(12) United States Patent
Arazi

(10) Patent No.: US 11,017,688 B1
(45) Date of Patent: May 25, 2021

(54) SYSTEM, METHOD, AND PROGRAM PRODUCT FOR INTERACTIVELY PROMPTING USER DECISIONS

(71) Applicant: Matan Arazi, Santa Monica, CA (US)

(72) Inventor: Matan Arazi, Santa Monica, CA (US)

(*) Notice: Subject to any disclaimer, the term of this patent is extended or adjusted under 35 U.S.C. 154(b) by 0 days.

(21) Appl. No.: 16/855,485

(22) Filed: Apr. 22, 2020

Related U.S. Application Data

(60) Provisional application No. 62/837,140, filed on Apr. 22, 2019.

(51) Int. Cl.
| | |
|---|---|
| *G09B 19/00* | (2006.01) |
| *G06Q 10/10* | (2012.01) |
| *G06Q 50/00* | (2012.01) |
| *H04W 4/029* | (2018.01) |
| *G16H 20/30* | (2018.01) |
| *G16H 20/60* | (2018.01) |
| *G06Q 30/02* | (2012.01) |

(52) U.S. Cl.
CPC .......... *G09B 19/00* (2013.01); *G06Q 10/109* (2013.01); *G06Q 30/0249* (2013.01); *G06Q 50/01* (2013.01); *G16H 20/30* (2018.01); *G16H 20/60* (2018.01); *H04W 4/029* (2018.02)

(58) Field of Classification Search
CPC .. G09B 19/00; G06Q 30/0249; G06Q 10/109; G06Q 50/01; G16H 20/30; G16H 20/60; H04W 4/029
See application file for complete search history.

(56) References Cited

U.S. PATENT DOCUMENTS

| | | | |
|---|---|---|---|
| 6,754,470 | B2 | 6/2004 | Hendrickson et al. |
| 7,967,731 | B2 | 6/2011 | Kil |
| 8,149,530 | B1 | 4/2012 | Lockton et al. |
| 8,162,756 | B2 | 4/2012 | Amaitis et al. |
| 8,312,173 | B2 | 11/2012 | Berg et al. |
| 8,381,108 | B2 | 2/2013 | Fuller et al. |
| 8,504,389 | B2 | 8/2013 | Saidel et al. |
| 8,560,498 | B2 | 10/2013 | Allen et al. |
| 8,600,774 | B2 | 12/2013 | Saidel et al. |
| 8,606,308 | B2 | 12/2013 | Simon et al. |
| 8,620,687 | B2 | 12/2013 | Saidel et al. |
| 8,622,837 | B2 | 1/2014 | Harris et al. |
| 8,768,728 | B2 | 7/2014 | Saidel et al. |

(Continued)

OTHER PUBLICATIONS

Python—Find pattern in time series graph with pandas—Stack Overflow, (Accessed Sep. 20, 2020) https://stackoverflow.com/questions/55057635/find-pattern-in-time-series-graph-with-pandas, 3 pages, Internet.

(Continued)

*Primary Examiner* — Masud Ahmed
(74) *Attorney, Agent, or Firm* — Amster, Rothstein & Ebenstein

(57) ABSTRACT

The present disclosure relates to a computer-implemented process for evaluating user activity, user preference, and/or user habit via one or more personal devices and providing precisely timed and situationally targeted prompts and stimuli for encouraging lifestyle choices and reinforcing health habits. It is an object of the present disclosure to provide a technological solution to the long felt need in health management services caused by the technical problem of procuring timely health management by encouraging healthy choices.

28 Claims, 71 Drawing Sheets

(56) References Cited

U.S. PATENT DOCUMENTS

| | | | |
|---|---|---|---|
| 8,799,019 B2 | 8/2014 | Saidel et al. | |
| 8,920,332 B2 * | 12/2014 | Hong | A61B 5/02427 600/500 |
| 8,945,017 B2 * | 2/2015 | Venkatraman | A61B 5/6831 600/500 |
| 9,044,171 B2 * | 6/2015 | Venkatraman | A61B 5/0002 |
| 9,069,380 B2 | 6/2015 | Rahman et al. | |
| 9,173,576 B2 | 11/2015 | Yuen et al. | |
| 9,173,577 B2 | 11/2015 | Yuen et al. | |
| 9,198,611 B2 | 12/2015 | Migita et al. | |
| 9,202,111 B2 | 12/2015 | Arnold et al. | |
| 9,215,286 B1 | 12/2015 | Schilit et al. | |
| 9,247,884 B2 | 2/2016 | Yuen et al. | |
| 9,274,747 B2 | 3/2016 | Fuller et al. | |
| 9,433,357 B2 | 9/2016 | Yuen et al. | |
| 9,642,209 B2 | 5/2017 | Eisele et al. | |
| 9,715,242 B2 | 7/2017 | Pillai et al. | |
| 9,830,426 B2 | 11/2017 | Arnold et al. | |
| 9,874,457 B2 | 1/2018 | Fung | |
| 9,931,539 B1 | 4/2018 | de Pablos et al. | |
| 10,268,660 B1 | 4/2019 | Krazi | |
| 10,375,135 B2 | 8/2019 | Lee et al. | |
| 10,398,389 B1 | 9/2019 | D'Alessandro et al. | |
| 10,477,640 B2 | 11/2019 | Eisele et al. | |
| 10,512,407 B2 * | 12/2019 | Richards | A61B 5/02427 |
| 10,545,132 B2 | 1/2020 | Guthrie et al. | |
| 10,579,866 B2 | 3/2020 | Bedrosian et al. | |
| 10,582,007 B2 | 3/2020 | Chander | |
| 10,599,116 B2 | 3/2020 | Pillai et al. | |
| 10,691,148 B2 | 6/2020 | Pillai et al. | |
| 10,712,722 B2 | 7/2020 | Pillai et al. | |
| 10,719,788 B2 | 7/2020 | Block et al. | |
| 10,825,356 B2 | 11/2020 | McNichol et al. | |
| 2008/0182542 A1 | 7/2008 | Choi et al. | |
| 2009/0054123 A1 | 2/2009 | Mityagin et al. | |
| 2009/0300143 A1 | 12/2009 | Musa et al. | |
| 2010/0029370 A1 | 2/2010 | Robinson et al. | |
| 2010/0178985 A1 | 7/2010 | Chickering et al. | |
| 2012/0166372 A1 | 6/2012 | Ilyas et al. | |
| 2012/0166373 A1 | 6/2012 | Sweeney et al. | |
| 2012/0191757 A1 | 7/2012 | Gross et al. | |
| 2012/0244504 A1 | 9/2012 | Wasserman | |
| 2013/0084882 A1 | 4/2013 | Khorashadi et al. | |
| 2013/0139259 A1 * | 5/2013 | Tegreene | H04N 21/4394 726/22 |
| 2013/0159310 A1 | 6/2013 | Birdwell et al. | |
| 2013/0176438 A1 | 7/2013 | Mate et al. | |
| 2013/0245930 A1 | 9/2013 | Husain et al. | |
| 2014/0142397 A1 | 5/2014 | Bedrosian et al. | |
| 2014/0142967 A1 | 5/2014 | Bedrosian et al. | |
| 2014/0302470 A1 * | 10/2014 | Zapantis | H04L 51/32 434/236 |
| 2015/0224364 A1 * | 8/2015 | Hsieh | G16H 40/67 700/275 |
| 2015/0364057 A1 * | 12/2015 | Catani | G16H 20/30 434/127 |
| 2016/0324463 A1 * | 11/2016 | Simpson | A61B 5/14532 |
| 2017/0053157 A1 | 2/2017 | Bedrosian et al. | |
| 2019/0065970 A1 * | 2/2019 | Bonutti | G06N 20/00 |
| 2019/0228856 A1 * | 7/2019 | Leifer | G16H 20/60 |

OTHER PUBLICATIONS

Time series modeling with Facebook Prophet, JR Kreiger, Towards Data Science, (Accessed Sep. 20, 2020) https://towardsdatascience.com/time-series-modeling-with-facebook-prophet-57f146a11d0d, 11 pages, Internet.

\* cited by examiner

Optional Second Personal User Device 10-1A

Processor(s) 702A | Memory 706A

Communication Portal 708A

Sensor Device(s) 704

| | |
|---|---|
| Location Sensor(s) 710 | Touch Screen Sensor(s) 736 |
| Accelerometer(s) 712 | Fingerprint Sensor(s) 738 |
| Altimeter(s) 714 | Barcode/QR code Sensor(s) 740 |
| Gyrometer(s) 716 | Barometer(s) 742 |
| Magnetometer(s) 718 | Heat Rate Sensor(s) 744 |
| Pedometer(s) 720 | Thermometer(s) 746 |
| Device Motion Sensor(s) 722 | Air Humidity Sensor 748 |
| Proximity Sensor(s) 724 | Geiger Counter(s) 750 |

Light Sensor(s) 726

Apple® Propriety HealthKit™ 728

Google® Propriety Google Fit™ 730

Global Positioning System Sensor(s) 732

Microphone(s) 734

Sensor Data Database 704-1

FIG. 2B

S1002: obtaining, at a personal information module, lifestyle information regarding a lifestyle of a first user S1004: storing, in memory operatively connected to the personal information module, the lifestyle information S1006 (optional): obtaining, at a social module, social information associated with the first user S1008 (optional): storing, in memory operatively connected to the social module, the social information S1010: filtering, by a situation module, the lifestyle information based at least on time, to provide a situation data set S1012: generating, by a stimulus module, a stimulus condition database including stimulus condition information S1014: storing, by the stimulus module, the stimulus database S1016: selecting, by a manager module, a first stimulus to be provided to the first user based at least on the situation data set, the stimulus information, and the stimulus condition information S1018: sending the first stimulus to a first computing device associated with the first user

CONTINUED WITH FIG. 10-B

FIG. 10-A

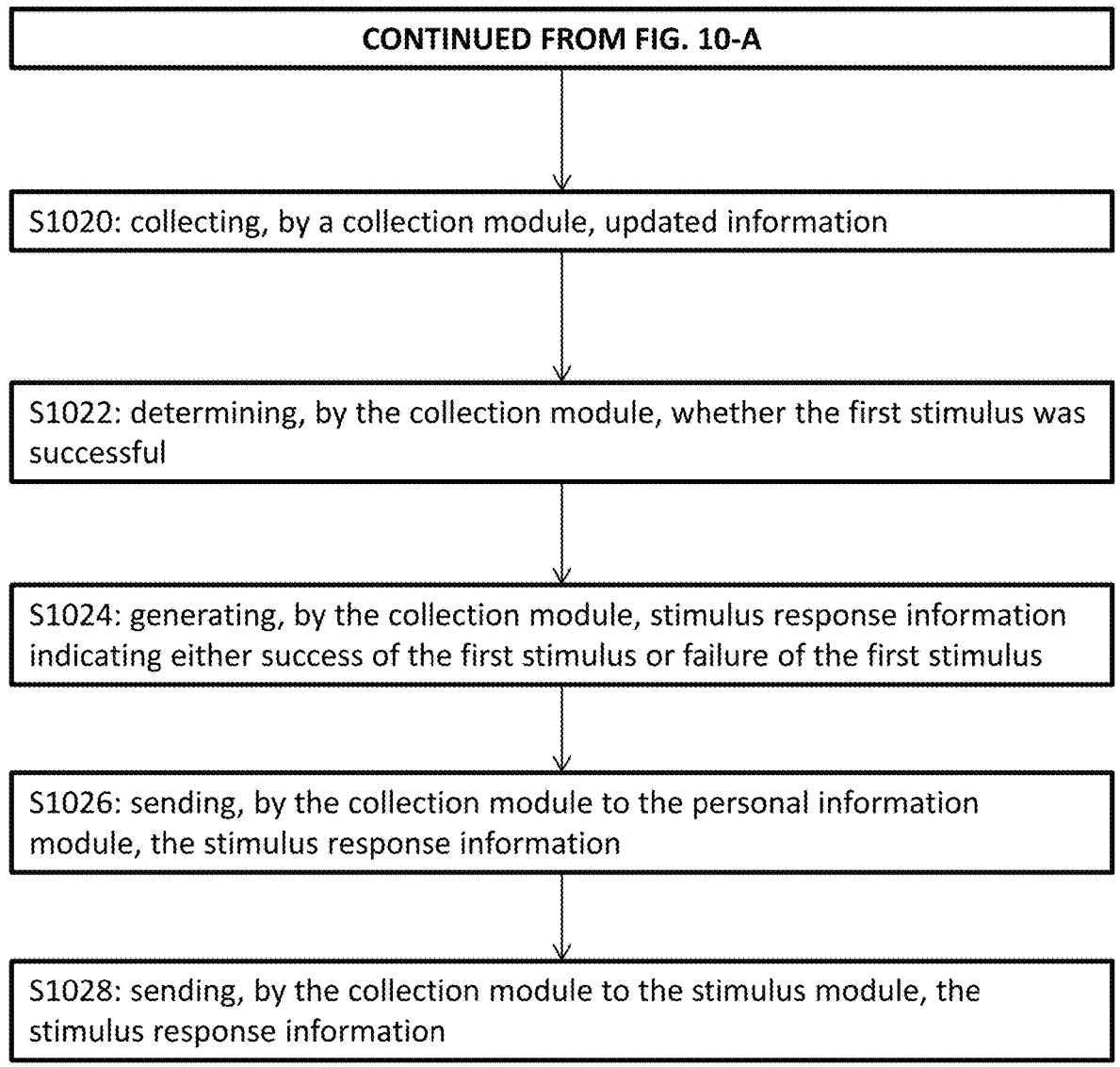
FIG. 10-B

S1010: providing, by the situation module 1016, a situation data set

S1202: accessing the lifestyle information provided by the personal information module 1002

S1204: arranging the lifestyle information based at least on chronology to include information from a first predetermined time period in a current state data set associated with a current state of the first user S1206: providing the situation information data set to a machine learning algorithm trained by prior lifestyle information arranged chronologically with situation provided as a label S1208: storing the situation data set associated with the first user

FIG. 12A

S1010: providing, by the situation module 1016, a situation data set

S1202': accessing the lifestyle information provided by the personal information module 1002

S1204': arranging the lifestyle information based at least on chronology to include information from a first predetermined time period in a current state data set associated with a current state of the first user S1206': access prior current state information associated with prior current states of the first user S1208': providing a situation data set associated with the first user, based on the current state data set and the prior current state information S1210': storing the situation data set associated with the first user

FIG. 12B

S1114: generating, by the training set module 1018, training data set 1018-1

S1210: accessing the stimulus information

S1212: filtering the stimulus information based at least on the stimulus information S1214: providing the training data set based on the application of the filter criteria to the stimulus information S1216: storing the training data set

FIG. 12C

S1116: selecting, by the manager module 1006, the first stimulus

S1218: receiving the situation data set from the situation module 1016

S1220: providing the situation data set to a second machine learning algorithm trained by the training data set with stimulus provided as a label

FIG. 12D

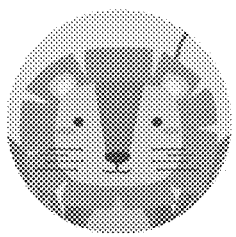
BOB SMITH
Power user
45 yrs    199 lb    5'7"    male
   
Employer: Not Defined
Insurer: Not Defined
Email address: bsmith@12345.com
LOGOUT
FIG. 13L

S2116: Predict one or more location data labels associated with one or more recurring locations

S2148: Obtain all identified recurring locations

↓

S2150: Compute hours of week

↓

S2152: Compare hours of week to data models

↓

S2154: For each match above a second threshold, confirm match

FIG. 21F

S2118: Confirm one or more predicted location data labels

OPTIONAL S2156: Obtain stimulus

↓

OPTIONAL S2158: Send stimulus to user

↓

OPTIONAL S2160: Receive response to stimulus

↓

S2162: Confirmed?

No → (loop back to S2156)
Yes → S2106

FIG. 21G

```
┌─────────────────────────────────────────────────────────────┐
│ S2164: Predict location-based event for each confirmed      │
│ location                                                    │
│   ┌─────────────────────────────────────────────────────┐   │
│   │ S2172: Obtain location data for each confirmed      │   │
│   │ location                                            │   │
│   └─────────────────────────────────────────────────────┘   │
│                            ↓                                │
│   ┌─────────────────────────────────────────────────────┐   │
│   │ S2174: Compute user location pattern(s)             │   │
│   └─────────────────────────────────────────────────────┘   │
│                            ↓                                │
│   ┌─────────────────────────────────────────────────────┐   │
│   │ S2176: Compare location patterns to data models     │   │
│   └─────────────────────────────────────────────────────┘   │
│                            ↓                                │
│   ┌─────────────────────────────────────────────────────┐   │
│   │ S2178: For each match above a third threshold,      │   │
│   │ confirm match                                       │   │
│   └─────────────────────────────────────────────────────┘   │
└─────────────────────────────────────────────────────────────┘
```

FIG. 21J

```
┌─────────────────────────────────────────────────────────────┐
│ S2166: Confirm each predicted location-based event          │
│     ┌───────────────────────────────────────────────────┐   │
│  ┌─▶│ OPTIONAL S2180: Obtain stimulus                   │   │
│  │  └───────────────────────────────────────────────────┘   │
│  │                         ↓                                │
│  │  ┌───────────────────────────────────────────────────┐   │
│  │  │ OPTIONAL S2182: Send stimulus to user             │   │
│  │  └───────────────────────────────────────────────────┘   │
│  │                         ↓                                │
│  │  ┌───────────────────────────────────────────────────┐   │
│  │  │ OPTIONAL S2184: Receive response to stimulus      │   │
│  │  └───────────────────────────────────────────────────┘   │
│  │                         ↓                                │
│  │           No          ◇                    Yes           │
│  └──────────────── S2186: Confirmed? ─────────┐             │
│                         ◇                     ↓             │
│                                            ┌──────┐         │
│                                            │S2110 │         │
│                                            └──────┘         │
└─────────────────────────────────────────────────────────────┘
```

FIG. 21K

S2202: Providing a lifestyle modification computer system to encourage a selected change in lifestyle related behavior S2204: obtaining, by a personal information module, raw time-stamped streaming data including a first set of time-stamped sensor data associated with a first time period, the first set of time-stamped sensor data being associated with a first location S2206: processing, in real-time by the personal information module of the lifestyle modification computer system, the second raw time-stamped streaming data to determine if the first location has a first location data label S2208: First location has a data label?

Yes → CONTINUE WITH FIG. 22B

No → CONTINUE WITH FIG. 22D

FIG. 22A

SYSTEM, METHOD, AND PROGRAM PRODUCT FOR INTERACTIVELY PROMPTING USER DECISIONS

REFERENCE TO RELATED APPLICATIONS

This application claims the benefit of and priority to each of U.S. Provisional Patent Application No. 62/837,140, filed on Apr. 22, 2019 and entitled "SYSTEM, METHOD AND PROGRAM PRODUCT FOR AN INTERACTIVE USER HEALTH DECISION PROMPTING PROCESS," the entire contents of each of which is hereby incorporated by reference herein.

FIELD

The present disclosure relates to a computer-implemented process for evaluating user activity, user preference, and/or user habit via an associated personal device and providing precisely timed and situationally targeted prompts and/or stimuli for encouraging lifestyle choices and reinforcing health habits.

BACKGROUND

Lifestyle and health management has been an established industry with extensive content in periodicals, books, membership services, and the like. A long felt need in this industry has been to address a fundamental issue with respect to any health management scheme, which is effective assistance in self-monitoring and health and lifestyle management. Certain programs have addressed this issue by introducing oversight and/or peer support. For example, services such as Weight Watchers® include periodic meetings for members of the program to offer guidance, support, and a certain degree of oversight. With technological advancements in personal devices, certain software applications ("apps") provide for recording user activity, journaling consumption, monitoring health parameters (e.g., heartrate), etc., which may be tied to traditional health management services like Weight Watchers® and other more modern technological solutions like MyFitnessPal® provided by Under Armor® and "Diabetes Prevention Program" provided by Lark™ (www.lark.com/dpp-diabetes-prevention-program/) to name a few.

Current technology relies largely upon self-reporting (e.g., meal and consumption journaling) with retrospective oversight. Such retrospective analysis, which may include some form of reward and punishment scheme, incentivizes inaccurate reporting (either on purpose or by accident) and fails to provide users with effective support at the moments when support is most needed. Indeed, applications today are not technologically capable of providing a real-time notification for an accurate and timely stimulus. Furthermore, the retrospective reporting gives rise to opportunities for users to cheat the system by inaccurate reportage after the fact. Current systems, methods, and program products are unable to evaluate user activity, user preference to provide precisely timed and situationally targeted prompts and/or stimuli for encouraging lifestyle choices and reinforcing health habits at or before a decision point is being made by a user.

SUMMARY

In view of the above, it is an object of the present disclosure to provide a technological solution to address the long felt need and technological challenges faced in health management services of procuring precisely timed health management directives, such as prompts, rewards, recommendations, challenges or other stimuli to users, such that positive choices are encouraged (and potentially, rewarded) at moments of decision, in contrast with conventional systems that are based on after-the-fact analysis, reward, and punishment. The present disclosure provides for an automated health care system using machine learning and/or heuristic systems that encourages individuals to make everyday choices by detecting situations in real time at or in advance of a decision point in being made by a user in which stimuli are most likely to be the most successful. Another advantage of the present disclosure is that by providing pre-emptive identification of user decision points and real time data capture, both the ability and inclination of users to provide inaccurate reporting is diminished. Collectively, these advantages work in favor of the users themselves as well because it makes it harder to effectively fool the system, method and program product described herein, thereby increasing user compliance and benefits from using the present disclosure.

In embodiments, a method comprises: (a) providing a lifestyle modification computer system comprising one or more computers and including at least: (1) a plurality of databases stored in respective memory operatively connected to the lifestyle computer system including: (A) a lifestyle database comprising: (i) first raw time-stamped streaming data including a plurality of sets of time-stamped sensor data obtained by a first user personal mobile device associated with a first user; and (ii) a respective location data label associated with each set of time-stamped sensor data; (B) a user profile database comprising: (i) location information including location data labels associated with the first user; (ii) event stream information including previously identified event streams associated with the first user and comprising a plurality of time-sequenced location data labels associated with the first user and respective type of stimulus information associated with each respective previously identified event stream; (iii) goal information indicating at least one selected goal in lifestyle behavior of the first user, wherein the at least one selected goal in lifestyle behavior is a subset of a plurality of goals in lifestyle behaviors organized by category of goal in lifestyle behavior; and (iv) budget information including an available budget to provide stimuli to the first user; (C) an available stimulus database comprising available stimulus information comprising a plurality of available stimulus items and for each available stimulus item of the plurality of available stimulus items comprising: (i) respective type of stimulus information including a respective categorization of the stimulation information associated with the at least one selected goal in lifestyle behavior; (ii) respective cost information including a respective cost associated with the respective stimulus item; and (iii) respective availability information including a respective time period when the respective stimulus item is available; and (D) a stimulus database comprising: (i) query information comprising: 1. a plurality of queries; 2. respective stimulus information associated with each query of the plurality of queries; and 3. respective outcome information associated with each query of the plurality of queries; (2) a plurality of modules including: (A) a personal information module; (B) a situation module; (C) a training set generation module; (D) a stimulus module; and (E) a manager module; (b) obtaining, by the personal information module of the lifestyle modification computer system from the first user personal mobile device, second raw time-stamped streaming data including a first set of time-stamped sensor data associated with a first time period, wherein the first set of time-stamped sensor data includes: (1) time-stamped location information associated with a location of the first user personal mobile device at a first time in the first time period; and (2) time-stamped motion information associated with movement of the first user personal mobile device at a first time in the first time period; (c) upon obtaining the second raw time-stamped streaming data, processing, in real-time by the personal information module of the lifestyle modification computer system, the second raw time-stamped streaming data by the steps of: (1) determining, in real-time, a first location data label associated with the location of the first user personal mobile device at the first time, wherein the determining step is made by comparing, at least the time-stamped location information with the location information associated with the first user stored in the user profile database to determine the first location data label; (2) updating the lifestyle database by storing the second raw time-stamped streaming data labelled with the first location data label; and (3) notifying the situation module that there is updated lifestyle information; (d) upon receiving the update notification, processing, in real-time by the situation module of the lifestyle modification computer system, the updated lifestyle information by performing, the steps of: (1) obtaining, by the situation module, the updated lifestyle information including the second raw time-stamped stream data with its associated first location data label and a second plurality of sets of time-stamped sensor data and corresponding location data labels, wherein the second plurality of time-stamped sensor data is a subset of the plurality of sets of time-stamped sensor data and each of the second plurality of sets of time-stamped sensor data is sequentially related by time interval and are within a threshold period of time; (2) generating, by the situation module, a first event stream organized by timestamps associated with each respective location data label corresponding to the second plurality of sets of time-stamped sensor data; (3) analyzing, by the situation module, the generated first event stream against event stream information obtained from the user profile database associated with the first user to determine a predicted event expected to occur within a second time period; (4) upon determining the predicted event expected to occur within the second time period, sending, from the situation module to the manager module, the generated first event stream as a first query to the manager module; (e) upon receipt of the first query, processing, in real-time by the manager module, the first query by the steps of. (1) providing, by the manager module, the first query as a data input to a first machine-learning algorithm with a training set provided by the training set module to generate first stimulus information to be sent to the first user personal mobile device, the first stimulus information including a first type of stimulus information indicating a first categorization of the first stimulus information associated with the at least one goal in lifestyle behavior; wherein the training set includes a plurality of the previously identified event streams associated with the first user, tagged with stimulus information indicating a respective stimulus offered to the first user and corresponding respective stimulus outcome information indicating one or more respective actions taken in response to the respective stimulus offered; (2) generating, by the manager module via the first machine-learning algorithm, the first stimulus information; and (3) sending the first stimulus information to the stimulus module of the lifestyle modification computer system; (f) upon receipt of the first stimulus information, processing, in real-time by the stimulus module, the first stimulus information to select a first stimulus including a first stimulus item to be sent to the first user personal mobile device, based on available stimulus items in the available stimulus database, and outcome information in the stimulus database indicating prior outcomes of one or more stimuli offered in association with prior event streams, wherein the first stimulus is a first type of stimulus, and wherein the first stimulus is selected from available stimulus items that are associated with both the first type of stimulus and outcome information indicating a positive outcome; and (g) sending, by the lifestyle modification computer system to the first user personal mobile device, the first stimulus, wherein the first stimulus is situationally targeted with respect to the at least one selected goal in lifestyle behavior such that the first stimulus is sent to provide a real-time notification to the first user via the personal mobile device; and (h) collecting, by the collection module, a first outcome associated with the first stimulus and causing the stimulus module to update the stimulus database with at least the first query, the first stimulus, and the first outcome.

In embodiments, the situational targeting of the first stimulus based on the predicted event, and wherein the predicted event is predicted in advance by the lifestyle modification computer system based on prior event streams. In embodiments, the method further comprises (i) obtaining, by the personal information module from the first user personal mobile device, third raw time-stamped streaming data including a second set of time-stamped sensor data associated with a third time period obtained by the first user personal mobile device, wherein the second set of time-stamped sensor data includes: (1) second time-stamped location information during the second time period associated with a second location of the first user personal mobile device at a second time in the second time period; and (2) second time-stamped motion information associated with movement of the first user personal mobile device at the second time in the second time period. In embodiments, the third raw time-stamped data includes additional data associated with the first user personal mobile device. In embodiments, the method further comprises: (j) upon obtaining the third raw time-stamped streaming data, determining, by the personal information module, that no location data label is associated with the second location, by processing the third raw time-stamped streaming data in real-time; and (k) sending, by the personal information module to a location module of the lifestyle modification computer system, the second time-stamped location information to establish a second location data label associated with the second location.

In embodiments, the method further comprises: (j) upon obtaining the third raw time-stamped streaming data, processing, in real-time by the personal information module of the lifestyle modification computer system, the third raw time-stamped streaming data by the steps of: (1) determining, in real-time, a second location data label associated with the second location of the first user personal mobile device at a second time in the second time period, wherein the determining step is made by comparing, at least the second time-stamped location information with the location information associated with the first user stored in the user profile database to determine the second location data label; (2) updating the lifestyle database by storing the third raw time-stamped streaming data labelled with the second location data label; and (3) notifying the situation module that there is updated lifestyle information; and (k) upon receiving the update notification, processing, in real-time by the situation module of the lifestyle modification computer system, the updated lifestyle information by performing the steps of: (1) obtaining, by the situation module, the updated lifestyle information including the third raw time-stamped stream data with its associated second location data label and a third plurality of sets of time-stamped sensor data and corresponding location data labels, wherein the third plurality of time-stamped sensor data is a subset of the plurality of sets of time-stamped sensor data and each of the third plurality of sets of time-stamped sensor data is sequentially related by time interval and within the threshold period of time; (2) generating, by the situation module, a second event stream organized by timestamps associated with each respective location data label corresponding to the third plurality of sets of time-stamped sensor data; (3) analyzing, by the situation module, the generated second event stream against event stream information obtained from the user profile database associated with the first user to determine no predicted event is expected to occur within a third time period; and (4) upon determining that no predicted event is expected to occur within the third time period, one of the following occurs: (i) the method ends; or (ii) the situation module notifies the personal information module to analyze the third raw time-stamped stream data for a third location.

In embodiments, the method further comprises (j) upon obtaining the third raw time-stamped streaming data, processing, in real-time by the personal information module of the lifestyle modification computer system, the third raw time-stamped streaming data by the steps of: (1) determining, in real-time, a second location data label associated with the second location of the first user personal mobile device at the second time period, wherein the determining step is made by comparing, at least the second time-stamped location information with the location information associated with the first user stored in the user profile database to determine the second location data label; (2) updating the lifestyle database by storing the third raw time-stamped streaming data labelled with the second location data label; and (3) notifying the situation module that there is updated lifestyle information; and (k) upon receiving the update notification, processing, in real-time by the situation module of the lifestyle modification computer system, the updated lifestyle information by performing, the steps of: (1) obtaining, by the situation module, the updated lifestyle information including the third raw time-stamped stream data with its associated second location data label and a third plurality of sets of time-stamped sensor data and corresponding location data labels, wherein the third plurality of time-stamped sensor data is a subset of the plurality of sets of time-stamped sensor data and each of the third plurality of sets of time-stamped sensor data is sequentially related by time interval and within the threshold period of time; (2) generating, by the situation module, a second event stream organized by timestamps associated with each respective location data label corresponding to the third plurality of sets of time-stamped sensor data; (3) analyzing, by the situation module, the generated second event stream against event stream information obtained from the user profile database associated with the first user to determine a second predicted event expected to occur within a third time period; (4) upon determining that the predicted event expected to occur within the third time period, sending, from the situation module to the manager module, the generated second event stream as a second query to the manager module; (1) upon receipt of the second query, processing, in real-time by the manager module, the second query by the steps of: (1) providing, by the manager module, the second query as a second data input to the first machine-learning algorithm with the training set provided by the training set module to receive an output from the first machine-learning algorithm; (2) determining, by the manager module, the output indicates that no stimulus information has been identified by the first machine-learning algorithm based on the second query as the second data input; and (3) sending, by the manager module to the stimulus module, the second query and the output; and (m) upon receipt of the second query and output, storing, by the stimulus module, the second query and the output in the stimulus database.

In embodiments, the method further comprises: (j) upon obtaining the third raw time-stamped streaming data, processing, in real-time by the personal information module of the lifestyle modification computer system, the third raw time-stamped streaming data by the steps of: (1) determining, in real-time, a second location data label associated with the second location of the first user personal mobile device at the second time period, wherein the determining step is made by comparing, at least the second time-stamped location information with the location information associated with the first user stored in the user profile database to determine the second location data label; (2) updating the lifestyle database by storing the third raw time-stamped streaming data labelled with the second location data label; and (3) notifying the situation module that there is updated lifestyle information; and (k) upon receiving the update notification, processing, in real-time by the situation module of the lifestyle modification computer system, the updated lifestyle information by performing, the steps of: (1) obtaining, by the situation module, the updated lifestyle information including the third raw time-stamped stream data with its associated second location data label and a third plurality of sets of time-stamped sensor data and corresponding location data labels, wherein the third plurality of time-stamped sensor data is a subset of the plurality of sets of time-stamped sensor data and each of the third plurality of sets of time-stamped sensor data is sequentially related by time interval and within the threshold period of time; (2) generating, by the situation module, a second event stream organized by timestamps associated with each respective location data label corresponding to the third plurality of sets of time-stamped sensor data; (3) analyzing, by the situation module, the generated second event stream against event stream information obtained from the user profile database associated with the first user to determine a second predicted event expected to occur within a third time period; and (4) upon determining that the predicted event expected to occur within the third time period, sending, from the situation module to the manager module, the generated second event stream as a second query to the manager module; (1) upon receipt of the second query, processing, in real-time by the manager module, the second query by the steps of: (1) providing, by the manager module, the second query as a second data input to the first machine-learning algorithm to generate second stimulus information to be sent to the first user personal mobile device, the second stimulus information including a second type of stimulus information indicating a second categorization of the second stimulus information associated with the at least one goal in lifestyle behavior; (2) generating, by the manager module via the first machine-learning algorithm, the second stimulus information; and (3) sending the second stimulus information to the stimulus module of the lifestyle modification computer system; (m) upon receipt of the first stimulus information, determining, in real-time by the stimulus module, a second stimulus corresponding to the second stimulus information is unavailable; and (n) upon determining the second stimulus is unavailable, storing, by the stimulus module, the second query and the second stimulus information.

In embodiments, the budget information further includes respective available budgets for each user of a plurality of users of an interactive electronic network associated with the lifestyle modification computer system, and wherein the plurality of users includes the first user. In embodiments, one or more users of the plurality of users is associated with a monthly budget. In embodiments, one or more users of the plurality of users associated with the same budget.

In embodiments, the budget information includes a budget for each at least one selected goal.

In embodiments, the at least one selected goal includes a plurality of selected goals.

In embodiments, the plurality of queries includes queries associated with one or more users associated with one or more goals in lifestyle behavior in the same category of goal in lifestyle behavior as the at least one goal in lifestyle behavior of the first user.

In embodiments, the respective outcome information for each query of the plurality of queries includes outcomes of one or more stimuli offered to one or more additional users associated with one or more goals in lifestyle behavior in the same category of goal in lifestyle behavior as the selected at least one goal in lifestyle behavior of the first user.

In embodiments, prior to step (d), the personal information module sends the second raw-time stamped streaming data with its associated first location data label to the situation module.

In embodiments, the obtained second plurality of sets of time-stamped sensor data and corresponding location labels includes less than all of the second plurality of sets of time-stamped sensor data within the threshold period of time.

In embodiments, the threshold period of time is one of the following: (i) 1 calendar day; (ii) 12 hours; (iii) 6 hours; (iv) 1 hour; and (v) 30 minutes.

In embodiments, the first event stream includes a plurality of event streams, each organized by timestamps associated with its respective location data label.

In embodiments, the first event stream is organized further by one or more of the following: (i) each event included in the first event stream's respective timestamp; and (ii) a routine associated with the first user.

In embodiments, the second period of time is less than 10 minutes.

In embodiments, the first stimulus is sent to a second user personal mobile device associated with a second user.

In embodiments, the first outcome is collected from at least one of the following: (i) the first user personal mobile device; (ii) a second electronic device associated with the first user; (iii) a second user personal mobile device associated with a second user; and (iv) a third party computer system.

In embodiments, the first stimulus is sent from the stimulus module to the manager module and then from the manager module to the first user personal mobile device.

In embodiments, the first stimulus is sent to the first user personal mobile device by the stimulus module.

In embodiments, the first stimulus is sent from the stimulus module to the collection module and then from the collection module to the first user personal mobile device.

In embodiments, the first machine-learning algorithm is utilizes a neural network. In embodiments, the first machine learning algorithm utilizes a deep learning neural network.

In embodiments, the training set further includes a plurality of previously identified event streams associated with a second user.

In embodiments, the method may be performed by a system configured to perform said method.

In embodiments, a lifestyle modification computer system comprises: (a) a plurality of databases stored in respective memory operatively connected to the lifestyle computer system including: (1) a lifestyle database comprising: (A) first raw time-stamped streaming data including a plurality of sets of time-stamped sensor data obtained by a first user personal mobile device associated with a first user and (B) a respective location data label associated with each set of time-stamped sensor data; (2) a user profile database comprising: (A) location information including location data labels associated with the first user; (B) event stream information including previously identified event streams associated with the first user and comprising a plurality of time-sequenced location data labels associated with the first user and respective type of stimulus information associated with each respective previously identified event stream; (C) goal information indicating at least one selected goal in lifestyle behavior of the first user, wherein the at least one selected goal in lifestyle behavior is a subset of a plurality of goals in lifestyle behaviors organized by category of goal in lifestyle behavior; and (D) budget information including an available budget to provide stimuli to the first user: (3) an available stimulus database comprising available stimulus information comprising a plurality of available stimulus items and for each available stimulus item of the plurality of available stimulus items comprising: (A) respective type of stimulus information including a respective categorization of the stimulation information associated with the at least one selected goal in lifestyle behavior; (B) respective cost information including a respective cost associated with the respective stimulus item; and (C) respective availability information including a respective time period when the respective stimulus item is available; and (4) a stimulus database comprising: (A) query information comprising: (i) a plurality of queries; (ii) respective stimulus information associated with each query of the plurality of queries; and (iii) respective outcome information associated with each query of the plurality of queries; (b) a plurality of modules including: (i) a personal information module, configured to perform the following steps: (A) obtaining, by the personal information module of the lifestyle modification computer system from the first user personal mobile device, second raw time-stamped streaming data including a first set of time-stamped sensor data associated with a first time period, wherein the first set of time-stamped sensor data includes: (i) time-stamped location information associated with a location of the first user personal mobile device at a first time in the first time period; and (ii) time-stamped motion information associated with movement of the first user personal mobile device at a first time in the first time period; (B) upon obtaining the second raw time-stamped streaming data, processing, in real-time by the personal information module of the lifestyle modification computer system, the second raw time-stamped streaming data by the steps of (i) determining, in real-time, a first location data label associated with the location of the first user personal mobile device at the first time, wherein the determining step is made by comparing, at least the time-stamped location information with the location information associated with the first user stored in the user profile database to determine the first location data label; (ii) updating the lifestyle database by storing the second raw time-stamped streaming data labelled with the first location data label; and (iii) notifying the situation module that there is updated lifestyle information; (2) a situation module configured to perform the following steps: (A) upon receiving the update notification, processing, in real-time by the situation module of the lifestyle modification computer system, the updated lifestyle information by performing, the steps of: (i) obtaining, by the situation module, the updated lifestyle information including the second raw time-stamped stream data with its associated first location data label and a second plurality of sets of time-stamped sensor data and corresponding location data labels, wherein the second plurality of time-stamped sensor data is a subset of the plurality of sets of time-stamped sensor data and each of the second plurality of sets of time-stamped sensor data is sequentially related by time interval and are within a threshold period of time; (ii) generating, by the situation module, a first event stream organized by timestamps associated with each respective location data label corresponding to the second plurality of sets of time-stamped sensor data; (iii) analyzing, by the situation module, the generated first event stream against event stream information obtained from the user profile database associated with the first user to determine a predicted event expected to occur within a second time period; and (iv) upon determining the predicted event expected to occur within the second time period, sending, from the situation module to the manager module, the generated first event stream as a first query to the manager module; (3) a training set generation module configured to provide a training set associated with a first machine-learning algorithm; (4) a manager module configured to perform the following steps: (A) upon receipt of the first query, processing, in real-time by the manager module, the first query by the steps of: (i) providing, by the manager module, the first query as a data input to a first machine-learning algorithm with the training set provided by the training set module to generate first stimulus information to be sent to the first user personal mobile device, the first stimulus information including a first type of stimulus information indicating a first categorization of the first stimulus information associated with the at least one goal in lifestyle behavior; wherein the training set includes a plurality of the previously identified event streams associated with the first user, tagged with stimulus information indicating a respective stimulus offered to the first user and corresponding respective stimulus outcome information indicating one or more respective actions taken in response to the respective stimulus offered; (ii) generating, by the manager module via the first machine-learning algorithm, the first stimulus information; and (iii) sending the first stimulus information to the stimulus module of the lifestyle modification computer system; (5) a stimulus module configured to perform the following steps: (A) upon receipt of the first stimulus information, processing, in real-time by the stimulus module, the first stimulus information to select a first stimulus including a first stimulus item to be sent to the first user personal mobile device, based on available stimulus items in the available stimulus database, and outcome information in the stimulus database indicating prior outcomes of one or more stimuli offered in association with prior event streams, wherein the first stimulus is a first type of stimulus, and wherein the first stimulus is selected from available stimulus items that are associated with both the first type of stimulus and outcome information indicating a positive outcome; and (B) sending, to the first user personal mobile device, the first stimulus, wherein the first stimulus is situationally targeted with respect to the at least one selected goal in lifestyle behavior such that the first stimulus is sent to provide a real-time notification to the first user via the personal mobile device; and (6) a collection module configured to perform the following steps: (A) collecting, by the collection module, a first outcome associated with the first stimulus and causing the stimulus module to update the stimulus database with at least the first query, the first stimulus, and the first outcome.

In embodiments, a computer device, associated with a first user, to encourage a selected change in health-related behavior of at least the first user of a plurality of users of an interactive electronic network, may comprise: (a) a plurality of sensors comprising: i. at least one accelerometer; ii. at least one gyrometer; iii. at least one pedometer; iv. at least one proximity sensor; v. at least one magnetometer sensor; vi. at least one light sensor; (b) a personal information module including first one or more processors operatively connected to a first memory device and first machine readable instructions, wherein the first one or more processors execute the first machine readable instructions to obtain and store in one or more lifestyle databases, lifestyle information associated with the first user, wherein the lifestyle information includes: i. identity information associated with an identity of the first user; ii. health-related attribute information associated with at least one health-related attribute of the first user; iii. health kit information associated with health conditions and/or actions effecting health of the first user; iv. sensor information associated the computer device, wherein the sensor information includes at least one of the following: (1) location information associated with location information and/or movement information of the computer device at a first respective time; (2) accelerometer information generated by the at least one accelerometer at a second respective time; (3) gyrometer information generated by the at least one gyrometer at third respective time; (4) pedometer information generated by the at least one pedometer at a fourth respective time; (5) proximity information generated by the at least one proximity sensor at a fifth respective time; (6) magnetometer information generated by the at least one magnetometer sensor at a sixth respective time; (7) orientation information associated with degrees of rotation the computer device makes around three physical axes at a seventh respective time; (8) light sensor information generated by the at least one light sensor at an eighth respective time; (9) altimeter information associated with a change in altitude pressure of the computer device at a ninth respective time; (10) motion information associated with acceleration, attitude, rotation, and magnetic data of the computer device at a respective time; v. prior purchase information associated with at least one of the following: (1) one or more purchases made by the first user; and (2) one or more purchases associated with the first user; vi. activity information indicative of at least one of the following: (1) one or more activities engaged in by the first user; and (2) one or more activities associated with the first user within; vii. budget information associated with an available budget for use in providing stimulus to the first user; and viii. goal information associated with the selected change in behavior; (c) a situation module including second one or more processors operatively connected to at least a second memory device and second machine readable instructions, the situation module operatively connected to the personal information module, wherein the second one or more processors execute the second machine readable instructions to provide a situation data set by: i. accessing the lifestyle information provided by the personal information module; ii. arranging the lifestyle information based at least on chronology to include information from a first predetermined time period to provide a current state data set associated with a current state of the first user; iii. arranging other lifestyle information from prior predetermined periods of time as prior lifestyle information; iv. providing the current state data set to a first machine learning algorithm trained by the prior lifestyle information arranged chronologically with situation provided as a label; wherein the first machine learning algorithm provides a situation data set associated a situation of the first user; v. storing the situation data set associated with the first user; (d) a stimulus module, including third one or more processors operatively connected to a third memory device and third machine readable instructions, wherein the third one or more processors execute the third machine readable instructions to provide a stimulus database using the second memory device, the stimulus database comprising stimulus information, wherein the stimulus information includes, for each prior stimulus of a plurality of prior stimuli: i. the respective prior stimulus; ii. a respective situation data set associated with the respective prior stimulus; and iii. respective stimulus response information associated with the respective prior stimulus; (e) a training set module, including fourth one or more processors operably connected to a fourth memory device and fourth machine readable instructions, the training set module operatively connected to the stimulus module, wherein the fourth one or more processors execute the fourth machine readable instructions to generate a training data set by: i. accessing the stimulus information; ii. filtering the stimulus information based at least on available stimulus information; iii. providing the training data set based on the application of filter criteria to the stimulus information; and iv. storing the training data set; (f) a manager module including fifth one or more processors operatively connected to at least a fifth memory device and fifth machine readable instructions, the manager module operatively connected to the situation module and the training set module, wherein the fifth one or more processors execute the fifth machine readable instructions to select the first stimulus by: i. receiving the situation data set from the situation module; ii. providing the situation data set to a second machine learning algorithm trained by the training data set with stimulus provided as a label, wherein the second machine learning algorithm selects the first stimulus and a time to display the first stimulus; iii. generating, first machine-readable display instructions including a first graphical user interface (GUI), wherein the first GUI represents the first stimulus; and iv. executing, by the computer device at the time, the first machine-readable display instructions, wherein, upon executing the first machine-readable display instructions, the computer device displays the first GUI on a display screen of the computer device; (g) a collection module including sixth one or more processors operatively connected to a sixth memory device and sixth machine readable instructions, wherein the sixth one or more processors execute the sixth machine readable instructions to: i. after the first stimulus is displayed by the display screen of the computer device, collect updated lifestyle information from at least one of: (1) the computer device; (2) a second computer device associated with the first user; and (3) a third computer device associated with a second user associated with the first user via social media, professional affiliation or the interactive electronic network, wherein the updated information includes at least updated lifestyle information; ii. determine, based at least on the updated lifestyle information, the first stimulus was successful; iii. generating, second machine-readable display instructions including a second GUI, wherein the second GUI represents stimulus response information associated with success of the first stimulus; iv. executing, by the computer device, the second machine-readable display instructions, wherein, upon executing the second machine-readable display instructions, the computer device displays the second GUI on a display screen of the computer device; and v. send the updated lifestyle information to the personal information module to be added to the lifestyle database.

In embodiments, the computer device further comprises: (h) a social module including seventh one or more processors operatively connected to at least a seventh memory device and seventh machine readable instructions, the social module operatively connected to the personal information module, wherein the seventh one or more processors execute the seventh machine readable instructions to obtain and store in one or more social databases, social information associated with the first user, wherein the social information includes: i. social network information, wherein the social network information comprises a second user that is a social network connection; and ii. professional colleague information, wherein the social module is operatively connected to the personal information module, and wherein the execution of the first machine readable instructions by the personal information module further includes: iv. accessing the social network information provided by the social module; v. filtering the social network information based at least on the time; and vi. providing the social network information to the personal information module and the lifestyle database. In embodiments, the at least one second user is a professional colleague connection of the first user. In embodiments, the third computer device is associated with the second user. In embodiments, the personal information module is operatively connected to the social module, wherein the first one or more processors execute the first machine readable instructions to provide the proximity information indicating when the first user is within a predetermined proximity of the second user by: i. accessing the social network information; ii. filtering the social network information based at least a current time; and iii. providing the proximity information based on: (1) the location information associated with the first user; and (2) location information associated with at least the second user. In embodiments, the proximity information is based on at least one of the following: (1) determining the third computer device is associated with the second user; (2) determining the third computer device is within range of the same cell tower as at least one of the computer device or the second computer device; (2) determining the third computer device associated with the second user is within a predetermined distance of at least one of the computer device or the second computer device; (3) determining the third computer device and at least one of the computer device or the second computer device are in a first building; (4) determining the third computer device and at least one of the computer device or the second computer device are within a first city block; (5) determining the third computer device and at least one of the computer device or the second computer device are in a first room of a second building; and (6) determining the third computer device and at least one of the computer device or the second computer device are within a first place of business.

In embodiments, the stimulus response information is further provided from: d. a fourth computer device associated with a third user of the interactive electronic network associated with the first user via professional association.

In embodiments, the stimulus response information is further provided from: d. a fourth computer device associated with a third user of the interactive electronic network, wherein the third user is not linked via social media or professional affiliation to the first user.

In embodiments, the stimulus response information is further provided from: d. a fourth computer device associated with a third user of the interactive electronic network, wherein the third user is associated with the first user via professional association; and e. a fifth computer device associated with a fourth user of the interactive electronic network, wherein the fourth user is not linked via social media or professional affiliation to the first user.

In embodiments, the stimulus response information is provided based on updated lifestyle information indicating whether the first stimulus provided positive results relative to the selected change.

In embodiments, the health-related attribute information includes at least one of: (1) heartbeat information; (2) respiratory information; (3) blood pressure information; (4) body temperature information; (5) height information; and (6) weight information. In embodiments, at least a portion of the health-related attribute information is provided by the first user via the computer device. In embodiments, at least a portion of the health-related attribute information is provided by at least one of the plurality of sensors. In embodiments, at least a portion of the health-related attribute information is provided by the first user via the second computer device. In embodiments, at least a portion of the health-related attribute information and/or health kit information is provided by one or more healthcare providers. In embodiments, at least a portion of the health-related attribute information is provided by the computer device in response to a survey provided on the computer device.

In embodiments, the first GUI comprises: (1) a first message based on at least the first stimulus and an impending first choice, wherein the impending first choice is based on at least the selected change; and (2) impending first choice information being based on at least the impending first choice and the selected change. In embodiments, the first-machine readable display instructions further include a notification instruction, wherein execution of the first-machine readable display instructions by the computer device causes a notification to be sent from the computer device to the second computer device In embodiments, the collection module: i. generates, after generating the stimulus response information; third machine-readable display instructions including a third GUI, wherein the third GUI comprises a first message based on at least one of: (1) the first stimulus, and (2) the stimulus response information; and ii. perform at least one of the following: (1) executing, by the computer device, the third machine-readable display instructions, wherein, upon executing the third machine-readable display instructions, the computing device displays the third GUI on the display screen of the computer device; and (2) sending, by the computer device to the second computer device, the third machine-readable display instructions, wherein, upon receiving the third machine-readable display instructions, the second computer device executes the third machine-readable display instructions which causes the third GUI to be displayed on a second display screen of the second computer device.

In embodiments, the computer device is at least one of a portable computer device and a wearable device. In embodiments, the portable computer device is at least one of a smart phone, a tablet, a phablet, or a laptop.

In embodiments, the second computer device is at least one of a portable computer device or a wearable device. In embodiments, the portable computer device is at least one of a smart phone, a tablet, a phablet, and a laptop.

In embodiments, the second computer device comprises at least one of: (1) an accelerometer; (2) a gyrometer; (3) a pedometer; (4) a magnetometer; (5) a light sensor; and (6) a proximity sensor.

In embodiments, the first machine learning algorithm utilizes a neural network. In embodiments, the first machine learning algorithm utilizes a deep learning neural network.

In embodiments, the second machine learning algorithm utilizes a neural network. In embodiments, the second machine learning algorithm utilizes a deep learning neural network.

In embodiments, each of the (1) location information; (2) accelerometer information; (3) gyrometer information; (4) pedometer information generated by at least one pedometer of the first user computer device at a respective fourth time; (5) proximity information; (6) magnetometer information; (7) orientation information; (8) light sensor information; and (9) altimeter information; and (10) motion information include a respective time stamp.

In embodiments, the prior lifestyle information includes time stamps that are prior to the first predetermined period of time.

In embodiments, at least a portion of the (1) location information; (2) accelerometer information; (3) gyrometer information; (4) pedometer information generated by at least one pedometer of the first user computer device at a respective fourth time; (5) proximity information; (6) magnetometer information; (7) orientation information; (8) light sensor information; and (9) altimeter information; and (10) motion information is provided by the second computer device.

In embodiments, a method for encouraging a selected behavior change in at least one user of an interactive electronic network includes: (a) receiving and storing, by a computing device in one or more databases, identity information associated with each user of a plurality of users of the interactive electronic network; (b) receiving and storing, by the computing device in the one or more databases, attribute information associated with physical attributes of each user of the plurality of users of the interactive electronic network; (c) receiving and storing, by the computing device in the one or more databases, health condition information associated with health conditions of each user of the plurality of users of the interactive electronic network; (d) receiving and storing, by the computing device in the one or more databases, location information associated with a respective location of each user of the plurality of users of the interactive electronic network; (e) receiving and storing, by the computing device in the one or more databases, movement information associated with movements made by each user of the plurality of users of the interactive electronic network; (f) receiving and storing, by the computing device in the one or more databases, sensor information associated with one or more devices of each user of the plurality of users of the interactive electronic network and/or any technology or functionality included within, attached to, or connected to one or more of such devices, the sensor information including data from one or more of an accelerometer, a light sensor, a compass, a vibration sensor, wireless association data, and a proximity sensor; (g) storing, by the computing device in the one or more databases, prior stimulus information associated with prior stimulus provided to each user of the plurality of users of the interactive network by the computing device; (h) storing, by the computing device in the one or more databases, stimulus result information associated with a level of success of the prior stimulus provided to each user of the plurality of users of the interactive network provided by the computing device; (i) accessing, from the one or more databases by the computing device, at least a subset of the identity information, attribute information, health condition information, location information, movement information, sensor information, wireless association data, prior stimulus information, stimulus result information and any other information related to data derived to facilitate the health management process of a first user of the plurality of users of the interactive electronic network; (j) determining, by the computing device, a first impending choice of the first user to be potentially influenced based on one or more of the identity information, attribute information, health condition information, location information, movement information, prior stimulus information and stimulus result information associated with the first user; (k) determining, by the computer device, a first stimulus to be sent to the first user, wherein the determining is based on one or more of the following: (i) the first impending choice of the first user; (ii) prior stimulus information related to the first user; (iii) prior stimulus success information related to the first user; and (iv) budget information related to cost of the first stimulus; (l) transmitting, by the computing device to a first user device associated with the first user, the first stimulus; (m) transmitting, after a period of time, by the computing device to the first user device, a first query regarding the first stimulus; (n) receiving, by the computing device from the first user device, a first reply to the first query; (o) re-accessing, by the computing device, after the period of time, at least a subset of the identity information, attribute information, health condition information, location information, movement information, prior stimulus information and stimulus result information of the first user of the plurality of users of the interactive electronic network; (p) analyzing, by the computing device, the first reply and at least the location information and movement information to determine whether the first stimulus was successful in changing the first behavior and generating first stimulus result information based on the analysis; (q) storing, by the computing device in the one or more databases, the first stimulus result information; (r) in the case where the first stimulus result information indicates no change in behavior, repeating step h. to step p. until the stimulus result indicates a change in the first behavior; and (s) revising one or more bases for the determining in step (k) based on the first stimulus result information, wherein the one or more bases include at least one of a predetermined period of time and a predetermined condition related to inhibiting stimuli that potentially influence one or more choices that are similar to the first impending choice.

In embodiments the method may further include (t) determining, by the computer system, the stimulus result indicates the change in the first behavior; (u) generating, by the computer system in response to determining the change in the first behavior, a first graphical user interface (GUI), wherein the first GUI includes a first message, wherein the first message is based on at least one of the change in the first behavior, the first behavior, the first stimulus, and the first impending choice; and (v) transmitting, by the computing device to the first user device via the interactive electronic network, the first GUI, wherein, upon receiving the first GUI, the first user device displays the first GUI on a display screen of the first user device. In embodiments, the step of determining the stimulus result indicates the change in the first behavior is based on at least one of the following: (i) location information associated with the first user; (ii) first user additional location information received by the computing device from the first user device, wherein the first user location information is received by the computing device after the computer device transmits the first stimulus; (iii) movement information associated with the first user; and (iv) first user additional movement information received by the computing device from the first user device, wherein the first additional movement information received by the computing device after the computer device transmits the first stimulus.

In embodiments, transmitting the first stimulus may further include (i) generating, by the computing device, a first graphical user interface (GUI), wherein the first GUI includes at least one of the following: (1) a first message, wherein the first message is based on at least one of the first stimulus and the first impending choice; and (2) first choice information, wherein the first choice information is based on at least the first impending choice; and (ii) transmitting, by the computing device to the first user device via the interactive electronic network, the first GUI, wherein, upon receiving the first GUI, the first user device displays the first GUI on a display screen of the first user device.

In embodiments, the first user device may include a portable computing device, such as a smart phone, and a wearable device. In embodiments identity information associated with the first user is received by the computing device from at least one of the smart phone and the wearable device, wherein the identity information is received via the interactive electronic network. In embodiments, attribute information associated with the first user is received by the computing device from at least one of the smart phone and the wearable device, wherein the identity information is received via the interactive electronic network. In embodiments, the location information associated with the first user is received by the computing device from at least one of the smart phone and the wearable device, wherein the identity information is received via the interactive electronic network. In embodiments, the movement information associated with the first user is received by the computing device from at least one of the smart phone and the wearable device, wherein the identity information is received via the interactive electronic network. In embodiments, the sensor information associated with the first user is received by the computing device from at least one of the smart phone and the wearable device, wherein the identity information is received via the interactive electronic network. In embodiments, the smart phone includes at least one of. (i) the accelerometer; (ii) the light sensor; (iii) the vibration sensor; and (iv) the proximity sensor. In embodiments, the smart phone may additionally or alternatively include other smart phone technology or functionality that produces health management related data. In embodiments, the wearable device includes at least one of (i) the accelerometer; (ii) the light sensor; (iii) the vibration sensor; and (iv) the proximity sensor. In embodiments, the wearable device may additionally or alternatively include other wearable device technology or functionality that produces health management related data.

In embodiments, the identity information associated with the first user is received by the computing device from the first user device via the interactive electronic network. In embodiments, the identity information associated with the first user is received by the computing device from one or more third-party devices or databases. In embodiments, the attribute information associated with the first user is received by the computing device from the first user device via the interactive electronic network. In embodiments, the location information associated with the first user is received by the computing device from the first user device via the interactive electronic network. In embodiments, the movement information associated with the first user is received by the computing device from the first user device via the interactive electronic network. In embodiments, the sensor information associated with the first user is received by the computing device from the first user device via the interactive electronic network.

In embodiments, the first user device includes at least one of: (i) the accelerometer; (ii) the light sensor; (iii) the vibration sensor; and (iv) the proximity sensor. In embodiments, a computing device for encouraging a selected choice by at least one user of the computing device may include: (a) one or more processor devices; (b) one or more sensor devices; and (c) a non-transitory computer-readable memory having stored thereon recorded sensor data from the one or more sensor devices and instructions for the one or more processor devices to perform the steps of: (i) receiving user identification information from the at least one user; (ii) transmitting, to the one or more server devices, the received user identification information; (iii) receiving, from one or more server devices, first machine-readable instructions to render a user permission input GUI, the user permission input graphical user interface comprising a graphical accept option to approve transmission of the recorded sensor data to the one or more server devices; (iv) rendering, in accordance with the first machine-readable instructions, the user permission input graphical user interface; (v) receiving an input of the graphical accept option; (vi) transmitting, to the one or more server devices, permission data associated with the input of the graphical accept option; (vii) receiving, from the one or more server devices, second machine-readable instructions to transmit at least a portion of the recorded sensor data at predetermined time intervals to the one or more server devices; (viii) transmitting, in accordance with the second machine-readable instructions, the at least a portion of the recorded sensor data to the one or more server devices at the predetermined time intervals; (ix) receiving, from the one or more server devices, third machine-readable instructions to render a user stimulus graphical user interface, the user stimulus graphical user interface comprising one or more graphical options for responding to a user stimulus; (x) rendering, in accordance with the third machine-readable instructions, the user stimulus graphical user interface; (xi) receiving a selection of the one or more graphical options; (xii) transmitting, to the one or more server devices, user response data associated with the selection of the one or more graphical options; and (xiii) upon a condition of the transmitted sensor data over a plurality of predetermined time intervals meets at least one criterion associated with the user stimulus and the transmitted user response data, receiving, from the one or more server devices, fourth machine-readable instructions to render a user reward notification or a user award notification. In embodiments, the process may further include (xiv) receiving and storing, identity information associated with the at least one user; (xv) receiving and storing attribute information associated with physical attributes of the at least one user; (xvi) receiving and storing health condition information associated with health conditions of the at least one user; (xvii) receiving and storing location information associated with a respective location of the at least one user; and (xviii) receiving and storing movement information associated with movements made by the at least one user.

In embodiments the one or more sensor devices is operatively connected to a first user device associated with the at least one user. In embodiments, the first user device includes a smart phone and a wearable device. In embodiments, the user identification information is received from by the computing device from at least one of the smart phone and the wearable device, wherein the user identification information is received via an interactive electronic network.

In embodiments, a computing device for encouraging a selected choice by at least one user of a plurality of remote computing devices and/or local computing devices (e.g., the user's phone), the computing device may include: (a) one or more processor devices; (b) a network communication interface to the plurality of remote computing devices and a plurality of third-party computing systems; and (c) a non-transitory computer-readable memory having stored thereon instructions for the one or more processor devices to perform the steps of: (i) receiving, from the plurality of remote computing devices, user identification information; (ii) transmitting, to the plurality of remote computing devices, first machine-readable instructions to render a user permission input graphical user interface, the user permission input graphical user interface comprising a graphical accept option to approve transmission of recorded sensor data at the respective remote computing device to the computing device; (iii) receiving permission data associated with the graphical accept option from one or more of the plurality of remote computing devices; (iv) transmitting, to the one or more of the plurality of remote computing devices, second machine-readable instructions to transmit at least a portion of the recorded sensor data at predetermined time intervals to the computing device; (v) receiving, from the one or more of the plurality of remote computing devices, the at least a portion of the recorded sensor data at the predetermined time intervals; (vi) storing, in one or more databases, the received sensor data in association with the received user identification information; (vii) retrieving, from the plurality of third-party computing systems, user attribute information in correspondence with the received user identification information; (viii) storing, in the one or more databases, the retrieved user attribute information in association with the corresponding user identification information; (ix) determining, based at least in part upon the stored sensor data and the stored user attribute information, one or more user stimuli for the respective one or more of the plurality of remote computing devices, each of the one or more user stimuli comprising at least one criterion for a positive result; (x) generating and transmitting, to the respective one or more of the plurality of remote computing devices, third machine-readable instructions to render a user stimulus graphical user interface, the user stimulus graphical user interface comprising one or more graphical options for responding to the respective one or more user stimuli; (xi) receiving, from the respective one or more of the plurality of remote computing devices, user response data associated with a selection of the one or more graphical options; (xii) determining, based at least in part upon the received user response data and the stored sensor data over a plurality of the predetermined time intervals, whether the at least one criterion for each of the one or more user stimuli has been met; and (xiii) upon a condition of determining that the at least one criterion has been met: (1) recording the positive result in the one or more databases in association with the corresponding user identification information; and (2) generating and transmitting, to the corresponding remote computing device, fourth machine-readable instructions to render a user reward notification. In embodiments, the non-transitory computer-readable memory may perform the following further steps: (xiii) upon a condition of determining that the at least one criterion has not been met: (1) recording a negative result in the one or more databases in association with the corresponding user information identification information; and (2) generating and transmitting, to the corresponding remote computing device, fifth machine-readable instructions to render a user negative response notification.

In embodiments, the at least one user includes a first user and wherein the plurality of remote computing devices includes a first user device associated with the first user. In embodiments the at least a portion of the recorded sensor data is received by the computing device from the first user device via an interactive electronic network. In embodiments, the first user device includes at least one of: (i) an accelerometer; (ii) a light sensor; (iii) a vibration sensor; and (iv) a proximity sensor. In embodiments the first user device includes (i) a smart phone and (ii) a wearable device. In embodiments the at least a portion of the recorded sensor data is received from by the computing device from at least one of the smart phone and the wearable device, wherein the user identification information is received via an interactive electronic network.

In embodiments, the at least a portion of the recorded sensor data includes at least one of the following: (i) motion data; (ii) types of motion data; (iii) sleep patterns data; and (iv) stress patterns data. In embodiments, the at least a portion of the recorded sensor data may additionally or alternatively include any other sensor data related to health management.

In embodiments, the at least a portion of the recorded sensor data comprises at least one of the following: (i) location data; (ii) acceleration data; (iii) altitude data; (iv) steps data; (v) heartrate data; and (vi) accuracy data. In embodiments, the at least a portion a portion of the recorded sensor data may additionally or alternatively comprise any other sensor data related to health management.

In embodiments, a computing device for encouraging a selected choice by at least one user of a plurality of remote computing devices, the computing device may include: (a) one or more processor devices; (b) a network communication interface to the plurality of remote computing devices and a plurality of third-party computing systems; and (c) a non-transitory computer-readable memory having stored thereon instructions for the one or more processor devices to perform: (i) a user information registration process that includes: (1) receiving, from the plurality of remote computing devices, user identification information; (2) retrieving, from one or more of the plurality of third-party computing systems, user attribute information in correspondence with the received user identification information; and (3) storing, in one or more user databases, the retrieved user attribute information in association with the corresponding user identification information; (ii) a user stimulus storing process that includes: (1) retrieving, from another one or more of the plurality of third-party computing systems, user stimulus information; and (2) storing, in one or more stimulus databases, the retrieved user stimulus information in association with one or more corresponding user attributes; (iii) a user stimulus serving process that includes: (1) receiving, from one of the plurality of remote computing devices, a query for a user stimulus, the query comprising at least one user stimulus parameter; (2) retrieving, from the one or more user databases, user attribute information based on the user identification information associated with the one remote computing device; (3) retrieving, from the one or more stimulus databases, information associated with a user stimulus based at least in part upon the at least one user stimulus parameter and a user attribute corresponding to the retrieved user attribute information; (4) transmitting, to the one remote computing device, the retrieved user stimulus information; (5) monitoring the one remote computing device for a positive result indication for the transmitted user stimulus information; and (6) upon a condition of receiving the positive result indication from the one remote computing device, updating the associated user attribute information in the one or more user databases and the associated user stimulus information in the one or more stimulus databases.

In embodiments, the user stimulus service process further includes (1) upon a negative condition of receiving a negative result indication from the one remote computing device, updating the associated user attribute information in the one or more user databases and the associated user stimulus information in the one or more stimulus databases.

In embodiments, the non-transitory computer-readable memory may further perform: (iv) a user notification process that includes: (1) upon the condition of receiving the positive result indication, generating and transmitting, to the one remote computing device, machine-readable instructions to render a user reward notification. In embodiments the user notification process further includes: (2) upon a condition of receiving a negative result indication, generating and transmitting, to the one remote computing device, machine-readable instructions to render a user negative notification.

In embodiments, a computing device for encouraging a selected choice by at least one user of a plurality of remote computing devices, the computing device may include: (a) one or more processor devices; (b) one or more sensor devices; and (c) a non-transitory computer-readable memory having stored thereon recorded sensor data from the one or more sensor devices and instructions for the one or more processor devices to perform the steps of: (i) receiving user identification information from the at least one user; (ii) transmitting, to the one or more server devices, the received user identification information; (iii) rendering a user permission input graphical user interface, the user permission input graphical user interface comprising a graphical accept option to approve access to the recorded sensor data; (iv) receiving an input of the graphical accept option; (v) monitoring at least a portion of the recorded sensor data at first predetermined time intervals; (vi) determining at least one user stimulus parameter based at least in part on the monitored sensor data; (vii) transmitting, to a remote computing device, a user stimulus query with the at least one user stimulus parameter; (viii) receiving, from the remote computing device, user stimulus information; (ix) rendering a user stimulus graphical interface based on the user stimulus information, the user stimulus graphical interface comprising a user information input related to a user stimulus; (x) receiving the user information input; (xi) determining a user stimulus result based on the received user information input; and (xii) transmitting, to the remote computing device, the determined user stimulus result.

In embodiments, the at least a portion of the recorded sensor data is recorded by one or more of the following: (1) an accelerometer; (2) a light sensor; (3) a vibration sensor; and (4) a proximity sensor.

In embodiments the at least one user includes a first user and wherein the remote computing device includes a first user device associated with the first user. In embodiments the at least a portion of the recorded sensor data is received by the computing device from the first user device via an interactive electronic network. In embodiments, the first user device includes at least one of: (i) an accelerometer; (ii) a light sensor; (iii) a vibration sensor; and (iv) a proximity sensor.

In embodiments, the first user device includes: (i) a smart phone; and (ii) a wearable device. In embodiments the at least a portion of the recorded sensor data is received from by the computing device from at least one of the smart phone and the wearable device, wherein the user identification information is received via an interactive electronic network.

In embodiments, the at least a portion of the recorded sensor data includes at least one of the following: (i) walking data; (ii) types of motion data; (iii) sleep patterns data; and (iv) stress patterns data.

In embodiments, the at least a portion of the recorded sensor data includes at least one of the following: (i) location data; (ii) acceleration data; (iii) altitude data; (iv) steps data; (v) heartrate data; and (vi) accuracy data.

In embodiments, a computing device for encouraging a positive choice by at least one user of the computing device may include: (a) one or more processor devices; (b) one or more sensor devices; and (c) a non-transitory computer-readable memory having stored thereon recorded sensor data from the one or more sensor devices and instructions for the one or more processor devices to perform the steps of: (i) receiving user identification information from the at least one user; (ii) transmitting, to the one or more server devices, the received user identification information; (iii) rendering a user permission input graphical user interface, the user permission input graphical user interface comprising a graphical accept option to approve access to the recorded sensor data; (iv) receiving an input of the graphical accept option; (v) retrieving at least a portion of the recorded sensor data and determining at least one user stimulus parameter based on the retrieved sensor data; (vi) transmitting, to a remote computing device, a user stimulus query with the at least one user stimulus parameter; (vii) receiving, from the remote computing device, user stimulus information; (viii) rendering a user stimulus graphical interface based on the user stimulus information, the user stimulus graphical interface comprising a graphical stimulus accept option; (ix) receiving an input of the graphical stimulus accept option; (x) monitoring at least a same or different portion of the recorded sensor data at predetermined time intervals; (xi) determining a user stimulus result based on the monitored sensor data; and (xii) transmitting, to the remote computing device, information associated with the determined user stimulus result.

In embodiments, the at least a portion of the recorded sensor data is recorded by one or more of the following: (1) an accelerometer; (2) a light sensor; (3) a vibration sensor; and (4) a proximity sensor.

In embodiments, the at least one user includes a first user and the remote computing device includes a first user device associated with the first user. In embodiments, the at least a portion of the recorded sensor data is received by the computing device from the first user device via an interactive electronic network. In embodiments, the first user device includes at least one of: (i) an accelerometer; (ii) a light sensor; (iii) a vibration sensor; and (iv) a proximity sensor.

In embodiments, the first user device includes (i) a smart phone and (ii) a wearable device. In embodiments, the at least a portion of the recorded sensor data is received from by the computing device from at least one of the smart phone and the wearable device, wherein the at least a portion of the recorded sensor is received via an interactive electronic network.

In embodiments, the at least a portion of the recorded sensor data includes at least one of the following: (i) walking data; (ii) types of motion data; (iii) sleep patterns data; and (iv) stress patterns data.

In embodiments, the at least a portion of the recorded sensor data includes at least one of the following: (i) location data; (ii) acceleration data; (iii) altitude data; (iv) steps data; (v) heartrate data; and (vi) accuracy data.

In embodiments, a system to encourage a selected change in health-related behavior of at least a first user of a plurality of users of an interactive electronic network includes: (a) a personal information module including first one or more processors operatively connected to a first memory device and first machine readable instructions, wherein the first one or more processors execute the first machine readable instructions to obtain and store in one or more lifestyle databases, lifestyle information associated with the first user, wherein the lifestyle information includes: i. identity information associated with an identity of the first user; ii. health-related attribute information associated with at least one health-related attribute of the first user; iii. health kit information associated with health conditions and/or actions effecting health of the first user; iv. sensor information associated with a first computer device associated with the first user, wherein the sensor information includes at least one of the following: (1) location information associated with location information and/or movement information of the first computer device at a first respective time; (2) accelerometer information generated by at least one accelerometer of the first computer device at a second respective time; (3) gyrometer information generated by at least one gyrometer of the first computer device at third respective time; (4) pedometer information generated by at least one pedometer of the first computer device at a respective fourth time; (5) proximity information generated by at least one proximity sensor of the first computer device at a fifth respective time; (6) magnetometer information generated by at least one magnetometer sensor of the first computer at a sixth respective time; (7) orientation information associated with degrees of rotation the first computer device makes around three physical axes at a seventh respective time; (8) light sensor information generated by at least one light sensor of the first computer device at an eight respective time; (9) altimeter information associate with a change in altitude pressure of the first computer device at a ninth respective time; (10) motion information associated with acceleration, attitude, rotation, and magnetic data of the first user computing device at a respective time; v. prior purchase information associated with purchases made by and/or associated with the first user; vi. activity information indicative of activities engaged in by and/or associated with the first user within; vii. budget information associated with an available budget for use in providing stimulus to the first user; and viii. goal information associated with the selected change in behavior; (b) a situation module including second one or more processors operatively connected to at least a second memory device and second machine readable instructions, the situation module operatively connected to the personal information module, wherein the second one or more processors execute the second machine readable instructions to provide a situation data set by: accessing the lifestyle information provided by the personal information module; i. arranging the lifestyle information based at least on chronology to include information from a first predetermined time period to provide a current state data set associated with a current state of the first user; ii. arranging other lifestyle information from prior predetermined periods of time as prior lifestyle information; iii. providing the current state data set to a first machine learning algorithm trained by the prior lifestyle information arranged chronologically with situation provided as a label; wherein the first machine learning algorithm provides a situation data set associated a situation of the first user; storing the situation data set associated with the first user; (c) a stimulus module, including third one or more processors operatively connected to a third memory device and third machine readable instructions, wherein the third one or more processors execute the third machine readable instructions to provide a stimulus database using the second memory device, the stimulus database comprising stimulus information, wherein the stimulus information includes, for each prior stimulus of a plurality of prior stimuli: i. the respective prior stimulus; ii. a respective situation data set associated with the respective prior stimulus; and iii. respective stimulus response information associated with the respective prior stimulus; (d) a training set module, including fourth one or more processors operably connected to a fourth memory device and fourth machine readable instructions, the training set module operatively connected to the stimulus module, wherein the fourth one or more processors execute the fourth machine readable instructions to generate a training data set by: i. accessing the stimulus information; ii. filtering the stimulus information based at least on available stimulus information; iii. providing the training data set based on the application of filter criteria to the stimulus information; and iv. storing the training data set; (e) a manager module including fifth one or more processors operatively connected to at least a fifth memory device and fifth machine readable instructions, the manager module operatively connected to the situation module and the training set module, wherein the fifth one or more processors execute the fifth machine readable instructions to select the first stimulus by: i. receiving the situation data set from the situation module; ii. providing the situation data set to a second machine learning algorithm trained by the training data set with stimulus provided as a label, wherein the second machine learning algorithm selects the first stimulus and a time to send the first stimulus to the first computing device associated with the first user; and iii. sending the first stimulus to the first computing device associated with the first user; (f) a collection module including sixth one or more processors operatively connected to a sixth memory device and sixth machine readable instructions, wherein the sixth one or more processors execute the sixth machine readable instructions to: i. after the first stimulus is transmitted to the first computing device associated with the first user, collect updated information from at least one of: (1) the first computer device associated with the first user; (2) a second computer device associated with the first user; and (3) a third computer device associated with a second user associated with the first user via social media, professional affiliation or the interactive electronic network, wherein the updated information includes at least updated lifestyle information; ii. determine, based at least on the updated lifestyle information, the first stimulus was successful; iii. generate stimulus response information associated with success of the first stimulus; iv. send the updated lifestyle information to the personal information module to be added to the lifestyle database; and v. send the stimulus response information, including the first stimulus and the situation data set, to the stimulus module to be added to the stimulus database.

In embodiments, the system includes a social module including seventh one or more processors operatively connected to at least a seventh memory device and seventh machine readable instructions, the social module operatively connected to the personal information module, wherein the seventh one or more processors execute the seventh machine readable instructions to obtain and store in one or more social databases, social information associated with the first user, wherein the social information includes: i. social network information, wherein the social network information comprises a second user that is a social network connection; and ii. professional colleague information, wherein the social module is operatively connected to the personal information module, and wherein the execution of the first machine readable instructions by the personal information module further includes: iv. accessing the social network information provided by the social module; v. filtering the social network information based at least on the time; and vi. providing the social network information to the personal information module and the lifestyle database.

In embodiments, the at least one second user is a professional colleague connection of the first user.

In embodiments, the third computer device is associated with the second user.

In embodiments, the personal information module is operatively connected to the social module, wherein the first one or more processors execute the first machine readable instructions to provide the proximity information indicating when the first user is within a predetermined proximity of the second user by, i. accessing the social network information; ii. filtering the social network information based at least on the time; and iii. providing the proximity information based on: (1) the location information associated with the first user; and (2) location information associated with at least the second user.

In embodiments, the proximity information is based on at least one of the following: (1) determining a computing device associated with the second user is within range of the same cell tower as at least one of the first computer device or the second computer device; (2) determining the computing device associated with the second user is within a predetermined distance of at least one of the first computer device or the second computer device; (3) determining the electronic device associated with the second user and at least one of the first computer device or the second computer device are in a first building; (4) determining the electronic device associated with the second user and at least one of the first computer device or the second computer device are within a first city block; (5) determining the electronic device associated with the second user and at least one of the first computer device or the second computer device are in a first room of a second building; and (6) determining the electronic device associated with the second user and at least one of the first computer device or the second computer device are within a first place of business.

In embodiments, the stimulus response information is further provided from: d. a fourth computer device associated with a third user of the interactive electronic network associated with the first user via professional association.

In embodiments, the stimulus response information is further provided from: d. a fourth computer device associated with a third user of the interactive electronic network, wherein the third user is not linked via social media or professional affiliation to the first user.

In embodiments, the stimulus response information is further provided from: d. a fourth computer device associated with a third user of the interactive electronic network associated with the first user via professional association; and e. a fifth computer device associated with a fourth user of the interactive electronic network, wherein the fourth user is not linked via social media or professional affiliation to the first user.

In embodiments, the stimulus response information is provided based on updated lifestyle information indicating whether the first stimulus provided positive results relative to the selected change.

In embodiments, the health-related attribute information includes at least one of: (1) heartbeat information; (2) respiratory information; (3) blood pressure information; (4) body temperature information; (5) height information; and (6) weight information.

In embodiments, at least a portion of the health-related attribute information and/or health kit information is provided by the first user via the first computer device.

In embodiments, at least a portion of the health-related attribute information and/or health kit information is provided by the first user via the second computer device.

In embodiments, at least a portion of the health-related attribute information and/or health kit information is provided by one or more healthcare providers.

In embodiments, at least a portion of the health-related attribute information and/or health kit information is provided by the first computer device in response to a survey provided on the first computer device.

In embodiment, the manager module sends the first stimulus to the first computer device by performing the following steps: i. generating, after selecting the first stimulus, first machine-readable display instructions including a first graphical user interface (GUI), wherein the first GUI represents the first stimulus and comprises: (1) a first message based on at least the first stimulus and an impending first choice, wherein the impending first choice is based on at least the selected change; and (2) impending first choice information being based on at least the impending first choice and the selected change; and ii. sending the first machine-readable instructions to the first computer device, wherein, upon receiving the first machine-readable instructions, the first computer device executes the first machine-readable instructions which causes the first GUI to be displayed on a display screen of the first computer device.

In embodiments, the first-machine readable display instructions further include a notification instruction wherein receipt of the first-machine readable display instructions by the first computer device causes a notification to be sent from the first computer device to the second computer device.

In embodiments, the collection module: i. generates, after generating the stimulus response information; display machine-readable instructions including a graphical user interface (GUI), wherein the GUI comprises a first message based on at least one of: (1) the first stimulus, and (3) the stimulus response information; and ii. sends the display machine-readable instructions to at least one of: (1) the first computer device; and (2) the second computer device, wherein, upon receiving the first machine-readable instructions, one or more of the first computer device and the second computer device executes the first machine-readable instructions which causes the GUI to be displayed on a display screen of at least one of: (1) the first computer device; and (2) the second computer device.

In embodiments, first computer device is at least one of a portable computing device and a wearable device.

In embodiments, the portable computing device is at least one of a smart phone, a tablet, a phablet, or a laptop.

In embodiments, the second computer device is at least one of a portable computing device or a wearable device.

In embodiments, the portable computing device is at least one of a smart phone, a tablet, a phablet, and a laptop.

In embodiments, the first computer device comprises at least one of: (1) an accelerometer; (2) a gyrometer; (3) a pedometer; (4) a magnetometer; (5) a light sensor; and (6) a proximity sensor.

In embodiments the second computer device comprises at least one of: (1) an accelerometer; (2) a gyrometer; (3) a pedometer; (4) a magnetometer; (5) a light sensor; and (6) a proximity sensor.

In embodiments, the first machine learning algorithm utilizes a neural network.

In embodiments, the first machine learning algorithm utilizes a deep learning neural network.

In embodiments, the second machine learning algorithm utilizes a neural network.

In embodiments, the second machine learning algorithm utilizes a deep learning neural network.

In embodiments, each of the (1) location information; (2) accelerometer information; (3) gyrometer information; (4) pedometer information generated by at least one pedometer of the first user computing device at a respective fourth time; (5) proximity information; (6) magnetometer information; (7) orientation information; (8) light sensor information; and (9) altimeter information; and (10) motion information include a respective time stamp.

In embodiments, the prior lifestyle information includes time stamps that are prior to the first predetermined period of time.

In embodiments, at least a portion of the (1) location information; (2) accelerometer information; (3) gyrometer information; (4) pedometer information generated by at least one pedometer of the first user computing device at a respective fourth time; (5) proximity information; (6) magnetometer information; (7) orientation information; (8) light sensor information; and (9) altimeter information; and (10) motion information are provided by the second computer system.

In embodiments, a system to encourage a selected change in health-related behavior of at least a first user of a plurality of users of an interactive electronic network includes: (a) a personal information module including a first one or more processors operatively connected to at least a first memory device and first machine readable instructions, wherein the first one or more processors execute the first machine readable instructions to obtain and store in one or more lifestyle databases, lifestyle information associates associated with the first user wherein the lifestyle information includes: i. identity information associated with an identity of the first user; ii. health-related attribute information associated with at least one health-related attribute of the first user; iii. health kit information associated with health conditions and/or actions effecting health of the first user; iv. sensor information associated with a first computer device associated with the first user, wherein the sensor information includes at least one of the following: (1) location information associated with location information and/or movement information of the first computer device at a first respective time; (2) accelerometer information generated by at least one accelerometer of the first computer device at a second respective time; (3) gyrometer information generated by at least one gyrometer of the first computer device at third respective time; (4) pedometer information generated by at least one pedometer of the first user computer device at a respective fourth time; (5) proximity information generated by at least one proximity sensor of the first computer device at a fifth respective time; (6) magnetometer information generated by at least one magnetometer sensor of the first computer device at a sixth respective time; (7) orientation information associated with degrees of rotation the first user computer device makes around three physical axes at a seventh respective time; (8) light sensor information generated by at least one light sensor of the first computer device at an eight respective time; (9) altimeter information associate with a change in altitude pressure of the first computer device at a ninth respective time; (10) motion information associated with acceleration, attitude, rotation, and magnetic data of the first computer device at a respective time; v. prior purchase information associated with purchases made by and/or associated with the first user; vi. activity information indicative of activities engaged in by and/or associated with the first user; and vii. budget information associated with an available budget for use in providing stimulus to the first user; viii. goal information associated with the selected change in behavior; (b) a situation module including second one or more processors operatively connected to at least a second memory device and second machine readable instructions, the situation module operatively connected to the personal information module, wherein the second one or more processors execute the second machine readable instructions to provide a situation data set by: i. accessing the lifestyle information provided by the personal information module; ii. arranging the lifestyle information based at least on chronology to include information from a first predetermined time period in a current state data set associated with a current state of the first user; iii. arranging other lifestyle information from prior predetermined periods of time as prior lifestyle information; iv. providing a situation data set associated with the first user based on the current state data set and the prior current state information; i. storing the situation data set associated with the first user; (c) a stimulus module including third one or more processors and operatively connected to at least a third memory device and third machine readable instructions, wherein the third one or more processors execute the third machine readable instructions to generate a stimulus database including: i. vendor stimulus information associated with available vendor stimulus offers; ii. cost information associated with a cost of each of the plurality of stimulus options; iii. prior stimulus information associated with a prior stimulus sent to the first user and an associated prior stimulus response associated with a response of the first user to the corresponding prior stimulus and associated prior situation data set; (d) a manager module including a fourth one or more processors and at least a fourth memory device and fourth machine readable instructions, wherein the fourth one or more processors execute the fourth machine readable instructions to: (1) select a first stimulus to be provided to the first user; and (2) send the first stimulus to the first computer device associated with the first user, wherein the manager module selects the first stimulus and a first time at which the first stimulus is sent to the first user based on at least one of the following: i. the situation data set; ii. the prior stimulus, associated situation data set and prior stimulus response information; iii. the prior purchase information and associated prior stimulus response information relevant to the prior purchase information; and iv. the activity information and associated prior stimulus response information relevant to the activity information; (e) a collection module including fifth one or more processors operatively connected to a fifth memory device and fifth machine readable instructions, the collection module operatively connected to the manager module, the personal information module and the stimulus module, wherein the fifth one or more processors, after the first stimulus is sent to the first computer device, execute the fifth machine readable instructions to: i. collect updated information from at least one of: a. the first computer device associated with the first user; b. a second computer device associated with the first user; and c. a third computer device associated with a second user linked via social media, professional affiliation or the interactive electronic network to the first user, wherein the updated information includes updated lifestyle information; ii. determine, based at least on the updated lifestyle information, the first stimulus was successful; iii. generate stimulus response information associated with success of the first stimulus; iv. send the updated lifestyle information to the personal information module to be added to the lifestyle database; and v. send the stimulus response information, including the first stimulus, the situation data set, to the stimulus module to be added to the stimulus database.

In embodiments the system includes a social module including one or more processors operatively connected to at least a sixth memory device including sixth machine readable instructions, wherein the social module is configured to execute the sixth machine readable instructions to receive and store in one or more social databases, social information associated with the first user, wherein the social information includes: i. social network information, wherein the social network information comprises a second user that is a social network connection of the first user, and ii. professional colleague information; wherein the social module is operatively connected to the personal information module and the execution of the first machine readable instructions by the personal information module includes: a. accessing the social network information; b. providing the social network information to the personal information module and including in in the lifestyle database.

In embodiments, the second user is a professional colleague connection of the first user.

In embodiments, the third computer device is associated with the at least one second user.

In embodiments, the personal information module is operatively connected to the social module and the first one or more processors execute the first machine readable instructions to provide the proximity information indicating when the first user is within a predetermined proximity of the second user by: i. accessing the social network information; ii. filtering the social network information based at least on the time; and vi. providing the proximity information based on: (1) the location information associated with the first user; and (2) location information associated with at least the second user.

In embodiments, the proximity information is based on at least one of: i. determining a first location at a second time of the first user based at least on the respective location information associated with the first computer device; ii. determining a second location at the second time of the second user device; iii. determining the second location is within the predetermined proximity of the first location; and iv. sending, from the manager module to the collection module, current proximity information indicating the second location is within the predetermined proximity of the first location, wherein, upon receipt of the current proximity information, the collection module stores the current proximity information.

In embodiments, the manager module is further configured to: (3) select a second stimulus to be provided to the first user; and (4) send the first stimulus to the first computer device associated with the first user at a selected time, wherein the manager module selects the second stimulus and the selected time at which the second stimulus is sent to the first computer device based on at least one of the following: i. current proximity information; ii. a second situation data set at the selected time; iii. each prior stimulus and the associated prior stimulus response information and situation data set; the prior purchase information and associated prior stimulus response information relevant to the prior purchase information; and the activity information and associated prior stimulus response information relevant to the activity information.

In embodiments the selected time is the same as the second time.

In embodiments, the stimulus response information is further provided from: d. a fourth computer device associated with a third user of the interactive electronic network associated with the first user via professional association.

In embodiments, the stimulus response information is further provided from: d. a fourth computer device associated with a third user of the interactive electronic network, wherein the third user is a social contact of the first user.

In embodiments, the stimulus response information is further provided from: d. a fourth computer device associated with a third user of the interactive electronic network wherein the third user is not linked via social media or professional affiliation to the first user.

In embodiments the stimulus response information is provided based on updated lifestyle information indicating whether the first stimulus provided positive results.

In embodiments, the manager module is further configured to: (3) select a second stimulus to be provided to the first user; and (4) send the second stimulus to the first computer device associated with the first user, wherein the manager module selects the second stimulus and a second time at which the second stimulus is sent to the first user based on at least one of the following: i. a second situation data set based at least on the lifestyle information; ii. the first stimulus, associated prior stimulus response information, and the situation data set; iii. the prior purchase information and associated prior stimulus response information relevant to the prior purchase information; and iv. the activity information and associated prior stimulus response information relevant to the activity information.

In embodiments the health-related attribute information includes at least one of: (1) heartbeat information; (2) respiratory information; (3) blood pressure information; (4) body temperature information; (5) height information; and (6) weight information.

In embodiments, at least a portion of the health-related attribute and/or health kit information is provided by the first user via the first computer device.

In embodiments, at least a portion of the health-related attribute and/or health kit information is provided by the first user via the second computer device.

In embodiments, at least a portion of the health-related attribute and/or health kit information is provided by one or more health care providers.

In embodiments, the manager module is configured to send the first stimulus to the first computer device by performing the following steps: i. generating, after selecting the first stimulus, GUI machine-readable instructions including a first graphical user interface (GUI), wherein the first GUI represents the first stimulus and comprises: (1) a first message based on at least the first stimulus and an impending first choice, wherein the impending first choice is based on at least the selected change; and (2) impending first choice information being based on at least the impending first choice and the selected change; and iii. sending the GUI machine-readable instructions to the first computer device, wherein, upon receiving the GUI machine-readable instructions, the first computer device executes the GUI machine-readable instructions which causes the first GUI to be displayed on a display screen of the first computer device.

In embodiments, the GUI machine-readable instructions further include a notification instruction wherein receipt of the GUI machine-readable instructions by the first computer device causes a notification to be sent from the first computer device to the second computer device.

In embodiments, the collection module is further configured to: i. generate, after generating the stimulus response information, GUI machine-readable instructions including a first graphical user interface (GUI), wherein the first GUI comprises a first message based on at least one of: (1) the first stimulus, and (2) the stimulus response information; and ii. sends the GUI machine-readable instructions to at least one of: (1) the first computer device; and (2) the second computer device, wherein, upon receiving the GUI machine-readable instructions, one or more of the first computer device and the second computer device executes the GUI machine-readable instructions which causes the first GUI to be displayed on a display screen of at least one of: (1) the first computer device; and (2) the second computer device.

In embodiments, the first computer device is at least one of a portable computing device and a wearable device.

In embodiments, the portable computing device is at least one of a smart phone, a tablet, a phablet, and a laptop.

In embodiments, the second computer device is at least one of a portable computing device and a wearable device.

In embodiments the portable computing device is at least one of a wearable device, a smart phone, a tablet, a phablet, or a laptop.

In embodiments, the first computer device comprises at least one of: (1) an accelerometer; (2) a gyrometer; (3) a pedometer; (4) a magnetometer; (5) a light sensor; and (6) a proximity sensor.

In embodiments, the second computer device comprises at least one of (1) an accelerometer; (2) a gyrometer; (3) a pedometer; (4) a magnetometer; (5) a light sensor; and (6) a proximity sensor.

In embodiments, each of the (1) location information; (2) accelerometer information; (3) gyrometer information; (4) pedometer information generated by at least one pedometer of the first user computing device at a respective fourth time; (5) proximity information; (6) magnetometer information; (7) orientation information; (8) light sensor information; and (9) altimeter information; and (10) motion information include a respective time stamp.

In embodiments, the prior lifestyle information includes time stamps that are prior to the first predetermined period of time.

In embodiments, at least a portion of the (1) location information; (2) accelerometer information; (3) gyrometer information; (4) pedometer information generated by at least one pedometer of the first user computing device at a respective fourth time; (5) proximity information; (6) magnetometer information; (7) orientation information; 8) light sensor information; and (9) altimeter information; and (10) motion information are provided by the second computing system.

In embodiments, a method to encourage a selected change in health-related behavior of at least a first user of a plurality of users of an interactive electronic network includes: (a) obtaining and storing, by a personal information module including a first one or more processors operatively connected to a first memory device and first machine readable instructions, in one or more lifestyle databases, lifestyle information associated with the first user, wherein the lifestyle information includes: i. identity information associated with an identity of the first user; ii. health-related attribute information associated with at least one health-related attribute of the first user; iii. health kit information associated with health conditions and/or actions effecting health of the first user; iv. sensor information associated with a first computer device associated with the first user, wherein the sensor information includes at least one of the following: (1) location information associated with location information and/or movement information of the first computer device at a first respective time; (2) accelerometer information generated by at least one accelerometer of the first computer device at a second respective time; (3) gyrometer information generated by at least one gyrometer of the first computer device at third respective time; (4) pedometer information generated by at least one pedometer of the first computer device at a respective fourth time; (5) proximity information generated by at least one proximity sensor of the first computer device at a fifth respective time; (6) magnetometer information generated by at least one magnetometer sensor of the first computer device at a sixth respective time; (7) orientation information associated with degrees of rotation the first computer device makes around three physical axes at a seventh respective time; (8) light sensor information generated by at least one light sensor of the first computer device at an eight respective time; (9) altimeter information associate with a change in altitude pressure of the first computer device at a ninth respective time; and (10) motion information associated with acceleration, attitude, rotation, and magnetic data of the first computer device at a respective time; v. prior purchase information associated with purchases made by and/or associated with the first user; vi. activity information indicative of activities engaged in by and/or associated with the first user; and vii. budget information associated with an available budget for use in providing stimulus to the first user; and viii. goal information associated with the selected change in behavior; (b) providing, by a situation module including second one or more processors operatively connected to at least a second memory device and second machine readable instructions, the situation module operatively connected to the personal information module, a situation information data set by: i. accessing the lifestyle information provided by the personal information module; ii. arranging the lifestyle information based at least on chronology to include information from a first predetermined time period in a current state data set associated with a current state of the first user; iii. accessing prior current state information associated with prior current states of the first user; iv. providing a situation data set associated with the first user, based on the current state data set and the prior current state information; and i. storing the situation data set associated with the first user; (c) generating and storing, by a stimulus module including a third one or more processors and operatively connected to at least a third memory device and third machine readable instructions, a stimulus database including: i. vendor stimulus information associated with available vendor stimulus offers; ii. cost information associated with a cost of each of the plurality of stimulus options; and iii. prior stimulus information associated with a prior stimulus sent to the first user and an associated prior stimulus response associated with a response of the first user to the corresponding prior stimulus and an associated prior situation data set; (d) selecting, by a manager module including fourth one or more processors operatively connected to a fourth memory device and fourth machine readable instructions, the manager module operatively connected to the situation module and the stimulus module, a first stimulus to be provided to the first user from the plurality stimulus options; wherein the manager module selects the first stimulus and a first time at which the first stimulus is sent to the first user based on at least one of the following: i. the situation data set; ii. each prior stimulus and associated prior stimulus response information and associated prior situation data set; iii. the prior purchase information and associated prior stimulus response information relevant to the prior purchase information; and iv. the activity information and associated prior stimulus response information relevant to the activity information; (e) sending, by the manager module to the first computing device associated with the first user, the first stimulus; (f) collecting, by a collection module including fifth one or more processors operatively connected to at least a fifth memory device and fifth machine readable instructions, the collection module operatively connected to the manager module, the personal information module and the stimulus module, updated lifestyle information from at least one of. i. the first computer device associated with the first user; ii. a second computer device associated with the first user; and iii. a third computer device associated with a second user linked via social media, professional affiliation or the interactive electronic network to the first user, (g) determining, by the collection module, based at least on the updated lifestyle information, the first stimulus was successful; (h) generating, by the collection module, stimulus response information associated with success of the first stimulus; (i) sending, by the collection module, the updated lifestyle information to the personal information module to be added to the lifestyle database; and (j) sending, by the collection module, the stimulus response information, including the first stimulus and the situation data set, to the stimulus module to be added to the stimulus database.

In embodiment, the method further comprises: (k) receiving, by a social module, social connection information, wherein, the social module includes fifth one or more processors operatively connected to at least a fifth memory device and, fifth machine-readable instructions, and wherein the social module is operatively connected to the personal information module and the situation module such that the personal information module and situation module are enabled to access and use of the social connection information.

In embodiments, the method further comprises: wherein, the social connection information is associated with the first user and includes social network connection information and professional colleague information, wherein the social network connection information is associated with at least one second user that is a social network connection of the first user, and (k) storing, by the social module in the fifth memory device, the social connection information, wherein the manager module selects the first stimulus and the first time based further on the social connection information.

In embodiments, the second user is a professional colleague connection of the first user.

In embodiments, the second user is a social connection of the first user.

In embodiments, the method further includes comprising: (k) prior to selecting the first stimulus, determining, by the situation module, when the first user is within a predetermined proximity of the second user, wherein the manager module selects the first stimulus and the time further based on at least a proximity of the second user to the first user.

In embodiments step (k) is determined by the situation module by performing the following steps: i. receiving, at the situation module, first location information from the personal information module, wherein the first location information indicates a first location of the first user at a second time, and wherein the first location information is based at least on respective location information of at least one of the first computer device and the second computer device, and ii. receiving, at the situation module, second distance information, wherein the second distance information indicates a second location of the second user at the second time, and wherein the second distance information is based at least on respective location information of an electronic device associated with the second user, and wherein, the second distance information enables the situation module to determine the second location at the second time; iii. accessing, by the situation module, the first distance information and the second distance information; iv. determining, by the situation module, the second location is within the predetermined distance of the first location, wherein the determination that the second location is within the predetermined distance from the first location results in the situation module generating utilizing current proximity information which indicates the second location is within the predetermined proximity of the first location.

In embodiments, the method further includes (1) selecting, by the manager module, a second stimulus to be provided to the first user from the plurality of stimulus options, wherein the manager module selects the second stimulus and a selected time at which the second stimulus is sent to the first user based on at least one of the following: i. the current proximity information; ii. a second situation data set at the selected time of the first user based at least on the lifestyle information; iii. each prior stimulus and associated prior stimulus response information and situation data set; iv. the prior purchase information and associated prior stimulus response information relevant to the prior purchase information; and v. the activity information and associated prior stimulus response information relevant to the activity information; and (vi) sending, by the manager module, the selected second stimulus to at least one of i. the first computer device; and ii. the second computer device.

In embodiments, the selected time is the same as the first time.

In embodiments, the updated information is further collected from: iv. a fourth computer device associated with a third user of the interactive electronic network associated with the first user via professional association.

In embodiments, the third user is not linked via social media or professional affiliation to the first user.

In embodiments, the stimulus response information is further collected from a fourth computer device associated with a third user of the interactive electronic network associated with the first user via professional association and/or social connection.

In embodiments the stimulus response information is provided based on updated lifestyle information indicating whether the first stimulus provided positive results.

In embodiments, the health-related attribute information includes at least one of: (1) heartbeat information; (2) respiratory information; (3) blood pressure information; (4) body temperature information; (5) height information; and (6) weight information.

In embodiments, at least a portion of the health-related attribute information and health kit information is provided by the first user via the first computer device.

In embodiments, at least a portion of the health-related attribute information and health kit information is provided by the first user via the second computer device.

In embodiments, at least a portion of the health-related attribute information and health kit information is provided by a healthcare provider.

In embodiments, the step of selecting a first stimulus includes: i. generating, by the manager module, GUI machine-readable instructions including a first graphical user interface (GUI), wherein the first GUI represents the first stimulus and comprises: (1) a first message based on at least the first stimulus and an impending first choice, wherein the impending first choice is based on at least the selected change; and (2) impending first choice information being based on at least the impending first choice and the selected change; and ii. sending the GUI machine-readable instructions from the manager module to the first computer device, wherein, upon receiving the GUI machine-readable instructions, the first computer device executes the GUI machine-readable instructions which causes the first GUI to be displayed on a display screen of the first computer device.

In embodiments, the GUI machine-readable instructions further include a notification instruction, and wherein receipt of the GUI machine readable instructions by the first computer device causes a notification to be sent from the first computer device to the second computer device.

In embodiments, the method includes: (k) generating, by the collection module, after generating the stimulus response information, GUI machine-readable instructions including a first graphical user interface (GUI), wherein the first GUI comprises a first message based on at least one of: i. the first stimulus, and iii. the stimulus response information; and sending the GUI machine-readable instructions to at least one of: i. the first computer device; and ii. the second computer device, wherein, upon receiving the GUI machine-readable instructions, one or more of the first computer device and the second computer device executes the GUI machine-readable instructions which causes the first GUI to be displayed on a display screen of at least one of: i. the first computer device; and ii. the second computer device.

In embodiments, the first computer device is at least one of a portable computing device and a wearable device.

In embodiments the portable computing device is at least one of a smart phone, a tablet, a phablet, and a laptop.

In embodiments, the second computer device is at least one of a portable computing device and a wearable device.

In embodiments the portable computing device is at least one of a smart phone, a tablet, a phablet, and a laptop.

In embodiments the first computer device comprises at least one of: (1) an accelerometer; (2) a gyrometer; (3) a pedometer; (4) a magnetometer; (5) a light sensor; and (6) a proximity sensor.

In embodiments, the second computer device comprises at least one of: (1) an accelerometer; (2) a gyrometer; (3) a pedometer; (4) a magnetometer; (5) a light sensor; and (6) a proximity sensor.

In embodiments, method for encouraging a selected change in health-related behavior of at least a first user of a plurality of users of an interactive electronic network, the method comprising: (a) providing a behavior modification system to encourage the selected change in health-related behavior the system including a plurality of processors and being operatively connected to one or more memory devices and a plurality of machine-readable instructions, wherein the one or more memory devices comprises at least one training data set for training one or more machine learning algorithms to receive one or more situation data sets and generate one or more stimuli, wherein a first training data set of the at least one training data set comprises a plurality of labels and corresponding tags for each label, wherein the one or more stimuli include corresponding one or more triggers, and wherein the one or more triggers, when activated, cause one or more computer devices to generate, in real-time, a notification associated with a respective one or more stimuli; (b) obtaining, by a first one or more processors of the plurality of processors, lifestyle information associated with the first user over a first amount of time, wherein the lifestyle information includes: i. identity information associated with an identity of the first user; ii. sensor information associated with a first computer device associated with the first user, wherein the sensor information includes at least one of the following: (1) location information associated with a location history of the first computer device; (2) motion information associated with movement of the first computer device between one or more locations in the location history of the first computer device; and (3) timestamp information indicating: A. a first plurality of time intervals indicating when the first computer device was obtaining location information and motion information; and B. a second plurality of time intervals indicating when the first computer device was not obtaining one or more of the following: a. location information; and b. motion information, wherein each time interval of the second plurality of time intervals includes a respective start time and a respective end time, wherein each respective start time is associated with a respective time interval of the second plurality of time intervals and indicates a respective beginning of the respective time interval, wherein each respective end time is associated with a respective time interval of the second plurality of time intervals and indicates a respective end of the respective time interval, wherein each time interval of the second plurality of time intervals includes a respective start location and a respective end location, wherein each respective start location is associated with a respective time interval of the second plurality of time intervals and indicates a respective location of the first device at a respective beginning of the respective time interval, and wherein each respective end location is associated with a respective time interval of the second plurality of time intervals and indicates a respective location of the first device at a respective ending of the respective time interval; iii. budget information associated with an available budget for use in providing stimulus to the first user; iv. activity information indicating one or more activities engaged in by the first user; and v. goal information associated with the selected change in behavior, wherein the lifestyle information is stored in a first memory device of the one or more memory devices; (c) generating, by a second one or more processors of the plurality of processors, a current state data set associated with a current state of the first user over the first amount of time by: i. arranging the lifestyle information based at least on chronology; ii. identifying a first plurality of stationary locations by determining that a first plurality of data points indicates the first user was present at plurality of stationary locations, wherein each of the first plurality of stationary locations includes a respective timestamp indicating a respective time the first user was stopped at a respective stationary location, and wherein the first plurality of stationary locations is stored in memory operatively connected to the second one or more processors; iii. identifying a second plurality of stationary locations by analyzing the second plurality of time intervals to determine, for each time interval of the second plurality of time intervals, the following: 1. a respective length of time associated with a respective time interval of the second plurality of time intervals based at least on a difference in time between a respective start time associated with the respective time interval and a respective end time associated with the respective time interval; and 2. a respective change in location associated with a respective time interval of the second plurality of time intervals based at least on a difference in distance between a respective start location associated with the respective time interval and a respective end location associated with the respective time interval, wherein each of the second plurality of stationary locations includes one or more start locations associated with one or more time intervals of the second plurality of time intervals such that each of the one or more time intervals is associated with: A. a respective length of time above a first predetermined threshold; and B. a respective change in location below a second predetermined threshold, wherein each of the second plurality of stationary locations includes a respective timestamp indicating a respective time the first user was stopped at a respective stationary location, and wherein the second plurality of stationary locations is stored in memory operatively connected to the second one or more processors; iv. identifying one or more recurring locations by analyzing the first plurality of stationary locations and the second plurality of stationary locations to determine the first user was present at one or more of the first plurality of stationary locations and the second plurality of stationary locations more than once, wherein each of the one or more recurring locations includes a respective plurality of timestamps indicating each respective time the first user was stopped at a respective recurring location, and wherein the one or more recurring locations is stored in memory operatively connected to the second one or more processors; v. determining, for each of one or more recurring locations of the one or more recurring locations, a respective potential location data label associated with a respective recurring location based at least on the lifestyle information associated with the first user and timestamps associated with the one or more recurring locations, wherein each respective recurring location is labelled with its potential location data label; vi. confirming each potential location data label of each respective recurring location by: 1. obtaining, for each potential location data label, first machine-readable instructions to display a first graphical user interface including a first prompt to confirm the respective potential location data label; 2. sending, by the system to the first computer device, the first machine-readable instructions such that the first computer device receives and executes the first machine-readable instructions causing the first graphical user interface to be displayed by the first computer device; 3. in the event a first response to the first prompt is received, performing the following steps: A. receiving, by the system from the first computer device, the first response to the first prompt indicating a respective confirmed location data label; and B. labelling the corresponding recurring location with the respective confirmed location data label, wherein, if the first response to the first prompt is not received, the respective recurring location remains labelled with its corresponding potential location data label; and vii. identifying, for each recurring location, a respective potential event; viii. confirming each potential event by: 1. obtaining, for each potential event, second machine-readable instructions to display a second graphical user interface including a second prompt to confirm the respective potential event; 2. sending, by the system to the first computer device, the second machine-readable instructions such that the first computer device receives and executes the second machine-readable instructions causing the second graphical user interface to be displayed by the first computer device; 3. in the event a second response to the second prompt is received, performing the following steps: A. receiving, by the system from the first computer device, the second response to the second prompt indicating a respective confirmed event; and B. labelling the corresponding recurring location with the respective confirmed event, wherein if the response to the second prompt is not received, the respective recurring location remains labelled with its corresponding respective potential event, wherein the current state data set comprises: 1. the labelled one or more recurring locations; and 2. timestamps associated with the one or more recurring locations wherein the current state data set is stored in a second memory device of the one or more memory devices; (d) obtaining by a third one or more processors of the plurality of processors, a first machine learning algorithm; (e) generating, by a fourth one or more processors of the plurality of processors, a situation data set by providing the current state data set to the first machine learning algorithm; (f) obtaining by a fifth one or more processors of the plurality of processors, a second machine learning algorithm trained by the first training data set; (g) generating, by a sixth one or more processors of the plurality of processors, a first stimulus by providing the situation data set to the second machine learning algorithm, wherein the first stimulus comprises a first trigger, wherein the first trigger is based on a predicted location associated with the first user, wherein the predicted location is within a radius of at least one of the one or more recurring locations, and wherein the predicted location is predicted, in advance, based on the labelled one or more recurring locations; and (h) sending, by a seventh one or more processors of the plurality of processors to the first computer device, the stimulus such that the first computer device displays a first notification associated with the first stimulus in real-time in response to the first trigger being activated.

In embodiments, the one or more recurring locations is identified by inputting the first plurality of stationary locations and the second plurality of stationary locations into a recurring location algorithm. In embodiments, the recurring location algorithm is a Density-Based Spatial Clustering of Applications with Noise algorithm.

In embodiments, the first trigger comprises a trigger activity comprising one or more of the following: (i) one or more trigger calendar dates; (ii) one or more trigger times; (iii) one or more trigger locations; (iv) one or more trigger activities; and (v) a combination thereof, wherein the first trigger is activated in real-time when the first computer device determines the first user has performed the trigger activity.

In embodiments, the first amount of time is a calendar day. In embodiments, the first amount of time is a calendar week day and a calendar weekend day. In embodiments, the first amount of time is a calendar week. In embodiments, the first amount of time is a calendar month. In embodiments, the first amount of time is one or more of the following: (i) at least one calendar week day; (ii) at least one calendar weekend day; (iii) at least one calendar week; (iv) at least one calendar month; (v) at least one calendar year; and (vi) a combination thereof.

In embodiments, step (b) through step (d) are repeated at least one time before the method proceeds to step (e).

In embodiments, the first prompt is a quiz. In embodiments, the second prompt is a quiz.

In embodiments, the one or more activities comprises one or more of the following: (i) waking up; (ii) eating breakfast; (iii) eating lunch; (iv) arriving at work; (v) one or more breaks at work; (vi) leaving work; (vii) eating dinner; (viii) entertainment; and (ix) falling asleep.

In embodiments, the first trigger comprises trigger biometric data such that the first trigger is activated upon the first computer device determining the one or more sensors has obtained data indicating the trigger biometric data is present in the first user.

In embodiments, identifying the first plurality of stationary locations further comprises for one or more of each of the first plurality of stationary locations: 1. obtaining, for each of the one or more, respective proximity information indicating that an additional user is within a predetermined radius of at least one additional user, wherein the at least one additional user is at least one of: A. a social network connection; and B. a professional colleague connection; 2. generating, for each of the one or more, a respective proximity indicator for each respective stationary location, wherein the respective proximity indicator comprises the at least one additional user, and wherein the respective proximity indicator is tagged as associated with the respective stationary location.

In embodiments, at least a portion of the lifestyle information is provided by the first computer device in response to a quiz provided on the first computer device.

In embodiments, the first machine learning algorithm utilizes Density-Based Spatial Clustering of Applications with Noise.

In embodiments, the first amount of time is a predetermined amount of time.

In embodiments, a method to encourage a selected change in health-related behavior of at least a first user of a plurality of users of an interactive electronic network includes: (a) obtaining and storing, by a personal information module including first one or more processors operatively connected to a first memory device and first machine readable instructions, in one or more lifestyle databases, lifestyle information associated with the first user, wherein the lifestyle information includes: i. identity information associated with an identity of the first user; ii. health-related attribute information associated with at least one health-related attribute of the first user; iii. health kit information associated with health conditions and/or actions effecting health of the first user; iv. sensor information associated with a first computer device associated with the first user, wherein the sensor information includes at least one of the following: (1) location information associated with location information and/or movement information of the first user computer device at a first respective time; (2) accelerometer information generated by at least one accelerometer of the first user computer device at a second respective time; (3) gyrometer information generated by at least one gyrometer of the first user computer device at third respective time; (4) pedometer information generated by at least one pedometer of the first user computer device at a respective fourth time; (5) proximity information generated by at least one proximity sensor of the first computer device at a fifth respective time; (6) magnetometer information generated by at least one magnetometer sensor of the first computer device at a sixth respective time; (7) orientation information associated with degrees of rotation the first user computer device makes around three physical axes at a seventh respective time; (8) light sensor information generated by at least one light sensor of the first user computer device at an eight respective time; (9) altimeter information associate with a change in altitude pressure of the first user computer device at a ninth respective time; (10) motion information associated with acceleration, attitude, rotation, and magnetic data of the first user computer device at a tenth respective time; v. prior purchase information associated with purchases made by and/or associated with the first user; vi. activity information indicative of activities engaged in by and/or associated with the first user within; vii. budget information associated with an available budget for use in providing stimulus to the first user; and viii. goal information associated with the selected change in behavior; (b) providing, by a situation module including second one or more processors operatively connected to at least a second memory device and second machine readable instructions, the situation module operatively connected to the personal information module, a situation data set by: i. accessing the lifestyle information provided by the personal information module; ii. arranging the lifestyle information based at least on chronology to include information from a first predetermined time period to provide a current state data set associated with a current state of the first user; iii. providing the situation information data set to a first machine learning algorithm trained by the prior lifestyle information arranged chronology with situation provided as a label; wherein the first machine learning algorithm provides a situation data set associated with the first user; and iv. storing situation data set associated with the first user; (c) providing, by a stimulus module including a third one or more processors operatively connected to a third memory device and third machine readable instructions, a stimulus database using the second memory device, the stimulus database comprising stimulus information, wherein the stimulus information includes, for each prior stimulus of a plurality of prior stimuli: i. the respective prior stimulus; ii. a respective situation information data set associated with the respective prior stimulus; and iii. respective stimulus response information associated with the respective prior stimulus; (d) generating, by a training set module including fourth one or more processors operably connected to a fourth memory device and fourth machine readable instructions, the training set module operatively connected to the stimulus module, a training data set by: i. accessing the stimulus information; ii. filtering the stimulus information based at least on available stimulus information; iii. providing the training data set based on the application of the filter criteria to the stimulus information; and iv. storing the training data set; (e) selecting, by a manager module including fifth one or more processors operatively connected to at least a fifth memory device and fifth machine readable instructions, the manager module operatively connected to the situation module and the training set module, the first stimulus by: i. receiving the situation data set from the situation module; ii. providing the situation data set to a second machine learning algorithm trained by the training data set with stimulus provided as a label, wherein the machine learning algorithm selects the first stimulus and a time to send the first stimulus to the first computing device associated with the first user; and iii. sending the first stimulus to the first computing device associated with the first user; (f) collecting, by a collection module including sixth one or more processors operatively connected to a sixth memory device and sixth machine readable instructions, after the first stimulus is transmitted to the first computing device associated with the first user, updated information from at least one of: (1) the first computer device associated with the first user; (2) a second computer device associated with the first user; and (3) a third computer device associated with a second user associated with the first user via social media, professional affiliation or the interactive electronic network, wherein the updated information includes at least updated lifestyle information; (g) determining, by the collection module, based at least on the updated lifestyle information, the first stimulus was successful; (h) generating, by the collection module, stimulus response information associated with success of the first stimulus; (i) sending, by the collection module to the personal information module the update lifestyle information to be added to the lifestyle database; and (j) sending, by the collection module to the stimulus module, the stimulus response information, including the first stimulus and the situation data set, to be added to the stimulus database.

In embodiments, the method includes: (k) obtaining and storing, by a social module including seventh one or more processors operatively connected to at least a seventh memory device and seventh machine readable instructions, the social module operatively connected to the personal information module and the situation module, social information associated with the first user, wherein the social information includes: i. social network information, wherein the social network information comprises a second user that is a social network connection; and ii. professional colleague information, wherein the social module is operatively connected to the personal information module, and the personal information module accesses the social network information provided by the social module; and the situation module filters the social network information based at least on the time and used it to provide the situation data set.

In embodiments, the second user is a professional colleague of the first user.

In embodiments, the third computer device is associated with the second user.

In embodiments, the personal information module is operatively connected to the social module, and the personal information module: i. receives the social network information; and ii. provide the proximity information indicating when the first user is within a predetermined proximity of the second user by: a. accessing the social network information; b. filtering the social network information based at least on the time; and c. providing the proximity information based on: (1) the location information associated with the first user; and (2) location information associated with at least the second user.

In embodiments, the proximity information is also based on at least one of the following: i. determining a computing device associated with the second user is within range of the same cell tower as at least one of the first computer device or the second computer device; ii. determining the computing device associated with the second user is within a predetermined distance of at least one of the first computer device or the second computer device; iii. determining the electronic device associated with the second user and at least one of the first computer device or the second computer device are in a first building; iv. determining the electronic device associated with the second user and at least one of the first computer device or the second computer device are within a first city block; v. determining the electronic device associated with the second user and at least one of the first computer device or the second computer device are in a first room of a second building; and vi. determining the electronic device associated with the second user and at least one of the first computer device or the second computer device are within a first place of business.

In embodiments the stimulus response information is further provided from: d. a fourth computer device associated with a third user of the interactive electronic network associated with the first user via professional association.

In embodiments the stimulus response information is further provided from: d. a fourth computer device associated with a third user of the interactive electronic network, wherein the third user is a social contact of the first user.

In embodiments the stimulus response information is further provided from: d. a fourth computer device associated with a third user of the interactive electronic network associated with the first user via professional association; and e. a fifth computer device associated with a fourth user of the interactive electronic network, wherein the fourth user is not linked via social media or professional affiliation to the first user.

In embodiments, the stimulus response information is provided based on updated lifestyle information indicating whether the first stimulus provided positive results relative to the selected change.

In embodiments, the health-related attribute information includes at least one of: (1) heartbeat information; (2) respiratory information; (3) blood pressure information; (4) body temperature information; (5) height information; and (6) weight information.

In embodiments, at least a portion of the health-related attribute information and/or health kit information is provided by the first user via the first computer device.

In embodiments, at least a portion of the health-related attribute information and/or health kit information is provided by the first user via the second computer device.

In embodiments, at least a portion of the health-related attribute information and/or health kit information is provided by one or more healthcare providers.

In embodiments, at least a portion of the health-related attribute information is provided by the first user in response to a survey provided on the first computer device.

In embodiments, the manager module sends the first stimulus to the first computer device by performing the following steps: i. generating, after selecting the first stimulus, first machine-readable instructions including a first graphical user interface (GUI), wherein the first GUI represents the first stimulus and comprises: (1) a first message based on at least the first stimulus and an impending first choice, wherein the impending first choice is based on at least the selected change; and (2) impending first choice information being based on at least the impending first choice and the selected change; and ii. sending the first machine-readable instructions to the first computer device, wherein, upon receiving the first machine-readable instructions, the first computer device executes the first machine-readable instructions which causes the first GUI to be displayed on a display screen of the first computer device.

In embodiments the first-machine readable instructions further include a notification instruction wherein, and wherein receipt of the first-machine readable instructions by the first computer device causes a notification to be sent from the first computer device to the second computer device.

In embodiments, the collection module: i. generates, after generating the stimulus response information, display machine-readable instructions including a first graphical user interface (GUI), wherein the first GUI comprises a first message based on at least one of: (1) the first stimulus, and (2) the stimulus response information; and ii. sends the display machine-readable instructions to at least one of: (1) the first computer device; and (2) the second computer device, wherein, upon receiving the first machine-readable instructions, one or more of the first computer device and the second computer device executes the first machine-readable instructions which causes the first GUI to be displayed on a display screen of at least one of: (1) the first computer device; and (2) the second computer device.

In embodiments, the first computer device is at least one of a portable computing device and a wearable device.

In embodiments, the portable computing device is at least one of a smart phone, a tablet, a phablet, and a laptop.

In embodiments, the second computer device is at least one of a portable computing device and a wearable device.

In embodiments, the portable computing device is at least one of a smart phone, a tablet, a phablet, and a laptop.

In embodiments, the first computer device includes at least one of: (1) an accelerometer; (2) a gyrometer; (3) a pedometer; (4) a magnetometer; (5) a light sensor; and (6) a proximity sensor.

In embodiments, the second computer device includes at least one of: (1) an accelerometer; (2) a gyrometer; (3) a pedometer; (4) a magnetometer; (5) a light sensor; and (6) a proximity sensor.

In embodiments, the first machine learning algorithm utilizes a neural network.

In embodiments, the first machine learning algorithm uses a deep learning neural network.

In embodiments, the second machine learning algorithm utilizes a neural network.

In embodiments, the second machine learning algorithm utilizes a deep learning neural network.

In embodiments, each of the (1) location information; (2) accelerometer information; (3) gyrometer information; (4) pedometer information generated by at least one pedometer of the first user computing device at a respective fourth time; (5) proximity information; (6) magnetometer information; (7) orientation information; (8) light sensor information; and (9) altimeter information; and (10) motion information include a respective time stamp.

In embodiments, the prior lifestyle information includes time stamps that are prior to the first predetermined period of time.

In embodiments at least a portion of the (1) location information; (2) accelerometer information; (3) gyrometer information; (4) pedometer information generated by at least one pedometer of the first user computing device at a respective fourth time; (5) proximity information; (6) magnetometer information; (7) orientation information; (8) light sensor information; and (9) altimeter information; and (10) motion information are provided by the second computing system.

Other features and advantages of the present disclosure will become readily apparent from the following detailed description and the accompanying drawings.

BRIEF DESCRIPTION OF THE DRAWINGS

The above and related objects, features and advantages of the present disclosure will be more fully understood by reference to the following, detailed description of the preferred, albeit illustrative, embodiment of the present disclosure when taken in conjunction with the accompanying figures, wherein:

FIG. 1A-1 is an exemplary block diagram of the system of FIG. 1 selecting a stimulus for a user associated with the first computer device and/or the second computer device in accordance with exemplary embodiments of the present invention;

FIG. 1A-2 is an exemplary block diagram of a first computer device selecting a stimulus for a user associated with the first computer device and/or the second computer device in accordance with exemplary embodiments of the present invention;

FIG. 1A-3 is another exemplary block diagram of a first computer device selecting a stimulus for a user associated with the first computer device and/or the second computer device in accordance with exemplary embodiments of the present invention;

FIG. 2B is an exemplary block diagram of an optional second personal user device in accordance with exemplary embodiments of the present invention;

FIG. 3 is an exemplary block diagram illustrating the structure of mobile application software for implementing an interactive user health decision prompting process in accordance with exemplary embodiments of the present invention;

FIG. 10-A is an exemplary flow chart illustrating a process for encouraging a selected change in behavior of at least a first user of a plurality of users of an interactive electronic network in accordance with exemplary embodiments of the present invention;

FIG. 10-B is an exemplary flow chart illustrating a continued process associated with the process illustrated in FIG. 10-A in accordance with exemplary embodiments of the present invention;

FIGS. 12A-12B are exemplary flow charts illustrating processes for a situation module providing a situation data set in accordance with exemplary embodiments of the present invention;

FIG. 12C is an exemplary flow chart illustrating a process for a training set module generating a training data set in accordance with exemplary embodiments of the present invention;

FIG. 12D is an exemplary flow chart illustrating a process for a manager module selecting a first stimulus in accordance with exemplary embodiments of the present invention;

FIGS. 13D-1-13D-2 are illustrative screenshots of exemplary graphical user interfaces in accordance with exemplary embodiments of the present invention;

FIGS. 13E-13L are illustrative screenshots of exemplary graphical user interfaces in accordance with exemplary embodiments of the present invention.

FIGS. 14D-1-14D-2 are exemplary flow charts illustrating a process of communicating with third-party systems to assist in the selection of a stimulus in accordance with exemplary embodiments of the present invention;

FIG. 15-1 is an exemplary block diagram illustrating a personal user device transmitting a request to the system in accordance with exemplary embodiments of the present invention;

FIG. 15-2 is an exemplary flow chart for processing the one or more requests of FIG. 15-1 in accordance with exemplary embodiments of the present invention;

FIGS. 15A-15G are exemplary flow charts of processes for responding to a request from a personal user device in accordance with exemplary embodiments of the present invention;

FIG. 19A is an exemplary data model representing a timeline of a recurring location over a week in accordance with exemplary embodiments of the present invention;

FIG. 19B is an exemplary timeline of a recurring location over a week in accordance with exemplary embodiments of the present invention;

FIGS. 21A-21M are exemplary flow charts of processes to generate a data set in accordance with exemplary embodiments of the present invention; and FIGS. 22A-22F are exemplary flow charts of processes for providing a stimulus to a personal user device in accordance with exemplary embodiments of the present invention.

DETAILED DESCRIPTION

The present disclosure relates to a computer-implemented process for evaluating user activity, user preference, and/or user habit via one or more personal devices and providing precisely timed and situationally targeted prompts and stimuli for encouraging lifestyle choices and reinforcing health habits. It is an object of the present disclosure to provide a technological solution to the long felt need in health management services caused by the technical problem of procuring timely health management by encouraging healthy choices.

Figure 1:
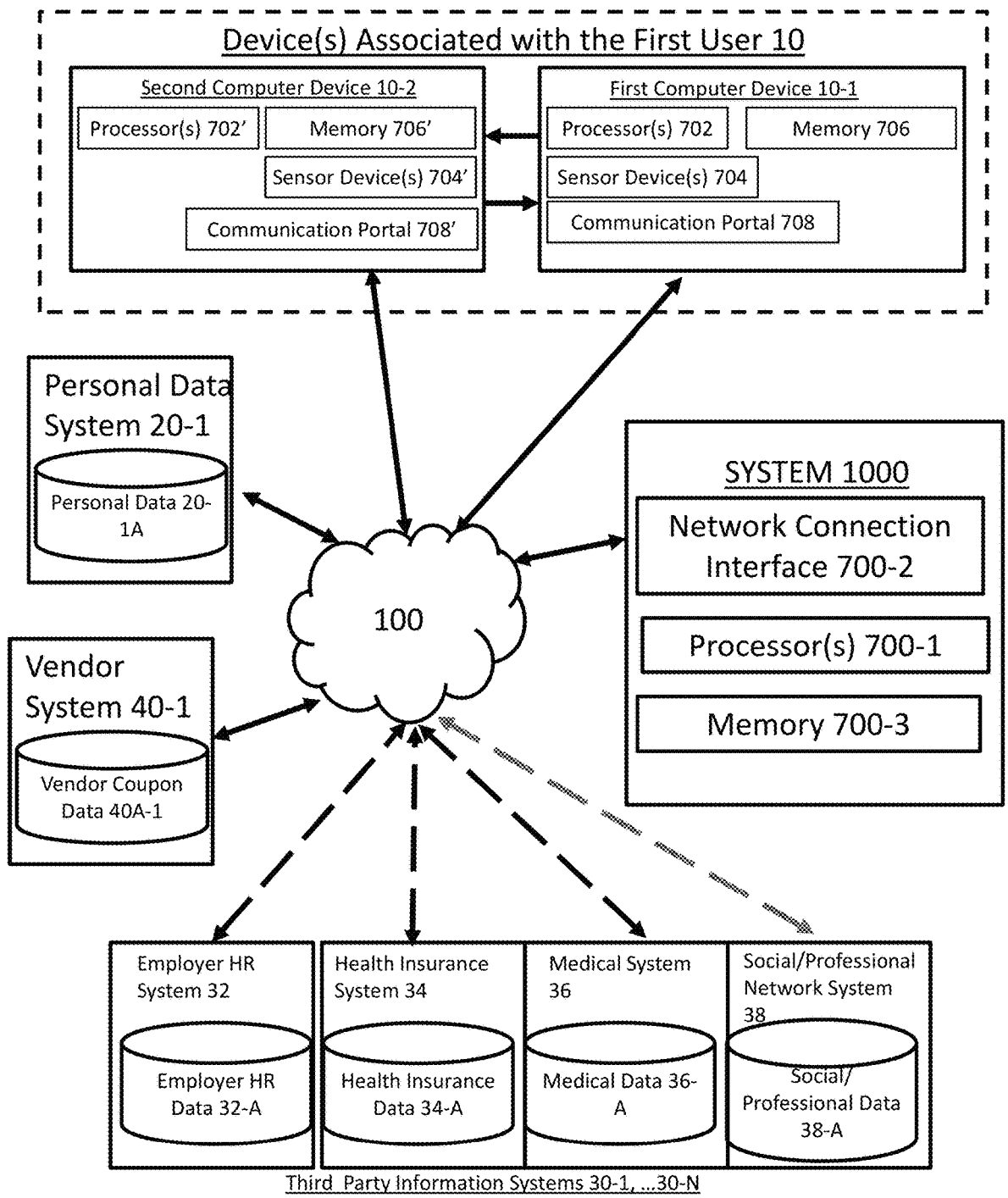
FIG. 1 is a schematic diagram illustrating system and apparatuses for implementing an interactive user health decision prompting process in accordance with exemplary embodiments of the present invention.

FIG. 1 shows, according to an exemplary embodiment, a system for obtaining, determining, and evaluating personal health and behavioral data from one or more devices associated with a user and for providing appropriate positive health choices via prompts and stimuli at the one or more devices in correspondence with the evaluated personal health and behavioral data.

The present invention is directed towards to a system, method, and program product that detects user behavior from e.g., a user's respective personal portable device, to predict and identify and provide in real-time contextually relevant stimulus (e.g., alerts/notifications to the user's personal portable device) to influence the user's behavior for predetermined goals, e.g., healthy lifestyle options.

As a preliminary step, a first user may create an account via a user interface provided by the system (e.g., via a website and/or mobile application, to name a few). The process of signing up, for example, may include providing information associated with the first user (e.g., credential information, name, height, weight, age, gender, and/or a combination thereof, to name a few), providing at least one goal, and/or granting the system access to data obtained and/or saved by one or more personal user devices associated with the first user (a more detailed description of creating an account is located below in connection with the description of FIG. 15B, the description of which applying herein). For the purposes of this example—the first user may have inputted at least its name—Bob—and its goal—to lose weight (a more detailed example regarding Bob is located below in connection with the description of Example 10, the description of which applying herein). In embodiments, the first user may be registered by another, e.g., employer, insurance company, family member, to name a few. Thus, for example, an employer may want to encourage employees to achieve certain goals, such as lifestyle goals that can result in better productivity, e.g., eating healthier, getting more exercise, sleeping a full night, to name a few. In embodiments, other third parties and goals may be involved without deviating from the scope or spirit of the present invention.

After the user is registered, the system will begin to collect and label historical data about the user. Examples of data, include, e.g., raw data streamed from a user's personal mobile device. For example, data may be collected over a time period, such as a certain number of days, a week, a month, multiple months, a year, or years to name a few, and labelled. In embodiments, labelling can include Location information, and Event information. Examples of Location information may include, e.g., user specific location associated location data labels (e.g., home, office, to name a few), public location associated location data labels (e.g., gym, grocery store, restaurant), and/or special location associated location data labels (e.g., airport, train, hospital, to name a few). Other types of location information can include stationary location (e.g., a location where the user has stopped for at least a minimum amount of time, typically when the user is not commuting), recurring location (e.g., a stationary location where the user has stopped more than a fixed number of times during a selected window of time (e.g., a few weeks/months, etc.), a recurring location with a predicted location data label (e.g., a location data label for a recurring location which has been predicted either by heuristic and/or machine learning algorithms, as a likely place to generate and send the user a stimulus associated with one or more designated goals), confirmed place (e.g., a predicted place associated with a stimulus that the user has acted in positive manner with respect to a designated goal), a place (e.g., a confirmed place that has been confirmed). The system, for example, may predict one or more location data labels associated with one or more recurring locations using one or more data models (e.g., the data model(s) depicted in connection with FIGS. 19A and/or 19B).

Examples of Events can include, e.g., wake up, having meals (e.g., breakfast, lunch, snake, dinner), clocking in/out from work, going out (e.g., in the evening), waking up, going to bed, attending a movie or play, to name a few. Other examples of events, including a predicted event (e.g., an event predicted by the heuristic and/or machine learning algorithms that can be used to generate a stimulus to confirm the hypothesis) and confirmed event (e.g., a predicted event where a stimulus was issued and tested positively in response to stimulus), and event (e.g., a confirmed event that is confirmed by a positive response to stimulus). Events, in embodiments, may be mapped out by the system in the form of a daily routine (e.g., the daily routines illustrated in connection with FIGS. 20A and 20B). The daily routine, in embodiments, may assist the system in predicting locations and/or events associated with a user's day. In embodiments this labelling may be done using a heuristic model and/or using a machine learning algorithm. In embodiments, because the data gathered may have gaps, gap filling algorithms can be used to fill in such gaps.

When enough data is collected, the present data can be fed into a heuristic (e.g., using data models and/or daily routines) and/or machine learning algorithm which can be used to predict user activity in advance. In embodiments, each user (or in some cases groups of users) will have one or more dedicated machine learning modules that can be used to predict that user (or group of users) present or future activities. In embodiments, different users (or groups of users) may have different models, some of which may be shared (for example, models may be shared between users that work together and frequently go out to lunch together during lunchtime on business days, to name a few). In embodiments where machine learning is used, the historical data with labels can be used as a training set for the machine learning algorithm. In embodiments, the historical data will include various data streaming from e.g., a user's mobile device (e.g., a mobile phone), and the labels will be answers (or responses) to stimuli. In embodiments, labels associated with one user may be applied to one or more other users.

As shown in FIG. 1, personal user devices 10-1 . . . 10-n, a personal data system 20, third-party user information systems 30-1 . . . 30-n, and vendor systems 40-1 . . . 40-n may be in communication with one another via a network 100. The network 100 may be the Internet, an intranet network, a local area network, other wireless, optical, or other hardwired connection or connections, or a combination of one or more thereof, by which individual components of the system may communicate. In embodiments, personal user devices 10-1 . . . 10-n may include personal computers and/or mobile devices, such as cellphones, smartwatches, other smart wearable devices, exercise equipment with user interfaces, and the like, with Internet access that are uniquely identifiable by Internet Protocol (IP) addresses, Internet cookies, Media Access Control (MAC) identifiers, or online personal accounts of the individual users associated with the personal user devices 10-1 . . . 10-n, either directly or through another personal device. Other personal user devices 10-1 . . . 10-n may include, for example, television set-top boxes, tablet computers, portable media devices, smart appliances and devices, personal medical devices, websites, and gaming consoles. Further exemplary personal user devices 10-1 . . . 10-n are described below in connection with FIG. 2A. Communications systems for facilitating network 100 can include hardware (e.g., hardware for wired and/or wireless connections) and/or software. In embodiments, communications systems can include one or more communications chipsets, such as a GSM chipset, CDMA chipset, LTE chipset, 4G/5G, Wi-Fi chipset, LiFi, Bluetooth chipset, to name a few, and/or combinations thereof. Wired connections may be adapted for use with cable, plain old telephone service (POTS) (telephone), fiber (such as Hybrid Fiber Coaxial), xDSL, to name a few, and wired connections may use coaxial cable, fiber, copper wire (such as twisted pair copper wire), and/or combinations thereof, to name a few. Communications systems for facilitating network 100 can include one or more of virtual networking, physical networking, software defined networking (SDN), and/or a combination thereof, to name a few. Wired connections may be provided through telephone ports, Ethernet ports, USB ports, and/or other data ports, such as Apple 30-pin connector ports or Apple Lightning connector ports, to name a few. Wireless connections may include cellular or cellular data connections and protocols (e.g., digital cellular, PCS, CDPD, GPRS, EDGE, CDMA2000, 1×RTT, RFC 1149, Ev-DO, HSPA, UMTS, 3G, 4G, and/or LTE, to name a few), Bluetooth, Bluetooth Low Energy, Wi-Fi, radio, satellite, optical connections, ZigBee communication protocols, to name a few. Communications interface hardware and/or software, which may be used to communicate over wired and/or wireless connections, may include Ethernet interfaces (e.g., supporting a TCP/IP stack), X.25 interfaces, T1 interfaces, and/or antennas, to name a few. Computer systems may communicate with other computer systems or devices directly and/or indirectly, e.g., through a data network 5, such as the Internet, a telephone network, a mobile broadband network (such as a cellular data network), a mesh network, Wi-Fi, LoRa, WAP, LAN, and/or WAN, to name a few. Further exemplary communication systems are described below in connection with FIG. 2A.

According to an exemplary embodiment of the present disclosure, users associated with and/or of the personal user devices 10-1 . . . 10-n may each be associated with a personal user profile account. In embodiments, one or more personal user profile account(s) may be is maintained at personal data system 20. Personal data system, in embodiments, may be operatively connected, mechanically coupled, and/or electrically coupled to computing device 700 (which is described in more detail below in connection with FIG. 2A). In addition, in an embodiment, one or more users may be associated with one or more additional user accounts which may be maintained at one or more third-party user information systems 30-1 . . . 30-n. In embodiments, third-party user information systems 30-1 . . . 30-n may include user accounts associated with one or more users associated with one or more the personal user devices 10-1 . . . 10-n—such as Apple ID, iCloud, Google (Android) Account, Microsoft Account, to name a few—social media services, such as Facebook, Twitter, Instagram, Snapchat, to name a few—or other entities associated with the users of the personal user devices—such as, employers, medical insurance companies, health service providers, sponsors, loyalty programs, to name a few. As shown in FIG. 1, in embodiments, third-party information systems 30-1 . . . 30-N may include employee HR systems 32 (with employer HR data 32-A), health insurance systems 34 (with health insurance data 34-A), medical system 36 (with medical data 36-A), social and/or professional network systems 38 (with social and/or professional data 38-A), to name a few.

In accordance with an exemplary embodiment of the present disclosure, users may be provided with an option to consent to share some or all of their personal data with one or more sponsors (of the various challenges and/or rewards/incentives), one or more employers, one or more medical insurance companies, and/or one or more health services providers, to name a few. The personal data, in embodiments, may be shared by one or more users via third-party user information systems 30-1 . . . 30-n. Additional challenges and rewards may be provided in exchange for a user consenting to share some or all of their personal data. In embodiments, the personal data shared may be protected by an enhanced security protocol that uses an improved block-chain-like algorithm, which may be provided among the personal user devices 10-1 . . . 10-n for recording data such as: user prompt and stimulus response transactions, possibly in a distributed multiparty smart contract and indelible ledger. Furthermore, in embodiments, when users are sharing personal data with third-party user information systems 30-1 . . . 30-n, an enhanced security protocol that uses an improved block-chain-like algorithm may be provided among the personal user devices 10-1 . . . 10-n for recording user prompt and stimulus response transactions in a distributed multiparty smart contract and indelible ledger. For the purposes of providing a technical solution to the technical problem of data security risks on the internet, each of the personal user devices 10-1 . . . 10-n may be provided with a unique key that is only available at the respective personal user device and only decrypted in a transient memory thereof after a user performs a biometric authentication process on the respective personal user device. All user actions, such as (1) user responses to prompts, directions, directives, instructions, or stimuli, (2) elections (e.g., accepting challenges, redeeming rewards, etc.), or (3) other actions such as changes in walking speed, going to a different restaurant, viewing personal data, etc., may be recorded using this indelible ledger functionality, which may form a master record against which a similar recorded history possibly maintained at personal data system 20 (and/or other locations) may be compared and verified.

Vendor systems 40-1 . . . 40-n may, in embodiments, include systems for maintaining online user accounts associated with one or more personal user devices 10-1 . . . 10-n at various vendors for goods and services that are associated with the users of personal user devices 10-1 . . . 10-n—for example, online marketplace accounts maintained at iTunes, Google Play, Amazon, to name a few, food and beverage vendors, such as, Starbucks, McDonalds, to name a few, exercise program or equipment memberships, such as, Peloton®, SoulCycle®, to name a few, pharmaceutical vendors, such as, CVS, Duane Reade, to name a few, general department stores, such as Macy's, etc., payment and/or financial transaction service vendors, such as Visa, AMEX, Square, and the like, to name a few. Vendor systems 40-1 . . . 40-n may, in embodiments, maintain incentive programs and discount information for products and services which may be related to particular prompts and stimuli that may be used to encourage particular positive choices. For example, as described in further detail below, when a user is detected to have visited the vendor to purchase and/or consume lower calorie or relatively healthier choices in response to a prompt and/or stimuli, the user may be rewarded with one or more of the following: discounts for items offered for sale by food vendors, incentive points, to name a few. Similarly, interchangeable credits or benefits may be associated with particular milestones achieved through recorded participation in exercise programs and/or equipment usage, to name a few. It is noted that based on consolidation of certain entities of various types, third-party user information systems 30-1 . . . 30-n and vendor systems 40-1 . . . 40-n may be owned and/or operated by the same, related, and/or associated corporate or other types of entities.

According to an exemplary embodiment of the present disclosure, personal data system 20 may communicate with personal user devices 10-1 . . . 10-n to obtain and/or store relevant user information and to cross-reference the obtained and/or stored information with similar or related information obtained and/or stored from personal user devices 10-1 . . . 10-n and/or at respective third-party user information systems 30-1 . . . 30-n and vendor systems 40-1 . . . 40-n, or other sources. Based on the aforementioned analysis of the obtained and/or stored user information, personal data systems 20-1 . . . 20-n may generate and/or transmit various prompts and/or stimuli to one or more personal user devices 10-1 . . . 10-n. The prompts and/or stimuli may be transmitted at appropriate times and locations in order to encourage users of the personal user devices 10-1 . . . 10-n to make positive lifestyle choices (e.g., a personal and/or conscious decision to perform a behavior that may decrease the risk of injury or disease). In embodiments, a positive lifestyle choice may refer to a decision by a user to act in a manner that may benefit a user's health, happiness, wellbeing, financial wellbeing, religious wellbeing, and/or social wellbeing, to name a few. The one or more users' responses to prompts and stimuli may be stored and analyzed which may assist in the determination of future prompts and stimuli to the particular users and/or their related users.

Figure 2A:
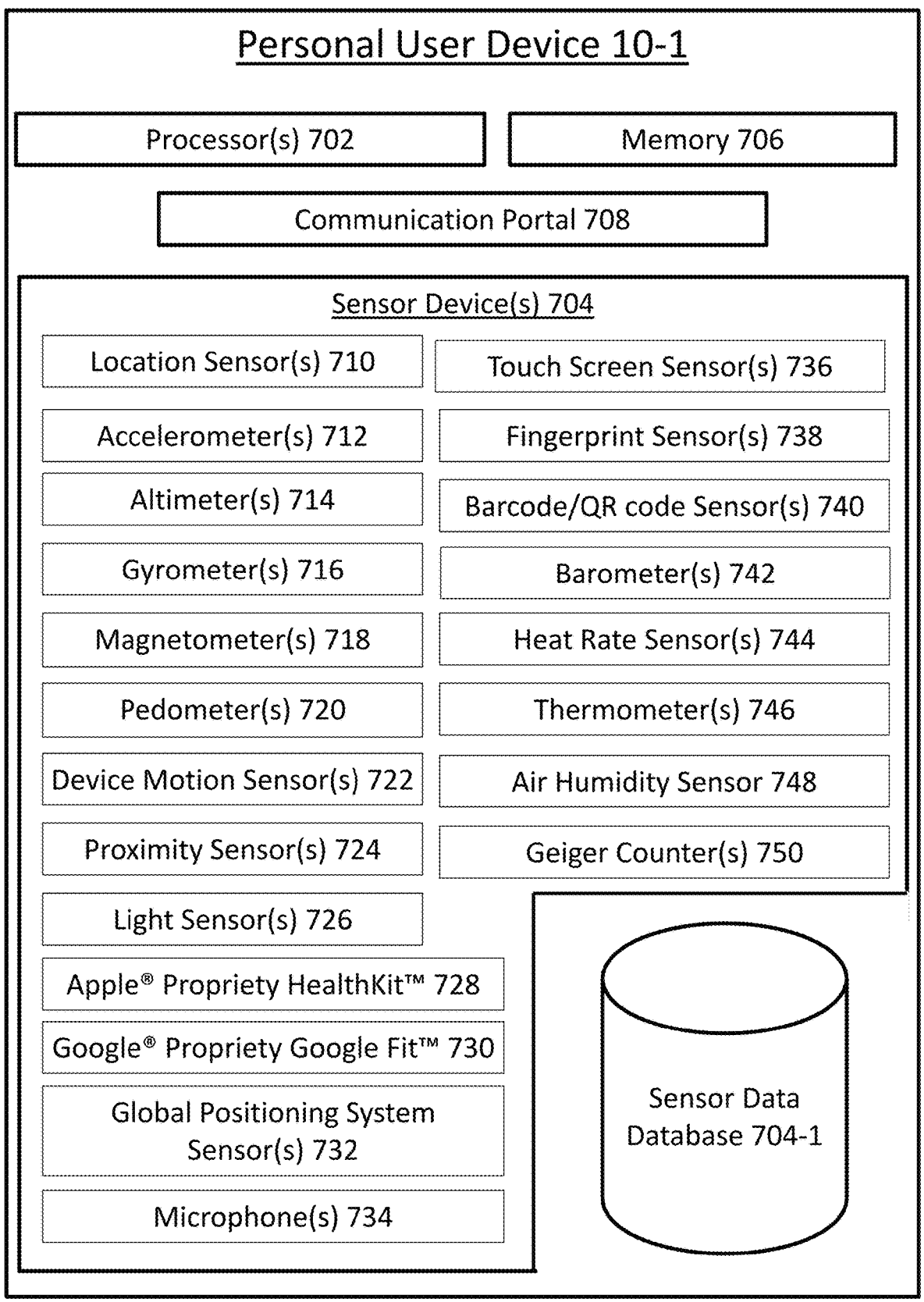
FIG. 2A is an exemplary block diagram of a personal user device in accordance with exemplary embodiments of the present invention.
Figure 2C:
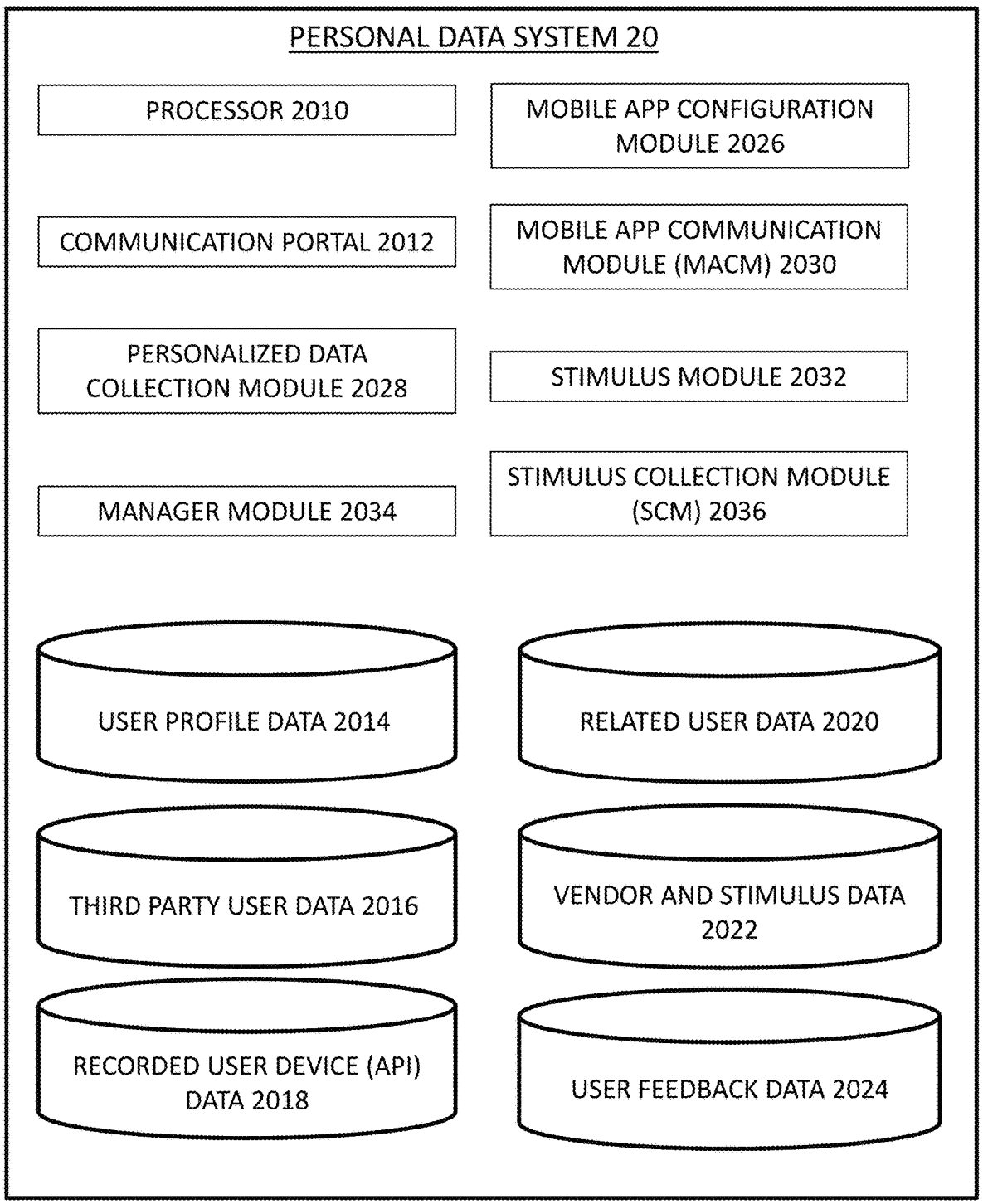
FIG. 2C is an exemplary block diagram illustrating a networked personal data system for implementing an interactive user health decision prompting process in accordance with exemplary embodiments of the present invention.
Figure 3:
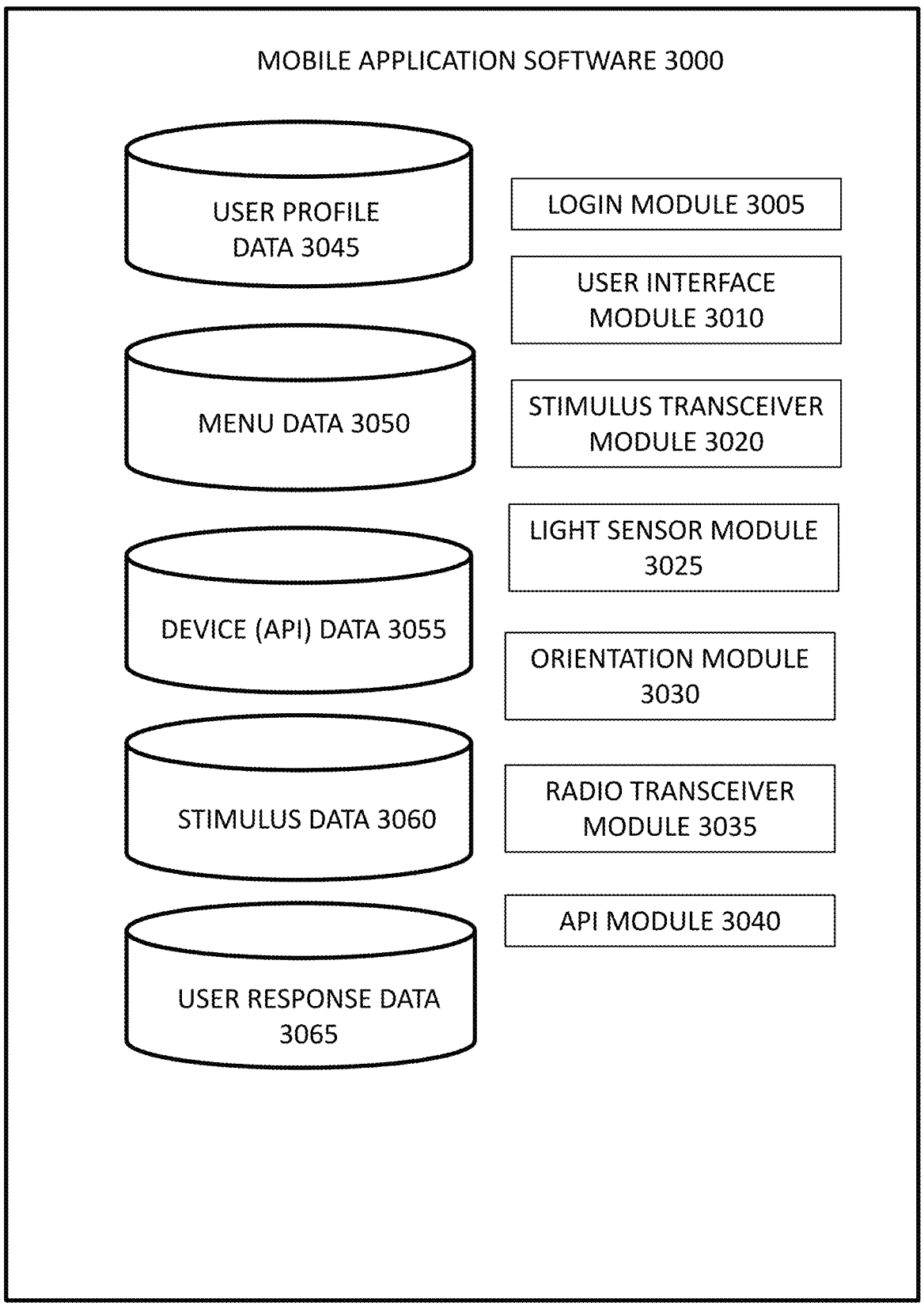

FIG. 2C is an exemplary block diagram of a personal data system in accordance with an exemplary embodiment of the present invention. Personal data system 20 may include a processor 2010, which may be embodied by a general purpose computer, a server, a mainframe computer, a computer with a specific purpose of maintaining personal user data and of communicating with personal user devices 10-1 . . . 10-n, third-party user information systems 30-1 . . . 30-n, and vendor systems 40-1 . . . 40-n, or a combination of one or more thereof. Processor 2010 may be integrated with or communicate through a communication portal 2012 with other systems and devices, such as personal user devices 10-1 . . . 10-n, third-party user information systems 30-1 . . . 30-n, and vendor systems 40-1 . . . 40-n via network 100. Processor 2010 may (by itself or in cooperation with other processors) maintain one or more databases associated with user profile data 2014, third-party user data 2016, recorded user device (including API) data 2018, related user data 2020, vendor and stimulus data 2022, user feedback data 2024 and other data related to the application. Further exemplary uses and examples of processors are described below in connection with FIG. 2A and apply herein.

User profile data 2014 may include one or more of user attribute information, health information, and/or other profile information of each user associated with personal user devices 10-1 . . . 10-n. In embodiments, user profile data 2014 may be maintained, stored, and/or organized under respective user accounts. In embodiments, user profile data 2014 may include a user reliability rating related to the reliability of each user's responses to prompts and stimuli. The user reliability rating may be verified and compared with other sources of information. According to an exemplary embodiment of the present disclosure, user profile data 2014 may include user information provided during a user registration process. For example, during an installation and/or first execution of application software (e.g., mobile application software 300, described below in connection with FIG. 3) on personal user devices 10-1 . . . 10-n. The user information provided may include one or more of the following: user personal details (e.g., height, weight, level of physical activity, health issues, genealogical/hereditary data (including propensity for genetic diseases), to name a few), name, email address, date of birth, and gender, to name a few. Additionally, the application software (e.g., mobile application software 3000) may be configured to store and/or relay device hardware information associated with personal user devices 10-1 . . . 10-n, such as device name, system name, system version, device model, device localized model, vendor identifier, login time, device boot-loader information, manufacturer, security patches installed, user network IP address, to name a few. The hardware information, in embodiments may be used for user identification/ verification, for service customization purposes, and/or for security purposes. User profile data 2014 may further include program-relevant information associated with each user, such as user statistics on stimulus/incentive program points consumed, remarks entered, stored user well-being statistics, to name a few. User profile data 2014 may include usage patterns, which, in embodiments, may refer to responses to notifications and/or alerts.

In embodiments, stored user well-being statistics may include data regarding: walking, running, cycling, exercising, types of motion (going up/down in elevators, escalators, stairs, and/or a combination thereof, to name a few), sleep patterns, and stress patterns, to name a few. Walking data may include: a number of steps (and/or other units of distance) as related to a period of time (a period of time may refer to a year, quarter, season, month (can also refer to type of month—e.g., birthday month), day (type of day—e.g., business day, holiday, weekend, week day, to name a few), portion of day (e.g., morning, afternoon, or night), and/or a period of time where the user is walking, to name a few), a maximum number of steps as related to the aforementioned period of time (maximum can refer to the maximum number of steps the user has done in the aforementioned period of time), a minimum number of steps as related to the aforementioned period of time (minimum can refer to the minimum number of steps a user has taken as related to the aforementioned period of time), an average number of steps as related to the aforementioned period of time (average can refer to the average number of steps a user has taken as related to the aforementioned period of time), a median number of steps as related to the aforementioned period of time, a start time of steps, an end time of steps, and a combination of the aforementioned types of walking data, to name a few. Walking data, in embodiments, may be used to determine when, if, and/or the type of prompts and/or stimuli that may be sent to a user. For example, if there is a period of time where the user is unusually sedentary, a prompt and/or stimulus may be transmitted to a user device that encourages the user to walk.

Types of motion data (e.g., walking, climbing, running, driving, cycling, ascending/descending) may include a number of stairs and/or flights of stairs a user has ascended and/or descended as related to a period of time (a period of time may refer to a year, quarter, season, month (can also refer to type of month—e.g., birthday month), day (type of day—e.g., business day, holiday, weekend, week day, to name a few), portion of day (e.g., morning, afternoon, or night), and/or a period of time where the user is ascending and/or descending stairs, to name a few), a maximum number of stairs and/or flights ascended and/or descended as related to the aforementioned period of time (maximum can refer to the maximum number of stairs and/or flights the user has ascended and/or descended in the aforementioned period of time), a minimum number of stairs and/or flights ascended and/or descended as related to the aforementioned period of time (minimum can refer to the minimum number of stairs and/or flights a user has ascended and/or descended as related to the aforementioned period of time), an average number of stairs and/or flights ascended and/or descended as related to the aforementioned period of time (average can refer to the average number of stairs and/or flights a user has ascended and/or descended as related to the aforementioned period of time), a median number of stairs and/or flights ascended and/or descended as related to the aforementioned period of time, a start time of ascended and/or descended stairs and/or flights, an end time of ascended and/or descended stairs and/or flights, a combination of the aforementioned types of motion data, to name a few. Also, comparison information on the availability of alternative means of traveling to the same location (floor, restaurant, work, home, to name a few). For example, comparison information may include using stairs to reach a specific destination instead of using an elevator and/or escalator. The user profile data 2014 may include indicia for encouraging a user to take the stairs instead of using an escalator or elevator to reach the same location, where possible and/or practicable. Possibility or practicality may be determined, in embodiments, on a case by case basis depending on information obtained and/or stored in user profile data 2014. For example, walking up six flights of stairs may be possible for one person, whereas six flights of stairs may be too much for another. Sleep patterns data, in embodiments, may include data associated with monitored motion of the user device over the course of a day; data associated with monitored heartrate of the user (where the heartrate is monitored by the user device); and/or orientation of the user device. In embodiments, sleep patterns data may be found by assigning a longest period of non-motion of the user device as sleep. If, in embodiments, sleep period is less than X hours (or is interrupted, or is not deep enough) then the data may indicate that the user did not sleep well. Stress pattern data, in embodiments, may include data associated with monitored device movement (e.g., whether the user device is shaking) while user is running mobile application software 3000 on their associated user device. The data may be used to determine a baseline of movement. The baseline of movement, in embodiments, may be compared with other movement data, allowing for the detection of stress patterns. In embodiments, stress patterns data may also include heartrate data.

Other user statistics may include user responses to stimuli, responses to challenges allotted, user responses to queries, user responses to quizzes, user remarks and/or comments, stimulus/incentive program points consumed, to name a few.

Third-party user data 2016 may include information received from and/or obtained through third-party user information systems 30-1 . . . 30-n which may be associated with the users of personal user devices 10-1 . . . 10-n. For example, third-party user data 2016 may include information on sponsored health incentive programs that are maintained at third-party user information systems 30-1 . . . 30-n, such as health incentive programs provided by employers, health insurance providers, and the like. Third-party user data 2016 may also include information provided and/or stored by users of personal user devices 10-1 . . . 10-n at various third-party services, such as review websites (e.g., Yelp®), group discount services (e.g., Groupon®), social media platforms, health management services, to name a few. In embodiments, third-party user data 2016 may include user survey information which may be provided as part of a sponsored and/or independent health management program. The user survey information may include a user's daily schedule and/or routine, sleep cycle, and/or food, venue, and/or activity reviews, to name a few. As part of a health management program, third-party user data 2016 may include potential (e.g., open tasks which may be completed by one or more users) and/or assigned tasks (e.g., open tasks which may be a part of a challenge accepted by a user) for health improvement, such as run/walk for a predetermined amount of distance, ride a bicycle to work, and/or take the stairs instead of the escalators and/or elevators where such choices are available, to name a few. Associated with such tasks (e.g., potential tasks, assigned tasks, to name a few) may be incentives for completion/compliance, such as available discount coupons at selected restaurants, points for user credits at vendors, and discounts for gym memberships with branches near (e.g., within a predetermined radius) frequently visited locations, to name a few. In embodiments, incentives may be rewarded to users upon a verified completion of tasks. In embodiments, third-party user data 2016 includes details about insurance providers, challenges provided by them, rewards, incentive, and users effected, to name a few.

In embodiments, the prompts and/or stimuli that are available and/or assigned to various users of personal user devices 10-1 . . . 10-*n*, together with the users' responses to the assigned prompts and/or stimuli that are input at personal user devices 10-1 . . . 10-*n* (together may be referred to as user interactions), may be part of health improvement and incentive programs which may be sponsored by third-party entities. Such information, therefore, may be maintained and/or organized in third-party user data 2016 in correspondence with such sponsored programs. Accordingly, third-party user data 2016 may include user interactions (stimuli/ responses) to note improvements, such as quizzes with query labels, options for user choice, user incentive points, start date, end date, times for answer, quiz popularity, and number of quiz users to name a few. Third-party user data 2016 may further include information and user interactions associated with challenges, such as challenge type, challenge label, challenge details, expiry time, average time to complete the challenge, average user behavior, challenge levels, number of users who have completed the challenge, number of users who have accepted the challenge and have not completed the challenge (which may represent a difficulty level of the challenge), number of rewards awarded, and user challenge points, to name a few. As non-exhaustive examples, information on incentive programs may include: a $400 per year bonus for more than 10,000 average daily steps maintained on Fitbit; reduced life insurance premiums if certain physical achievements are met (e.g., run a mile in less than 9 minutes, etc.); and/or discounts to for healthier options, such as egg whites instead of eggs, to name a few.

Recorded user device (API) data 2018 may include some or all of the information that may be autonomously and/or semi-autonomously recorded at personal user devices 10-1 . . . 10-*n* without active responses from the users at the user interfaces of these devices. For example, recorded user device (API) data 2018 may include low accuracy location (e.g., cellular network triangulation); high accuracy location (e.g., a combination of GPS and at least one other sensor, e.g., WiFi); multi-dimensional accelerometer data (time-series); multi-dimensional compass data; multi-dimensional proximity data; light sensor data; wireless network association data; Bluetooth® association data; calendar/email/messaging data and activity; presence/group data; and device API data, to name a few. In embodiments, this information may be collected and/or received after consent is given by a user at the time of downloading and/or first execution of mobile application software 3000. In embodiments, recorded user device (API) data 2018 may include information used to generate user profile data 2014: data associated with high and low accuracy location; data associated with an accelerometer; data associated with a light sensor; data associated with a body proximity sensor, WiFi association, audio data, to name a few, which may be used to determine user motion patterns such as walking, running, climbing stairs, using escalators, user sleep patterns, or user stress patterns, to name a few. Recorded user device (API) data 2018, may be dependent upon the model and/or make of personal user device 10-1 . . . 10-*n*. For example, personal user device 10-1 may, in embodiments, not have a light sensor. Additionally, recorded user device (API) data 2018 may be dependent on what a user consents to. For example, a user may not consent to sharing location data. Recorded user device (API) data 2018 may include user-provided information that is integrated into the recorded user device (API) data 2018 with various sensor-detected recorded data (e.g., data associated and/or gathered by one or more sensors operatively connected to personal user device 10-1 . . . 10-*n*).

Referring to FIG. 2A, an exemplary personal user device 10-1 communicating with optional second personal user device 10-1A and/or computing device 700 over network 100 is shown. In embodiments, a user may have one or more personal user devices. For example, a user may have a cell phone (e.g., personal user device 10-1) and a wearable device (e.g., optional second personal user device 10-1A). In embodiments, the user may be encouraged to make a positive choice (e.g., eat healthier) through the help of the cell phone, wearable device, and/or computing device 700. In this example, the user may frequent the same Unhealthy Restaurant every day for lunch. This information regarding the user's eating habits may be determined and/or confirmed by computing device 700, the cell phone (exemplary personal user device 10-1), and/or the wearable device (optional second personal user device 10-1A) using one or more location sensor(s) 710, acting in concert with mobile application software 3000 over network 100. The information may also be determined using the mobile application software 3000. In embodiments, the user may consent to the mobile application software 3000 accessing information from the cell phone. The information may be stored either locally, remotely, or a combination of both and may be stored in connection with other applications on the cell phone. For example, other applications may include, location applications, calendar applications, electronic mail applications, social media applications, and banking applications, to name a few. Thus, computing device 700, the cell phone (exemplary personal user device 10-1), and/or the wearable device (optional second personal user device 10-1A) may determine that the user is frequenting Unhealthy Restaurant every day for lunch by checking the user's calendar or social media applications (using calendar events or locations that the user has checked-in to using social media) and checking the user's receipts (using the electronic mail applications or banking applications) to determine that the user has been to Unhealthy Restaurant and is buying food at Unhealthy Restaurant. Additionally, this information regarding the user's eating habits may be Continuing the example, in response to determining and/ or confirming the information regarding the user's unhealthy eating habits, computing device 700, the cell phone (exemplary personal user device 10-1), and/or the wearable device (optional second personal user device 10-1A), through mobile application software 3000, may want to encourage the user to eat at a healthier restaurant. In this example, the computing device 700 may find a close, healthier alternative—e.g., Healthy Restaurant which may be within walking distance of Unhealthy Restaurant.

Continuing the example, the computing device 700, using its one or more processor(s) 700-1 and network connection interface 700-2, may generate and transmit a suggestion for the user to make a positive choice, eat at Healthy Restaurant. The suggestion may be transmitted to the cellphone (personal user device 10-1) and/or the wearable device (optional second personal user device 10-1A) via network 100.

Figure 8A:
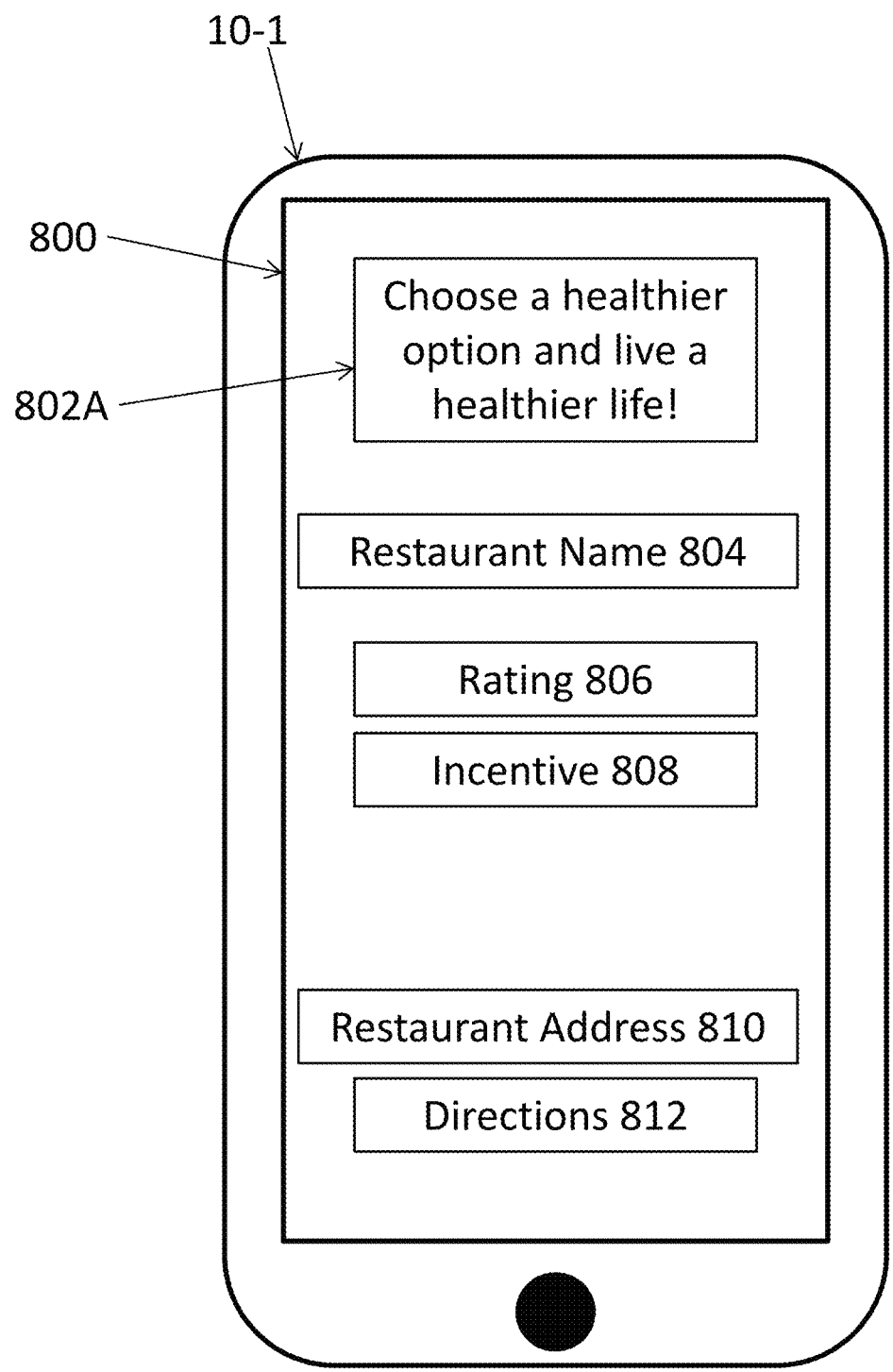
FIGS. 8A and 8B are exemplary graphical user interfaces (GUIs) showing exemplary suggestions of positive choices in accordance with exemplary embodiments of the present invention.
Figure 8B:
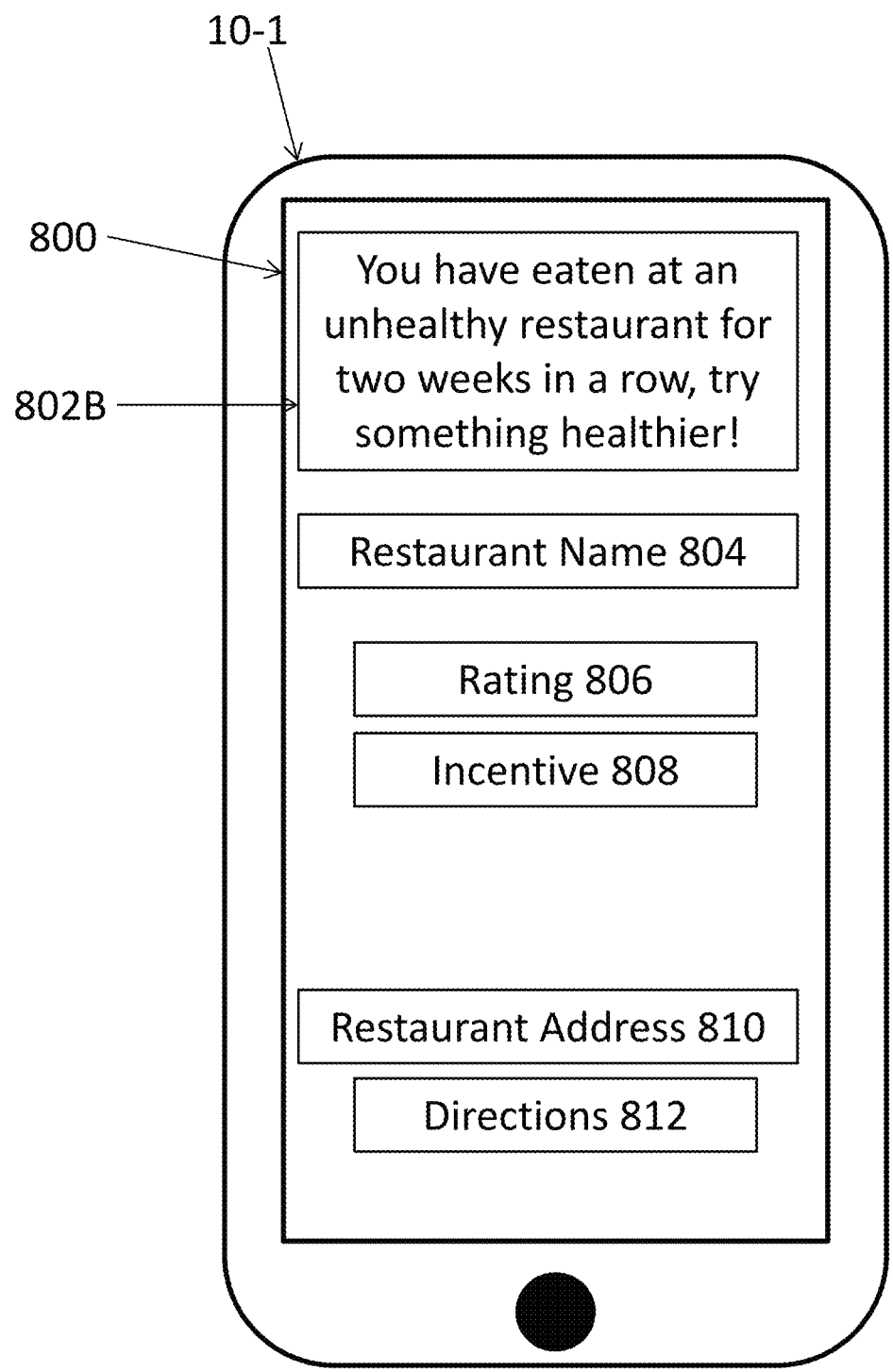

Continuing the example, the suggestion may be received by the cell phone (exemplary personal user device 10-1), and/or the wearable device (optional second personal user device 10-1A). Referring to FIGS. 8A and 8B, once received, the cell phone (exemplary personal user device 10-1) may display the suggestion. The personal user device 10-1 may display the suggestion on a display screen 800 of personal user device 10-1. The suggestion, in embodiments, may include a message (802A of FIG. 8A and 802B of FIG. 8B), a restaurant name 804, a rating 806 of the restaurant, an incentive 808 to encourage a positive choice, the restaurant address 810, and directions 812 to the restaurant. The suggestion, in embodiments, may further include reviews of the restaurant and a menu of the restaurant. For example, the suggestion may include the name "Healthy Restaurant," ratings and reviews of Healthy Restaurant, a menu from Healthy Restaurant, the location of Healthy Restaurant, directions to Healthy Restaurant, an incentive to eat at Healthy Restaurant, and a message for encouragement. The message may be simple, as in FIG. 8A, for example, "Choose a healthier option and live a healthier life." The message may also be more pointed, as shown in FIG. 8B, including pertinent facts, for example "You have eaten at Unhealthy Restaurant every weekday for the past two weeks, why not try something healthier like Healthy Restaurant." The incentive 808 may be used to encourage the user to eat at Healthy Restaurant instead of Unhealthy Restaurant. For example, incentive 808 may be one or more of the following: a coupon, an offer of goods and/or services, an offer of money, an offer of a gift certificate, and/or an offer to accumulate a certain number of points, to name a few. The points system, in embodiments, may be used for one or more of the following: to allow a user to reach a goal of healthy actions, to allow a user to compete with friends and/or family that are also using mobile application software 3000, and to allow third-party companies, such as insurance companies, to give rebates or cash back to the user based on the amount of confirmed healthy actions the user is making, to name a few. The incentive 808 may also include information from the user's friends and/or family. For example, incentive 808 may be, a message that states, "Your friend Charley is eating at Healthy Restaurant, would you like to join him?" In this embodiment, Charley, the user's friend, may be another user associated with another personal user device that, in concert with computing device 700, may be encouraged to make one or more positive choices. As another example, incentive 808 may be a message that states, "Your friend Keith has already reached his healthy goal, catch up!"

Continuing the example, after the cell phone (exemplary personal user device 10-1), and/or the wearable device (optional second personal user device 10-1A) have received and/or displayed the received suggestion, the computing device 700, the cell phone (exemplary personal user device 10-1), and/or the wearable device (optional second personal user device 10-1A) may confirm that the user has made the positive choice, eating at Healthy Restaurant instead of Unhealthy Restaurant. The confirmation of the user's healthy action may be completed in a similar manner as determining and/or confirming the user's old eating habits. Additionally, the confirmation may come by determining whether the user has used incentive 808. For example, the computing device 700 may receive confirmation from the cell phone (exemplary personal user device 10-1), and/or the wearable device (optional second personal user device 10-1A) by receiving confirmation data. The confirmation data may be transmitted in response to incentive 808 being utilized. For example, if incentive 808 is an offer of a coupon for 10% off at Healthy Restaurant, when the coupon is used by the user at Healthy Restaurant, data may be transmitted to computing device 700, confirming that the User has taken the healthy suggestion. In embodiments, the confirmation data may be transmitted from the cell phone (exemplary personal user device 10-1), and/or the wearable device (optional second personal user device 10-1A) to the computing device 700 via network 100.

Continuing the example, once it has been confirmed that the user has made a positive choice by eating at Healthy Restaurant, the computing device 700, using its one or more processor(s) 700-1 and network connection interface 700-2, may generate and transmit a confirmation message for the user, congratulating the user for making a positive choice. The confirmation message may be transmitted to the cellphone (personal user device 10-1) and/or the wearable device (optional second personal user device 10-1A) via network 100.

Figure 8C:
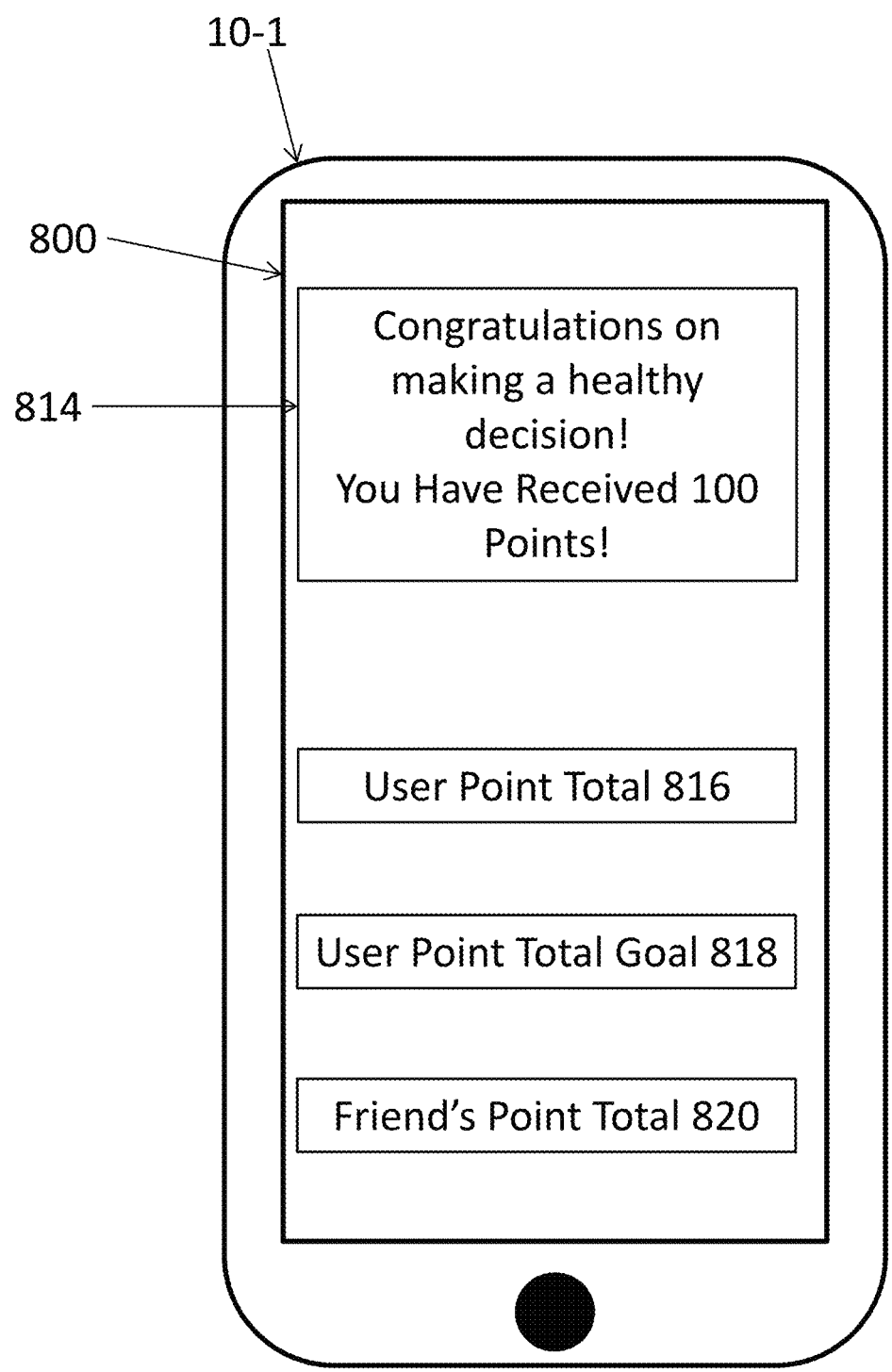
FIG. 8C is an exemplary GUI showing an exemplary confirmation message in accordance with exemplary embodiments of the present invention.

Continuing the example, the confirmation message may be received by the cell phone (exemplary personal user device 10-1), and/or the wearable device (optional second personal user device 10-1A). Referring to FIG. 8C, once received, the cell phone (exemplary personal user device 10-1) may display the confirmation message using the display screen 800 of personal user device 10-1. The confirmation message, in embodiments, may include a congratulatory message 814, user point total 816, user point total goal 818, and friend's point total 820. The congratulatory message 814, may read "Congratulations on making a healthy decision!" The congratulatory message 814, in embodiments, if the incentive 808 included points, may continue with "You have received 100 points!" The points, in embodiments, may be relative to the type of healthy decision the user has made. For example, there may be more points associated with a two-hour work-out then there would be for taking the stairs instead of an elevator. The points received by the user may, in embodiments, be totaled and displayed by the cell phone (exemplary personal user device 10-1) as user point total 816. The user point total 816 may be compared to the user point total goal 818. In embodiments, the user point total goal 818 may be a goal set by the user. In embodiments, the user point total goal 818 may be set by a third-party. For example, an insurance company may require a certain amount of healthy actions before giving the user a rebate or cash-back on the user's insurance premium. In embodiments, users may compete with friends and/or family, to see who has the healthier actions. The user's friend's and/or family's point total may be displayed on the cell phone (exemplary personal user device 10-1) as friend's point total 820. In embodiments, friend's point total 820 may include the user's ranking among other users in the area, state, country, or world. The user's ranking, in embodiments, may be in the form of a number (e.g., you rank $15^{th}$ in Manhattan) or percentile (e.g., you are in the 23 percentile in New York). An exemplary interface depicting a user's stats is located in connection with FIGS. 9F and 9G.

Referring back to FIG. 1, personal user device 10-1 and/or optional second personal user device 10-1A, as used herein, may, in embodiments, correspond to any suitable type of electronic device including, but are not limited to, desktop computers, mobile computers (e.g., laptops, ultrabooks), mobile phones, portable computing devices, such as smart phones, tablets and phablets, televisions, set top boxes, smart televisions, personal display devices, large scale display devices (e.g., billboards, street signs, etc.), personal digital assistants ("PDAs"), gaming consoles and/or devices, virtual reality devices, smart furniture, smart household devices (e.g., refrigerators, microwaves, etc.), smart vehicles (e.g., cars, trucks, motorcycles, etc.), smart transportation devices (e.g., boats, ships, trains, airplanes, etc.), wearable devices (e.g., watches, pins/broaches, headphones, etc.), smart security systems, and/or smart accessories (e.g., light bulbs, light switches, electrical switches, etc.), to name a few. In some embodiments, personal user device 10-1 and/or optional second personal user device 10-1A may be relatively simple or basic in structure such that no, or a minimal number of, mechanical input option(s) (e.g., keyboard, mouse, track pad) or touch input(s) (e.g., touch screen, buttons) are included. For example, personal user device 10-1 and/or optional second personal user device 10-1A may be able to receive and output audio, and may include power, processing capabilities, storage/memory capabilities, and communication capabilities. However, in other embodiments, personal user device 10-1 and/or optional second personal user device 10-1A may include one or more components for receiving mechanical inputs or touch inputs, such as a touch screen and/or one or more buttons.

Personal user device 10-1 and/or optional second personal user device 10-1A may, in embodiments, be a voice activated electronic device. A voice activated electronic device, as described herein, may correspond to any device capable of being activated in response to detection of a specific word (e.g., a word, a phoneme, a phrase or grouping of words, or any other type of sound, or any series of temporally related sounds). For example, a voice activated electronic device may be one or more of the following: Amazon Alexa-enabled devices, Amazon Echo®; Amazon Echo Show®; Amazon Echo Dot®; Smart Television (e.g., Samsung® Smart TVs); Google Home®; Apple Siri-enabled devices; "OK Google" enabled devices; Voice Controlled Thermostats (e.g., Nest®; Honeywell® Wi-Fi Smart Thermostat with Voice Control), smart vehicles, smart transportation devices, wearable devices (e.g., Fitbit®), and/or smart accessories, to name a few.

Personal user device 10-1 and/or optional second personal user device 10-1A may include one or more processor(s) (702 and 702A respectively), one or more sensor device(s) (704 and 704A respectively), memory (706 and 706A respectively), and communication portal (708 and 708A respectively).

One or more processor(s) (702 and 702A), which may be referred to herein collectively as processor(s) 702, may include any suitable processing circuitry capable of controlling operations and functionality of personal user device 10-1 and optional second personal user device 10-1A, as well as facilitating communications between various components within personal user device 10-1 and optional second personal user device 10-1A. In some embodiments, processor(s) 702 may include a central processing unit ("CPU"), a graphic processing unit ("GPU"), one or more microprocessors, a digital signal processor, or any other type of processor, or any combination thereof. In some embodiments, the functionality of processor(s) 702 may be performed by one or more hardware logic components including, but not limited to, field-programmable gate arrays ("FPGA"), application specific integrated circuits ("ASICs"), application-specific standard products ("AS-SPs"), system-on-chip systems ("SOCs"), and/or complex programmable logic devices ("CPLDs"). Furthermore, each of processor(s) 702 may include its own local memory, which may store program systems, program data, and/or one or more operating systems. However, processor(s) 702 may run an operating system ("OS") for personal user device 10-1 and optional second personal user device 10-1A, and/or one or more firmware applications, media applications, and/or applications resident thereon. In some embodiments, processor(s) 702 may run a local client script for reading and rendering content received from one or more websites. For example, processor(s) 702 may run a local JavaScript client for rendering HTML or XHTML content received from a particular URL accessed by personal user device 10-1 and optional second personal user device 10-1A. Processor(s) 702 may be similar to processor 2010 described in connection with FIG. 2C, the description of which applies herein.

One or more sensor device(s) (704 and 704A), which may be referred to herein collectively as sensor device(s) 704, may provide the recorded user device (API) data 2018. Sensor device(s) 704, referring to FIGS. 7D and 7E, may include one or more processor(s) (732 and 732A respectively), the sensor (734 and 734A respectively), memory (736 and 736A respectively), and communication circuitry (738 and 738A respectively). One or more processor(s) (732 and 732A respectively), memory (736 and 736A respectively), and communication circuitry (738 and 738A respectively) may be similar to one or more processor(s) 702, memory 706, and communications portal 708, described in connection with FIGS. 2A and 2B, the description applying herein.

Referring to FIGS. 2A and 2B, sensor device(s) 704 may include one or more of the following sensors from the following non-exhaustive list of sensors: (1) one or more location sensor(s) 710, (2) one or more accelerometer(s) 712, (3) one or more altimeter(s) 714, (4) one or more gyrometer(s) 718, (5) one or more magnetometer(s) 718, (6) one or more pedometer(s) 720, (7) one or more device motion sensor(s) 722, (8) one or more proximity sensor(s) 724, (9) one or more light sensor(s) 726, (10) Apple® Proprietary HealthKit™ 728, and (11) a Google® Proprietary Google Fit™ 730 or other equivalent systems (such as those by Samsung or others).

In embodiments, the one or more location sensor(s) 710 may provide one or more of the following data types: longitude data (e.g., the longitude of a geographical coordinate of a user device); latitude data (e.g., the latitude of a geographical coordinate of a user device); altitude data (e.g., the altitude of a user device, which may be measured in meters, feet, and miles, to name a few); speed data (e.g., the instantaneous speed of the device(s), which may be measured in meters per second, feet per second, kilometers per hour, and miles per hour, to name a few); course data (e.g., the direction in which the device(s) are traveling, which may be measured in degrees and may be relative to due north and which may have a value of −1 when the value is not determined by the sensor); bearing data (e.g., a user's relative position or movement in degrees); and timestamp data (e.g., the time and/or date at which data is observed by the one or more location sensor(s) 710) to name a few. In embodiments, as with any of the sensors of the device, data from the one or more location sensor(s) 710 may be compared with or used in concert with data from other sensors of the device and/or other device(s) that are also sensing data to improve reliability, consistency, and/or accuracy of the data being provided by the device.

In embodiments, the one or more accelerometer(s) 712 may provide one or more of the following data types: X-X-axis acceleration data in G's (e.g., gravitational force); Y-Y-axis acceleration in G's (e.g., gravitational force); Z-Z-axis acceleration data in G's (e.g., gravitational force); Accuracy data (e.g., a representation of the confidence of the accelerometer in the data being presented); and timestamp data (e.g., the time at which data is observed by the one or more accelerometer(s) 712), to name a few. In embodiments, the accuracy data may be on a scale from 0 to 1, where 1 is the highest amount of confidence and 0 is the lowest amount of confidence. The scale at which the accuracy data may be computed on may include: 0 to 1; 0 to 10; 0 to 100; 0 to 1,000, etc., to name a few. In embodiments, as with any of the sensors of the device, data from the one or more accelerometer(s) 712 may be compared with or used in concert with data from other sensors of the device and/or other device(s) that are also sensing data to improve reliability, consistency, and/or accuracy of the data being provided by the device.

In embodiments, the one or more altimeter(s) 712 may provide one or more of the following data types: relative altitude data (e.g., the altitude in relation to another point or the change in altitude since the last observation of the altimeter measured in meters, feet, kilometers, or miles, to name a few); pressure data (e.g., the pressure at the location of the altimeter device, measured in newton per meter squared, kilopascals, etc. to name a few); and timestamp data (e.g., the time and/or date at which data is observed by the one or more altimeter(s) 712), to name a few. In embodiments, as with any of the sensors of the device, data from the one or more altimeter(s) 712 may be compared with or used in concert with data from other sensors of the device and/or other device(s) that are also sensing data to improve reliability, consistency, and/or accuracy of the data being provided by the device.

In embodiments, the one or more gyrometer(s) 716 may provide one or more of the following data: X-Axis location (e.g., the location of the one or more gyrometer(s) 716 on the x-axis relative to a point); Y-Axis location (e.g., the location of the one or more gyrometer(s) 716 on the y-axis relative to a point); Z-Axis location (e.g., the location of the one or more gyrometer(s) 716 on the z-axis relative to a point); and timestamp data (e.g., the time and/or date at which data is observed by the one or more gyrometer(s) 716), to name a few. In embodiments, the point at which the one or more gyrometer(s) 716 is measuring the X, Y, or Z axis, may be, in embodiments, sea level, mean sea level, ground level (e.g., for above ground level (ABL) measurements), and a point selected by the user of the device, to name a few. In embodiments, as with any of the sensors of the device, data from the one or more gyrometer(s) 716 may be compared with or used in concert with data from other sensors of the device and/or other device(s) that are also sensing data to improve reliability, consistency, and/or accuracy of the data being provided by the device.

In embodiments, the one or more magnetometer(s) 718 may provide one or more of the following data: strength of a magnetic field relative to the X-Axis; direction of the magnetic field relative to the X-Axis; strength of a magnetic field relative to the Y-Axis; direction of the magnetic field relative to the Y-Axis; strength of a magnetic field relative to the Z-Axis; direction of the magnetic field relative to the Z-Axis; and timestamp data (e.g., the time and/or date at which data is observed by the one or more magnetometer(s) 718), to name a few. In embodiments, the relative strength and direction may be observed from a point measured relative to the current surroundings of the one or more magnetometer(s) 718, relative to data retrieved by other sensors (e.g., the one or more accelerometer(s) 712, or the one or more location sensor(s) 710), or relative to a point selected by the user of the user device, to name a few.

In embodiments, the one or more pedometer(s) 720 may provide one or more of the following data types: start date data (e.g., a time and/or date at which the one or more pedometer(s) 720 begins sensing data); end date data (e.g., a time and/or date at which the one or more pedometer(s) 720 stops sensing data); steps data (e.g., the number of steps taken by the user); distance data (e.g., the estimated distance traveled by the user which may be measured in meters, feet, kilometers, or miles, to name a few); distance data (e.g., the estimated distance traveled by the user which may be measured in meters, feet, kilometers, or miles, to name a few); floors ascended data (e.g., an approximate number of floors or stories a user has ascended); and floors descended data (e.g., an approximate number of floors or stories a user has descended). In embodiments, as with any of the sensors of the device, data from the one or more pedometer(s) 720 may be compared with or used in concert with data from other sensors of the device and/or other device(s) that are also sensing data to improve reliability, consistency, and/or accuracy of the data being provided by the device (e.g., the one or more location sensor(s) 710, the one or more accelerometer(s) 712, the one or more altimeter(s) 714, to name a few). For example, floors ascended data sensed by the one or more pedometer(s) 720 may be compared to one or more altitude values sensed by the one or more location sensor(s) 710. The one or more pedometer(s) 720 may sense that a user is beginning to ascend floors, logging the start time in start date data. The user may climb two flights of stairs and stop. As the user stops, the one or more pedometer(s) 720 may sense the stopping and log the two flights of stairs in floors ascended data and the end time in end date data. At the same time, the one or more location sensor(s) 710 may also log the change in altitude over the start and end times. The values of "two flights of stairs" form the one or more pedometer(s) 720 and change in altitude from the one or more location sensor(s) 710 may be compared to increase the reliability, consistency, and/or accuracy of the data in order to improve the quality of the user experience.

In embodiments, the one or more device motion sensor(s) 722 may provide one or more of the following data types: user acceleration data (e.g., the acceleration of a device associated with a user); magnetic field data (e.g., the vector quantity of a magnetic field with respect to the device); gravity acceleration data (e.g., the vector quantity of gravity acceleration expressed in the reference frame of the device); rotation rate data (e.g., the rate of rotation represented in velocity, acceleration, direction of velocity, and/or direction of acceleration); and timestamp data (e.g., the time and/or date at which data is observed by the one or more device motion sensor(s) 722), to name a few. In embodiments, as with any of the sensors of the device, data from the one or more device motion sensor(s) 722 may be compared with or used in concert with data from other sensors of the device and/or other device(s) that are also sensing data to improve reliability, consistency, and/or accuracy of the data being provided by the device.

In embodiments, the one or more proximity sensor(s) 724 may provide one or more of the following data types: distance data (e.g., the distance of a device in relation to a point, which may be for example a user's ear and/or another device which also may be providing data); accuracy data (e.g., a representation of the confidence of the one or more proximity sensor(s) 724 in the data being presented); and timestamp data (e.g., the time at which data is observed by the one or more proximity sensor(s) 724), to name a few. In embodiments, the accuracy data may be on a scale from 0 to 1, where 1 is the highest amount of confidence and 0 is the lowest amount of confidence. The scale at which the accuracy data may be computed on may include: 0 to 1; 0 to 10; 0 to 100; 0 to 1,000, etc., to name a few. In embodiments, as with any of the sensors of the device, data from the one or more proximity sensor(s) 724 may be compared with or used in concert with data from other sensors of the device and/or other device(s) that are also sensing data to improve reliability, consistency, and/or accuracy of the data being provided by the device.

In embodiments, the one or more light sensor(s) 726 may provide one or more of the following data types: value data (e.g., data that may indicate whether light is present or whether there was a change in the lighting, the change in lighting may be a change in brightness, color, or type of lighting); accuracy data (e.g., a representation of the confidence of the one or more light sensor(s) 726 in the data being presented); and timestamp data (e.g., the time at which data is observed by the one or more light sensor(s) 726), to name a few. In embodiments, the accuracy data may be on a scale from 0 to 1, where 1 is the highest amount of confidence and 0 is the lowest amount of confidence. The scale at which the accuracy data may be computed on may include: 0 to 1; 0 to 10; 0 to 100; 0 to 1,000, etc., to name a few. In embodiments, as with any of the sensors of the device, data from the one or more light sensor(s) 726 may be compared with or used in concert with data from other sensors of the device and/or other device(s) that are also sensing data to improve reliability, consistency, and/or accuracy of the data being provided by the device.

In embodiments, Google® Proprietary Google Fit™ and Apple® Proprietary HealthKit™ or similar/equivalent platforms may be configured to function as platforms that aggregate data from many sources (including, but not limited to, sensors) and then optionally process it. They can be queried upon user permission and/or can export data to files or other systems. In embodiments, the Apple® Proprietary HealthKit™ 728 platform may provide one or more of the following data types: Characteristic Data (e.g., data that does not typically change over time (e.g., blood type, height, gender, race, date of birth, to name a few) and data that may, in embodiments, be entered manually by a user); Quantity Data (e.g., data that represents samples that contain a numeric value (e.g., calories consumed for example) and data that may, in embodiments, be entered manually by a user); Category Data (e.g., data that contains an option from a short list of possible values (e.g., sleep analysis, resting heartrate, to name a few)); Correlation Data (e.g., data that contains a plurality of quantity data and/or category data (e.g., calories consumed in a meal where the meal has multiple types of food having different amounts of calories); and Workout Data (e.g., data sensed by the device that is related to exercise (e.g., heartrate, calories burned, time duration of exercise, weight of user, type of exercise activity and details thereof (e.g., amount of weight lifted, type of sport being played, etc. to name a few), to name a few. In embodiments, as with any of the sensors of the device, data from the Apple® Proprietary HealthKit™ 728 platform may be compared with or used in concert with data from other sensors of the device and/or other device(s) that are also sensing data to improve reliability, consistency, and/or accuracy of the data being provided by the device.

In embodiments, the Google® Proprietary Google Fit™ 730 platform may provide one or more of the following data types: weight data (e.g., the weight of the user); height data (e.g., the height of the user), step count (e.g., the number of steps taken by the user); speed data (e.g., the instantaneous speed of the device(s), which may be measured in meters per second, feet per second, kilometers per hour, and miles per hour, to name a few); activity segment data (e.g., a value, which may be predetermined, that represents the type of activity the user is engaged in, which may be manually inputted and/or selected by the user); nutrition data (e.g., the amount of calories consumed, the type of food being consumed, to name a few); heartrate data (e.g., the heartrate of the user); metabolic rate data (e.g., the rate at which metabolism occurs in the user); body fat data (e.g., the body fat of the user, the body mass index of the user, to name a few); cycling data (e.g., data related to a user riding a manually or semi-manually operated vehicle (e.g., a bicycle, a tricycle, a unicycle, a motorized bicycle, to name a few); distance data (e.g., the estimated distance traveled by the user which may be measured in meters, feet, kilometers, or miles, to name a few); hydration data (e.g., the amount of water consumed by the user); power data (e.g., the amount of power generated by the user during an activity); activity exercise data (e.g., a user's continuous workout routine, which may be either manually, semi-manually, or automatically inputted); and timestamp data (e.g., the time at which data is observed by the Google® Proprietary Google Fit™ 730 platform), to name a few. In embodiments, the cycling data, may include one or more of the following types of data: pedaling cadence data (e.g., the pace and/or consistency of one or more of wheels on a manually or semi-manually operated vehicle; pedaling cumulative data (e.g., the total amount of rotations of one or more of wheels on a manually or semi-manually operated vehicle); wheel revolution data (e.g., data regarding the rotations of one or more of wheels on a manually or semi-manually operated vehicle); wheel rotations-per-minute (RPM) data (e.g., the rotations per minute of one or more of wheels on a manually or semi-manually operated vehicle), to name a few. In embodiments, as with any of the sensors of the device, data from the Google® Proprietary Google Fit™ 730 platform may be compared with or used in concert with data from other sensors of the device and/or other device(s) that are also sensing data to improve reliability, consistency, and/or accuracy of the data being provided by the device. Similarly, in embodiments, it is understood that other platforms (different from Google Fit and/or Apple HealthKit) may be provided by one or more other vendors, such as S Health.

In embodiments, sensor device(s) 704 may be operatively connected, electrically coupled, and/or mechanically coupled to personal user device 10-1 and/or optional second personal user device 10-1A.

Referring to FIGS. 2A-2B, as mentioned above, personal user device 10-1 and/or optional second personal user device 10-1A may include memory (706 and 706A respectively). Memory 706 and 706A, which may be referred to herein collectively as memory 706, may include one or more types of storage mediums such as any volatile or non-volatile memory, or any removable or non-removable memory implemented in any suitable manner to store data for personal user device 10-1 and/or optional second personal user device 10-1A. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 706 may be implemented as computer-readable storage media ("CRSM"), which may be any available physical media accessible by processor(s) 702 to execute one or more instructions stored within memory 706. In some embodiments, one or more applications (e.g., mobile application software 3000, gaming, music, video, calendars, lists, banking, social media etc.) may be run by processor(s) 702 and may be stored in memory 706.

In embodiments, as mentioned above, personal user device 10-1 and/or optional second personal user device 10-1A may include communications circuitry (708 and 708A respectively). Communications portal 708 and 708A, which may be referred to herein collectively as communications portal 708, may include any circuitry allowing or enabling one or more components of personal user device 10-1 and/or optional second personal user device 10-1A to communicate with one another, with computing device 700, and/or with one or more additional devices, servers, and/or systems. As an illustrative example, data retrieved from the one or more sensor device(s) 704 may be transmitted over a network 100, such as the Internet, to computing device 700 using any number of communications protocols. For example, network(s) 100 may be accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between personal user device 10-1 and/or optional second personal user device 10-1A and computing device 700. In some embodiments, personal user device 10-1 and/or optional second personal user device 10-1A and computing device 700 may communicate with one another via a web browser using HTTP. Various additional communication protocols may be used to facilitate communications between personal user device 10-1 and/or optional second personal user device 10-1A and/or computing device 700, include the following non-exhaustive list, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), optical, BitTorrent, FTP, RTP, RTSP, SSH, and/or VOIP.

Communications portal 708 may use any communications protocol, such as any of the previously mentioned exemplary communications protocols. In some embodiments, personal user device 10-1 and/or optional second personal user device 10-1A may include one or more antennas to facilitate wireless communications with a network using various wireless technologies (e.g., Wi-Fi, Bluetooth, radiofrequency, etc.). In yet another embodiment, personal user device 10-1 and/or optional second personal user device 10-1A may include one or more universal serial bus ("USB") ports, one or more Ethernet or broadband ports, and/or any other type of hardwire access port so that communications portal 708 allows personal user device 10-1 and/or optional second personal user device 10-1A to communicate with one another or with one or more communications networks.

Referring to FIG. 1, computing device 10-1 ... 10-n may include one or more processor(s) 700-1, a network connection interface 700-2 and memory 700-3, to name a few. In embodiments, the one or more processors(s) 700-1 may be similar to processor(s) 702 described above in connection with FIGS. 2A-2B, the description applying herein. In embodiments, the network connection interface 700-2 may be similar to communications portal 708 described above in connection with FIGS. 2A-2B, the description applying herein. In embodiments, memory 700-3 may be similar to memory 706 described above in connection with FIGS. 2A-2B, the description applying herein. In embodiments, computing device 700 may include personal data system 20. Personal data system 20 may, in embodiments, be stored in memory 700-3. In embodiments, computing device 700 may be one or more electronic devices that may be mechanically, operatively, and/or electrically connected to one another.

Referring back to FIG. 2C, related user data 2020 may include associations among one or more of the users of personal user devices 10-1 ... 10-n. For example, the associations may be through employment, familial relationship, membership, social media, physical location, hobbies in common, health conditions in common, to name a few. Personal data system 20 may store an independent network of user associations that may be defined and/or organized by the users of personal user devices 10-1 ... 10-n. For example, personal data system 20 may store a form of a social network service related to health improvement which, in embodiments, may be tied to a subscription service. Such related users may foster teamwork and/or encouragement to make positive choices associated with the prompts and/or stimuli provided in detail below. Additionally, such related users may, in embodiments, also form a network of other sources of information, which may be used to verify the factual accuracy of user responses received from personal user devices 10-1 ... 10-n. In embodiments, related user data 2010 includes: user age, electronic-mail identification, roles, groups attached, emergency contact number, address, basic details, a list of followers (associated with either mobile application software 3000 or another application such as Twitter®), one or more common entities between other users having information included in user profile data 2014, to name a few, forming one or more clusters.

Vendor and stimulus data 2022 may be a repository of information on prompts and/or stimuli that may be available for transmission to personal user devices 10-1 ... 10-n. As will be described in further detail below, certain prompts and/or stimuli may be tied to particular vendors, such as food choice discounts, membership discounts, task challenges, and/or incentive programs, to name a few.

Figures 1, 1A:
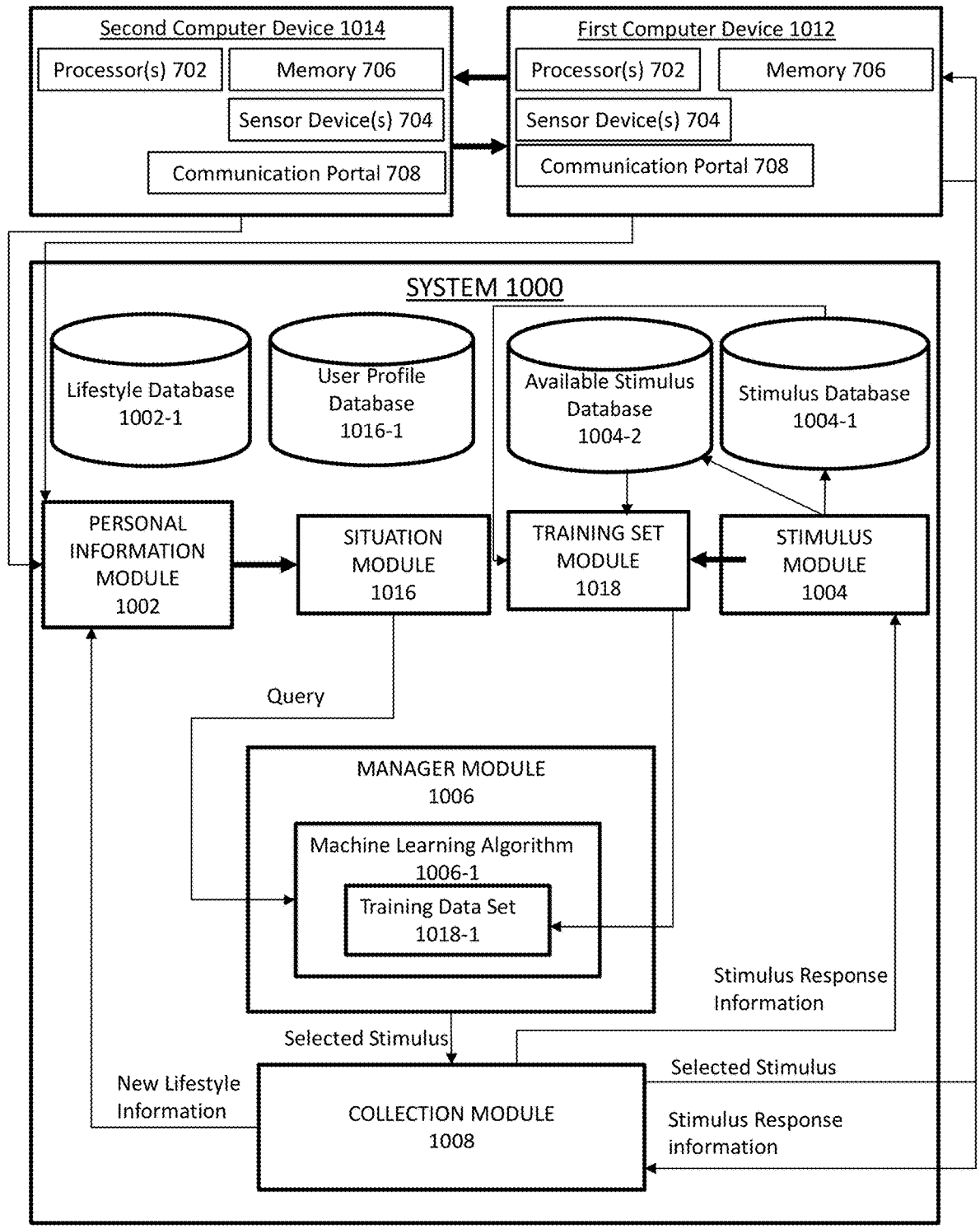

FIG. 1 is an exemplary block diagram illustrating devices associated with a first user and third-party vendors both supplying information to the system of FIG. 1A. In embodiments, system 1000 may receive information to: select a behavior of one or more users, select a change in behavior of one or more users, and/or cause a change in behavior of one or more users. The information received by system 1000, may, in embodiments, be obtained from one or more sources, including, for example, a first computer device 1012 associated with a first user, a second computer device 1014 associated with the first user, and one or more third-party vendor(s) 1016, to name a few. In embodiments, the information received by the system 1000 may be obtained from information stored in memory of the system 1000.

The process of obtaining information by the system 1000 may begin with the devices associated with the first user 1400 (first computer device 1012, second computer device 1014) obtaining data. The data obtained, in embodiments, may include one or more of the following: sensor data, connection data, calendar data (e.g., from Apple Proprietary HealthKit 728 and/or Google Proprietary Google Fit 730), identity data (e.g., from Apple Proprietary HealthKit 728 and/or Google Proprietary Google Fit 730), health-related attribute data (e.g., from Apple Proprietary HealthKit 728 and/or Google Proprietary Google Fit 730), prior purchase data, activity data, goal data, user preferences data, contact data (e.g., from Apple Proprietary HealthKit 728 and/or Google Proprietary Google Fit 730) and/or medical data (e.g., from Apple Proprietary HealthKit 728 and/or Google Proprietary Google Fit 730). In embodiments, each piece of data, when obtained, may include the relative data gathered and a relative timestamp. The timestamp may indicate one or more of the following: when the data was obtained, when the data was created, and/or when the data was sent to the system 1000. When data is sent from the aforementioned one or more sources, in embodiments, each piece of data may include the obtained data and the relative timestamp associated with the relative piece of data.

The obtained data, in embodiments, may be sent by the source of the data to the system 1000 via network 100. In embodiments, the system 1000 may receive the obtained data at the personal information module 1002. The system may also store the received obtained data, in embodiments, in the lifestyle database 1002-1. Once received and stored by the system 1000, in embodiments, the obtained data may be organized by the relative timestamp and/or time sliced based on the relative timestamp. For example, the lifestyle database 1002-1 may organize the obtained data by user and, within each user's information, by relative timestamp. Continuing the example, the lifestyle database 1002-1 may organize the obtained data that was created at the most recent time to the obtained data that was created at the least recent time. In embodiments, the lifestyle database 1002-1 may include one or more databases. For example, the lifestyle database may include databases specific to each user of the interactive online network. Each user database may include a plurality of databases. For example, a first database may include all of the obtained information that is associated with the user. A second database, for example, may include all of the obtained data that is considered present. The present data may be changed and updated based on time and information and/or data obtained by the system 1000.

Data may be considered present, in embodiments, if the timestamp associated with the obtained data indicates a time that is within a predetermined time frame. If, for example, the respective timestamp indicates the respective data is present, then the respective data may be stored in the second database and the first database. If, for example, the respective timestamp indicates that the respective data is not present, the data may only be stored in the first database.

The predetermined timeframe may vary based on: user preferences, the type of stimulus to be sent, the type of behavior that is going to be changed, the type of change in the behavior, and the lifestyle information 1308A. For example, if the type of behavior to be changed is related to a user's diet, the predetermined time frame may be based on when the user typically eats. Thus, if a user typically eats breakfast between 7 AM and 8 AM, typically eats lunch between 11 AM and 1 PM, and typically eats dinner between 6 PM and 8 PM, the predetermined timeframe may be between 7 AM and 8 AM, between 11 AM and 1 PM, and between 6 PM and 8 PM. As another example, if the type of behavior to be changed is related to a user's sedentary lifestyle, the predetermined timeframe may be based upon how often a healthy person is typically moving around during the day—which for this example, may be every two hours. Thus, the predetermined time frame may be the past two hours. If, for example, the user does not exercise or move around at all, making the task of moving around every two hours a difficult change, the system 1000 may take that into account and alter the predetermined timeframe to better suit the user. For example, the user who does not exercise may have a predetermined time frame of four hours where the user who exercises, but not frequently, may have a predetermined time frame of two hours.

As mentioned above, the process of obtaining information by the system 1000 may begin with the devices associated with the first user 1400 (first computer device 1012, second computer device 1014) obtaining data. Again, as mentioned above, the data obtained, in embodiments, may include one or more of the following: sensor data, connection data, calendar data, identity data, health-related attribute data, prior purchase data, activity data, goal data, user preferences data, and/or medical data. In embodiments, the first computer device 1012 and/or the second computer device 1014 may obtain sensor data by implementing one or more sensor(s) devices 704 which are one or more of: operatively connected to the first computer device 1012 and/or the second computer device 1014, mechanically coupled to the first computer device 1012 and/or the second computer device 1014, and/or electronically coupled to the first computer device 1012 and/or the second computer device 1014.

For example, the location of the first user may be obtained by determining the location of one or more of the first computer device 1012 or the second computer device 1014. The location information, which may be obtained from a location sensor (e.g., location sensor 710), may be obtained and demonstrated as below:

```
"fields": {
"TypeID": "location",
"documentid": "id:location:location::5&J519clHl~f0.4e8d-81>
8a-ce7a4e189954",
·latlong·· {
"y": 28628487,
"x": 77377167
},
"latlong.position": "<position x=\"773771671" y=\"28628487\"
"latlong=\"N28 628487;E77.377167\"/>",
"distance": "0.0",
"speed": "0.0",
"altitude": "0.0",
"course": "0",
"accuracy":· "23.323",
"bearing":· "0.0",
"data_timestamp·: ·2018-11).05 13:55:47"
}
```
Fields Description TypeID : Name of the sensor's document
Documentid: Unique id of the document
latlong/latlong.posttion: User latitude and longitude details
Distance: The distance covered between last latlong and current latlong.
Speed: The speed of last distance covered
Course: Direction in which the device is traveling, measured in degrees and relative to due north (iOS field)
Accuracy: Estimated horizontal accuracy of this location, radial, in meters.
Searing: Get the bearing, in degrees.
Data_timestamp: The lime when data is collected.

In embodiments, location data may also be provided as below:

LOCATION

Latitude: The latitude of the geographical coordinate.
Longitude: The longitude of the geographical coordinate.
Altitude: The altitude, measured in meters.
Speed: The instantaneous speed of the device, measured in meters per second (−1 when value not determined by sensor).
Course: The direction in which the device is traveling, measured in degrees and relative to
due north (−1 when value not determined by sensor)
Time: Time when the value was recorded (in UTC)
Sample Data

```
{
"latlong": {
 "y": 34200301,
 "x": -11686983
},
```

LOCATION

"latlong.position": "<position x-\"-1:8686983\"
y=\ " 34208301 \" latlong=\ "N34.208301; W118.686983\" />",
"distance": "11.5",
"speed": " 5.5.",
"altitude": "2.4",
"course": " 0",
"accuracy": "1 ",
"bearing": " 0.0",
"status": "1",
"timestamp" : "2018- 07-1818:13:36-07"

As another example, accelerometer data may be obtained from accelerometer(s) 712 and demonstrated as below:

ACCELEROMETER

"fields": {
"TypeID": "accelerometer",
"documentid": "id:accelerometer:accelerometer::
7t215386-6f5d-42ae-a7b2-55fd93d6ae90",
·latlong·· {
"y": "-0.02813042",
"x": "-0.545878",
"z": "10.0748005"
"data_timestamp":· "2018-10-05 13:56:24",
"accuracy": "3"}
Fields Description TypeID : Name of the sensor's document
Documentid: Unique Id of the document
X : Movement In x-direction
Y : Movomant In y- direction
Z : Movement In z- direction
Accuracy: Accuracy of sensor in degrees
Data_timestamp: The time when data is collected Accelerometer data, in embodiments, may also be provided as below:

ACCELEROMETER

X: X-axis acceleration in G's (gravitational force).
Y: Y-axis acceleration in G's (gravitational force).
Z: Z-axis acceleration in G's (gravitational force).
Accuracy: Confidence of sensor while recording value 0 < value,1 where 1 is the highest
Timestamp: Time when value was recorded (in UTC)
Sample Data {
"x": "-0.01959228515625",
"y": "-0. 65719604q921875",
"z": "-0.7764129638671875",
"timestamp": "2018-10-05 02:09:14 PM"
}

As another example, gyrometer data may be obtained from gyrometer(s) 716 and demonstrated as below:

"fields": {
"TypeID": "gyrometer",
"documentid": "id.gyrometer.gyrometer::
b6903a86c3564df4b96a-76b35ef7f6a2",
"x":· "-0.0051661744",
"y": · "0.0056897732",
"z": · "-0.023073252",
"timestamp": "2018-10-08 08:52:11",
"accuracy": "3"
Fields Description TypeID: Name of the sensor's document
Documentid: Unique id of the document
X: Movement In x-direction
Y: Movement In y-direction
Z: Movement in z-direction
Accuracy: Accuracy of sensor in degrees
Data_timestamp: The time when data is collected In embodiments gyrometer data may also be provided as below:

GYROMETER

Indicating the instantaneous rotation around the device's three primary axes.
X: The value for the X-axis.
Y: The value for the Y-axis.
Z: The value for the Z-axis.
Timestamp: Time when the value was recorded (in UTC)
Sample Data {
"x": "-0.140344+2833943173",
"y": "0.2508010651293402",
"z": "-0.01562742927658497",
"timestamp": "2018-10-05 02:08:44 PM"
}

As yet another example, altimeter data may be obtained by altimeter(s) 714 and demonstrated as below:

ALTIMETER

Relative altitude: The change in altitude (in meters) since last observation.
Pressure: The recorded pressure, in kilopascals.
Timestamp: Time when the value was recorded (in UTC)
Sample Data {
    "relativeAltitude": "0",
    "pressure": "97.78125";
    "timestamp": "2018-10-05 02:09:14 PM"
}

As yet another example, pedometer data may be obtained from pedometer(s) 720 and demonstrated as below:

"fields": {
"TypeID": "pedometer",
"documentid": "id.pedometer.pedometer::ade45296-b017-4a03-bf83-7ae342e9b2b8"
"numberOfSteps": "23"
"startDate": "0000-00-00 00:00:00",
"endDate": "2018-10-08 08:52:10",
"distance": "1 0.01794"
"floorsAscended": "0",
"floors Descended": "0"
"accuracy" "3"
}
Fields Description TypeID: Name of the sensor's document
Documentid: Unique id of the document
Number of steps: Number of steps taken by user
Start date: Time when user starts taking steps.
End date: Time when user ends taking steps
Distance: Total distane covered between start date and end date by user
Floor Ascended: Stairs ascended by user (IOS field)
Floor Descended: Stairs descended by user (IOS field)
Accuracy: Accuracy of sensor in degrees
Data_timestamp: The time when data is collected In embodiments, pedometer data may also be provided as below:

---
PEDOMETER

StartDate: The start time for the pedometer data.
EndDate: The end time for the pedometer data.
NumberOfSteps: The number of steps taken by the user.
Distance: The estimated distance (in meters) traveled by the user.
FloorsAscended: The approximate number of floors ascended by walking.
FloorsDescended: The approximate number of floors descended by walking/
Sample Data {
"numberofsteps": "4335",
"startdate": "2018-10- 04 08:19:21 PM";
"enddate": "2018-10-05 02:07:47 PM"
"floorsascended": "5",
"floorsdescended": "5"
}

---

As yet another example, proximity data may be obtained from proximity sensor(s) 724 and demonstrated as below:

---
"fields": {
"TypeID": "proximity"
"documentid": "id.proximity.proximity::046cc0bd-783c-4799-b300-59bffa0fb78f",
"timestamp": "2018-10-05 08:52:11",
"accuracy": "3",
"timestamp": "2018-10-05 13:07:21",
"accuracy": "3",
"distance": "0.01794"
}
Fields Description TypeID: Name of the sensor's document
DocumentId: Unique Id of the document
Distance: Distance between user's ear and device in centimeters
Accuracy: Accuracy of sensor
Data_timestamp: The time when data is collected.

---

As yet another example, magnetometer data may be obtained by magnetometer(s) 718 and demonstrated as below:

---
"fields": {
"TypeID": "magneto",
"documentid": "id.magneto.magneto::e9670oee-012-44ef-88be-8e8b5c8d0005",
"x": "–30.69985",
"y": "35.999153",
"z": "1.5998943",
"data timestamp": "2018-10-05 13:56:22",
"accuracy": "3"
}
Fields Description TypeID: Name of the sensor's document
Documentid: Unique id of the document
X: Magnetic field in x-direction
Y: Magnetic field in y-direction
Z: Magnetic field in z-direction
Accuracy: Accuracy of sensor
Data_timestamp: The time when data is collected

---

As yet another example, orientation data may be obtained from one or more of location sensor(s) 710, altimeter(s) 714, and/or GPS sensor(s) 732 and demonstrated as below:

---
"fields": {
"TypeID": "orientation",
"documentid": "id.orientation.orientation::655edb32-f257-4832-81ca-851349791e31",
"azimuth": "40.426517",
"pitch": "3.0703373",
"roll": "0.184349.27
"data timestamp": "2018-10-05 13:55:26",
"accuracy": "3"
}
Fields Description TypeID: Name of the sensor's document
Documentid: Unique id of the document
Azimuth: Angle around z-axis in degrees
Pitch: Angle around x-axis in degrees
Roll: Angle around y-axis in degrees
Accuracy: Accuracy of sensor
Data_timestamp: The time when data is collected

---

As yet another example, ambient light data may be obtained from light sensor(s) 726 and demonstrated as below:

---
"fields": {
"TypeID": "lightsensor",
"documentid": "id.lightsensor.lightsensor::9676e7ab-b6bd-4e17-9c29-1da9b5a5db85",
"value": "87",
"data_timestamp": "2018-10-05 13:56:25",
"accuracy": "3"
}
Fields Description TypeID: Name of the sensor's document
Documentid: Unique id of the document
Value: Value of illumination
Accuracy: Accuracy of sensor
Data_timestamp: The time when data is collected.

---

As yet another example, magnetometer data may be obtained from magnetometer(s) 718 and demonstrated as below:

---
MAGNETOMETER

X: Strength and direction of the magnetic field relative to X-axis.
Y: Strength and direction of the magnetic field relative to Y-axis.
Z: Strength and direction of the magnetic field relative to Z-axis.
Timestamp: Time when the value was recorded (in UTC)
Sample Data {
"x": "–6. 7296142578125",
"y": "–145. 9888458251953",
"z": "–221.2802734375",
"timestamp": "2018-10-05 02:09:14 PM"
}

---

In embodiments, the above data may be synthesized by the first computer device 1012 and/or the second computer device 1014 to determine a relative motion of the device. The relative motion of the device, may be presented as below:

---
DEVICE MOTION

Deliver acceleration, altitude, rotation, and magnetic field data that is adjusted for gravity and other forms of bias.
The orientation of a body relative to a given frame of reference.
UserAccelerationX

| DEVICE MOTION |
| --- |
| UserAccelerationY |
| UserAccelerationZ |
| magneticFieldX |
| magneticFieldY |
| magneticFieldZ |
| magneticFieldAccuracy |
| gravityAccelerationX |
| gravityAccelerationY |
| gravityAccelerationZ |
| gravityAccelerationVal |
| gravityAccelerationAccuracy |
| gravityAccelerationGravity |
| rotationRateX |
| rotationRateY |
| rotationRateZ |
| altitudeYaw |
| altitudePitch |
| altitudeRoll |
| Timestamp |
| User Acceleration: The acceleration that the user is giving to the device. |
| MagneticField: Returns the magnetic field vector with respect to the device |
| GravityAcceleration: The gravity acceleration vector expressed in the device's reference frame |
| RotationRate: The rotation rate of the device. |
| Tlmestamp: Time when value was recorded (in UTC). |
| Sample Data |
| "UserAccelerationX": "−0.09066414833068848", "UserAccelerationY": "−0.03947654366493225", "UserAccelerationZ": "0.014531254768371582", "magneticFieldX": "0", "magneticFieldY": "0", "magneticFieldZ": "0", "magneticFieldAccuracy": "−1", "gravityAccelerationX": "0.7662622928619385", "gravityAccelerationY": "0.24646201729774475", "gravityAccelerationZ": "0.5933789610862732", "rotationRateX": "−0.0028715217486023903", "rotationRateY": "0.024384722113609314", "rotationRateZ": "−0.04633328691124916", "altitudeYaw": "0.499791142067002", "altitudePitch": "−0.24902795648517945", "altitudeRoll": "2.229719542586098", "Timestamp": "2018-10-05 02:08:44 PM" |

In embodiments, the system 1000 may also obtain connection data. Connection data may refer to the reliability and/or speed of the wireless and/or wired connection between the system 1000 and one or more of the first computer device 1012, the second computer device 1014, one or more devices associated with the third-party vendor(s) 1016, and/or one or more devices associated with the plurality of users of the interactive online network. In embodiments, the connection information may be used to provide context to the data and/or timestamp of the data received by the system 1000. Furthermore, in embodiments, the connection information may be used to calculate a time lag computation that may be used to determine the reliability of the data received and whether it is present data or not present data.

In embodiments, the system 1000 may also obtain calendar data. Calendar data in embodiments, may refer to data that indicates one or more user(s)' schedule. For example, the first user may store and/or enter their respective schedule using the first computer device 1012, the second computer device 1014, and/or an electronic device associated with the first computer device 1012 and/or the second computer device 1012, to name a few. In embodiments, calendar data may be sent from an electronic device associated with the first user (e.g., the first user may store and/or enter their respective schedule using the first computer device 1012, the second computer device 1014, and/or an electronic device) to the system 1000. In embodiments, this type of data may be sent as the data is entered and/or stored, or periodically. In embodiments, this data may require a user to give permissions to the system 1000 to access the data. In embodiments, this data may be manually entered into the system 1000 by a user via network 100.

In embodiments, the system 1000 may also obtain health-related attribute data 1312A. In embodiments, the system 1000 may obtain the health-related attribute data 1312A from one or more of the first computer device 1012 and/or the second computer device 1014. In embodiments, the health-related attribute data 1312A may be obtained in a similar manner as described above with calendar data and/or the sensor data (e.g., via heart rate sensor(s) 744). In embodiments, the system 1000 may obtain the health-related attribute data from one or more of the first computer device 1012 and/or the second computer device 1014 via quiz data supplied by either structured inputs by the first user or un-structured inputs by the first user. In embodiments, quiz data may refer to data received by the system as a result of a user answer a question. The question may be similar to the exemplary questions illustrated in connection with FIGS. 9C (structured input) and 9D (un-structured input). Structured inputs, in embodiments, may refer to responses to queries (the quiz), where the user chooses the response from a list of possible responses.

Figure 9A:
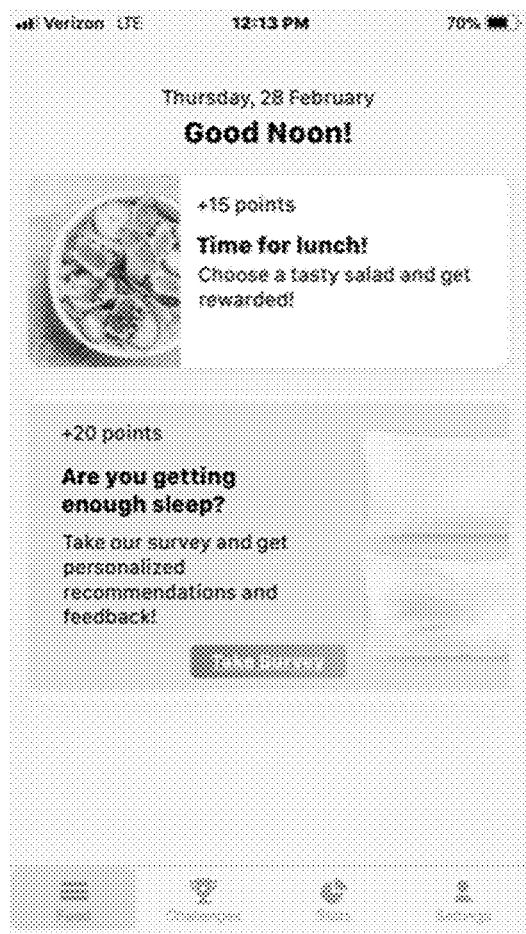
FIGS. 9A-9G are illustrative screenshots of exemplary graphical user interfaces in accordance with exemplary embodiments of the present invention.
Figure 9B:
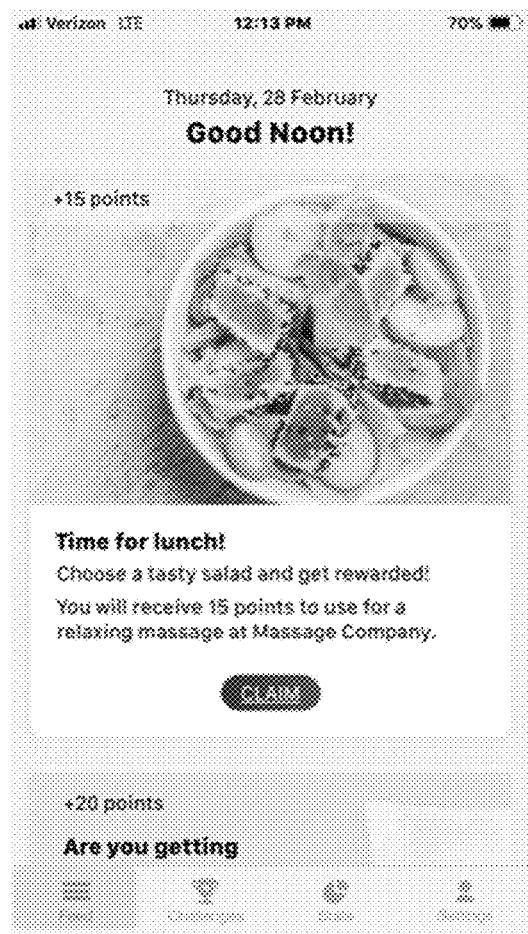
Figure 9C:
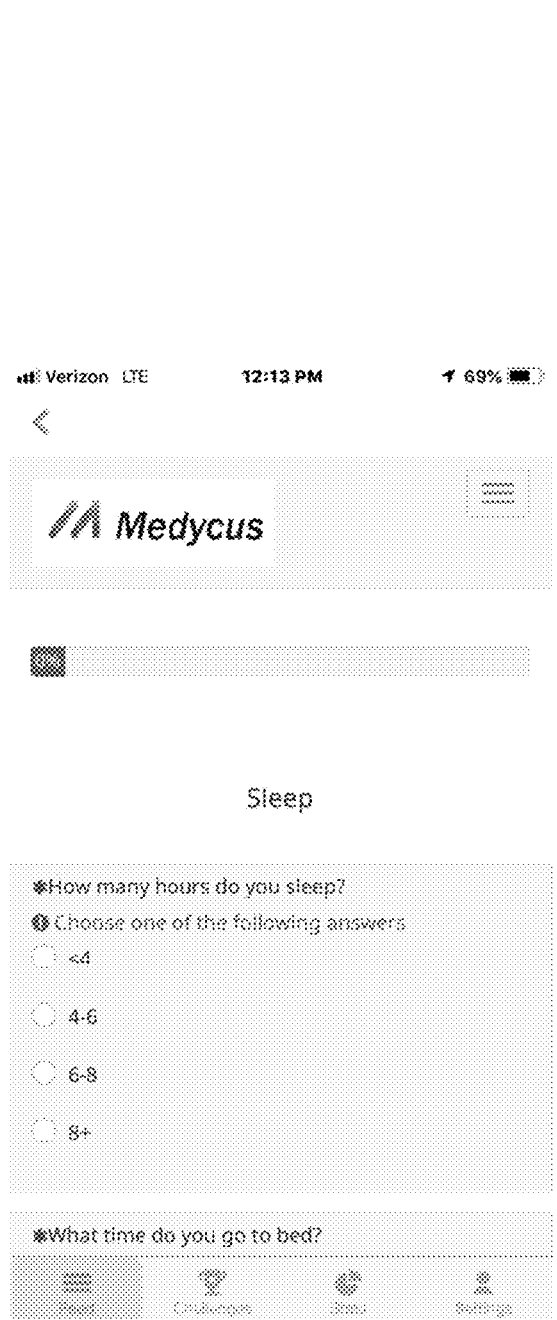

For example, as shown in FIG. 9C, the system 1000 may quiz a user with regards to how much sleep the user typically gets. The structured response, for example and as shown in FIG. 9C, may be less than four hours, four to six hours, six to eight hours, or eight plus hours. The user, continuing the example, may select one of the choices and submit their respective health-related attribute information with regards to the system 1000. In embodiments, when the response is received by the personal information module 1002, the system 1000 may extract the multiple-choice option associated with the response the user has given and store the information in the lifestyle information database 1002-1.

Figure 9D:
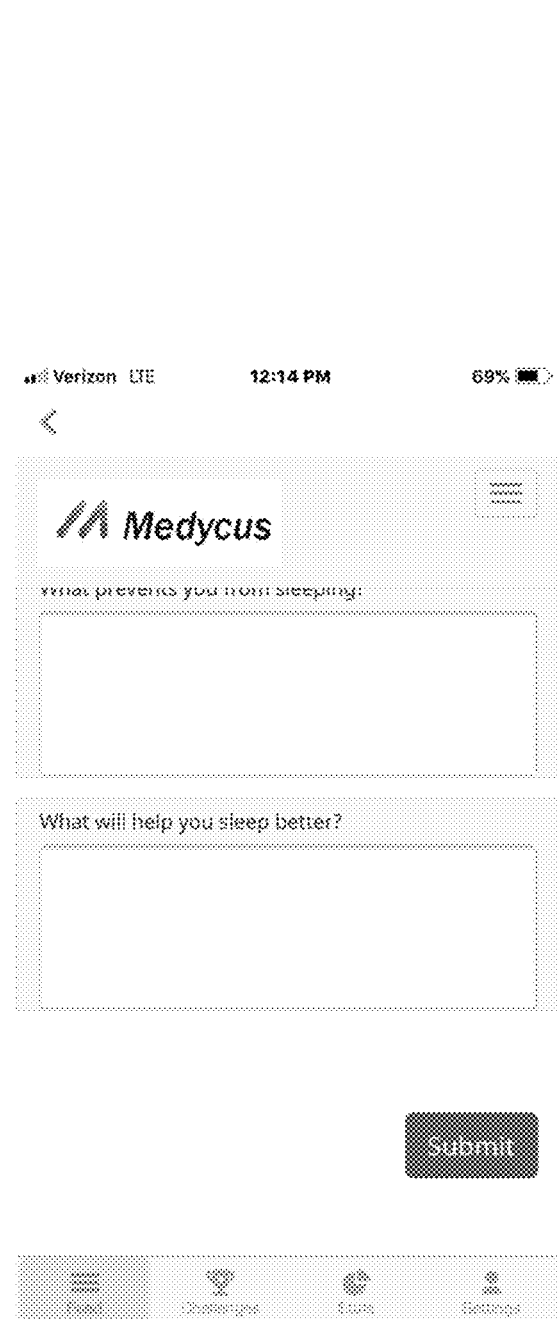
Figure 9E:
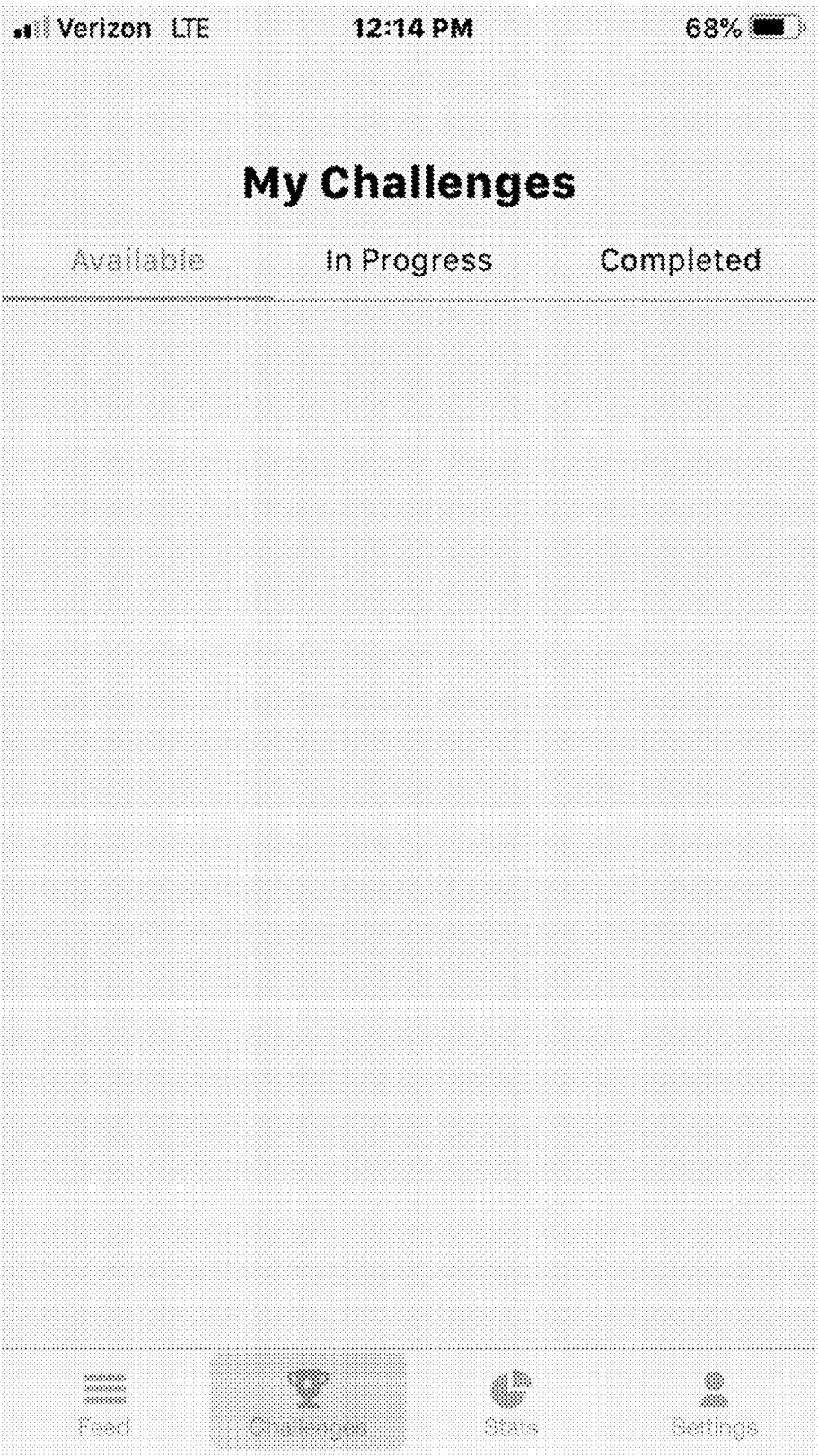
Figure 9F:
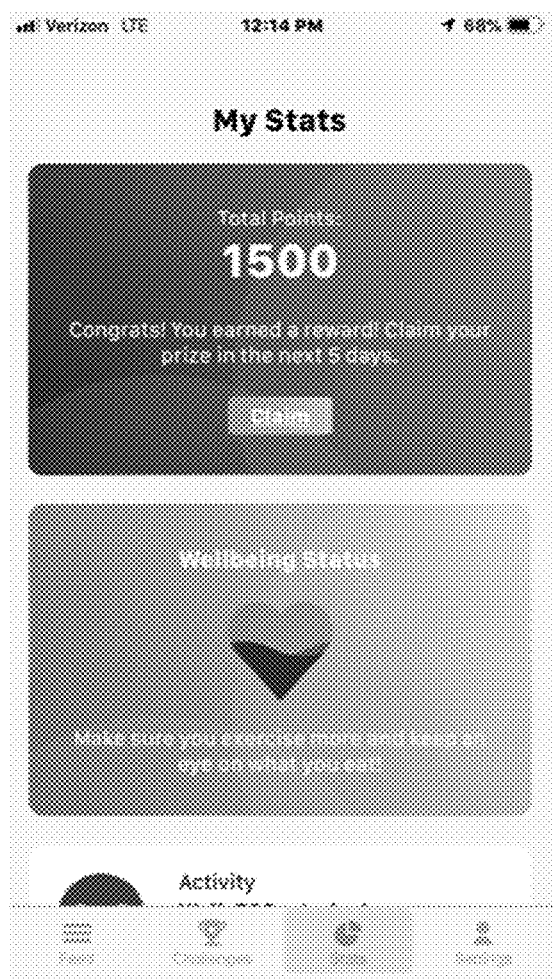
Figure 9G:
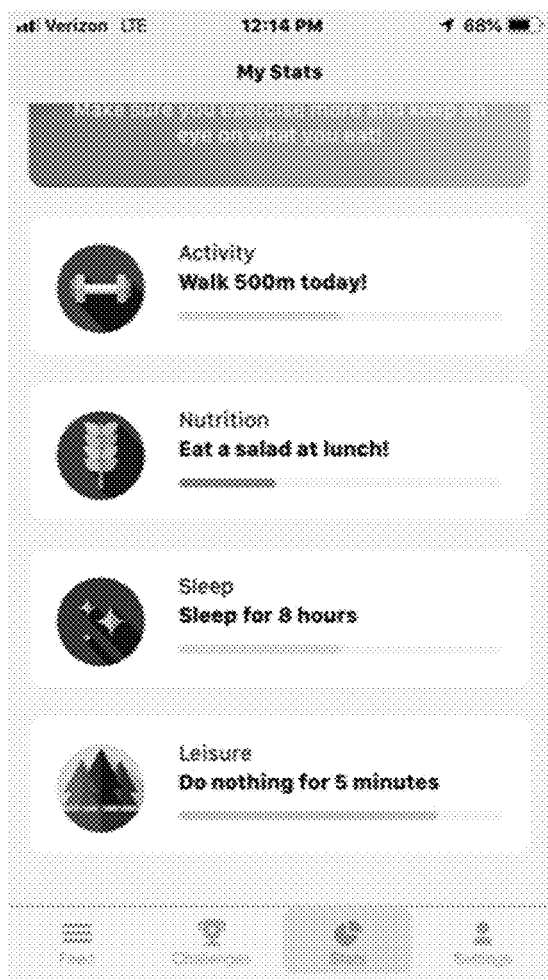

As another example, as shown in FIG. 9D, the system 1000 may quiz a user with regards to what would help the user with their respective sleep habits. The un-structured response, may be text data, audio data, image data, video data, and/or a combination thereof input by the user associated with the device that received the quiz. The audio data, in embodiments, may include one or more of the following types of audio data: RAW, AU/SND, WAVE, AIFF, MP3, OGG, and/or RAM, to name a few. The image data, in embodiments, may include one or more of the following types of image data: TIFF, JPEG, GIF, PNG, and/or RAW, to name a few. The video data, in embodiments, may include one or more of the following types of video data: WEBM, FLV, AVI, Quicktime, MP4, MPG, WMV, MOV, 3GP, Advanced Streaming Format, to name a few.

As another example, the first computer device 1012 and/or the second computer device 1014 may communicate with each other and/or with one or more additional devices to gather data (e.g., sleep data, success of stimulus, sensor data, lifestyle data, and/or a combination thereof, to name a few) associated with the first user. For example, sleep data may be obtained from a CPAP or BIPAP machine to determine use of sleep aids and/or success of a stimulus regarding sleep habits of a first user. As another example, one or more Internet of Things (IoT) devices may be utilized to gather data, deliver one or more stimuli, and/or trigger one or more stimuli. Examples of such IoT devices include one or more of the following: smart appliances (e.g., smart refrigerators), smart security systems (e.g., security cameras, motion detectors, etc.), biometric monitoring devices, commercial wearable devices, smart assistants (e.g., Google Home, Echo, Echo Show), smart thermostats (e.g., Nest), smart cars, and/or smart televisions, to name a few.

For exemplary purposes, the following is a process that the system 1000 may perform for the purposes of analyzing text data. In embodiments, the system 1000 may receive text data that represents the text of a response to a quiz. The one or more processor(s) 700-1 of the system 1000 may, in embodiments, may analyze the text data. The analysis of the text data may begin with the one or more processor(s) 700-1 parsing out the text data into grammatical objects to determine sentences within the text data. The grammatical objects may be further used to parse out each sentence within the text data to determine portions of each sentence associated with nouns, verbs, prepositions, etc. In embodiments, once each sentence is parsed out, the one or more processor(s) 700-1 of the system 1000 may determine the meaning of each sentence. In embodiments, the one or more processor(s) 700-1 of the system 1000 may determine that the sentence can have more than one meaning. In those cases, the one or more processor(s) 700-1 of the system 1000 may rank the more than one meaning of each sentence, the ranking being by which meaning the one or more processor(s) 700-1 of the system 1000 has the highest likelihood of being correct. In embodiments, the system 1000 may use one or more language models to determine the correct meaning of the ranked meanings.

Once the meanings of each sentence have been determined by the system 1000, the system 1000 may store the meanings of each sentence in the lifestyle database 1002-1. In embodiments, the meanings may be stored with the quiz questions. Moreover, the system 1000 may generate a list of details associated with the response to the quiz by analyzing the meanings of each sentence, both individually and collectively.

For exemplary purposes, the following is a process that the system 1000 may perform for the purposes of analyzing audio data. In the case of video data, the system 1000 may extract the audio data of the video data (if applicable) and perform the same process that follows. In embodiments, the system 1000 may receive audio data that represents the audio of the response to the quiz. The one or more processor(s) 700-1 of the system 1000 may, in embodiments, analyze the audio data. The one or more processor(s) 700-1 of the system 1000 may be enabled to perform speech-to-text functionality on audio data. In embodiments, the one or more processor(s) 700-1 of the system 1000 may implement any suitable computer implemented speech to text technique may be used to convert the received audio data into text, such as SOFTSOUND speech processing technologies available from the Autonomy Corporation, which is headquartered in Cambridge, England, United Kingdom. Once the audio data has been processed by the speech-to-text functionality of the one or more processor(s) 700-1 of the system 1000, the resulting text data may be analyzed in a similar manner as stated above.

For exemplary purposes, the following is a process that the system 1000 may perform for the purposes of analyzing image data. In the case of video data, the system 1000 may extract the image data of the video data (if applicable) and perform the same process that follows. In embodiments, the system 1000 may receive image data that represents an image associated with or the subject of the response to the quiz. The one or more processor(s) 700-1 of the system 1000 may, in embodiments, analyze the image data. The one or more processor(s) 700-1 of the system 1000 may be enabled to perform one or more of the following: 2D object recognition, 3D object recognition, image segmentation, motion detection (e.g., single particle tracking), video tracking, optical flow, 3D Pose Estimation, and/or automatic number plate recognition, to name a few.

In embodiments, the system 1000 may obtain the health-related attribute data 1312A and/or medical data from one or more of the third-party vendor(s) 1016. In embodiments, this health-related attribute data may be obtained from one or more insurance providers (e.g., health insurance data 1404) and/or one or more medical providers (e.g., medical data 1406). The data may be obtained by the system 1000 sending a request to the aforementioned one or more insurance providers and/or one or more medical providers and receiving the data as a response to that request. In embodiments, the request sent by the system 1000 may also include necessary consent forms that enable the one or more insurance providers and/or one or more medical providers to provide such data.

In embodiments, the system 1000 may also obtain user preference data. User preference data may be obtained in the quiz manner mentioned above. User preference data may include any data that indicates a preference of the user, for example, what time the user would like to receive stimuli, what kind of behavior the user would like to change (e.g., goal data), who the user is trying to change with (e.g., another user—a second user—of the plurality of users), what the user likes, what the user dislikes, and/or the amount a user can afford to spend, to name a few.

Examples of stimuli include alerts (phone notifications, app alerts, etc.) based on location and food choices, such as suggesting a user to choose stairs, cycle or walk to a workplace or prompting a user to choose particular menu items when the user is detected to be at a restaurant, quizzes that prompt the user to respond, to name a few. A more detailed description of stimuli and/or prompts (including alerts) is located below in connection with the description of FIGS. 8A-8C and 9A-9F.

Vendor and stimulus data 2022 may include standard incentives. Standard incentives, in embodiments, may include information regarding incentive type (Food discount, membership subscription), incentive label, incentive claiming period, to name a few.

In embodiments, vendor and stimulus data 2022 may include location-based incentives where a user's location and/or path of daily activity or daily activities is tracked and, based on the user's location, one or more notification(s) may be used to inform a user of possible best eating option(s) to avoid skipping a meal and/or suggest a healthier option. Additionally, a user may be alerted to take stairs on reaching a specific location, if it is determined that, based on vendor and/or stimulus data 2022, such an option is available, possible, and/or practical at the user's location. As another example, vendor and/or stimulus data 2022 may offer a membership discount if a user were to use a bicycle as transportation to work instead of other motorized vehicles (e.g., a car, truck, SUV, motorcycle, to name a few) on a user's route to his or her workplace for the day. As yet another example, vendor and/or stimulus data 2022 may offer a specific priced coupon to the user's favorite shop upon completing a specific task, such as 5000 steps, or another one-time or periodic activity or consumption limit goal (e.g., falling asleep at a specific time, being active for a certain period of time, taking the stairs at work instead of an elevator, to name a few). Stimulus data 2022 may be similar to incentive 808, described below in connection with FIGS. 8A-8B, the description of which applies herein.

User feedback data 2024 may be a collection of some or all of the user responses to prompts and/or stimuli received from personal user devices 10-1 . . . 10-*n*. In embodiments, user feedback data 2024, together with third-party user data 2016, recorded user device data 2018, and/or related user data 2020, may inform and/or refine user profile data 2014 in connection which may allow more accurate, appropriate and/or more effective prompts and/or stimuli for particular users of personal user devices 10-1 . . . 10-*n*.

In embodiments, user feedback data 2024 may include at least one of: mobile application usage patterns; challenge response data (e.g., expired, open, and/or active challenges) claim response data; survey response data; quiz response data; user behavior pattern; responses to notifications; responses to alerts; responses to stimuli; and/or responses to prompts, to name a few. The user feedback data 2024 may correspond with third-party user data 2016 to relate feedback to challenges, quiz presented, surveys taken, and/or rewards claimed. In embodiments, feedback data 2024 may be organized in key-value pairs responses or in other data structures.

Processor 2010 may execute and/or be operatively connected to one or more modules, such as, for example, mobile application (app) configuration module 2026, personalized data collection module 2028, mobile app communication module 2030, and stimulus module 2032. These modules may be implemented as combinations of software, hardware, and/or firmware. For example, the module software may include instructions in one or more suitable languages and may be stored on one or more computer readable storage media which can be accessed and/or executed by one or more processors (e.g., processor 2010, processor(s) 702, to name a few). These modules may form particular elements that perform respective functions related to the methods and processes described in further detail below according to embodiments of the present invention. In embodiments, various algorithmic processes may be implemented for the purpose of processing user feedback data 2024, third-party user data 2016, recorded user device (API) data 2018, related user data 2020, and/or user profile data 2014.

Algorithmic processes which are described below and may be implemented in embodiments of the present invention may include one or more of the following: (1) a recommendation genetic algorithm for determining incentives on offer to various users of the personal user devices 10-1 . . . 10-*n*; (2) a data clustering algorithm for determining associations within data associated with users of the personal user devices 10-1 . . . 10-*n*; and/or (3) a combination thereof, to name a few.

In embodiments, a recommendation genetic algorithm may include one or more of the following: applying reinforcement learning on user behavior as recorded in one or more of user feedback data 2024, third-party user data 2016, recorded user device (API) data, related user data 2020, and user profile data 2014; and assigning classifications (autotagged, inferred or manually tagged by an operator, by a user, or by a related user) to the recorded data and processing the results using a gradient boosting algorithm, such as XGBoost, to name a few.

Corresponding to the above, a multi-agent system may be implemented to allow different algorithms to compete for classifications and/or predictions, which in embodiments, may be confirmed by human tagging. Human tagging, in embodiments, may be completed by one or more users. one or more related users, one or more operators, and/or one or more third parties, to name a few.

In addition, in embodiments, time series data from all sensors may be analyzed using dynamic time warping (DTW), and/or similar processes, to build human behavioral models at personal data system 20 and/or to detect deviances from typical (and/or expected) behavior. The results can be used to affect user reliability (giving rise to sending stimuli to user only when an exception is detected, or to ask a second user about a first user's behavior). The results may also give rise to not sending stimuli and/or prompts to a user when an exception is not detected. The resulting data may also be corrected for, say, seasonality or other repetitive independent cycles, using anomaly detection and other software tools. For example, prompts and/or stimuli encouraging a user to go for a run may not be sent if there is a blizzard in the location of the user.

The above incentive determination may further be supplemented by incentive cost analyses using a gradient boosting algorithm, such as XGBoost and the like. For example, an optimized differentiable loss function may be provided to calculate a lowest-cost incentive that would still achieve a desired behavioral change for a user based on the user's analyzed behavioral profile. Correspondingly, for incentive provider bidding, such an optimized differentiable loss function may be used for determining a minimal price at which a starting bid from an incentive provider (such as a retailer and the like) may be accepted. In either case, processor 2010 of personal data system 20 may execute the analytical processes over time and/or over cycles to minimize payouts for incentives to users and maximize minimum bids from incentive providers, while maintaining one or more predetermined incentive efficacy thresholds across all users of personal user devices 10-1 . . . 10-*n*.

In embodiments, the above determination may be further supplemented by a data clustering algorithm, such as density-based spatial clustering of applications with noise (DBSCAN). Data clustering algorithms such as DSCAN, in embodiments, may enable the system 1000 to make associations, find patterns, and/or predict trends. For example, DSCAN may analyze the user's positive and negative user feedback data 2024 to better the timing and/or targeting of stimuli.

Figures 1, 1A, 2:
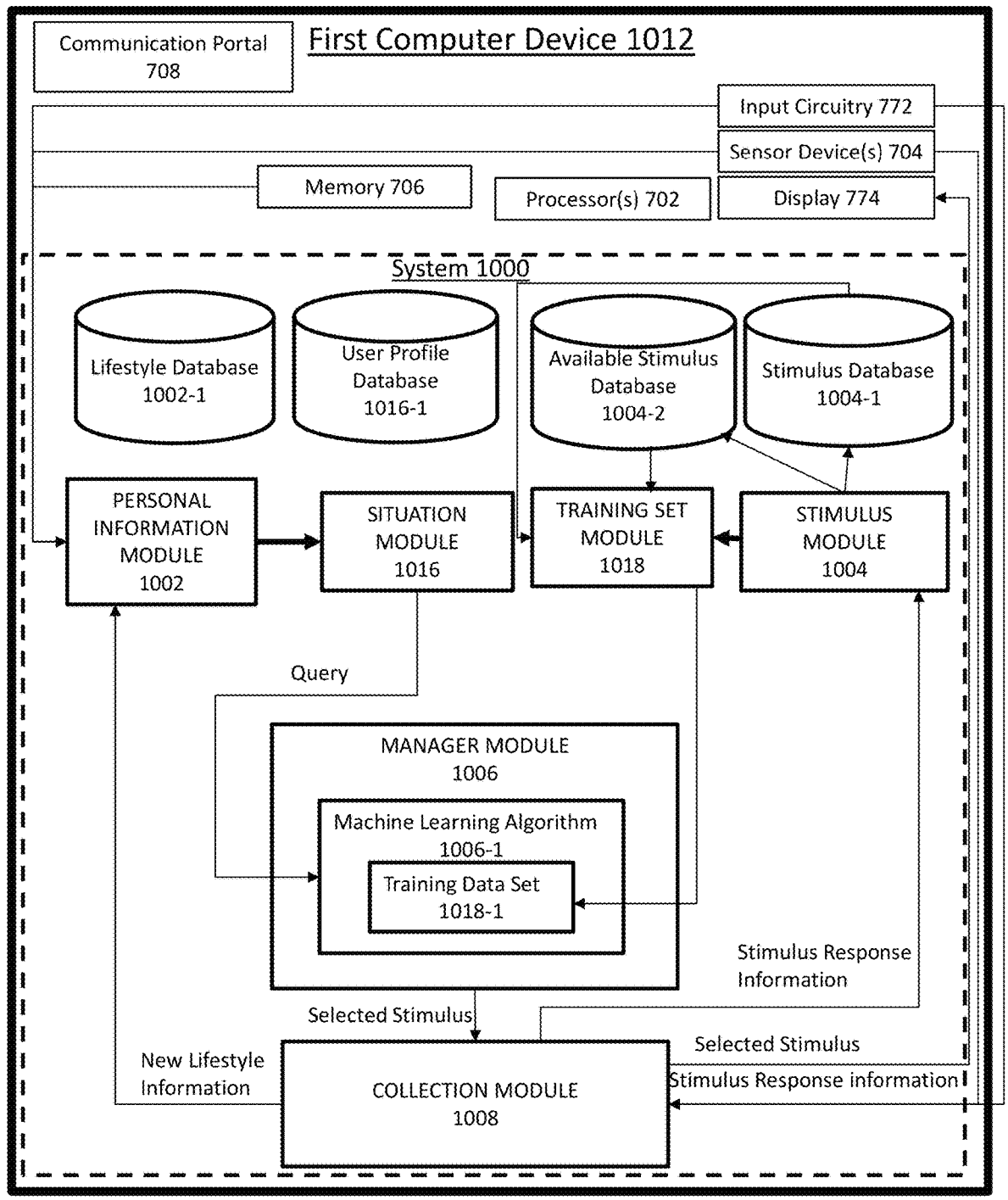
Figures 1, 1A, 2, 3:
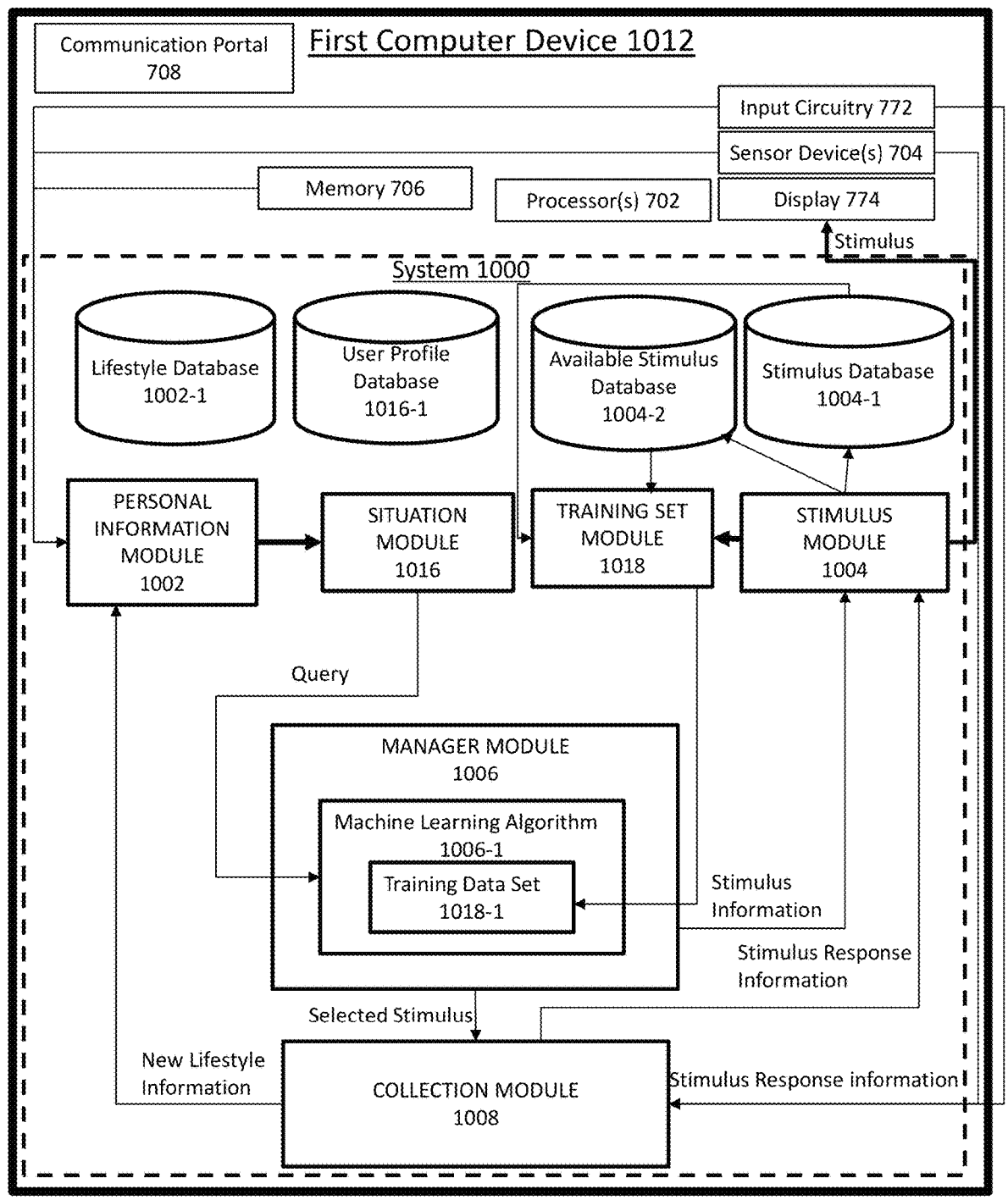

FIG. 3 is an exemplary block diagram illustrating the structure of mobile application software for implementing an interactive user health decision prompting process in accordance with exemplary embodiments of the present invention. In embodiments, the personal user devices 10-1 . . . 10-*n* may have downloaded mobile application software 3000 into memory of the personal user devices 10-1 . . . 10-*n* (e.g., memory 706). The personal user devices 10-1 . . . 10-*n* may be operatively connected via a network 100 to a personal data system 20. As shown in FIG. 3, mobile application software 3000 may be organized by various functional modules. In embodiments, the various functional modules of mobile application software 3000 may include: such as login module 3005, user interface module 3010, personalized data collection module 3015, stimulus transceiver module 3020, light sensor module 3025, orientation module 3030, and radio transceiver module 3035. Concurrently, mobile application software 3000 may store data locally in memory of the personal user devices 10-1 . . . 10-*n* which may allow for use by the various modules and/or for communication with personal data system 20 (e.g., transmitting messages and/or data from personal user devices 10-1 . . . 10-*n* to computing device 700 which may include personal data system 20). Such data may be organized, for example, into user profile data 3045, menu data 3050, device (API) data 3055, stimulus data 3060, and user response data 3065.

Figure 4A:
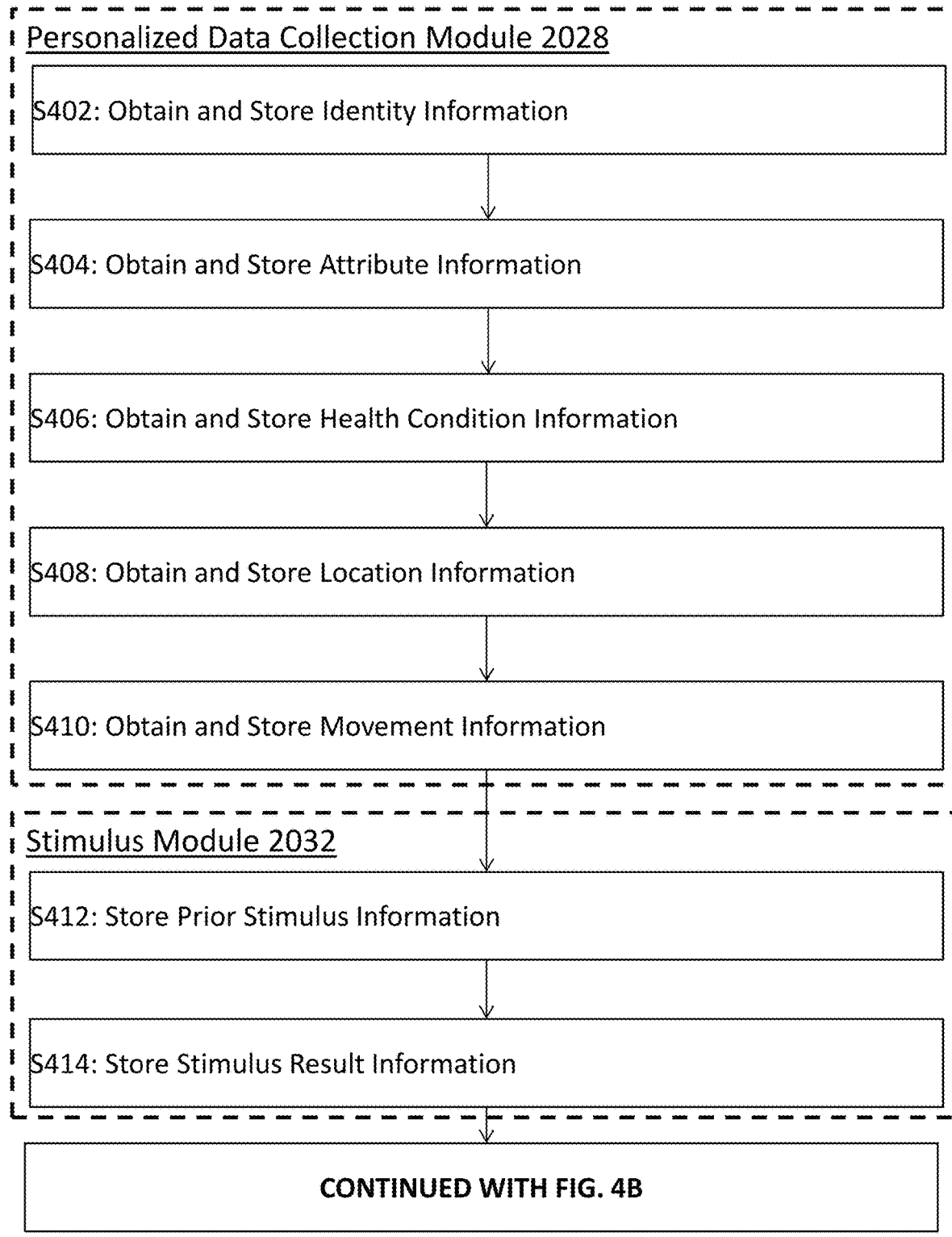
FIGS. 4A and 4B are exemplary flow charts illustrating a process for implementing an interactive user health decision prompting process in accordance with exemplary embodiments of the present invention.
Figure 4B:
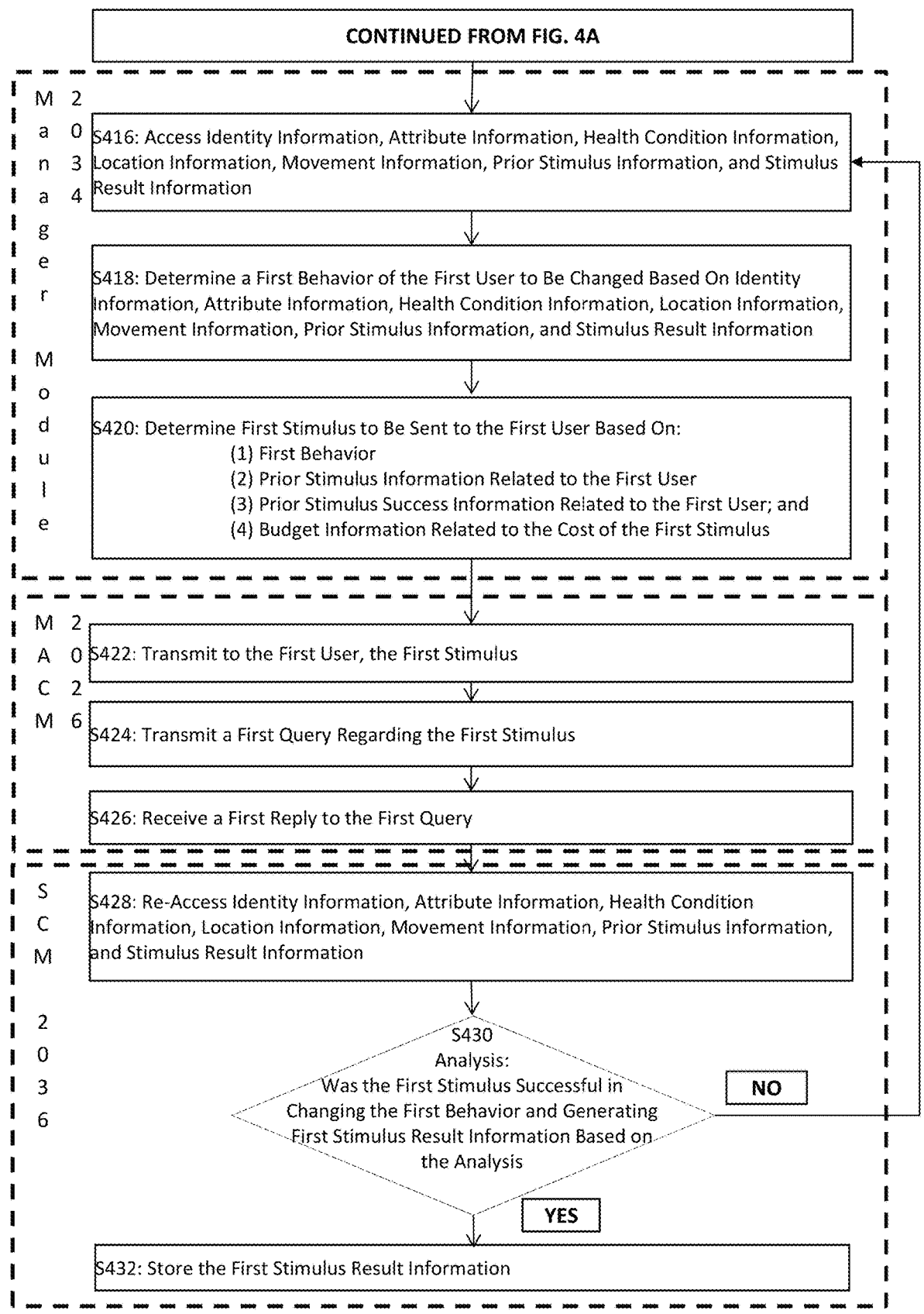

FIGS. 4A and 4B together form a flow chart illustrating an exemplary process for implementing a user stimulus program in accordance with embodiments of the present invention. The process shown in FIGS. 4A and 4B may begin at step S402. At step S402, personal data system 20 may receive and/or stores identity information associated with a user of one or more of personal user devices 10-1 . . . 10-n. For example, the identity information may be received by a computing device associated with the personal data system 20 working in concert with one or more processor(s) (e.g., processor 2010, processor(s) 700-1). The one or more processor(s) may be executing mobile app communication module 2030 and communicating with personal user devices 10-1 . . . 10-n via communication portal 2012 and network 100. Correspondingly, a user account may be maintained such that identity information may be stored together with other information. For example, the identity information may be maintained as user profile data 2014 at personal data system 20, as described above in connection with FIG. 2C.

The process may continue at step S404 where attribute information associated with one or more user(s) is received and/or stored by the computing device 700. In embodiments, the attribute information may be provided by the user via a manual entry at personal user devices 10-1 . . . 10-n in response to a predetermined questionnaire and/or interactive data entry program. For example, the attribute information may be input via user interface module 3010 of mobile application software 3000. Such attribute information may include one or more of the following: height, weight, dietary exercise habits, and/or sleep habits to name a few. The attribute information, in embodiments may be stored as user profile data 2014 at personal data system 20. In embodiments, attribute information may be received by computing device 700 from personal user devices 10-1 . . . 10-n. The personal user devices 10-1 . . . 10-n may receive manual entries in response to a predetermined questionnaire, as shown in FIGS. 9C and 9D.

Next, at step S406, in embodiments, health condition information may be received by a computing device 700. In embodiments, health condition information may be retrieved from one or more third-party sources, with consent from the user, by personalized data collection module 2028 at personal data system 20 from third-party systems 30-1 . . . 30-n maintained at, for example, health service providers, insurance companies, and the like. Health condition information may include medical history, health insurance information, medical test results to name a few. Correspondingly, historical device API data from personal user devices 10-1 . . . 10-n may also be obtained and/or stored to form user profile data 2014. For example, users' histories of daily activity recorded by personal user devices 10-1 . . . 10-n— i.e., device (API) data 3055 may be retrieved via API module 3040 by mobile application software 3000 and relayed to personal data system 20 for storing as part of recorded user device (API) data 2018.

At step S408, location information associated with the one or more user devices 10-1 . . . 10-n is retrieved and/or stored by a computing device 700. In embodiments, the location information may include vicinity location data, such as cellular network triangulation data. In embodiments, location data may be obtained by a combination of different device locator techniques, including one or more of GPS, triangulation, WiFi network location information, wireless location information, optical location information, Bluetooth® association data, light sensor data, camera images, multi-dimensional accelerometer data (time series), multi-dimensional compass data, and/or multi-dimensional proximity data, to name a few. In embodiments, the location information is transmitted by orientation module 3030 and/or radio transceiver module 3035 of mobile application software 3000 to personal data system 20, where it is stored as recorded user device data 2018. In embodiments, location information may be associated with vendor information. For example, when a user of one or more of personal user devices 10-1 . . . 10-n visits a particular vendor (either physically or virtually using one or more personal user devices 10-1 . . . 10-n and/or electronic devices associated with the one or more personal user devices 10-1 . . . 10-n), the location information retrieved from the personal user device 10-1 and transmitted to the personal data system 20 may be correlated to the visited vendor. Processor 2010, via stimulus module 2032, may query vendor and stimulus data 2022 to identify any appropriate prompts and/or stimuli for the user of the personal user device 10-1 at the visited vendor. Additionally, personal data system 20 may communicate with the corresponding vendor system 40-1 . . . 40-n to retrieve updated vendor information, and related prompt and stimulus information, that are offered by the vendor, as described below at step S412. In embodiments, personal data system 20 may query vendor systems 40-1 . . . 40-n at ad hoc and/or predetermined intervals for updated stimulus information, such stimulus information may be particular: challenges, discounts, benefit point systems, associated with the goods and services provided by the vendors, to name a few. In embodiments, the prompts and stimuli may be provided by one or more sponsors of particular users of personal user devices 10-1 . . . 10-n, or by other entities. Thus, stimulus module 2032 may include processes for querying third-party user systems 30-1 . . . 30-1 associated with the user sponsor(s) for updated sponsorship information, such as general budgets for stimuli, particular vendors at which users are eligible for stimuli, to name a few. Additionally, in embodiments, when a user visits a particular vendor, the aforementioned example may similarly apply to competitors of the visited vendor and/or comparable vendors to the visited vendor. For example, if a user visits a GAP® store, Old Navy® may provide users with prompts and/or stimuli to encourage a user to shop at Old Navy® instead of shopping at GAP®. As another example, a user's employer may sponsor incentive programs for encouraging positive lifestyle choices that may include gym membership discounts, food choice discounts, activity challenges, to name a few. The vendor and stimulus data 2022 may be timely updated and related to up-to-date and relevant user data. For example, one or more of user profile data 2014, third-party user data 2016, recorded user device data 2018, related user data 2020, and/or user feedback data 2024 may be timely updated and related to up-to date and relevant user data by stimulus module 2032 such that appropriate stimuli may be identified and provided to particular users.

Next, at step S410, personal data system 20 of computing device 700 may retrieve movement information from user devices 10-1 . . . 10-n and/or store the retrieved movement information. Such information may include: a time series record of the above-noted location information, and user device API information (e.g., user activity record under Apple HealthKit®, Google Fit®, to name a few), to name a few. Correspondingly, a user's movement (movement information associated with a user) may be used to determine a prompt and/or stimulus that may be independent from the location of the user. For example, if a user has determined to have moved outdoors, a stimulus for maintaining a walk of a certain distance and duration based on the user's profile may be generated by stimulus module 2032 and transmitted via mobile app communication module 2030 to stimulus transceiver module 3020.

In embodiments, steps S408 and/or S410 may include receiving additional user data from personal user devices 10-1 . . . 10-*n*. In embodiments, the additional user data may be received by personal user devices 10-1 . . . 10-*n* via a manual input from a user associated with the personal user devices 10-1 . . . 10-*n*. The additional user data may serve as self-reporting on activity and habits. As will be described in further detail below, one or more user interface schemes may be executed to receive such input, say, as part of the prompts and/or stimuli transmitted to personal user devices 10-1 . . . 10-*n*. The additional user information may be stored as complementary data to the device-recorded location and movement information. In embodiments, the device-recorded location and movement information may be compared with the additional user information for verifying the accuracy of the recordings and/or user reliability. User reliability determinations may form a key component of the prompt and/or stimulus program, exemplary embodiments of which will be described in further detail below.

Next, at step S412, prior stimulus information for each of the users associated with the personal user devices 10-1 . . . 10-*n* is recorded and stored at personal data system 20 of computing device 700. In embodiments, prior stimulus information may be stored locally on the personal user devices 10-1 . . . 10-*n*. When the prior stimulus information is stored locally, step S412 may include additional steps of the computing device 700 retrieving the information from personal user devices 10-1 . . . 10-*n* by receiving the data over network 100. Prior stimulus information may include stimulus information associated with the user that has been already transmitted to the user associated with the personal user devices 10-1 . . . 10-*n*. In embodiments, the prior stimulus information may be prior stimulus information for another user that is associated with the user of the personal user devices 10-1 . . . 10-*n*. In embodiments, step S412 may be omitted. For example, if it is a user's first time using the mobile application software 3000, there would be no prior stimulus information to store.

Correspondingly, at step S414, responses and/or results from prior stimuli are stored at personal data system 20 of computing device 700, along with the prior stimulus information. In embodiments, as with the prior stimulus information, prior stimulus results and/or responses may be stored locally on the personal user devices 10-1 . . . 10-*n*. When the prior stimulus results and/or responses are stored locally, step S414 may include additional steps of the computing device 700 retrieving the information from personal user devices 10-1 . . . 10-*n* by receiving the data over network 100. In embodiments, a direct network connection, for example, between personal user devices 10-1 . . . 10-*n* and personal data system 20 need not be maintained at all times for mobile application software 3000 to function properly. User interface module 3010 may independently interact with the user and record appropriate stimulus responses from the user as user response data 3065. Likewise, "past" stimuli that the user has responded to may also be recorded as part of stimulus data 3060. Stimulus data 3060 may include both such "past" stimuli and/or planned stimuli that have not been initiated yet, which may be pre-loaded from personal data system 20 during a previous communication via network 100. Thus, once a connection is reestablished between personal user devices 10-1 . . . 10-*n* and personal data system 20 via network 100, personal user devices 10-1 . . . 10-*n* may transmit the recorded information to personal data system 20. The efficacy of various stimuli can be evaluated based on user attributes and responses, and future stimuli may be adjusted accordingly. The efficacy of various stimuli can further be evaluated based on the context or situation in which stimuli were presented to the user and the users' actions (or lack thereof) in response, and future stimuli (along with the situational context in which they may be presented) may be adjusted accordingly. As with step s 4.6, in embodiments, step S414 may be omitted. For example, if it is a user's first time using the mobile application software 3000, there would be no prior stimulus result information to store.

The process of FIG. 4A may continue with FIG. 4B. In embodiments, the process next advances to executing a stimulus determination and transmission program, as shown in FIG. 4B. At step S416, the stored user information is accessed by computing device 700, at personal data system 20. The stored user information, in embodiments, may include, for example: identity information, attribute information, health condition information, prior stimulus information, and/or stimulus result information, to name a few. As illustrated and described above in connection with FIG. 2C, the stored user information may be stored and organized into user profile data 2014, third-party user data 2016, recorded user device data 2018, and/or user feedback data 2024. Additionally, location information and/or movement information may be received by computing device 700 from personal user devices 10-1 . . . 10-*n* via network 100. Personal user devices 10-1 . . . 10-*n* may receive location information and/or user information from one or more of light sensor module 3025, orientation module 3030, radio transceiver module 3035, and/or API module 3040, any of which may be mechanically coupled to, electrically coupled to, or operatively connected with personal user devices 10-1 . . . 10-*n*. The aforementioned modules and/or sensor device(s) 704 may cooperate to detect and store, from corresponding hardware sensors (e.g., sensor(s) 704) and software applications (e.g., mobile application software 3000) of personal user devices 10-1 . . . 10-*n*, low accuracy location (e.g., cellular network triangulation); high accuracy location (e.g., a combination of GPS and at least one other sensor, e.g., WiFi); multi-dimensional accelerometer data (timeseries); multi-dimensional compass data; multi-dimensional proximity data; light sensor data; wireless association data; optical association data; Bluetooth association data; calendar data (e.g., date and/or event entries); electronic-mail data (e.g., data retrieved from electronic mail of one or more users associated with the personal user devices 10-1 . . . 10-*n*); messaging data (e.g., data retrieved from messages stored locally on the personal user devices 10-1 . . . 10-*n* (e.g., SMS messages, MMS messages, and voice-mail messages, to name a few), messages stored on a network associated with accounts (e.g., social media accounts) associated with the user(s) of the personal user devices
10-1 . . . 10-*n*, to name a few); activity data; presence data; group data; and/or device API data, to name a few.

Continuing with step S418, based on the retrieved user information, personal data system 20 identifies and/or determines one of more behaviors (e.g., a First Behavior) of each user that can and/or may be influenced using the available prompts and stimuli. These behaviors, as generally mentioned throughout the present disclosure of this invention, may include: eating behaviors; exercise behaviors; sleeping behaviors; stress behaviors; shopping behaviors; social behaviors (e.g., meeting new people, trying new activities, exploring new locations, being more generous, volunteering personal time, to name a few); and communication behaviors (e.g., being more polite, being more honest, being nicer to people, forgiving people, to name a few), to name a few. In embodiments, the type of behavior to be changed may be determined based on one or more of the following: default and/or predetermined settings; user profile data 2014; related user data 2020; third-party user data 2016; vendor and stimulus data 2022; recorded user device (API) data 2018; user feedback data 2024; and/or settings selected by the user which indicate what behaviors the user would like to change, to name a few.

Next, at step S420, computing device 700, through processor(s) 702 and/or processor 2010 and/or stimulus module 2032 may determine the first stimulus to be sent to the personal user devices 10-1 . . . 10-$n$. In embodiments, the computing device 700 may query the vendor and stimulus data 2022 in order to identify and/or determine one or more prompts and/or stimuli (e.g., a First Stimulus) for each user (e.g., a First User) based at least in part on: (1) behaviors (e.g., First Behavior) identified at step S418; (2) "Prior Stimulus Information" of each user (e.g., First User), including, for example, prior prompts and stimuli that were transmitted to the personal user devices 10-1 . . . 10-$n$, identified in step S412; (3) "Prior Stimulus Success Information Related to the First User," including records of past prompts and/or stimuli that were transmitted to user devices 10-1 . . . 10-$n$ and that evoked positive responses from the corresponding users, which positive responses may be verified against recorded data from personal user devices 10-1 . . . 10-$n$ and/or third-party and vendor information from third-party user information systems 30-1 . . . 30-$n$ and vendor systems 40-1 . . . 40-$n$, respectively, identified in step S414; and (4) "Budget Information Related to the Cost of the First Stimulus," which may refer to one or more costs associated with providing the prompts and/or stimuli to the user. In embodiments, the budget information may be evaluated in the context of a likelihood of success based on past successes under item (3). In embodiments, the budget information may include cost information associated with prompts and/or stimuli that are at least in part provided by various vendors via the respective vendor systems 40-1 . . . 40-$n$. For example, a stimulus may be a discount and/or incentive related to certain goods or services provided by the various vendors, such as a discount for a healthy salad choice at a fast food restaurant, that may form an encouragement towards positive choices by a user. The budget information may also relate to a sponsored incentive program maintained at third-party user information systems 30-1 . . . 30-$n$. For example, the third-party user information systems 30-1 . . . 30-$n$ may be, as mentioned earlier, one or more of the following: a health incentive program sponsored by an employer, health insurance provider, to name a few. In embodiments, the cost and budget information may be evaluated in the context of information maintained at third-party user information systems 30-1 . . . 30-$n$ to ensure or increase the likelihood that providing the prompts and/or stimuli would maintain the associated sponsored program(s) within a predetermined budget.

It is understood that some or all components of personal data system 20 may be physically or logically operative in any type of computing device (e.g., computing device 700) which may be a personal user device as well, and that any processing may occur on any processor connected to network 100.

Once one or more prompts and/or stimuli (e.g., "First Stimulus") have been determined, at step S422, the identified prompts and/or stimuli (e.g., "First Stimulus") are transmitted to respective personal user devices 10-1 . . . 10-$n$ via network 100. Exemplary transmitted prompts and/or stimuli are described in more detail above in connection with FIGS. 8A-8B, the descriptions of which apply herein. Additionally, exemplary transmitted prompts and/or stimuli are shown in connection with FIGS. 9A and 9B.

Next, at step S424, personal data system 20 may transmit queries (e.g., "First Query") to personal user devices 10-1 . . . 10-$n$ via network 100. In embodiments, the queries may regard the prompts and/or stimuli that have been transmitted at step S422. In embodiments, the queries may be transmitted at specified times, predetermined intervals, and/or a predetermined time after the original prompts and/or stimuli were transmitted, to name a few.

After transmitting the queries, the computing device 700, using personal data system 20 may monitor for responses (e.g., "First Reply") from personal user devices 10-1 . . . 10-$n$ to the queries ("First Query") that were transmitted at step S424. Monitoring, by the computing device 700 may be active (e.g., computing device 700 communicating with personal data system 20 to determine if anything has been received, the communications being at either predetermined intervals of time, at certain points in time, to name a few) and/or passive monitoring (e.g., computing device 700 waits until communication is received from a user device). Monitoring may also include analyzing all communication received from personal user devices 10-1 . . . 10-$n$ to determine whether the communication is in fact a response to the queries.

At step S426, personal data system 20 of computing device 700 may receive one or more responses to the first query (e.g., "First Reply"). The one or more responses may be sent from the personal user devices 10-1 . . . 10-$n$ via network 100. The one or more responses, in embodiments may be sent manually, automatically, and/or semi-automatically from personal user devices 10-1 . . . 10-$n$. For example, mobile application software 3000 may include software that causes personal user devices 10-1 . . . 10-$n$ to automatically send a reply upon one or more of the following: personal user devices 10-1 . . . 10-$n$ determines that the first behavior was changed; the user has completed as much of the first behavior as they wish and stops for an amount of time (which may be predetermined, either by, for example, settings of the mobile application software 3000 and/or settings that were inputted manually by the user); and/or the personal user devices 10-1 . . . 10-$n$ determine that nothing has happened for a predetermined amount of time. As another example, the user may manually input a response stating that the first behavior change was completed. In embodiments, personal data system 20 may not receive a message. For example, personal user devices 10-1 . . . 10-$n$ were shut off and thus cannot send any messages. If a message is not received, the computing device 700 may determine that the first behavior change was not successful. In embodiments, if a message is not received, the computing device 700 may generate a message to send to the personal user devices 10-1 . . . 10-$n$. The message may be: a notification that the first behavior change was not completed; a message of encouragement (e.g., "It is OK, no one changes in a day, keep trying!" or "Your friend has already completed this task, are you really going to let your friend beat you?"; and/or an offer of additional incentives (e.g., "10% off the salad was not enough, how about 12% off?", to name a few.

When one or more responses ("First Reply") are received at step S426, personal data system 20 of computing device 700 may proceed to step S428 where the computing device may re-access relevant user information for the received one or more responses. Relevant user information may include Identity Information, Attribute Information, Health Condition Information, Location Information, Movement Information, Prior Stimulus Information, and/or Stimulus Result Information, to name a few.

Once the relevant user information is re-accessed, personal data system 20 of computing device 700 may proceeds to step S430 and analyze the received one or more responses to determine whether the prompts and/or stimuli ("First Stimulus") corresponding to the received one or more responses can be considered successes in changing the behaviors identified and determined at step S418. For example, if the first behavior change was for the user to walk 10,000 steps, the one or more responses may indicate whether the user has completed 10,000 steps. If the user has completed 10,000 steps, in this example, the computing device 700 may determine that the first behavior change was a success. If, however, the user has not completed 10,000 steps, the computing device 700 may determine that the first behavior change was not a success. This, in embodiments, may be a sliding scale. For example, if the user typically only walks 2,500 steps a day and reached 7,500 steps, the computing device may determine that the first behavior change was a partial success. A partial success may indicate to the computing device 700 that the first behavior is a behavior that can be changed and may continue to work with the user to finally reach the goal (e.g., 10,000 steps).

If the results of the analysis conducted at step S430 indicate that the prompts and stimuli ("First Stimulus") were not successful ("NO"), then the process may return to step S416 to restart the stimulus determination and transmission program based on the same behavior—or one or more different behaviors—and corresponding prompts and/or stimuli. In embodiments, returning to step S416 may include updating "Prior Stimulus Information" in order to reconsider the appropriate prompts and/or stimuli for affecting a particular behavior change. In embodiments, if the results of the analysis indicate the prompts and/or stimuli were not successful, the computing device 700 may generate GUI and/or a message (which may be included in GUI) to send to the personal user devices 10-1 . . . 10-n. The message may be: a notification that the first behavior change was not completed; a message of encouragement (e.g., "It is OK, no one changes in a day, keep trying!" or "Your friend has already completed this task, are you really going to let your friend beat you?"; and/or an offer of additional incentives (e.g., "10% off the salad was not enough, how about 12% off?", to name a few.

If the results of the analysis conducted at step S430 indicate that the prompts and/or stimuli ("First Stimulus") were successful ("YES"), then personal data system 20 proceeds to step S432 and stores the positive results for future reference in determining additional prompts and stimuli (e.g., "Prior Stimulus Success Information Related to the First User"). If the results of the analysis indicate that the prompts and/or stimuli were successful, the computing device 700 may generate and transmit GUI and/or a message reflecting the success. A more detailed explanation of generating and transmitting the GUI and/or message is located above in connection with the description of FIG. 8C, the description of which applies herein.

In embodiments, the steps of the process(es) described above in connection with FIGS. 4A and 4B may be rearranged and/or omitted.

In accordance with an exemplary embodiment of the present disclosure, the prompts and/or stimuli may be in the form of one or more yes/no or multiple-choice questions, which may be further used to gauge user reliability with reference to other sources of information regarding a user's response to the one or more questions. For example, questions transmitted to personal user devices 10-1 . . . 10-n of related users that may be in the proximity at the time of the user's response. Additionally, the prompts and/or stimuli may include essay entries and challenges for users to accept. In embodiments, entries may include, for example, venue reviews, description of preferred activities at respective locations, to name a few. In embodiments, challenges may include, for example, "run 1 mi in the next 20 minutes." Rewards (e.g., incentive 808 described above in connection with FIGS. 8A-8B, the descriptions of which applying herein) may be given to users in return for stimulus responses. Rewards may also be determined based on user profile information. For example, user archetypes may indicate certain users reacting best to small and frequent financial rewards, whereas a different user (or user archetype profile) may react best to larger and less frequent financial rewards, and a third user may react best to particular products associated with personal sentiment which may be, for example, a branded baseball hat of a favorite team. Such user archetypes may be persistently refined at personal data system 20 by personalized data collection module 2028 continually collecting user stimulus and response information in relation to context data, such as location, date and time information, related users in proximity, etc., and/or compiling updated user profile data 2014. Based on the updated user profile data 2014, stimulus module 2032 may continually improve upon the efficacy of the prompts and stimuli that are generated for particular users. In embodiments, the reward system may be independent of existing third-party reward systems.

In embodiments, if a challenge is accepted, then a user may be provided with a prescribed amount of time (or other parameters, for example, location, competition with other users, to name a few) to perform the challenge. Some challenges may last weeks or longer, some may be available only in certain locations, and/or some may be only available if a certain number of users participate and accept the challenge, to name a few (or any combinations thereof). Once a challenge is accepted and a user performs the challenge successfully the user may be given the reward as offered in the stimulus. The reward may also be dependent upon a user reliability rating, which may rely at least in part on confirmation of the challenge completion via other information sources such as a related user in proximity to the challenge completion.

Figure 5:
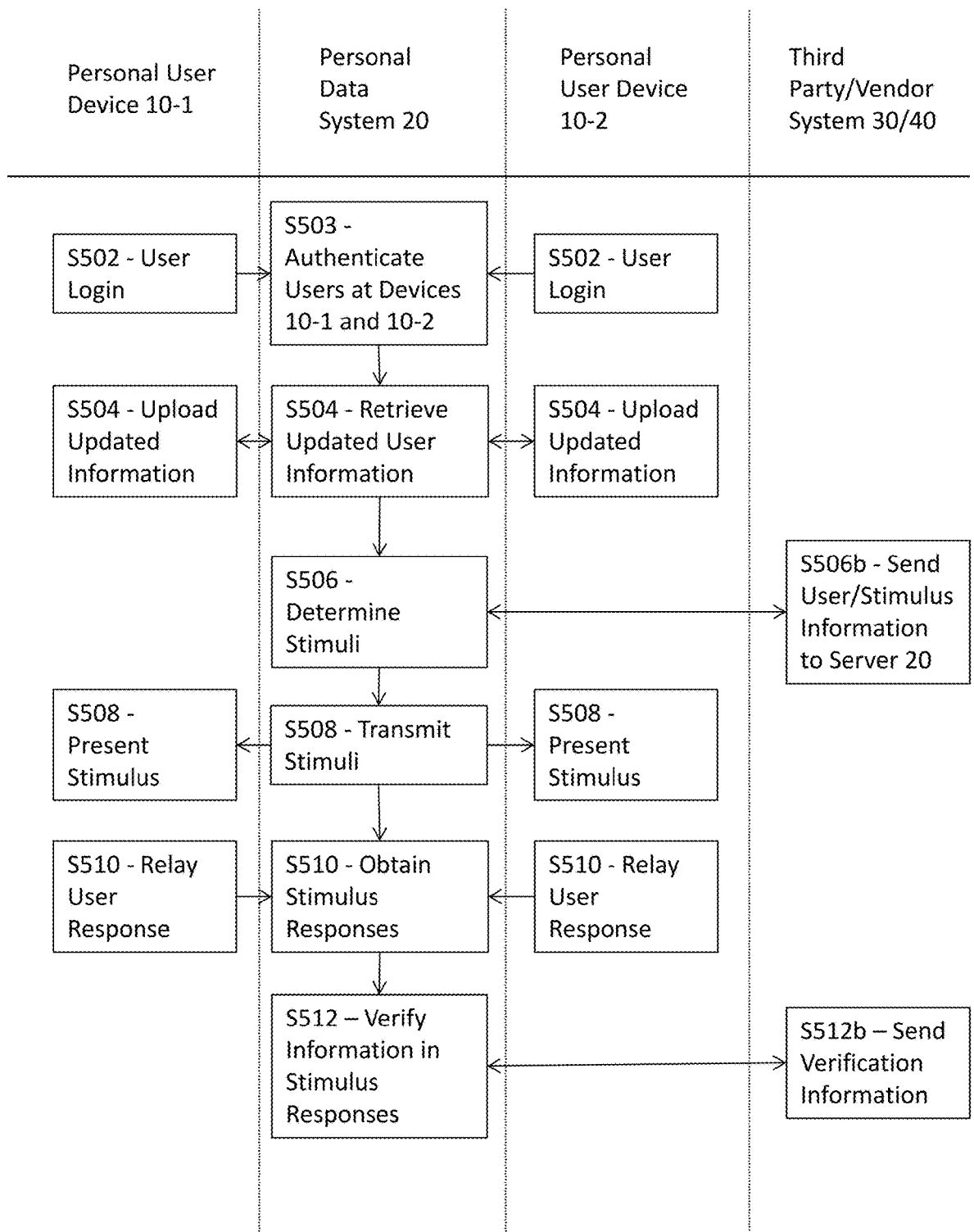
FIG. 5 is an exemplary flow chart illustrating a process and respective apparatuses for implementing an interactive user health decision prompting and verification process in accordance with exemplary embodiments of the present invention.

FIG. 5 illustrates process 500 for providing prompts and/or stimuli, as described above, to a plurality of the personal user devices 10-1 . . . 10-n, where the responses from these devices are verified against one another and, optionally or alternatively, third-party user information systems 30-1 . . . 30-n and vendor systems 40-1 . . . 40-n in accordance with an embodiment of the present invention. Process 500 may be initiated at step S502 by respective one or more users at personal user devices 10-1 . . . 10-n by logging into mobile application software 3000. For example, a user may log into mobile application software 3000 via login module 3005 illustrated above in FIG. 3. In embodiments, step S502 may be included in the process(es) described above in connection with FIGS. 4A and 4B (e.g., step S502 may occur before step s4.1 described above in connection with FIG. 4A).

Next, at step s503, personal data system 20 of computation device 700 may authenticate the users at personal user devices 10-1 and 10-2. Authentication, in embodiments, may implement tokenization, a two-step verification process, biometric data, and/or security questions, to name a few. In embodiments, step S503 may be included in the process(es) described above in connection with FIGS. 4A and 4B (e.g., step S503 may occur before step s4.1 described above in connection with FIG. 4A). In embodiments, personal user devices 10-1 and/or 10-2 may include each or either include a first user device (e.g., a cell phone) and a second user device (e.g., optional second personal user device 10-1A).

Process 500, in embodiments, may continue with step S504. At step S504 personal data system 20 of computation device 700 may retrieve updated user information. Updated user information, in embodiments may include querying personal user devices 10-1 and 10-2 for recorded information since a previous communication, as described above. Step S504 may be similar to steps s4.1-S416 described above in connection with FIGS. 4A-4B, the descriptions of which applying herein.

Once updated user information is retrieved, personal data system 20 of computation device 700 may, in embodiments, proceed to step s506. At step s506, the computation device 700 may determine appropriate prompts and/or stimuli for the respective users at personal user devices 10-1 and/or 10-2, as described above. In embodiments, the prompts and/or stimuli may be related and/or associated to one another if and when the users at the personal user devices 10-1 and 10-2 are associated with one another. For example, co-workers or associates under the same sponsorship program and/or social media acquaintances (e.g., Facebook® Friends, Twitter® followers, Instagram® followers, to name a few), to name a few, maintained at one or more of the third-party user information systems 30-1 . . . 30-n may be determined as associated and/or related to one another. Thus, at step s506b shown in FIG. 5, the third-party user information system 30 may be queried by personal data system 20 of computation device 700 for information relevant to determining the prompts and/or stimuli for the users of personal user devices 10-1 and/or 10-2. Additionally, the prompts and/or stimuli provided to the users may further be related to one another based on a proximity of the respective personal user devices 10-1 and 10-2. For example, if the users of these devices are dining together at a restaurant, which may be indicated by data retrieved from one or more proximity sensor(s) 724, their prompts and/or stimuli may be related to either or both of them. Thus, at step s506b shown in FIG. 5, a vendor system 40 may be queried for updated information relevant to the vendor and/or to verify the location of the personal user devices 10-1 and/or 10-2. Based on the information retrieved and recalled at personal data system 20, respective prompts and/or stimuli for personal user devices 10-1 and/or 10-2 are identified and/or determined at step s506. Step S506 may be similar to step S418 described above in connection with FIG. 4B, the description of which applying herein.

Once determined, the prompts and/or stimuli may be generated and/or transmitted to personal user devices 10-1 and 10-2 via network 100 at step s508. Correspondingly, the prompts and/or stimuli are presented to the users at personal user devices 10-1 and 10-2. A more detailed description of the prompts and/or stimuli generated and/or transmitted is located above in connection with FIGS. 8A-8B, the descriptions of which apply herein. Moreover, step S508 may be similar to step S422 described above in connection with FIG. 4B, the description of which applying herein.

In embodiments, after transmitting stimuli form the computing device 700 to personal user devices 10-1 and 10-2, the computing device may transmit a first query regarding the first stimulus to user devices 10-1 and 10-2 via network 100 (similarly to step S424 described above in connection with FIG. 4B, the description of which applies herein). In embodiments, the first query may be the same in substance for both user devices 10-1 and 10-2. In embodiments, the first query may include a first user query and a second user query. The first user query may be directed particularly to the first user of user device 10-1. The second query may be directed particularly to the second user of user device 10-2. Directed queries, in embodiments, may use information specific to the user accounts associated with the user devices 10-1. The information specific to the user accounts may, in embodiments, be obtained by the computing device 700 using personal data system 20 (e.g., user profile data 2014; third-party user data 2016; recorded user device3 (API) data 2018; related user data 2020; vendor and stimulus data 2022; and/or user feedback data 2024). In embodiments, the information specific to the user accounts may be obtained by the computing device 700 using: mobile application software 3000 (data (e.g., user profile data 3045, menu data 3050; device (API) data 3055; stimulus data 3060; user response data 3065; login module 3005) and/or modules of mobile application software 3000); third-party user information systems 30-1 . . . 30-n; and/or vendor systems 40-1 . . . 40-n, to name a few.

Next, at step s510, user responses to the prompts and/or stimuli are received from personal user devices 10-1 and 10-2 by personal data system 20 of computing device 700, as described above in connection with FIGS. 1-3 the description of which applying herein. Moreover, step S510 may be similar to step S426 described above in connection with FIG. 4B, the description of which applying herein.

Next, at step s512, personal data system 20 of computing device 700 may verify the information contained in the user responses. For instance, continuing the example of the users dining together, the user responses may contain information regarding menu items ordered and consumed by the respective users and user responses, thus, may be verified against one another regarding, say, the items ordered, and portions consumed. The verification may be in the form of: images taken by the users; the user associated with personal user device 10-1 verifying the actions of the user associated with personal device 10-2; the user associated with personal user device 10-2 verifying the actions of the user associated with personal device 10-1; and/additional information that may be monitored (e.g., receipts from a banking application or electronic mail application which indicate what was purchased), to name a few, Additionally, as shown in FIG. 5, process 500 may further include step s512b where the response information is further verified against information recorded at third-party user information systems 30-1 . . . 30-n and/or vendor systems 40-1 . . . 40-n. In embodiments, users of personal user devices 10-1 and 10-2 may be provided with interactive options via mobile application software 3000, and user interface module 3010 thereof. The interactive options, in embodiments, may request and/or receive permission from personal data system 20 (e.g., user settings and consent stored on personal data system 20) to query transaction information maintained at these systems for step s512b verification purposes. Step S512 may be similar to step S428 described above in connection with FIG. 4B, the description of which applying herein.

In embodiments, process 500 may continue with steps S430-S432 described above in connection with FIG. 4B, the description of which applying herein. Additionally, the steps of process 500 may be rearranged or omitted in embodiments.

Figure 6:
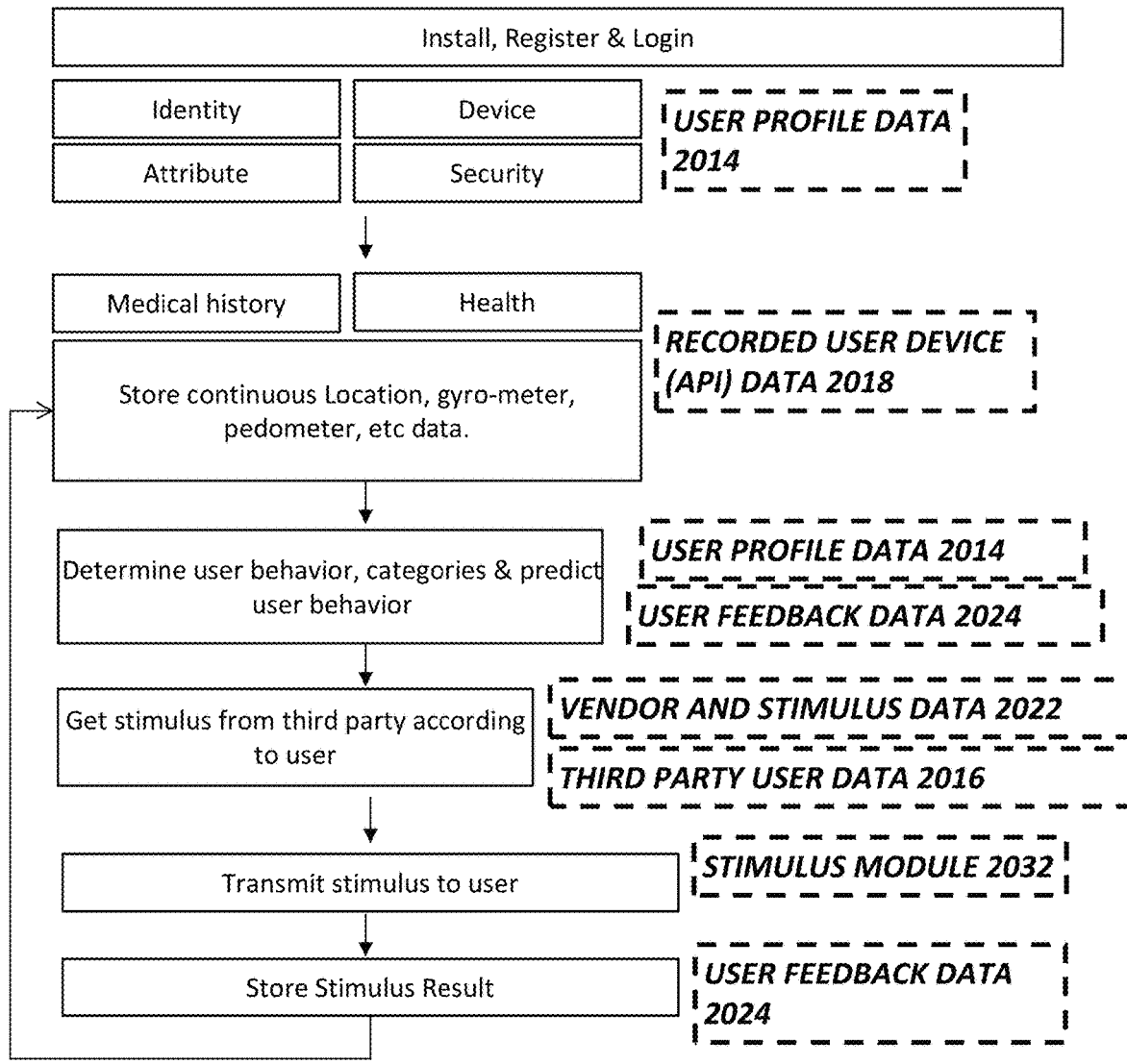
FIG. 6 is an exemplary flowchart illustrating a data flow process in accordance with exemplary embodiments of the present invention.

FIG. 6 is an exemplary flowchart illustrating a data flow process according to embodiments of the present invention. The data flow process shown in FIG. 6 may be similar to steps s4.1-S414 described above in connection with FIG. 4A and step S504 of process 500, described above in connection with FIG. 5, the descriptions of which applying herein. As shown in FIG. 6, the process begins with a user installing mobile application software 3000 on personal user device(s) 10-1 . . . 10-*n*, registering a user account, and/or logging in. Data permissions may be requested from the user. Additionally, the user may be requested to, and provide basic information, such as identity, attribute, device, security, medical history, and health, to name a few. The data permissions and basic information may be added to personal data system 20 in user profile data 2014.

Next, continuous sensor data may upload commences to personal data system 20, which is stored in recorded user device (API) data 2018. Based on the user data, which is continuously or periodically updated on demand or based on predetermined conditions, the process may proceed to an analysis. The analysis, in embodiments may determine user patterns and/or behaviors, while updating user profile data 2014 and user feedback data 2024 as appropriate. As a result of the analysis. triggers on stimuli, incentives, and/or challenges may be identified and/or generated based on vendor stimulus data 2022 and/or third-party user data 2016, such as healthcare provider, association, group, to name a few, to improve overall user behavior. Concurrently, users may be assigned appropriate tags to help third parties decide on appropriate challenges for the user.

The identified stimuli are associated with the users by stimulus module 2032 and transmitted to their respective personal user devices 10-1 . . . 10-*n*. The user feedback and corresponding stimulus results are retrieved to track behavior change/track impact of incentives. User feedback is stored in user feedback data 2024. Rewards redemption analysis may be conducted and behavior change by the user may be recorded. Based on the updated user feedback data 2024 and user profile data 2014, the process repeats to identify and generate new and updated challenges to continue improving overall user behavior.

In embodiments, as illustrated in FIG. 1, a system 1000 may be configured to communicate via network 100 with a plurality of user devices associated with a plurality of user devices 10-1 . . . 10-*n* associated with corresponding users of an interactive electronic network. Each user may have one or more associated user devices 10-1, 10-2, to name a few. In embodiments, the plurality of user devices may include the first computer device 10-1, the second computer device 10-2, and a third computer device 10-3 (not shown). In embodiments, the system 1000 may be configured to communicate with one or more third-party information systems 30-1 . . . 30-*n* via network 100. Moreover, in embodiments, the first computer device 10-1, and the second computer device 10-2 may be configured to communicate with the third-party information system(s) 40-1, 40-2, 40-3 via network 100. The first computer device 10-1 and the second computer device 10-2 may be associated with a first user of the plurality of users of the interactive electronic network. For example, the first computer device 10-1 may be the first user's portable computing device (e.g., a smart phone, tablet, phablet, or laptop, to name a few) and the second computer device 10-2 may be the first user's wearable device (e.g., a fitness tracker). The third computer device, in embodiments, may be associated with a second user which is linked via social media, professional affiliation, or the interactive electronic network. For example, the by the system 1000 may associate users (e.g., the first user and the second user) based on one or more of the following: lifestyle information, social information, prior stimulus information, vendor stimulus information, cost information, budget information, user preferences, and/or third-party information (which are described below in more detail, the descriptions of which applying herein). The third-party information, may, in embodiments, include customer information collected by consumer interviews, indirect tracking (e.g., through the use of loyalty programs), and/or by appending sources of customer data to specific customers, to name a few. For example, if the first user and the second user each have a habit of buying the same specific type of shoe once a month, the system 1000, may associate the first user and the second user, regardless of whether the users know each other.

FIG. 1A-1 is an exemplary block diagram of the system 1000 in accordance with exemplary embodiments of the present invention. In embodiments the system 1000 may encourage a selected change in behavior of at least a first user of a plurality of users of an interactive electronic network. The behavior, in embodiments, may be health-related, commercial related, and/or philanthropy related, to name a few.

The system 1000, in embodiments, may include one or more of the following: personal information module 1002 and operatively connected lifestyle database 1002-1, stimulus module 1004 and operatively connected stimulus database 1004-1 and available stimulus database 1004-2, manager module 1006, situation module 1016 and operatively connected user profile database 1016-1, collection module 1008, an optional social module, situation module 1016, and/or training set module 1018. As described above, the system 1000 may be configured to communicate with the first computer device 10-1 and/or the second computer device 10-2 via network 100.

In embodiments, the personal information module 1002 may include one or more processors and a first memory device. The first memory device, in embodiments, may be separate from the personal information module 1002. In those embodiments, the personal information module 1002 may be operatively connected to the first memory device. In embodiments, the personal information module 1002 may further include communications circuitry. The one or more processors, first memory device, and communications circuitry may be similar to processor(s) 703, memory 706, and communications portal 708 respectively described above in connection with FIGS. 2A-2B, the descriptions of which applying herein.

Figure 1B:
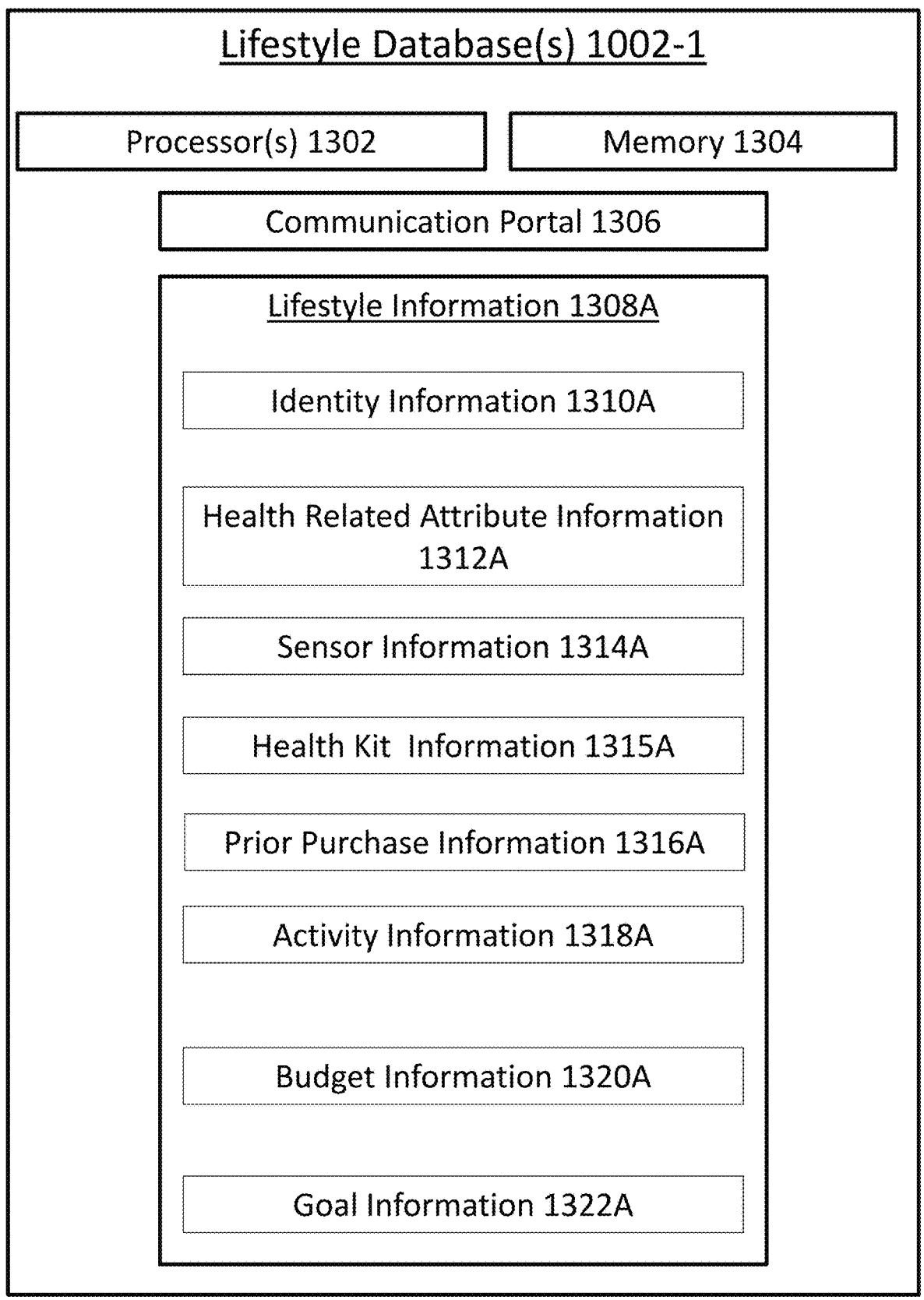
FIG. 1B is an exemplary block diagram of one or more lifestyle databases in accordance with exemplary embodiments of the present invention.
Figure 1C:
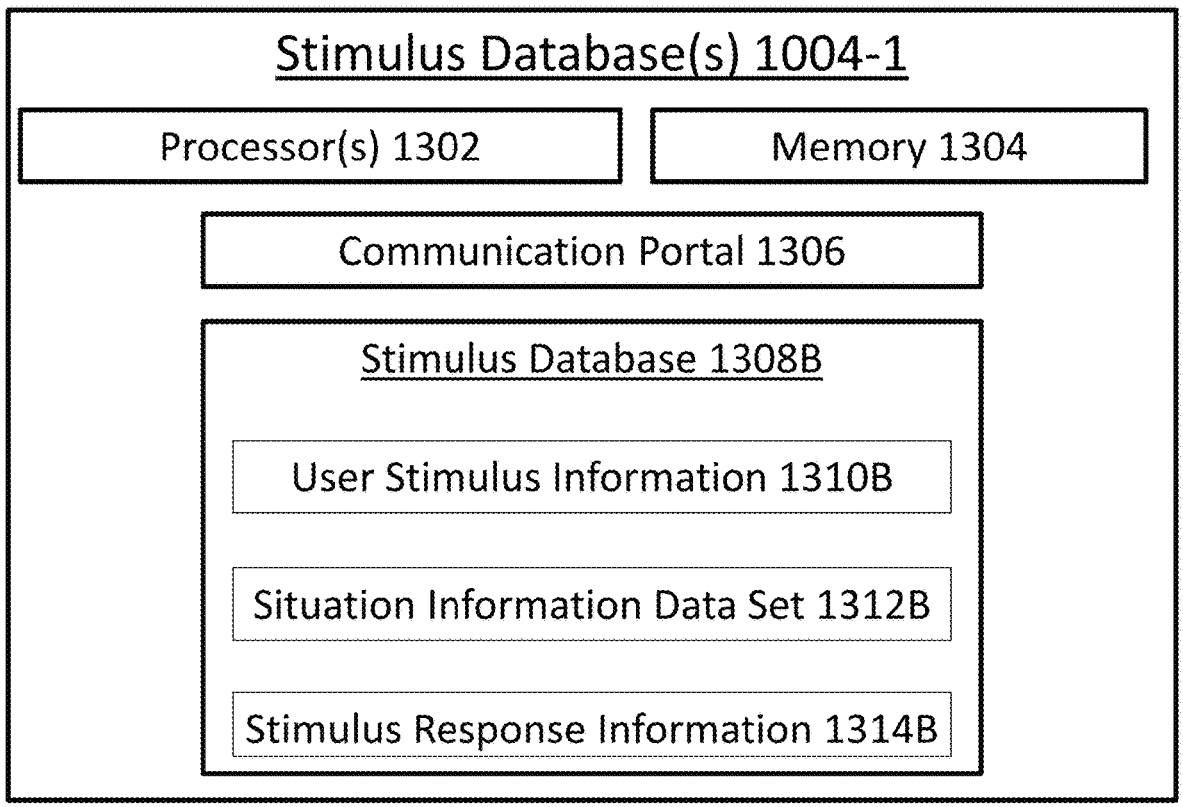
FIG. 1C is an exemplary block diagram of one or more stimulus databases in accordance with exemplary embodiments of the present invention.
Figure 1D:
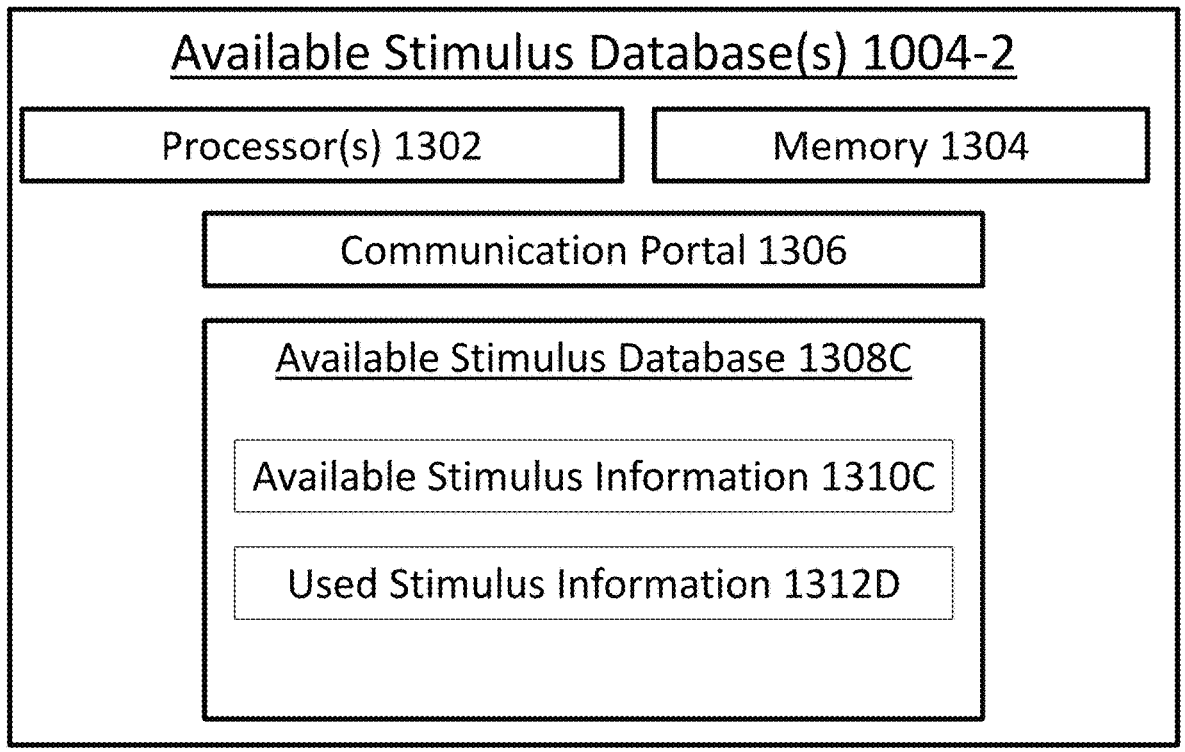
FIG. 1D is an exemplary block diagram of one or more available stimulus databases in accordance with exemplary embodiments of the present invention.
Figure 1E:
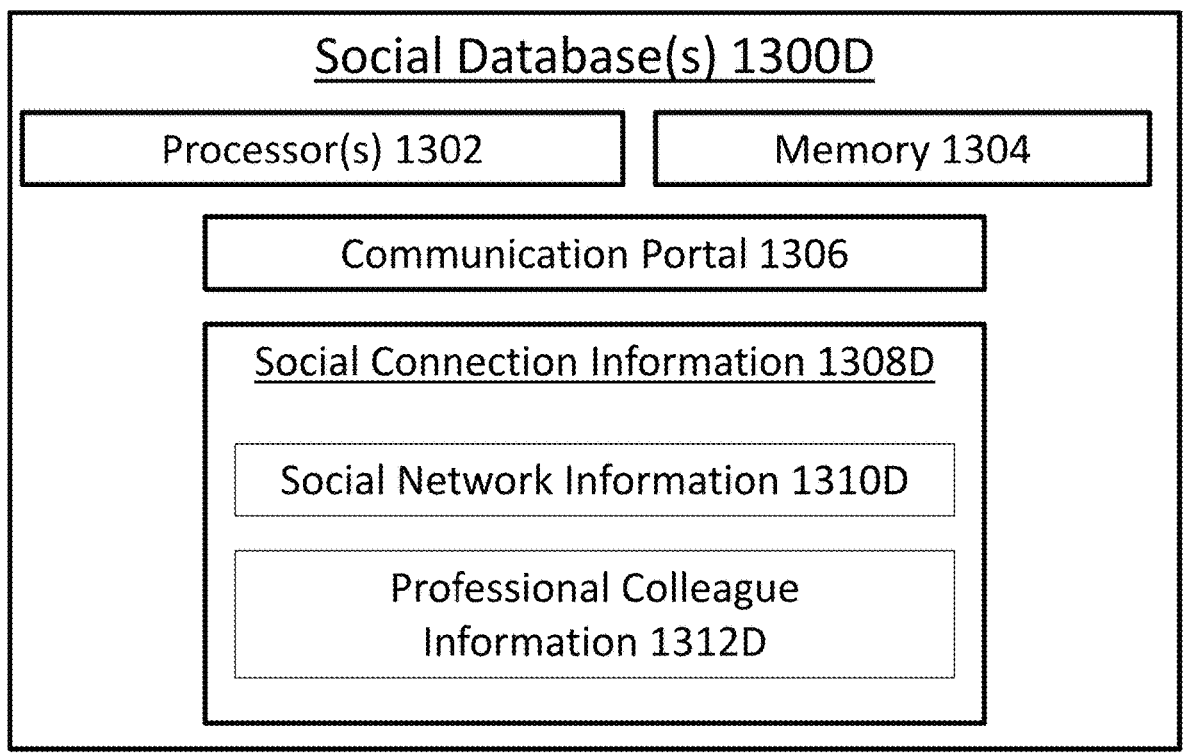
FIG. 1E is an exemplary block diagram of one or more social databases in accordance with exemplary embodiments of the present invention.
Figure 1F:
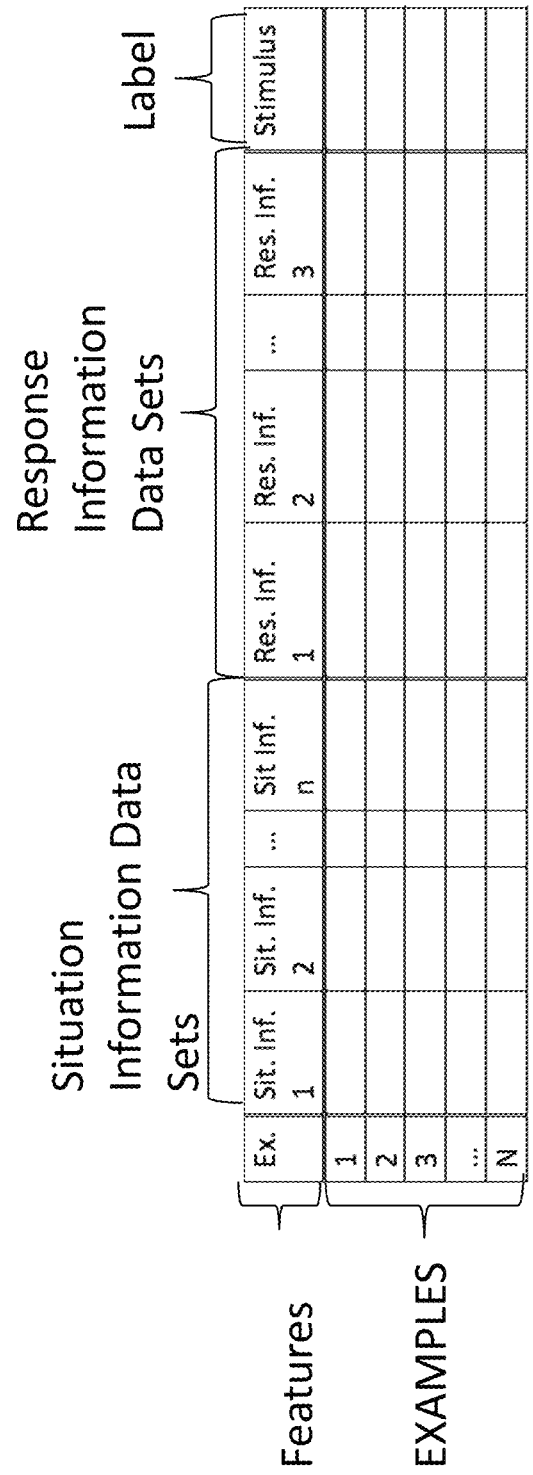
FIG. 1F illustrates exemplary one or more training data sets in accordance with exemplary embodiments of the present invention.

In embodiments, the personal information module 1002, may be configured to receive lifestyle information. Lifestyle information, in embodiments, can include information which relate to a lifestyle of a respective user. The lifestyle of a user, in embodiments, may refer to the user's daily schedule, daily diet, interests, dislikes, current health and/or a combination thereof, to name a few. Referring to FIG. 1B, lifestyle information 1308A may include one or more of the following: identity information 1310A, health-related attribute information 1312A, sensor information 1314A, health kit information 1315A, prior purchaser information 1316A, activity information 1318A, budget information 1320A, and/or goal information 1322A, to name a few.

In embodiments, identify information 1310A generally related to information that identifies a specific user. For example, identity information may include, a name or names associated with a user (e.g., first name, middle name, last name, etc.), a user account associated with a user; an e-mail address associated with a user; biometric data associated with a user (e.g., finger print, palm print, retinal scan, facial recognition scan, audio sampling of user's voice, image of user's face or other body part, etc.); gender information of the user associated with the user device; birth date and/or age of the user associated with the user device; personal data of a user associated with the user device, which is either volunteered by the user or received via access that is consented to by the user; past and/or present location information associated with the user device (usually with a corresponding time stamp); identification information related to a user device associated with a user of the plurality of users (e.g., metadata, device type, etc.), electronic identification (e.g., electronic identification card, electronic signature, etc.), to name a few. In embodiments, identity information may be similar to the identity information described above in connection with FIGS. 4A-B, the description of which applying herein.

Health-related attribute information, in embodiments may be associated with past health conditions, present health conditions, or potential future health risks. For example, health-related information may include chronic health conditions (e.g., osteoporosis, asthma, to name a few). As another example, health-related information may include acute health conditions (e.g., a broken bone, torn muscle, to name a few). In embodiments, health-related information may include actions effecting the health of the user. For example, health-related information may include exercise habits and/or habits effecting the user (e.g., smoking, drug abuse, caffeine intake, hydration, to name a few).

In embodiments, sensor information 1314A may be received from one or more user devices associated with a respective user and may include information derived from readings of the sensor device(s) 704, described above in connection with FIGS. 2A-2B, the description of which applying herein. For example, sensor information may include one or more of the following: accelerometer information generated by at least one accelerometer (e.g., accelerometer(s) 712), light sensor information generated by at least one light sensor (e.g., light sensor(s) 726), compass information generated by at least one compass (e.g., magnetometer(s) 718), wireless association information generated by at least one wireless transceiver (e.g., communication portal 708), proximity information generated by at least one proximity sensor (e.g., proximity sensor(s) 724), gate information (e.g., gate sensor to determine if a user has overate), and/or location information generated by at least one location sensor (e.g., location sensor(s) 710), to name a few.

In embodiments, health-kit information 1315A, such as Apple® Proprietary HealthKit™ 728 and/or Google® Proprietary Google Fit™ 730, may include one or more of health-related data sets as may be available from a user's personal device and/or other health records as authorized by the user to be used by the system, such as: heartbeat information, respiratory information, blood pressure information, body temperature information, height information, weight information. blood sugar information, cardiac information, kidney information, liver information, and/or brain information, to name a few. In embodiments, health-related attribute information 1312A may be similar to the attribute information and/or health condition information described above in connection with FIGS. 4A-B, the description of which applying herein.

Prior purchase information, in embodiments, may be past purchases of a user or purchases associated the user. For example, prior purchase information may include: meal purchases, entertainment purchases (e.g., movies, concerts, shows, television, internet, to name a few), communication purchases (e.g., phone, mail, internet), item purchases (e.g., shoes, clothes, electronics, to name a few), major purchases (e.g., house, cars, boats, to name a few), travel purchases (e.g., vacations, bus pass, subway card, gas, flights, to name a few), and/or miscellaneous purchases (e.g., a pack of gum, candy, cell phone charger, to name a few), to name a few. A purchase may be associated with a user if, for example, the purchase is either for the user (e.g., a gift) or made by the user through a third-party (e.g., a mortgage for a house, a loan for business, a loan for a car, to name a few).

Activity information, in embodiments, may include information that is associated with one or more activities undertaken by a user. For example, activity information may include: daily activities (e.g., eating, walking to work, daily exercise, sleep patterns, to name a few), weekly and/or monthly activities (e.g., intramural sports, weekend activities, to name a few), and/or goal activities (e.g., activities that a user prepares for, for example, a marathon). As an example, activity information may include a user's reservation at a local restaurant. As another example, activity information may include a trip the user is planning on taking to the Bahamas.

In embodiments, budget information 1320A may be associated with an available budget as of a given time for one or more stimulus options. In embodiments, budget information 1320A, may comprise data associated with an original budget for a specified time period, amounts spent during that time period, and an amount left to be spent for the remainder of the time period.

In embodiments, goal information 1322A may be associated with one or more goals related to the respective users. In embodiments, goal information 1322A may be related to changes in a respective user physical and/or mental situation. For example, goal information could include such goals as losing a specific amount of weight, taking a certain number of steps in a day, meditating for at least a specified time period each day, to name a few.

The above lifestyle information, in embodiments, may be used to determine situation information. Situation information, in embodiments, may refer to what the user is experiencing and/or is likely to do. For example, a user who is at work at 11:45 AM may soon want to go to lunch. In this example, based on the time and location information, the situation information may indicate that the user is about to go to lunch. As another example, the user may always eat fast-food for lunch on Fridays, thus on Friday at lunch time, the situation information may indicate that the user is going to drive to the local fast-food restaurant. Situation information, in embodiments, may be based on one or more of the lifestyle information, the time, and/or information received from vendors, to name a few.

In embodiments, the above-mentioned situation information may be generated and/or determined by the situation module 1016. The situation module 1016 may include one or more processors and a sixth memory device. The sixth memory device, in embodiments, may be separate from the situation module 1016. In those embodiments, the situation module 1016 may be operatively connected to the sixth memory device. In embodiments, the situation module 1016 may further include communications circuitry. The one or more processors, second memory device, and communications circuitry may be similar to processor(s) 703, memory 706, and communications portal 708 respectively described above in connection with FIGS. 2A-2B, the descriptions of which applying herein.

In embodiments, the stimulus module 1004 may include one or more processors and a second memory device. The second memory device, in embodiments, may be separate from the stimulus module 1004. In those embodiments, the stimulus module 1004 may be operatively connected to the second memory device. In embodiments, the stimulus module 1004 may further include communications circuitry. The one or more processors, second memory device, and communications circuitry may be similar to processor(s) 703, memory 706, and communications portal 708 respectively described above in connection with FIGS. 2A-2B, the descriptions of which applying herein.

The stimulus module 1004, in embodiments, may be configured to generate a plurality of stimulus options. In embodiments, the generated plurality of stimulus options may be tailored to a specific user. The plurality of stimulus options, in embodiments, may be generated based on one or more of the following: the lifestyle information, vendor stimulus information associated with available vendor stimulus offers, cost information associated with a cost of the plurality of stimulus options, budget information associated with an available budget for one or more stimulus options, prior stimulus options, vendor information (e.g., store hours, store locations, products and/or services offered by the vendor, to name a few) and/or the aforementioned situation information. The plurality of stimulus options, in embodiments, may be similar to the stimulus options described above, the description of which applying herein.

In embodiments, the manager module 1006 may include one or more processors and a third memory device. The third memory device, in embodiments, may be separate from the manager module 1006. In those embodiments, the manager module 1006 may be operatively connected to the third memory device. In embodiments, the manager module 1006 may further include communications circuitry. The one or more processors, third memory device, and communications circuitry may be similar to processor(s) 703, memory 706, and communications portal 708 respectively described above in connection with FIGS. 2A-2B, the descriptions of which applying herein.

The manager module 1006, in embodiments, may be configured to select a first stimulus from the plurality of stimulus options. In embodiments, the manager module may otherwise provide the first stimulus. The selection of the stimulus, in embodiments, may be based on at least one of: the aforementioned situation information, the prior stimulus information, the prior purchase information, the activity information, the lifestyle information, vendor stimulus information associated with available vendor stimulus offers, and/or cost information associated with a cost of the plurality of stimulus options, to name a few. The time associated with the budget information may be indicated by a timestamp which may indicate the time at which the budget was calculated. The cost information, in embodiments, may refer to the cost administrators of the system 1000 may pay to provide the stimulus. The budget information, in embodiments, may refer to the amount of money the administrators of system 1000 may be able to pay for the stimulus. In embodiments, the selected stimulus may be further based on user preferences. For example, a user may want to change a specific behavior, for example, eating habits. If the user has selected this specific behavior change, then the managing module 1006 may select stimuli that are tailored to the user's specific request. In embodiments, the user may select from a range of behaviors to change.

The manager module 1006, in embodiments, may be configured to select a time to send the selected stimulus to a particular user. The selected time, may refer to the time at which the managing module 1006 may send the selected stimulus to a device associated with the user to receive the selected stimulus. This selection may be based on at least one of: the aforementioned situation information, the prior stimulus information, the prior purchase information, the activity information, the lifestyle information, vendor stimulus information associated with available vendor stimulus offers and/or cost information associated with a cost of the plurality of stimulus options, to name a few. In embodiments, the time may be selected based on user preferences. For example, the user may only want to receive a stimulus during a certain point of the day or time range within a day, week, month, season or year, to name a few.

The manager module 1006, in embodiments, may be configured to send the selected stimulus to an electronic device associated with the aforementioned particular user. In embodiments, the manager module 1006 may transmit a selected stimulus at the selected time to a device associated with a user the selected stimulus is provided for.

In embodiments, the collection module 1008 may include one or more processors and a fourth memory device. The fourth memory device, in embodiments, may be separate from the collection module 1008. In those embodiments, the collection module 1008 may be operatively connected to the fourth memory device. In embodiments, the collection module 1008 may further include communications circuitry. The one or more processors, fourth memory device, and communications circuitry may be similar to processor(s) 703, memory 706, and communications portal 708 respectively described above in connection with FIGS. 2A-2B, the descriptions of which applying herein.

The collection module 1008, in embodiments, may be configured to updated information and/or collect stimulus response information. Stimulus response information may include the effect a stimulus had on a particular user. For example, if the system 1000 is trying to get the user to eat healthier, the system 1000 may send stimuli that give coupons for healthy meals. If those coupons are used, the collection module 1008 may receive information indicating that the stimulus used resulted in a positive result—e.g., the user used the coupon for a healthy meal which indicates the user had a healthy meal. The stimulus response information may be stored such that the collection module 1008 may be used by the manager module 1006 to determine what kind of stimulus has worked in the past.

In embodiments, the social module 1010 may include one or more processors and a fifth memory device. In embodiments, the social module 1010 may further include communications circuitry. The one or more processors, fifth memory device, and communications circuitry may be similar to processor(s) 703, memory 706, and communications portal 708 respectively described above in connection with FIGS. 2A-2B, the descriptions of which applying herein.

In embodiments, the social module 1010 may include information related to a user's social media accounts. For example, the social module 1010 may include social information that includes social media friends, followers, connections, and/or professional colleagues. For example, the social information may include a second user that is a social network connection of the first user. The social information may also include information related to social media, which may include, a user's likes, dislikes, opinions, where the user has checked in, where the user would like to go, and/or a user's employment history, to name a few. The information collected by the social module 1010 may be used by the manager module 1006 to select a stimulus.

In embodiments, the training set module 1018 may include one or more processors and a seventh memory device. The seventh memory device, in embodiments, may be separate from the training set module 1018. In those embodiments, the training set module 1018 may be operatively connected to the seventh memory device. In embodiments, the training set module 1018 may further include communications circuitry. The one or more processors, seventh memory device, and communications circuitry may be similar to processor(s) 703, memory 706, and communications portal 708 respectively described above in connection with FIGS. 2A-2B, the descriptions of which applying herein.

In embodiments, the personal information module 1002, stimulus module 1004, manager module 1006, collection module 1008, and/or social module 1010 may be operatively connected one another. In embodiments, the personal information module 1002, stimulus module 1004, manager module 1006, collection module 1008, and/or social module 1010 may be one or more electronic devices.

The system 1000, may communicate with one or more electronic devices associated with one or more users of an interactive electronic network via a network. In embodiments, the system 1000 may communicate and/or utilize one or more microservices. Referring to FIG. 1A, the system 1000 may communicate with first computer device 10-1 and second computer device 10-2 via network 100. In embodiments, the first computer device 10-1 may be associated with a first user. In embodiments the second computer device 10-2 may be associated with a first user. In embodiments, both the first computer device 10-1 and the second computer device 10-2 may be associated with a first user. In embodiments, the first computer device 10-1 and the second computer device 10-2 may be associated with a first user and a third computer device (not shown) may be associated with a social media connection of first user. The third computer device may be similar to the first computer device 10-1 and the second computer device 10-2, the descriptions of which applying herein. The exemplary block diagram shown in FIG. 1A-1 may be similar to the exemplary block diagram described in connection with FIG. 2A, the description of which applying herein (e.g., the computing device 700 may be similar to system 1000, personal user device 10-1 may be similar to first computer device 10-1, and optional second personal user device 10-1A may be similar to second computer device 10-2).

Figure 13A:
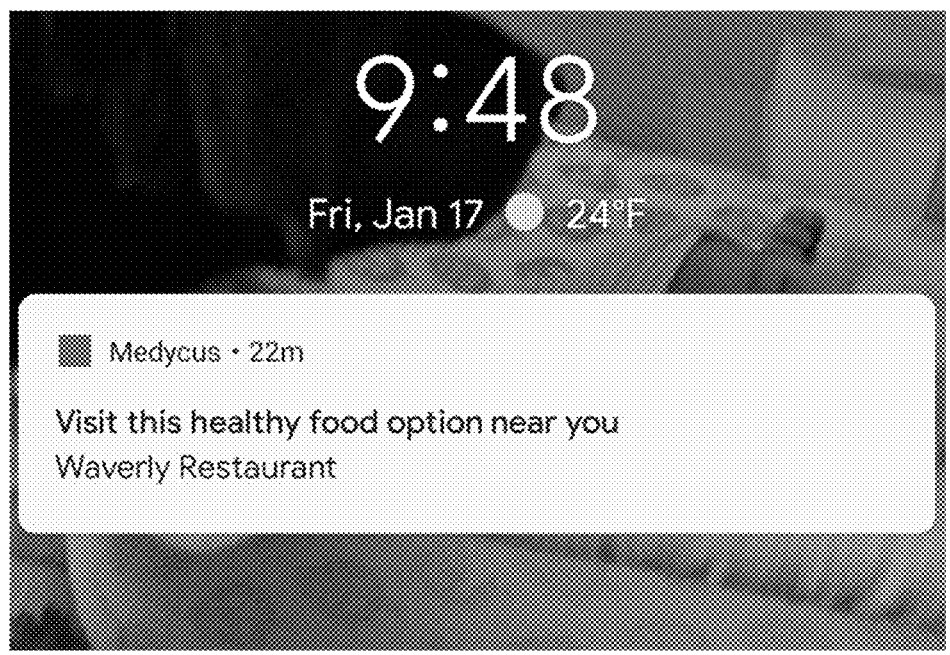
FIGS. 13A-C are illustrative screenshots of exemplary graphical user interfaces in accordance with exemplary embodiments of the present invention.
Figure 13B:
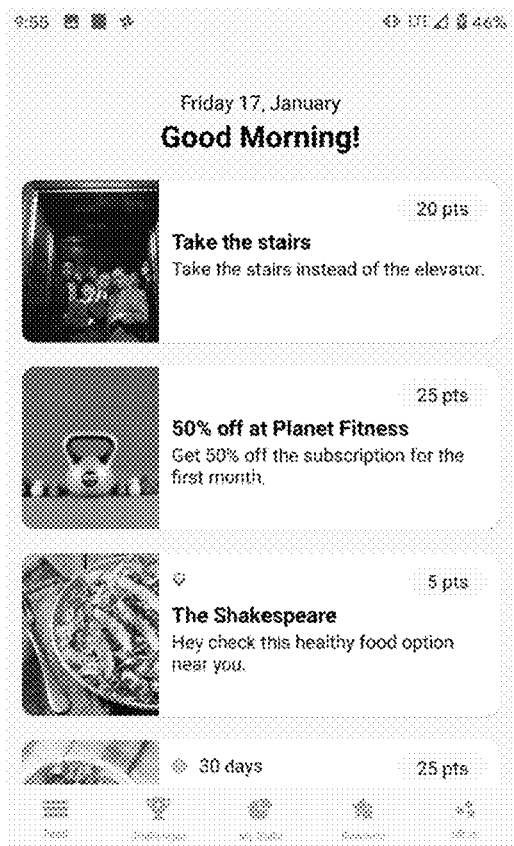
Figure 13C:
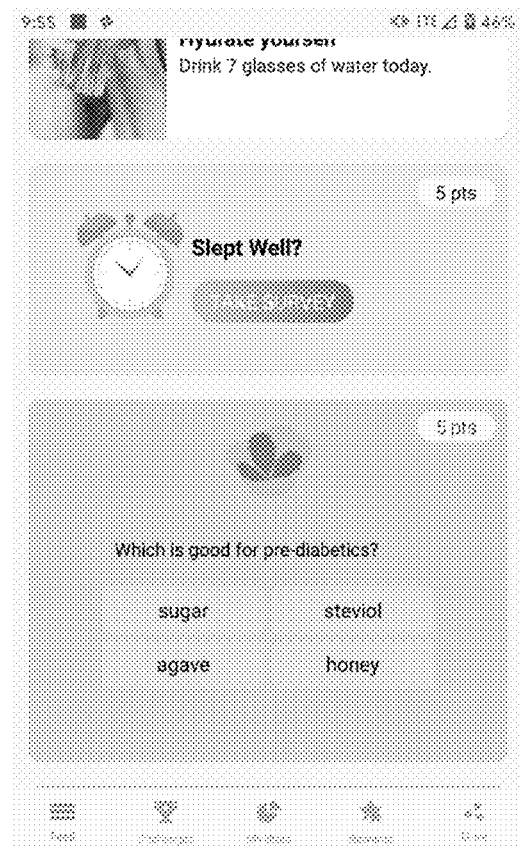
Figures 1, 13D:
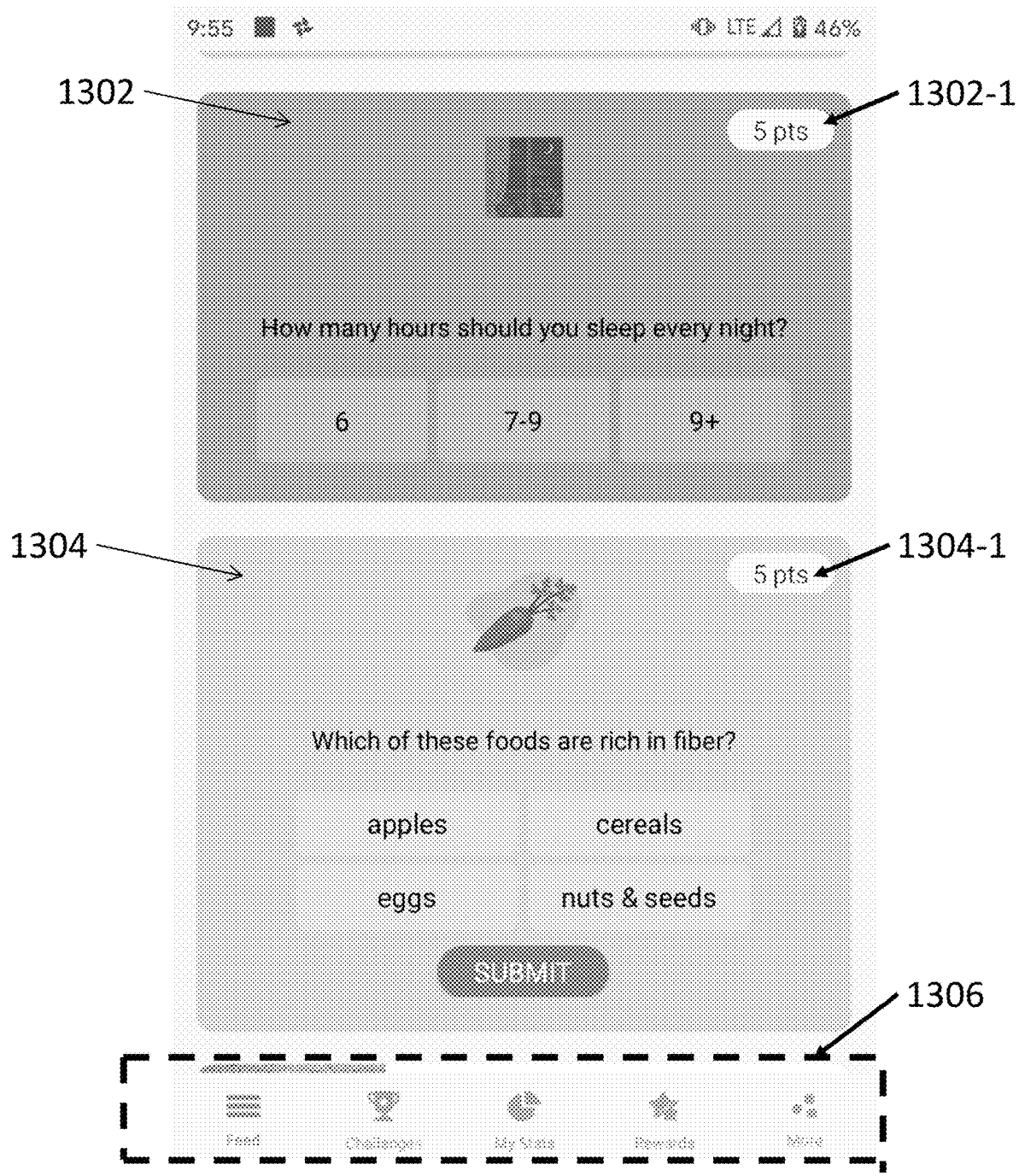
Figures 2, 13D:
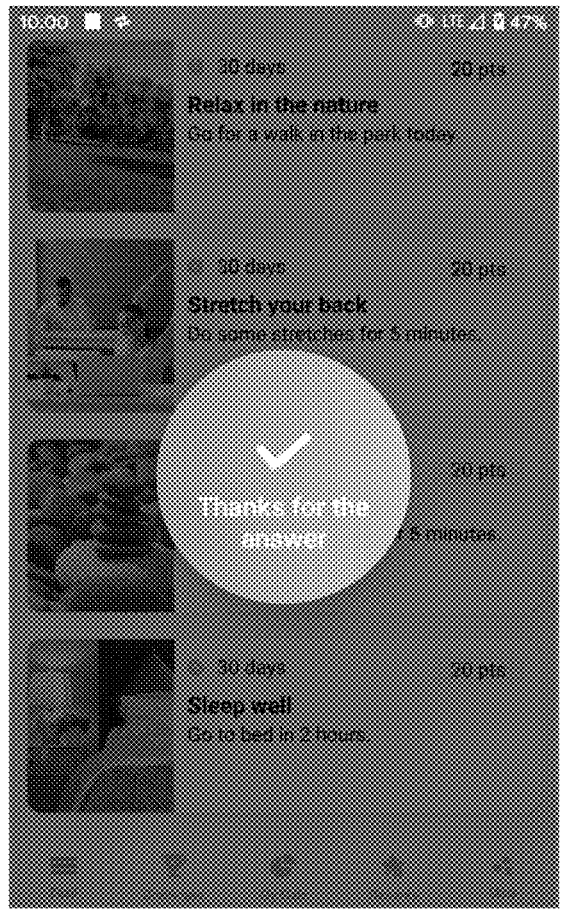

In embodiments, the system 1000, as described above and herein, may select and send a stimulus to one or more of the first computer device 10-1 and the second computer device 10-2, the stimulus being sent for the purpose of encouraging a selected change. This process, referring to FIG. 10-A, may, in embodiments, begin with the first user either creating an account with a mobile application. The process of creating an account, in embodiments, may include the first user inputting and/or verifying user login credentials which may include one or more of the following: username, password, e-mail address, phone number, one or more answers to security questions, biometric data, and/or a combination thereof, to name a few. With an account created, in embodiments, the first user may login to the mobile application using the aforementioned user login credentials. In embodiments, once the first user has logged into the mobile application on the first computer device 10-1, the first computer device 10-1 may display a graphical user interface. For example, the graphical user interface may be a display of the first user's feed (e.g., feed 1306-1 shown in connection with FIGS. 13D-1 and 13E) as shown in the illustrative screenshots of FIGS. 13B, 13C, and 13F. Referring to FIG. 13D-1, the feed 1306-1 may include one or more preloaded stimuli. The one or more preloaded stimuli, may, in embodiments, offer points and/or rewards for completing one or more surveys. The one or more surveys, in embodiments, may be designed to gather lifestyle information from the first user. For example, First Survey 1302 may offer the first user a First Reward 1302-1 of five points for answering the question "How many hours should you sleep every night?". This question, in embodiments, may be designed to gather information regarding the first user's knowledge of a healthier lifestyle and/or to gather information regarding the first user's preferences with regards to sleep. As another example, Second Survey 1304 may offer the first user a Second Reward 1304-1 of five points for answering the question "Which of these foods are rich in fiber". If, for example, the first user does not answer correctly, the system 1000 may use that lack of knowledge to generate stimuli that teach healthier habits. When a survey is answered, in embodiments, the system 1000 may generate and send a notification, as shown in connection with the illustrative screenshot of FIG. 13D-2. In embodiments, a survey may be presented to the user as a quiz.

This process, referring to FIG. 10-A, in embodiments, may begin and/or continue with a step S1002. At step S1002, in embodiments, the personal information module receives the aforementioned lifestyle information regarding the lifestyle of the first user. In embodiments, as discussed above, lifestyle information may include one or more of the following: identity information, health-related attribute information, health-related information, sensor information, prior purchaser information, budget information, and/or activity information, to name a few.

In embodiments, the lifestyle information may be received, received after a request is sent by the system 1000, collected, and/or obtained from one or more sources of information. In embodiments, the lifestyle information may be received from the first computer device 10-1, the second computer device 10-2, the aforementioned third computer device, one or more vendor databases, the aforementioned social information, one or more healthcare providers, one or more insurance companies, and/or one or more public sources of information, including government institutions and internet search engines. For example, the identity information and health-related attribute information by be received from the first computer device 10-1 via network 100. The first user may type in their name, e-mail address, height, weight and age in response to a prompt by a mobile application associated with the system 1000 or from another mobile application associated with the first user and the first computer device 10-1. As another example, the second computer device 10-2 may provide health-related attribute information to the system 1000. The second computer device 10-2, may include sensors that are configured to record one or more of the following: heartbeat information of the first user, respiratory information of the first user, blood pressure information of the first user, body temperature information of the first user, height information of the first user, and/or weight information of the first user, to name a few. This information, which may be collected via sensor device(s) 704(A) of the second computer device 10-2, may be sent from the second computer device 10-2 to the personal information module 1002 via the system 1000. In embodiments, the second computer device 10-2 may send lifestyle information to either, or both, the first computing device 10-1 and the personal information module 1002. In embodiments, if the second computer device 10-2 only sends information to the first computer device 10-1, the first computer device 10-1 may send information collected by the second computer device 10-2 to the personal information module 1002 via the system 1000. This may be the case, for example, if the second computer device 10-2 is operatively connected to the system 1000 via the first computer device 10-1. As yet another example, prior purchase information may be obtained, collected, and/or received from third-party databases. For example, a loyalty program with a particular store may gather prior purchase information relating to the first user. This prior purchase information may be obtained, collected, and/or received by the system 1000. As yet another example, personal information may be obtained, collected, and/or received from one or more healthcare providers and/or insurance providers.

Figure 13E:
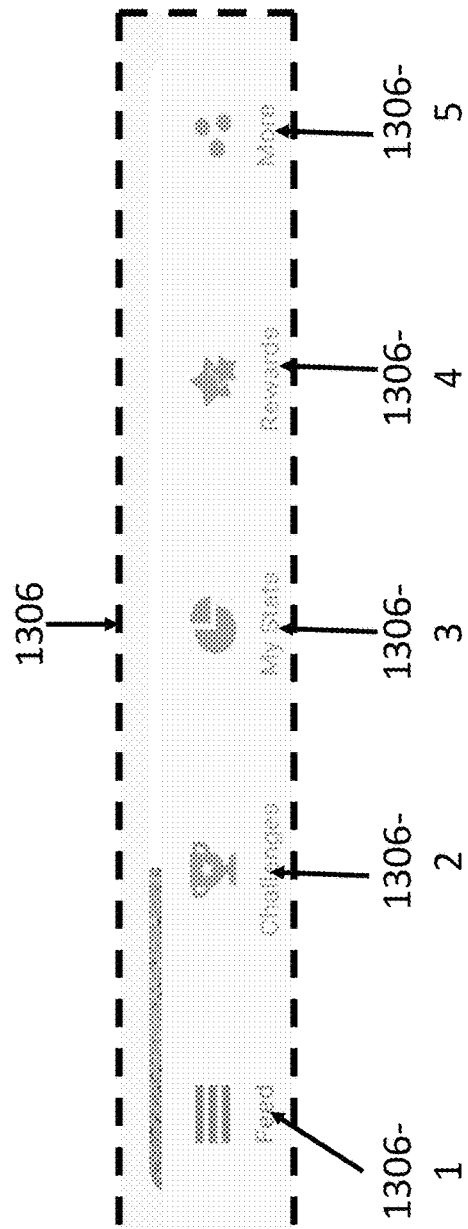
Figure 13F:
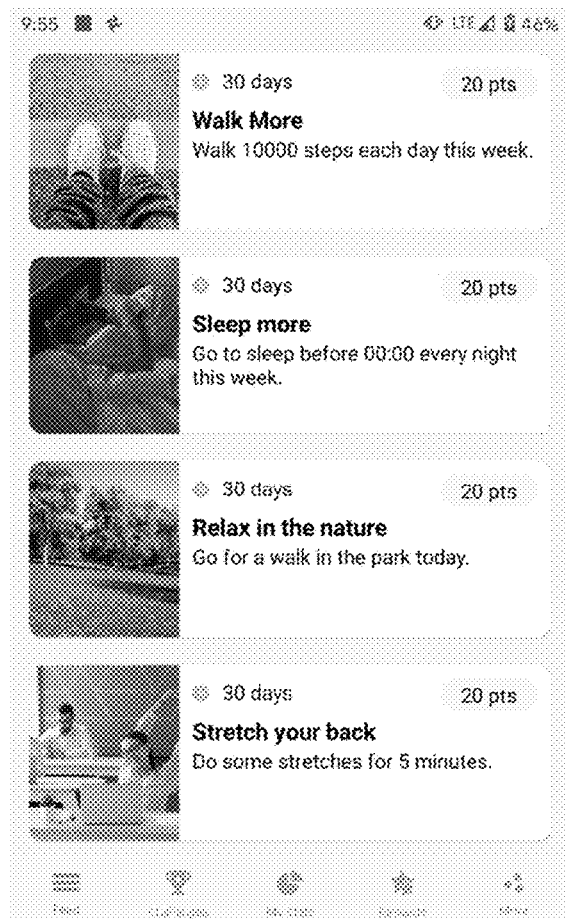

The inputted lifestyle information in embodiments, may be viewable on the aforementioned mobile application. For example, referring to FIG. 13L, the first user (e.g., "Bob Smith") may be able to view one or more of the following: the first user's age, weight, height, gender, employer, insurer, and/or e-mail address to name a few. The data collected and/or displayed by the system 1000, in embodiments, may be public (e.g., any user can view, all collected data can be used), semi-private (e.g., only some users can view, only some of the collected data can be used), and/or private (e.g., no other users can see the data, only some and/or none of the collected data can be used). For example, as shown in FIG. 13I, the first user may select which kind of data may be shared. As shown in the illustrative screenshot of FIG. 13I, in embodiments, the first user may select to share the collected and/or inputted health data (e.g., health-related attribute information, health-related information, sensor information). In embodiments, the first user may select to share the collected and/or inputted lifestyle data (e.g., identity information, health-related attribute information, health-related information, sensor information, prior purchaser information, budget information, and/or activity information, to name a few). In embodiments, the mobile application may have more categories to select to share and/or consolidate the categories into one. The first user, in embodiments, may also be able to view the inputted and/or collected data over a period of time (e.g., last month, last year, and/or all data, as shown in connection with FIG. 13I, to name a few) and whether that data was shared.

In embodiments, referring to FIG. 13D-1, the first user may be able to interact with the mobile application using the Menu 1306. Referring to FIG. 13E, the Menu 1306 may include one or more of the following: Feed 1306-1, My Challenges 1306-2, My Stats 1306-3, My Rewards 1306-4; and/or More 1306-5, to name a few. The Feed 1306-1 may be similar to the illustrative screenshots of FIGS. 13B, 13C, 13D-1, and/or 13F, to name a few. In embodiments, the first user may select My Challenges 1306-2 on Menu 1306.

Figure 13G:
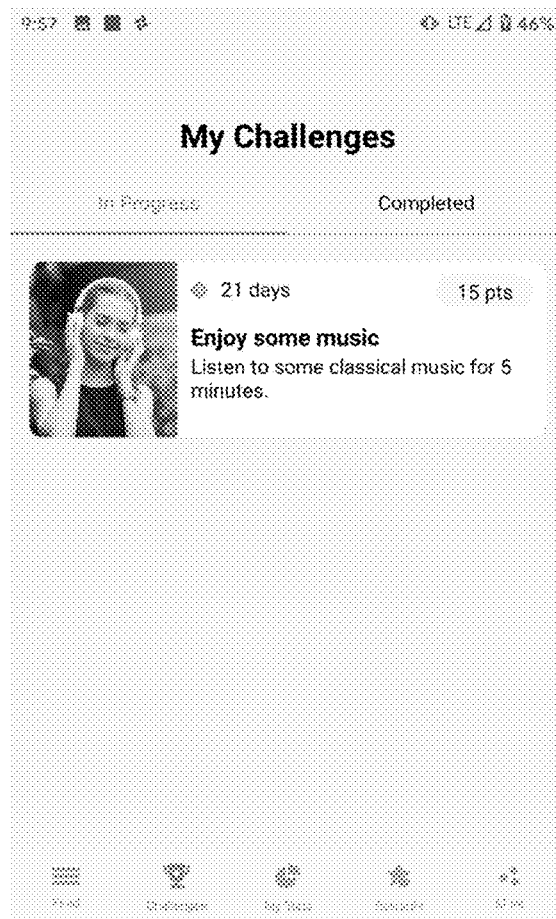

Referring to FIG. 13G, My Challenges 1306-2, when selected, may display the first user's stimuli (e.g., challenges) that are in progress and/or have been completed. Each challenge (e.g., stimulus) listed with the My Challenges 1306-2 may include information that may include one or more of the following: the challenge title, information regarding what the challenge is and how to complete it, a deadline for completing the challenge, the amount of points and/or reward associated with the challenge, when the challenge was accepted, and/or when the challenge was completed, to name a few. For example, referring to FIG. 13G, the first user has one exemplary challenge in progress. The exemplary challenge in progress "Enjoy Some Music" (the title), as shown in FIG. 13G, may be to "Listen to some classical music for 5 minutes" (the challenge information) within 21 days (the deadline) for 15 points (the reward). In embodiments, the five minutes of classical music may be provided by the system 1000 and/or a third-party via the system 1000.

Figure 13H:
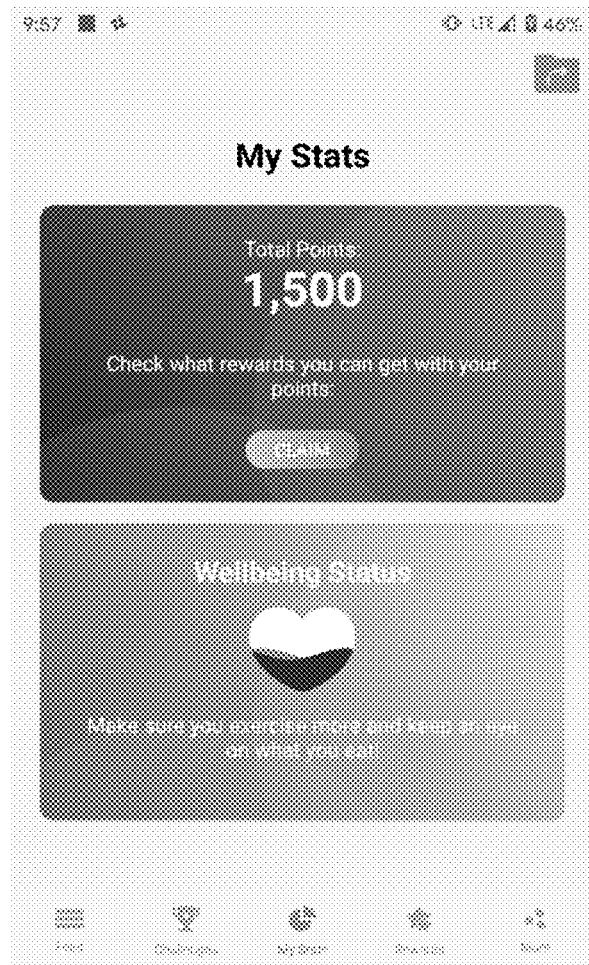
Figure 13I:
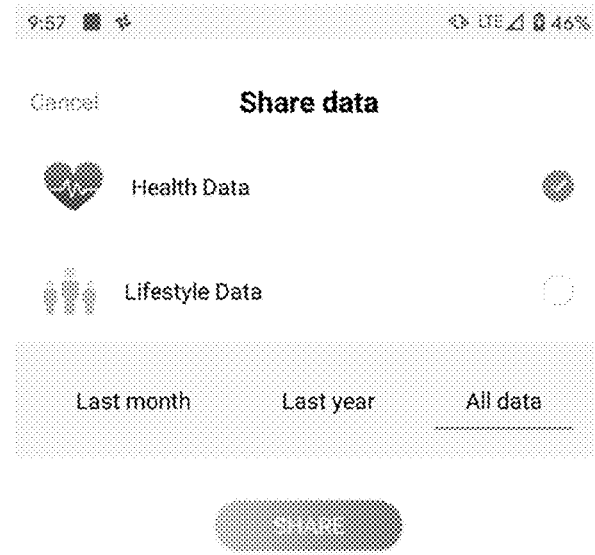

Referring to FIG. 13H, the first user may be able to access and/or view collected, accumulated, and/or inputted statistics under the My Stats 1306-3 tab. The My Stats 1306-3 tab may include the amount of points accumulated by the first user, a well-being status, and/or the first user's lifestyle information, to name a few. The well-being status, in embodiments, may refer to a calculation performed by the system 1000 that measures the health (e.g., mental, physical, and/or spiritual, to name a few) of the first user. In embodiments, the well-being status calculation may be based on one or more of the following: Physical Health (e.g., body mass index, heart rate, blood pressure, to name a few), Mental Health (e.g., sleep patterns, stress patterns (e.g., measured by blood pressure, heartrate, and/or sleep), to name a few), Education (e.g., information collected with identity information 1310A and/or third-party information from social media, to name a few), Material Living Standards (e.g., lifestyle information 1308, prior purchase information 1316A, information collected through answers to one or more preloaded stimuli—e.g., surveys, to name a few), activity information 1318A, and/or social connections (e.g., marital status, social and/or professional information associated with the first user input by the user and/or collected via social media, to name a few), to name a few. For example, if the first user has a healthy body mass index score, is active, and has friends, the first user's well-being score may be high. As another example, if the first user has a high body mass index score, is not active, makes a lot of purchases, and does not have friends, the first user's well-being score may be low. As another example, if the first user has a healthy body mass index score, is active, but has no friends, the first user's well-being score may be medium. The well-being score, in embodiments, may be a sliding scale and/or a point total, to name a few.

Figure 13J:
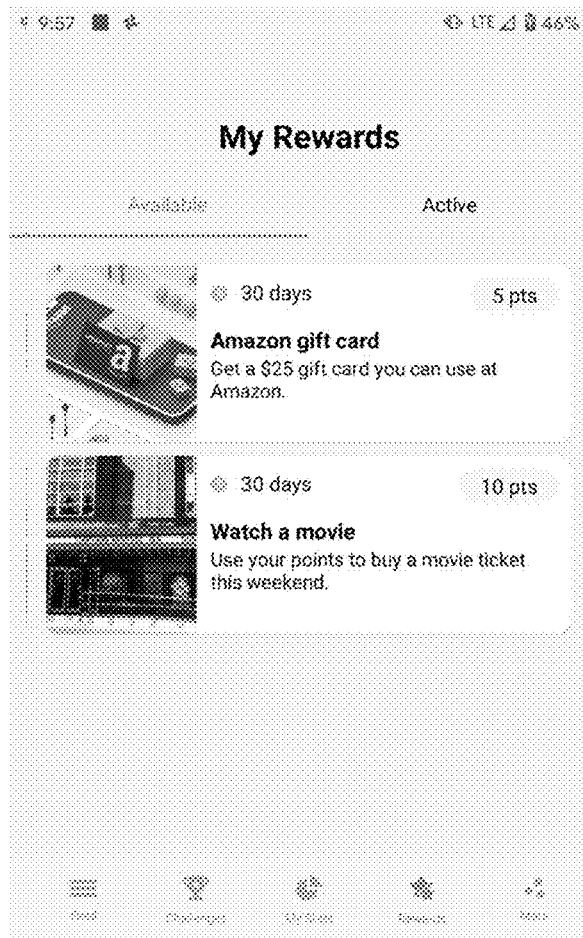
Figure 13K:
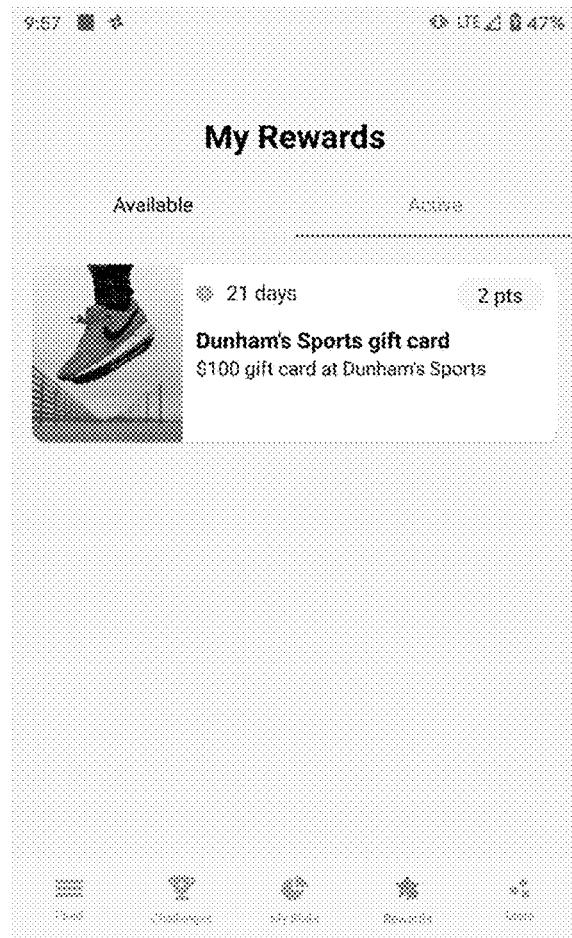

In embodiments, referring to FIGS. 13J and 13K, the first user may be able to access and/or view the first user's rewards by selecting the My Rewards 1306-4 tab on the Menu 1306. The My Rewards 1306-4 tab may include available rewards (shown in FIG. 13J) and/or active rewards (shown in FIG. 13K). In embodiments, available rewards may refer to rewards the first user has already earned and can use. In embodiments, active rewards may refer to rewards the first user is in the process of earning. In embodiments, active rewards may refer to rewards that are currently being used by the first user.

In embodiments, referring to FIG. 13L, the user may be able to access and/or view additional information by selecting the More 1306-5 tab on the Menu 1306. For example, the More 1306-5 tab may display information associated with the user which may include one or more of the following: name, nickname, weight, height, gender, age, goals, employer, insurer, contact information, friends, and/or nearby friends, to name a few. In embodiments, the user may be able to edit and/or confirm settings and/or privacy settings associated with the first user's account under the More 1306-5 tab.

In embodiments, as shown in FIG. 1A-2, the first computer device 1012 may include system 1000. Where the first computer device 1012 includes the system 1000, in embodiments, the system 1000 may operate in a similar manner as discussed in connection with FIG. 1A-1, however, the information obtained from the first computer device 1012 may be obtained internally by the system 1000. For example, the personal information module 1002 may receive lifestyle information from one or more of the following: sensor device(s) 704, memory 706, and/or input circuitry 772, to name a few. Input circuitry 772, in embodiments, may include circuitry allowing or enabling one or more users to input information into the first computer device 1012. Information obtained or stored by the first computer device (e.g., via sensor device(s) 704, memory 706, and/or input circuitry 772, to name a few) may be transmitted to personal information module 1002 and/or stored in lifestyle database 1002-1. As another example, stimulus response information may be received by the collection module 1008 from one or more of the following: sensor device(s) 704, memory 706, and/or input circuitry 772, to name a few.

Moreover, where the first computer device 1012 includes the system 1000, in embodiments, the system 1000 may transmit selected stimuli internally to the display 774 of the first computer device 1012. For example, stimuli selected by the system 1000 and sent to the first computer device 1012, by the collection module 1008, may instead be transmitted from the collection module 1008 to display 774 of the first computer device 1012. The display 774 may be similar to the display screen 800 of personal user device 10-1, described in connection with FIGS. 8A-8C, the description of which applying herein. Continuing the example, the selected stimuli may be received by the display 774 and displayed on display 774.

The process described in connection with FIG. 10-A may continue at a step S1004. At step S1004, in embodiments, the lifestyle information is stored in memory of the personal information module. In embodiments, the lifestyle information is stored into one or more lifestyle information databases. The one or more lifestyle databases, in embodiments, may be stored on the first memory device. A database, as described herein may be similar to memory 700-3 described above.

As step S1006 (which may be optional), in embodiments, the system 1000 may receive, at a social module, social and/or professional information associated with the first user. In embodiments, the social information may be from a social network such as Facebook. In embodiments, professional information may be from a professional network such as LinkedIn. Other social and/or professional networks may also be used to supply social and/or professional information related to the user and or the user's social and/or professional connections. In such embodiments, the social and/or professional information may be sorted in memory operatively connected to the social module.

At step S1010, in embodiments, the system 1000 may filter, by a situation module, the lifestyle information based at least on time, to provide a situation data set. In embodiments, as mentioned above, the lifestyle information 1308, which may be stored in the lifestyle database 1002, may include lifestyle information associated with one or more users, such as the first user, which, for example, may include: identity information 1310A associated with an identity of the first user; health-related attribute information 1312A associated with at least one health-related attribute of the first user; health kit information 1315A associated with health conditions and/or actions effecting health of the first user; sensor information 1314A associated with one or more computer devices associated with one or more users, such as the first user; prior purchase information 1316A associated with purchases made by and/or associated with the first user; activity information 1318A indicative of activities engaged in by and/or associated with the first user within; budget information 1320A associated with an available budget for use in providing stimulus to the first user; and goal information 1322A associated with the selected change in behavior, to name a few. Time, may, in embodiments, be used to filter the lifestyle information to provide a situation data set. For example, if the activity information associated with the first user indicates a workout within a predetermined amount of time, e.g., within the past hour, the situation module may filter out exercise related activities.

At step S1012, in embodiments, the system 1000 may generate, by a stimulus module, a stimulus condition database including stimulus condition information. In embodiments, the stimulus condition database may refer to the training data set 1018-1 as described in connection with FIG. 1A-1 and FIG. 1A-2, the description of which applying herein. At step S1014, system 1000 may store, by the stimulus module, the stimulus database.

At step S1016, in embodiments, a manager module in system 1000 may select a first stimulus to be provided to the first user based at least on the situation data set, the stimulus information, and the stimulus condition information. In embodiments, the first stimulus may be selected based on the training data set 1018-1 of the system 1000, information associated with the first user from the stimulus database 1004-1, information associated with the first user from the lifestyle database 1002-1, information associated with the first user from the user profile database 1016-1, and/or information associated with the first user from the available stimulus database 1004-2, to name a few. For example, if the first user is a 40 year old male that would like to eat healthy (information stored on the lifestyle database 1002-1 and/or the user profile database 1016-1), the system 1000 may use the training data set 1018-1 being processed by the machine learning algorithm 1006-1 to determine a stimulus for the first user based on the first user's information (40 year old male) and the first user's goal (eat healthy). Continuing the example, the pool of stimuli (stored on the stimulus database 1004-1) that can be selected may be narrowed by the machine learning algorithm 1006 using the available stimulus database 1004-2 (e.g., the available stimulus database 1004-2 may indicate which stimuli are available for use with the first user). A more detailed description of generating a data set (e.g., training data set 1018-1) to be input into and/or to train the machine learning algorithm 1016-1 is located below in connection with the description of FIGS. 21A-21M, the descriptions of which applying herein. The machine learning algorithm 1016-1, in embodiments, may need to be trained using information associated with the first user (e.g., lifestyle information, stimulus information, etc., to name a few). An exemplary process for training the machine learning algorithm 1016-1 and/or a machine learning algorithm in accordance with exemplary embodiments of the present invention is described in connection with FIG. 16 (e.g., steps S1604-S1610, step S1612, etc.).

Figure 16:
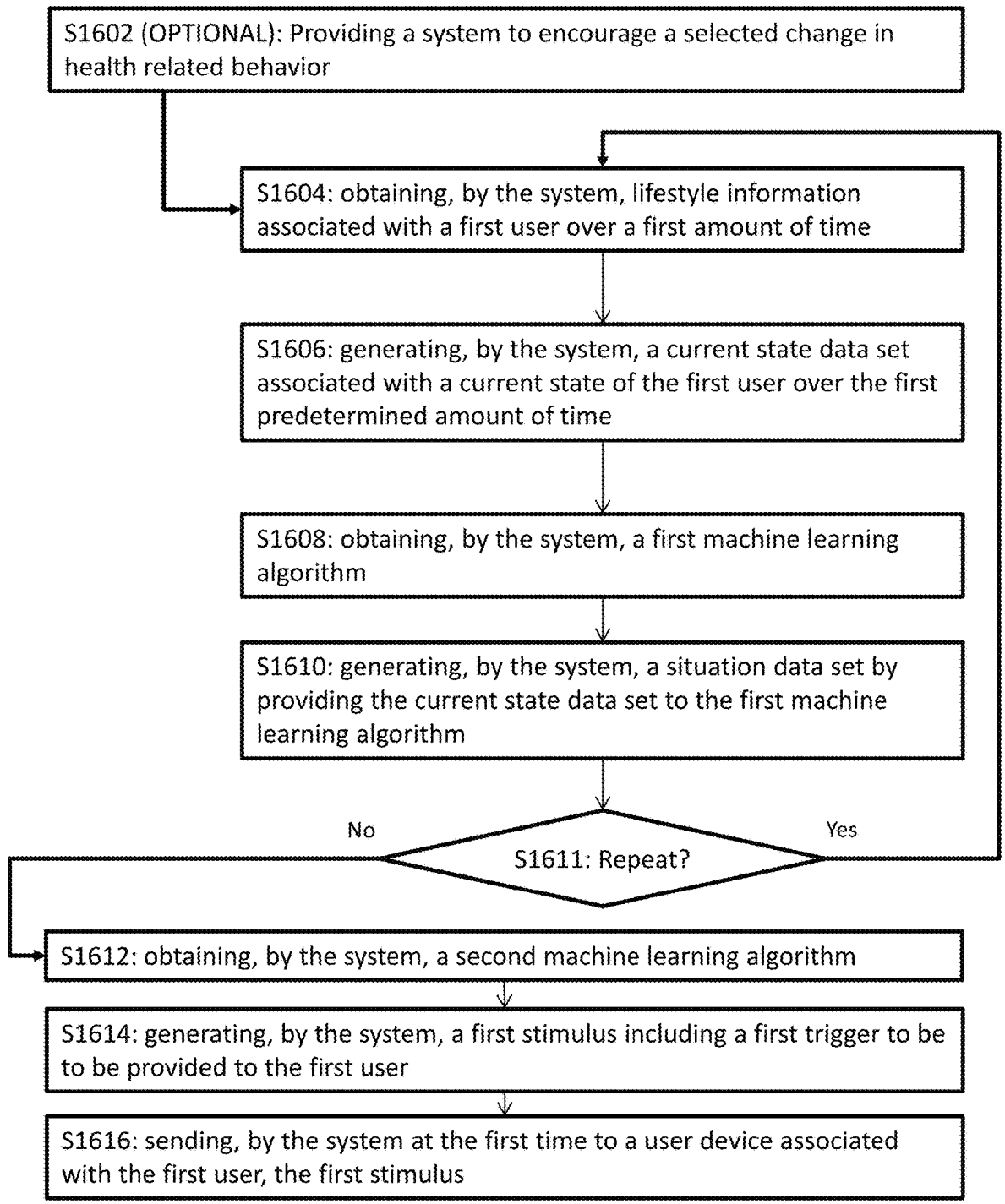
FIG. 16 is an exemplary flow chart of a process for providing a stimulus to a personal user device in accordance with exemplary embodiments of the present invention.

Referring to FIG. 16, the process, in embodiments, may optionally begin with step S1602. At step S1602, in embodiments, a system (e.g., the system 1000 and/or the system 1000-A) to encourage a selected change in health-related behavior is provided. The system provided may be the system 1000 described above in connection with FIGS. 1, and 1A-1F and/or the system 1000-A described in connection with FIGS. 17 and 17A-G, the descriptions of each applying herein. For example, the system may include (as shown in connection with FIG. 17, a user manager 1702 (which may be operable to manage one or more of the modules of the system 1000-A and/or which may be similar to manager module 1006 described above in connection with FIGS. 1A-1 and 1A-2, the description of which applies herein), memory 1704 (which may be similar to the one or more memory devices operably connected to the system 1000 described above in connection with FIGS. 1A-1 and 1A-2, the description of which applying herein), one or more modules (e.g., first module 1708-A, second module 1708-B, third module 1708-C . . . N-module 1706-N, to name a few), and/or a function library 1708 (e.g., one or more modules which utilize data sets provided by the one or more modules to select a stimulus and trigger), to name a few. As another example, the system may be operatively connected to one or more memory devices. The one or more memory devices, in embodiments, may include one or more of the following: one or more training data sets (e.g., training data set(s) 1018-1), one or more machine learning algorithms, one or more stimuli, and/or one or more triggers corresponding to each (and/or some) of the one or more stimuli. The one or more training sets, in embodiments, may be generated by step S1604 and S1606 (i.e. the current state data set, in embodiments, may be a training data set on a first iteration of steps S1604-S1610 and the second iteration may result in the generation of the current state data set). The one or more triggers, in embodiments, may correspond to machine-readable instructions that include one or more events based on a prediction of anticipated behavior based on past events, such that when one or more of the one or more events occurs, a notification for a corresponding stimuli is presented to a user via an associated device in real-time.

The process may continue (and/or begin) with step S1604. At step S1604, in embodiments, the system obtains (e.g., via personal information module 1002 and/or user manager 1702) lifestyle information associated with the first user over a first amount of time. The lifestyle information obtained by the system, for example, may be information that is used to generate data sets for the purposes of predicting behavior to better encouraging a change in said behavior to achieve one or more goals associated with the first user. The data obtained may be data previously gathered and stored by a user device associated with the first user over the first amount of time or the data may be gathered by the system in substantially real-time (e.g., the system receives and/or monitors data gathered by the first user's associated device as the first user's device is gathering the data). For the purposes of the process described in connection with FIG. 16, the system obtains data from the first user's device over a week in substantially real time.

The system, in embodiments, may collect (and, in step S1606 below, label) historical data about the first user. Examples of data, include, e.g., raw data streamed from a user's personal mobile device. For example, data may be collected over a time period, such as a certain number of days, a week, a month, multiple months, a year, or years to name a few (and labelled). The lifestyle information, in embodiments, may include one or more of the following: identity information 1310A associated with the first user, sensor information 1314A associated with the first user, and/or timestamp information associated with the data obtained that is associated with the first user, to name a few. The timestamp information, in embodiments, may include a first plurality of time intervals and/or a second plurality of time intervals, to name a few. The first plurality of time intervals may include one or more intervals of time where the system 1000 was obtaining lifestyle information from the first user device. during the first predetermined period of time. The second plurality of time intervals may include one or more intervals of time where the system could not obtain at least a portion (e.g., location information, motion information) of the lifestyle information during the first predetermined period of time. In embodiments, the second plurality of time intervals may include one or more gaps of data (e.g., a gap may refer to an interval of time of the second plurality of time intervals). Each time interval, in embodiments, may have a respective beginning and a respective end. Each respective beginning may, in embodiments and where feasible, include a corresponding beginning location (e.g., the location of the first user device at the beginning of the interval of time). Each respective end may, in embodiments and where feasible, include a corresponding end location (e.g., the location of the first user device at the end of the interval of time).

The system, in embodiments, may gather two types of information—motion information and location information in chronological order- to build a data set to describe the first user's daily activities. The motion information and location information, in embodiments, enable the system to determine locations the user has been over the first amount of time, such as, a few days, a week, or multiple weeks or months to name a few. The motion and location information (e.g., raw data), may have gaps (as described above). The gaps, continuing the example, are also used by the system to build the aforementioned data set.

In embodiments, the lifestyle information obtained by the system may be a stream of raw data (e.g., the data gathered by the first user device) over time. In embodiments, the first user device (and/or any other device associated with the first user) may only give edges of raw data. For example, the raw data obtained by the system from the first user device (e.g., a smart phone) may have gaps that appear when the user is not moving or is in a stationary location. The raw data obtained by the system, for example, the system may collect information associated with movements of the first user (e.g., motion information 770) and locations of the first user (e.g., location information 752) over a calendar week. In embodiments, the system may store the lifestyle information in one or more databases (e.g., lifestyle database 1002-1).

In embodiments, the lifestyle information may be obtained by a first user device (e.g., first computer device 1012, personal user device 10-1, to name a few), one or more electronic devices associated with the first user, one or more healthcare providers, and/or one or more electronic devices associated with a second user, to name a few. The first amount of time, in embodiments, may refer to one or more of the following: a day, a week, a month, a year, multiple amounts of time, and/or a combination thereof, to name a few. In embodiments, the lifestyle information may be obtained, in embodiments, in a similar manner as described in connection with FIGS. 1, 1A-1, 1A-2, 1B 10-A-10-B, and 11A-11B, the descriptions of which applying herein. The lifestyle information described herein may be similar to the lifestyle information 1308A described in connection with FIGS. 1, 1A-1, 1A-2, 1B 10-A-10-B, and 11A-11B, the descriptions of which applying herein. The first user device, in embodiments, may be similar to the first computer device 1012 described in connection with FIGS. 1, 1A, and 1B, the second computer device 1014 described in connection with FIGS. 1 and 1A, the personal user device 10-1 described in connection with FIG. 2A, and/or the second personal user device 10-1A described in connection with FIG. 2B, the descriptions of which applying herein. In embodiments, step S1604 may be similar to step S1102 described in connection with FIG. 11A, the description of which applying herein.

The process illustrated in FIG. 16 may continue with a step S1606. At step S1606, in embodiments, the system 1000 may generate a current state data set associated with a current state of the first user (and/or a training data set associated with the first user) over the first amount of time. The system turns raw data into information (e.g., via filtering and/or analysis) and transforms the information into knowledge of the first user. In embodiments, generating a current state data set (and/or training data set) may be accomplished by one or more modules of the system. For example, referring to FIG. 17, the first module 1708-A may receive the stream of raw data, raw data with gaps, and/or edges of raw data from the module manager 1702-B of the user manager 1702 of the system 1000-A. The first module, referring to FIG. 17A, may be the location module 1710. The raw data obtained in step S1604 may be analyzed and filtered by the location module 1710 using heuristics 1710-F (and/or machine learning algorithm 1710-G).

In embodiments, the raw data may be filtered by the location module 1710 from raw data to stationary locations, then from stationary locations to recurring locations, then from recurring locations to recurring locations with a confirmed location data label. In embodiments, the location module 1710 may utilize heuristics 1710-F to filter the raw data into a series of data points indicating stationary locations. The series of data points may include coordinates and/or a time stamp indicating the time (and/or time range) the first user was located at the stationary location.

Exemplary Filtering of Raw Data to Determine Stationary Locations

Heuristics 1710-F, in embodiments, may filter the raw data by determining data points within the raw data which indicate the first user has stopped at a stationary location. The determination, in embodiments, may be made based on one or more rules stored in heuristics 1710-F. The one or more rules, in embodiments, may include a minimum amount of time, a maximum amount of time, a radius, excluded locations (e.g., excluding locations such as highways which may cause the first user to stop in, for example, a traffic jam), and/or a combination thereof, to name a few. For example, the location module 1710 may determine that if the first user has spent at least 30 minutes within a 100-foot radius around location A, location A is a stationary location associated with the first user. If the raw data indicates that the first user has spent 2 days within a 100-foot radius around location A, in embodiments, the location module 1710 may determine that location A is not a stationary location (e.g., the first user is likely not to have spent 2 days in the same location, the first user device may be lost and/or not with the first user). In embodiments, if location A is on a list of excluded locations (e.g., stored in memory and/or obtained from one or more of the following: third-party systems 1412, vendor system 40-1, third-party information systems 30-1 . . . 30-N, and/or a combination thereof, to name a few), the location module 1710 may determine that location A is not a stationary location (e.g., traffic on a highway, phone is not with the first user, subway car not moving, etc.).

Heuristics 1710-F, in embodiments, may filter the raw data by analyzing edges of gaps within the raw data which may indicate a stationary location. Gaps within the raw data, as mentioned above, in embodiments may be caused by the first user device being powered off, software within the first user device preventing the continuous collection of data, and/or a combination thereof, to name a few. The location module 1710 (e.g., via heuristics 1710-F and/or machine learning algorithm 1710-G), in embodiments, may analyze the data surrounding the gaps to determine whether first user was either at or close to (e.g., within a predetermined radius) the same location at the end of the gap of time and, if within the predetermined radius, the system may determine whether first was in the same location for a predetermined period of time (e.g., indicating a stationary location). Gaps of data, in embodiments, may be analyzed using heuristics 1710-F. Heuristics 1710-F, in embodiments, may utilize one or more of the following to determine whether the gap indicates a stationary location: Optimal Interpolation, multiple imputation, interpolation, extrapolation, average method, a grown rate method, and/or a combination thereof, to name a few. Each of the stationary locations, in embodiments, may be stored with motion data associated with the movement of the first user device before the stationary location (and/or after the stationary location).

In embodiments, this process of determining stationary locations may continue until all of the collected raw data over the first period of time has been analyzed. In embodiments, as stationary locations are determined, the stationary locations may be sent to a second module to for the purposes of filtering the stationary locations into recurring locations. In embodiments, each stationary location may be stored by the system. In embodiments, data associated with each stationary location may be sent from the location module 1710 to stationary location(s) 1716-A of location function library 1708-A.

The location module 1710, in embodiments, may include one or more of the following: routine 1710-A (e.g., to determine and/or storing a routine of the first user using— e.g.,—using a stream of stationary locations), setup 1710-B, one or more data models 1710-C (e.g., models used by the location module 1710 to predict location data labels of locations and/or activities based on a comparison between one or more data models and the raw data and/or filtered data), quiz information 1710-D (e.g., machine-readable instructions representing one or more stimuli used by the location module 1710 to confirm stationary, recurring, and/ or predicted locations), scheduling information 1710-E (e.g., information regarding a schedule of stimuli to be presented to the first user by the location module 1710), heuristics 1710-F (e.g., one or more algorithms designed to filter the raw data), and/or machine learning algorithm 1710-G (e.g., one or more machine learning algorithms designed to filter the raw data—e.g., DBSCAN may be used to determine recurring locations).

Exemplary Filtering of Stationary Locations to Recurring Locations

In embodiments, the filtered raw data of stationary locations may be further filtered by the system from stationary locations to recurring locations. Recurring locations, in embodiments, may refer to a stationary location where the first user has stopped more than a fixed number of times during a window of time (e.g., the first amount of time, a day, a week, a few weeks/months, and/or a combination thereof, to name a few). The location module 1710 (and/or an additional location module not shown—e.g., a location module dedicated to filtering stationary locations to recurring locations), may analyze the stationary location data and determine whether any of the stationary locations are recurring locations. This determination, in embodiments, may be made via heuristics 1710-F, the machine learning algorithm (e.g., via DBSCAN), and/or a combination thereof.

In embodiments, this process of determining recurring locations may continue until all of the stationary locations over the first period of time have been analyzed. Each recurring location, in embodiments, may be graphed over time (e.g., a times stream) to present a pattern of movement (e.g., a routine) to use past locations to predict future locations. Similarly, each corresponding event (described in more detail below) may be graphed over time to present a pattern of events (e.g., a routine) to use past events to predict future events. For example, a first user may leave its home to go to work every weekday at 7:00 AM. The system, continuing the example, may store 7:00 AM as a "transition point" in the first user's routine. A transition point, in embodiments, may be used by the system to anticipate intervals of time to trigger a stimulus. Continuing the example, the first user may always stop at an unhealthy restaurant for breakfast on the way to work. The system, may determine that 6:55 AM may be an effective time to send a stimulus, offering a coupon for a healthier restaurant on the way to the first user's office. As another example, the system may also determine that the first user waking up may be a good trigger, using sensor data to provide a real-time notification upon the first user waking up. As another example, the system may use one or more of the following to determine what activity will trigger a stimulus (e.g., a trigger activity) and/or when a stimulus would be most effective: one or more transition points, one or more anticipated transition points, one or more anticipated arrivals, one or more deviations from a user's routine, and/or a combination thereof.

The above described pattern of movement (and/or pattern of events), in embodiments, may be organized and/or stored by routine 1710-A (routine 1712-A, and/or routine 1714-A). In embodiments, the recurring locations may be organized by the location module 1710. The organization, in embodiments, may assist in the prediction of the location data label associated with each recurring location (and/or stationary location). In embodiments, the organization may be organized by type of event likely to occur at such a location—e.g., a location-based event (e.g., working out at the gym, seeing a movie, working at a place of employment, going shopping, etc.) and/or a time-based event (e.g., waking up, eating breakfast, eating lunch, eating dinner, going to sleep, etc.). Organizing by type of event, in embodiments, may assist in the prediction of an event occurring at each recurring location (and/or stationary location). In embodiments, as recurring locations are determined, the recurring locations may be organized by type of recurring location—e.g., user-specific places, public places, and/or special places.

In embodiments, data associated with each recurring location may be sent from the location module 1710 to recurring location(s) 1716-B of location function library 1708-A.

Exemplary Filtering of Recurring Locations to Confirmed Locations

As mentioned above in connection with step S1604, the collected lifestyle information may be labelled by the system. In embodiments, labelling can include Location information and/or Event information (described in more detail below). Examples of Location information may include, e.g., user specific locations (e.g., home, office, to name a few), public locations (e.g., gym, grocery store, restaurant), and/or special locations (e.g., airport, train, hospital, to name a few). The location module, in embodiments, may organize each recurring location (and/or stationary location) into user-specific locations, public locations, and/or special locations.

Based on the organization category and/or the time associated with the recurring location (e.g., when the first user was present at the recurring location), in embodiments, the location module 1710 may predict a location data label for each recurring location (if feasible). For example, if a recurring location is a public place and the timestamp associated with the public place is 12:30 PM, the location module 1710 may determine the predicted location data label associated with the location is a restaurant. The location module 1710, in embodiments, may predict location data labels of location(s) based on when the first user is present and how often the first user is present. For example, if the first stationary location of the day is the same as the last stationary location of the day, the system may predict that said recurring location is the first user's home. The location module 1710, in embodiments, may predict location data labels of location(s) based on one or more of the following: information obtained from other users associated with the system (e.g., the recurring location for the first user was already confirmed as a church by a second user), third-party systems 1412 (e.g., FourSquare, Google Maps, etc.), vendor system 40-1 (e.g., GrubHub, Uber Eats, etc.), third-party information systems 30-1 . . . 30-N (e.g., Hospitals, Offices, etc.), data models 1710-C, category of location, time associated with the location, and/or a combination thereof, to name a few. In embodiments, location data labels confirmed by other users, third-parties, vendors, and/or a combination thereof, may substitute for confirming a predicted location data label of a location and/or a predicted corresponding activity. In embodiments, data associated with each location data label associated with recurring locations may be sent from the location module 1710 to possible location data labels 1716-C of location function library 1708-A.

Figure 19A:
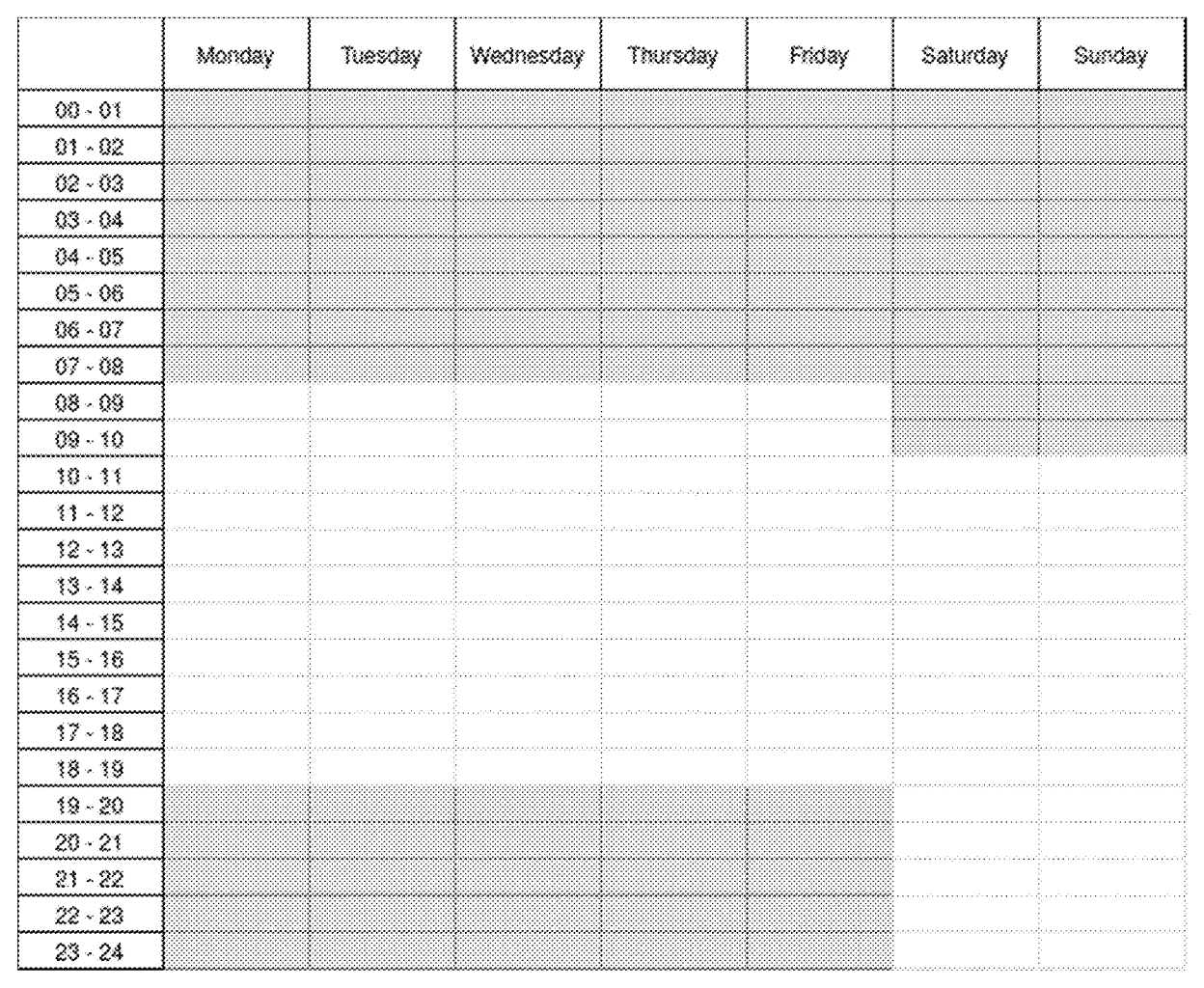
Figure 19B:
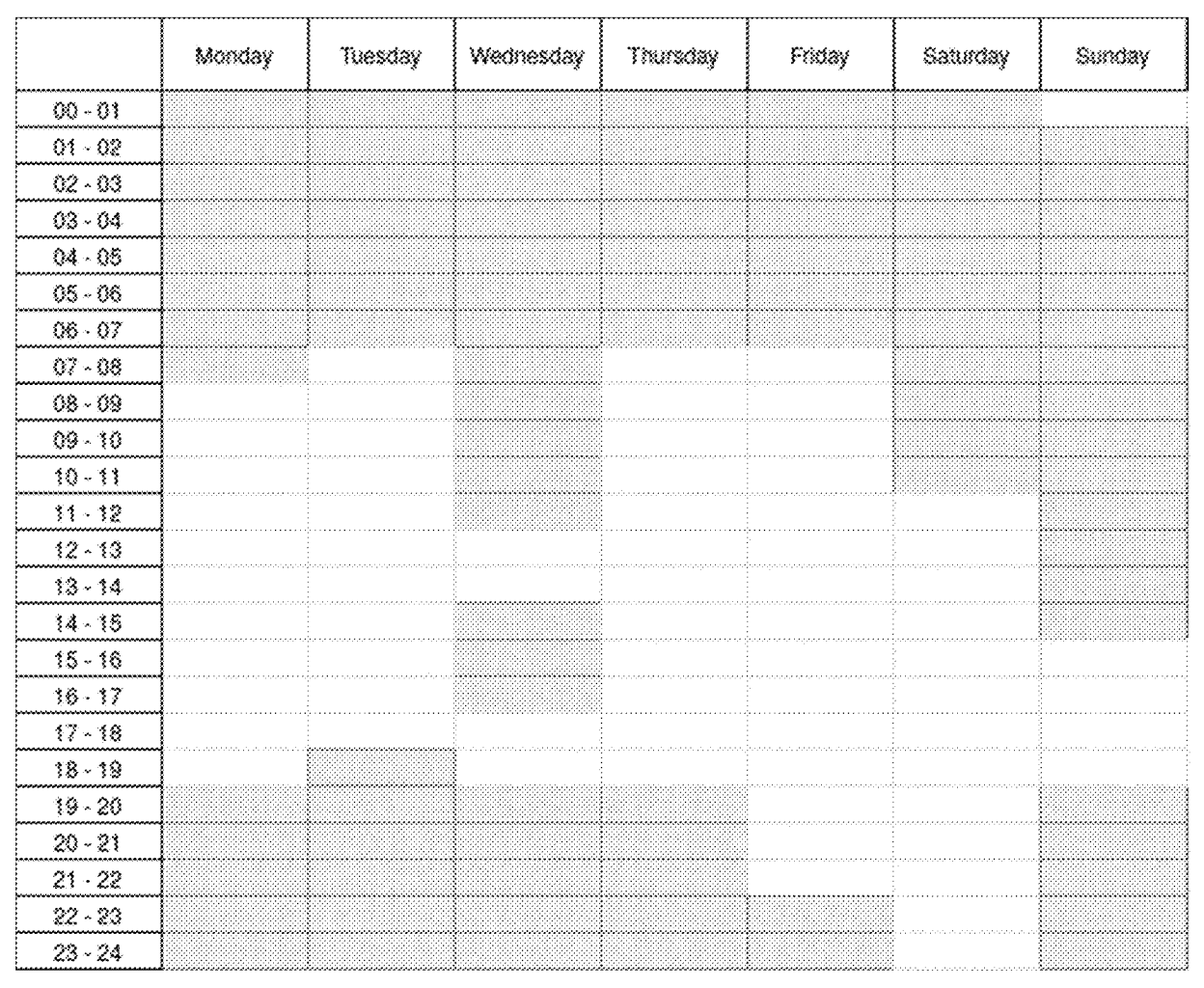

An exemplary data model is illustrated in FIG. 19A. Referring to FIG. 19A, a timeline of a model recurring location is depicted in matrix form over a week (e.g., the first amount of time). The location module 1710, in embodiments, may utilize the data model of FIG. 19A by generating a timeline for a determined recurring location in a similar format over a similar amount of time. For example, referring to FIG. 19B, the location module 1710 may generate a timeline of a determined recurring location in a format similar to the format shown in connection with FIG. 19A. The location module 1710, in embodiments, may compare the matrix of FIG. 19B to the matrix of FIG. 19A. If the location module 1710 determines the similarity between the model and the recurring location timeline are above a predetermined threshold, the location data label associated with the data model of FIG. 19A may be used as the label for the recurring location of FIG. 19B.

Each predicted location data label, in embodiments, may be confirmed by the system (e.g., via location module 1710 and/or an additional module dedicated to labelling). In embodiments, confirming one or more predicted location data labels may be accomplished by one or more of the following: a prompt, a quiz, a stimulus, purchase information (e.g., via prior purchase information 1316A (e.g., using a purchase made by the first user and/or a person within proximity of the first user to confirm the location data label and/or event associated with the recurring location)), social media information (e.g., via social connection information 1308D (e.g., a social connection and/or a professional colleague post an activity corresponding to a checked in location) and/or using social media to confirm an event associated with the confirmed location data label of a location the first user checked into), information from one or more additional users (e.g., if a second user has already confirmed an activity and/or location data label associated with the first user's recurring location, the system may use the second user's confirmed activity to confirm the predicted activity and/or location data label associated with the first user's recurring location), and/or a combination thereof, to name a few. For example, the system (e.g., via the location module 1710) may obtain and/or generate a quiz, stimulus, and/or prompt using quiz information 1710-D to supply necessary information and/or machine-readable instructions. For example, for a location predicted to be the first user's home, the location module 1710 may generate and send the following stimulus to the first user device:

Is the Location one of the following?
A: Your home
B: Your office
C: None of the above In response, continuing the example, the first user may select one or more of the options, resulting in a response being sent from the first user device to the system. For example, the user may confirm the system's prediction, selecting A. If the stimulus response received by the system confirms the system's predicted location data label, the location module 1710 (and/or the system) may label the recurring location with the confirmed location data label (e.g., the Location is the first user's Home). As additional examples, the user may contradict the system's predicted location data label, selecting B or C. If, for example, the stimulus response indicates the Location is not the first user's home and, is instead the first user's office, the location module 1710 (and/or the system) may label the recurring location with "Office" (e.g., the Location is the first user's Office). If, for example, the stimulus response indicates the Location is not the first user's home or office, the location module 1710 may make an additional predicted location data label and/or filter out the recurring location from the filtered data. In embodiments, the system may not require a stimulus to confirm the location data label of a stationary and/or recurring location.

The process of confirmation may continue until each predicted location data label is either confirmed or contradicted. In embodiments, each recurring location with a confirmed location data label may be filtered as a confirmed place. In embodiments this labelling may be done using a heuristic model (e.g., via heuristics 1710-F) and/or using a machine learning algorithm (e.g., via machine learning algorithm 1710-G). In embodiments, data associated with each confirmed place may be sent from the location module 1710 to confirmed locations 1716-D of location function library 1708-A. While only a multiple-choice stimulus is shown above, it is understood that the stimulus can be in other formats such as fill in the blank (e.g., the following address is your home, e.g., FIG. 9D), true or false (e.g., please confirm that the Location is your home), to name a few.

Figures 20A, 20B:
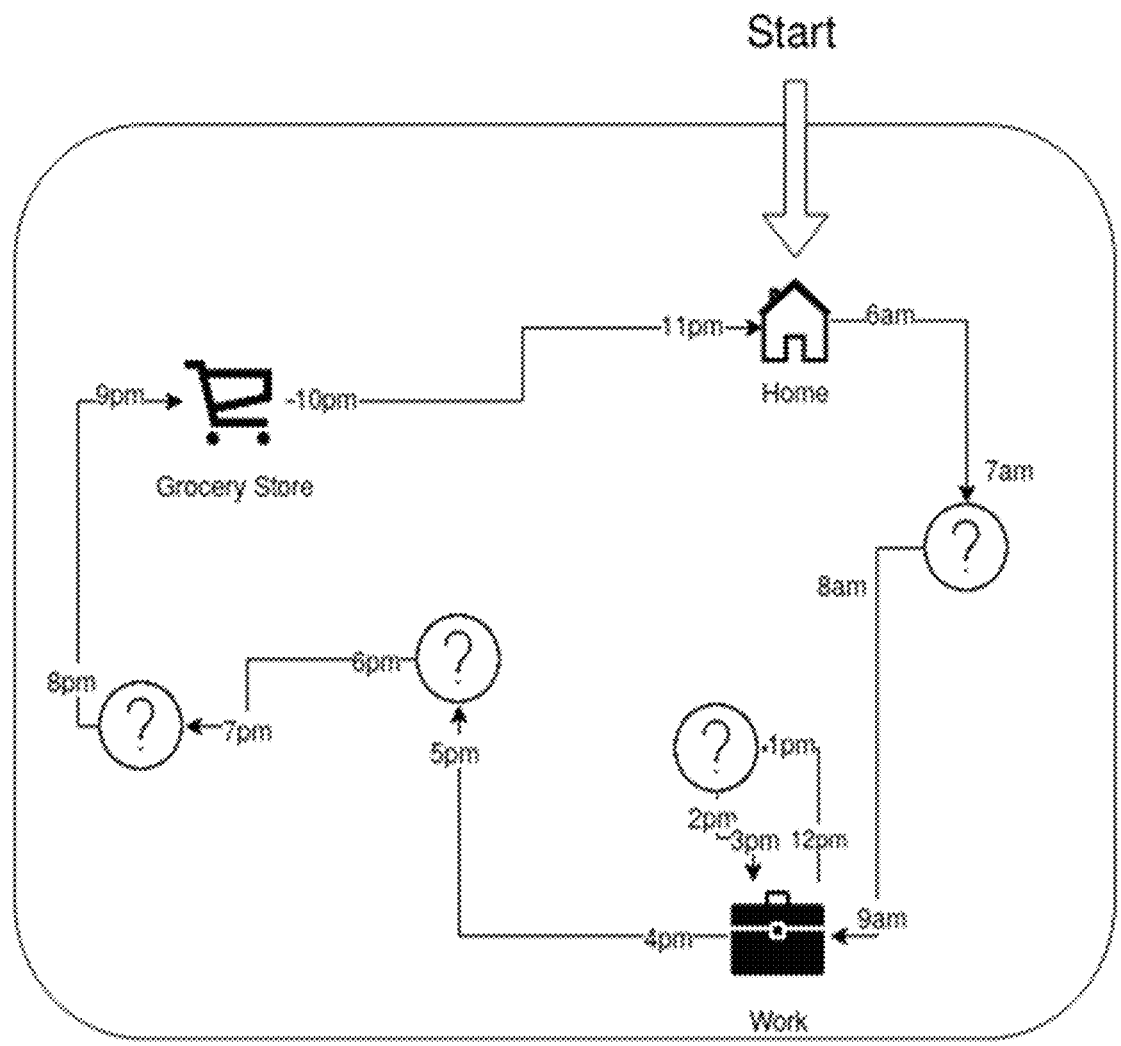
FIG. 20A is an exemplary routine of a user in accordance with exemplary embodiments of the present invention.
FIG. 20B is the exemplary routine of FIG. 20A displayed in a secondary manner in accordance with exemplary embodiments of the present invention.

In embodiments, to assist in predicting future locations and/or future events in advance, based on past locations and/or events (e.g., as described above with triggers), the location module 1710 may generate a daily routine (e.g., an event stream) associated with the first user. For example, referring to FIG. 20A, the location module 1710 may generate the routine illustrated in FIG. 20A to represent a daily routine of the first user. Each confirmed location and corresponding time may be utilized in the daily routine (e.g., home at 6 AM, work at 9 AM, grocery store at 9 PM, and home at 11 PM). In embodiments, a portion of the recurring locations may be contradicted, confirmed, and/or not able to be determined. As shown in FIG. 20A, each of the aforementioned portion of recurring locations may be represented by a question mark. FIG. 20B, in embodiments, is an event time stream displaying the routine displayed in FIG. 20A. Referring to FIG. 20B, in embodiments, the routine may be a sequence of time slots reporting confirmed locations associated with the user—each time slot being filled with a value representing one or more of the following—commuting—"C" (e.g., representing a time slot where the user is commuting to a location); Known Location—H for home, W for Work, and G for Grocery store, etc. (e.g., representing confirmed locations); and/or Unknown Locations—"?" (e.g., location contradicted, location unconfirmed, the user stopped but the location module 1710 does not have any additional data—e.g., a friend's house, etc.). In embodiments, each location represented by a "?" may be determined via one or more stimuli generated by the location module 1710 and sent to the first user device.

Exemplary Labelling of Recurring Locations with Events

As mentioned above, the collected lifestyle information may be labelled with Event information. The system may organize each recurring location (and/or stationary location) by type of event likely to occur at such a location—e.g., a location-based event (e.g., working out at the gym, seeing a movie, working at a place of employment, going shopping, etc.) and/or a time-based event (e.g., waking up, eating breakfast, eating lunch, eating dinner, going to sleep, etc.). In embodiments, the user manager 1702 may send each recurring location associated with a location-based event to the location-based events module 1712. In embodiments, the user manager 1702 may send each recurring location associated with a time-based event to the time-based event module 1714. In embodiments, some or all of the recurring locations may be sent to both the location-based events module 1712 and/the time-based events module 1714.

The location-based events module 1712 (e.g., via heuristics 1712-F and/or machine learning algorithm 1712-G) may predict an event for each recurring location sent to the location-based events module 1712 based one on or more of the following: labels associated with the recurring location, sensor data, location data, time data, information obtained from other users associated with the system (e.g., the recurring location for the first user was already confirmed as being associated with the event of working out by a second user), third-party systems 1412 (e.g., FourSquare, Google Maps, etc.), vendor system 40-1 (e.g., GrubHub, Uber Eats, etc.), third-party information systems 30-1 . . . 30-N (e.g., Hospitals, Offices, etc.), data models 1712-C, and/or a combination thereof, to name a few. For example, if a Recurring Location has a label of movie theater, the location-based events module 1712 may predict the event associated with the Recurring Location is watching a movie. As another example, if a Recurring Location occurs at a time of an increased heart rate and a lot of steps detected by one or more sensors of the first user device, the location-based events module 1712 may predict the event associated with the Recurring Location is working out. In embodiments, data associated with each event associated with recurring locations may be sent from the location-based events module 1712 to possible location data labels 1716-C of location function library 1708-A and/or to an event function library (e.g., the reciprocal library to the location function library 1708-A for events).

In embodiments, each event may be predicted using (and/or assisted by) one or more of the following: data models (e.g., the data models of FIGS. 19A and 19B); routines (e.g., the routines of FIGS. 20A and 20B); and/or a combination thereof, to name a few. For example, referring to FIG. 20B, the time slotted sequence—HHHHH-CUCWWWWWC????CH-HHHIH—may be represented by a unique string—e.g.,—HIHHHHIIHCWWWWWWWCHIIIIHHHHH.

In embodiments, each time slot being filled with a value representing one or more of the following—commuting—"C" (e.g., representing a time slot where the user is commuting to a location); Known Location—H for home, W for Work, and G for Grocery store, etc. (e.g., representing confirmed locations); and/or Unknown Locations—"?" (e.g., location contradicted, location unconfirmed, the location is unknown, the user stopped but the location module 1710 does not have any additional data—e.g., a friend's house, to name a few). In embodiments, each location represented by a "?" may be determined via one or more stimuli generated by the location module 1710 and sent to the first user device. In embodiments, each letter may be a code, letters, numbers, and/or a combination thereof which may be used to refer to one or more of the following: a location, a transition point, a trigger, an unknown, a commute, and/or a combination thereof, to name a few.

Once represented in a string, for example, the system may identify events by comparing patterns (e.g., event rules) in routines representing the first user's location(s) during the day. For example, if the first user had lunch outside the office, the system may identify the lunch by matching modelled lunchtime slots (e.g., from 11 AM to 3 PM) with a pattern (e.g., event rule) defined as an exemplary occurrence of the following sequence of events The user was in the office
The user wasn't in the office
The user was in the office again If, in embodiments, the pattern (event rule) matches the first user's location string, the system may predict that the event was lunch outside (e.g., which may be followed by a generated stimulus to ask if the user was having lunch at that time). In embodiments, the heuristic pattern matching may be implemented by the system via the use of regular expressions, which may result in a flexible and/or generalizable manner of predicting events using past locations and events.

As another example, a sequence of HHH-FIHHCWWBWWBWCHHHHHHHH, where B indicates a 15 minute break (measured by showing the first user's location leaving the office, then moving to a frequently-visited public area (e.g., a garden outside an office building) and coming back may be indicative of a smoking break where the user steps outside for 15 minutes to smoke and comes back into to the office. Upon observing this a sub-sequence (pattern) of "WBW . . . WBW . . . WBW", the system, in embodiments, may generate and send a stimulus to the first user asking if they smoke. This information can then be stored in the first user's profile to enable specific recommendations for smokers to be sent only to users that smoke.

Each predicted event associated with a recurring location, in embodiments, may be confirmed by the system (e.g., via location-based events module 1712 and/or an additional module dedicated to labelling). In embodiments, confirming one or more predicted events may be accomplished by one or more of the following: a prompt, a quiz, a stimulus, purchase information (e.g., via prior purchase information 1316A (e.g., using a purchase made by the first user and/or a person within proximity of the first user to confirm the location data label and/or event associated with the recurring location)), social media information (e.g., via social connection information 1308D (e.g., a social connection and/or a professional colleague post an activity corresponding to a checked in location) and/or using social media to confirm an event associated with the confirmed location data label of a location the first user checked into), information from one or more additional users (e.g., if a second user has already confirmed an activity and/or location data label associated with the first user's recurring location, the system may use the second user's confirmed activity to confirm the predicted activity and/or location data label associated with the first user's recurring location), and/or a combination thereof, to name a few. For example, For example, the system (e.g., via the location-based event module 1712) may obtain and/or generate a quiz, stimulus, and/or prompt using quiz information 1712-D to supply necessary information and/or machine-readable instructions. For example, for an event predicted to be the first user's daily workout, the location-based events module 1712 may generate and send the following stimulus to the first user device:

Were you just working out?
A: Yes
B: No

In response, continuing the example, the first user may select one or more of the options, resulting in a response being sent from the first user device to the system. For example, the user may confirm the system's prediction, selecting A. If the stimulus response received by the system confirms the system's predicted event, the location-based module 1712 (and/or the system) may label the recurring location with the confirmed event (e.g., the Recurring Location is associated with the event of Working Out). As another example, the user may contradict the system's predicted location data label, selecting B. If, for example, the stimulus response indicates the Recurring Location is not associated with Working Out, the location-based events module 1712 may make an additional predicted event. In embodiments, the system may not require a stimulus to confirm events associated with a stationary and/or recurring location.

The process of confirmation may continue until each predicted event associated with the location-based event module 1712 is either confirmed or contradicted. In embodiments, each recurring location with a confirmed associated event may be filtered as a confirmed place and/or a confirmed event. In embodiments this labelling may be done using a heuristic model (e.g., via heuristics 1712-F) and/or using a machine learning algorithm (e.g., via machine learning algorithm 1712-G). In embodiments, data associated with each confirmed place (and/or confirmed event) may be sent from the location-based event module 1710 to confirmed locations 1716-D of location function library 1708-A and/or to an event function library (e.g., the reciprocal library to the location function library 1708-A for events). While only a true or false type of question is shown, however, in embodiments, the stimulus can be in other formats such as fill in the blank (e.g., the following address is your home _____), multiple choice, to name a few.

The location-based events module 1712 (shown in connection with FIG. 17B), in embodiments, may include one or more of the following: routine 1712-A (e.g., to determine and/or storing a routine of location-based events of the first user using—e.g.,—using a stream of location-based events), setup 1712-B, one or more data models 1712-C (e.g., models used by the location-based events module 1712 to predict location-based events based on a comparison between one or more data models and the stationary and/or recurring locations), quiz information 1712-D (e.g., machine-readable instructions representing one or more stimuli used by the location-based events module 1712 to confirm events associated with stationary, recurring, predicted, and/or confirmed locations), scheduling information 1712-E (e.g., information regarding a schedule of stimuli to be presented to the first user by the location-based events module 1712), heuristics 1710-F (e.g., one or more algorithms designed to predict and/or confirm location-based events), and/or machine learning algorithm 1710-G (e.g., one or more machine learning algorithms designed to predict and/or confirm location-based events).

The time-based events module 1714 (e.g., via heuristics 1714-F and/or machine learning algorithm 1714-G) may predict an event for each recurring location sent to the time-based events module 1714 based one on or more of the following: labels associated with the recurring location, sensor data, location data, time data, information obtained from other users associated with the system (e.g., the recurring location for the first user was already confirmed as being associated with the event of working out by a second user), third-party systems 1412 (e.g., FourSquare, Google Maps, etc.), vendor system 40-1 (e.g., GrubHub, Uber Eats, etc.), third-party information systems 30-1 . . . 30-N (e.g., Hospitals, Offices, etc.), data models 1714-C, and/or a combination thereof, to name a few. For example, if a Recurring Location has a label of restaurant and an associated time of 8:00 AM, the time-based events module 1712 may predict the event associated with the Recurring Location is eating breakfast. As another example, if a Recurring Location occurs at a time of a decreased heart rate and a lack of movement for a period of time detected by one or more sensors of the first user device, the time-based events module 1714 may predict the event associated with the Recurring Location is sleeping. In embodiments, data associated with each event associated with recurring locations may be sent from the time-based events module 1714 to possible location data labels 1716-C of location function library 1708-A and/or to possible events 1718-A of the event function library 1718.

Each predicted event associated with a recurring location, in embodiments, may be confirmed by the system (e.g., via time-based events module 1714 and/or an additional module dedicated to labelling). Confirmation of a predicted event, in embodiments, may accomplished via one or more of the following: a prompt, a quiz, a stimulus, and/or a combination thereof, to name a few. The confirmation, in embodiments, may be generated by the time-based event module 1714 using quiz information 1714-D to supply necessary information and/or machine-readable instructions. For example, for an event predicted to be the first user's sleep, the time-based events module 1714 may generate and send the following stimulus to the first user device:

Were you just sleeping?
A: Yes
B: No

In response, continuing the example, the first user may select one or more of the options, resulting in a response being sent from the first user device to the system. For example, the user may confirm the system's prediction, selecting A. If the stimulus response received by the system confirms the system's predicted event, the time-based module 1714 (and/or the system) may label the recurring location with the confirmed event (e.g., the Recurring Location is associated with the event of Sleeping). As another example, the user may contradict the system's predicted location data label, selecting B. If, for example, the stimulus response indicates the Recurring Location is not associated with Sleeping, the time-based events module 1714 may make an additional predicted event. This process of confirmation may continue until each predicted event associated with the time-based event module 1714 is either confirmed or contradicted. In embodiments, each recurring location with a confirmed associated event may be filtered as a confirmed place and/or a confirmed event. In embodiments this labelling may be done using a heuristic model (e.g., via heuristics 1714-F) and/or using a machine learning algorithm (e.g., via machine learning algorithm 1714-G). In embodiments, data associated with each confirmed place (and/or confirmed event) may be sent from the time-based event module 1714 to confirmed locations 1716-D of location function library 1708-A and/or to confirmed events 1718-B of the event function library 1718.

While only a true or false type of question is shown, it is understood that the stimulus can be in other formats such as fill in the blank (e.g., the following address is your home _____ ), multiple choice, etc.

The time-based events module 1714 (shown in connection with FIG. 17C), in embodiments, may include one or more of the following: routine 1714-A (e.g., to determine and/or storing a routine of time-based events of the first user using—e.g.,—using a stream of time-based events), setup 1714-B, one or more data models 1714-C (e.g., models used by the time-based events module 1714 to predict time-based events based on a comparison between one or more data models and the stationary and/or recurring locations), quiz information 1714-D (e.g., machine-readable instructions representing one or more stimuli used by the time-based events module 1714 to confirm events associated with stationary, recurring, predicted, and/or confirmed locations), scheduling information 1714-E (e.g., information regarding a schedule of stimuli to be presented to the first user by the time-based events module 1714), heuristics 1714-F (e.g., one or more algorithms designed to predict and/or confirm time-based events), and/or machine learning algorithm 1714-G (e.g., one or more machine learning algorithms designed to predict and/or confirm time-based events).

Figure 17:
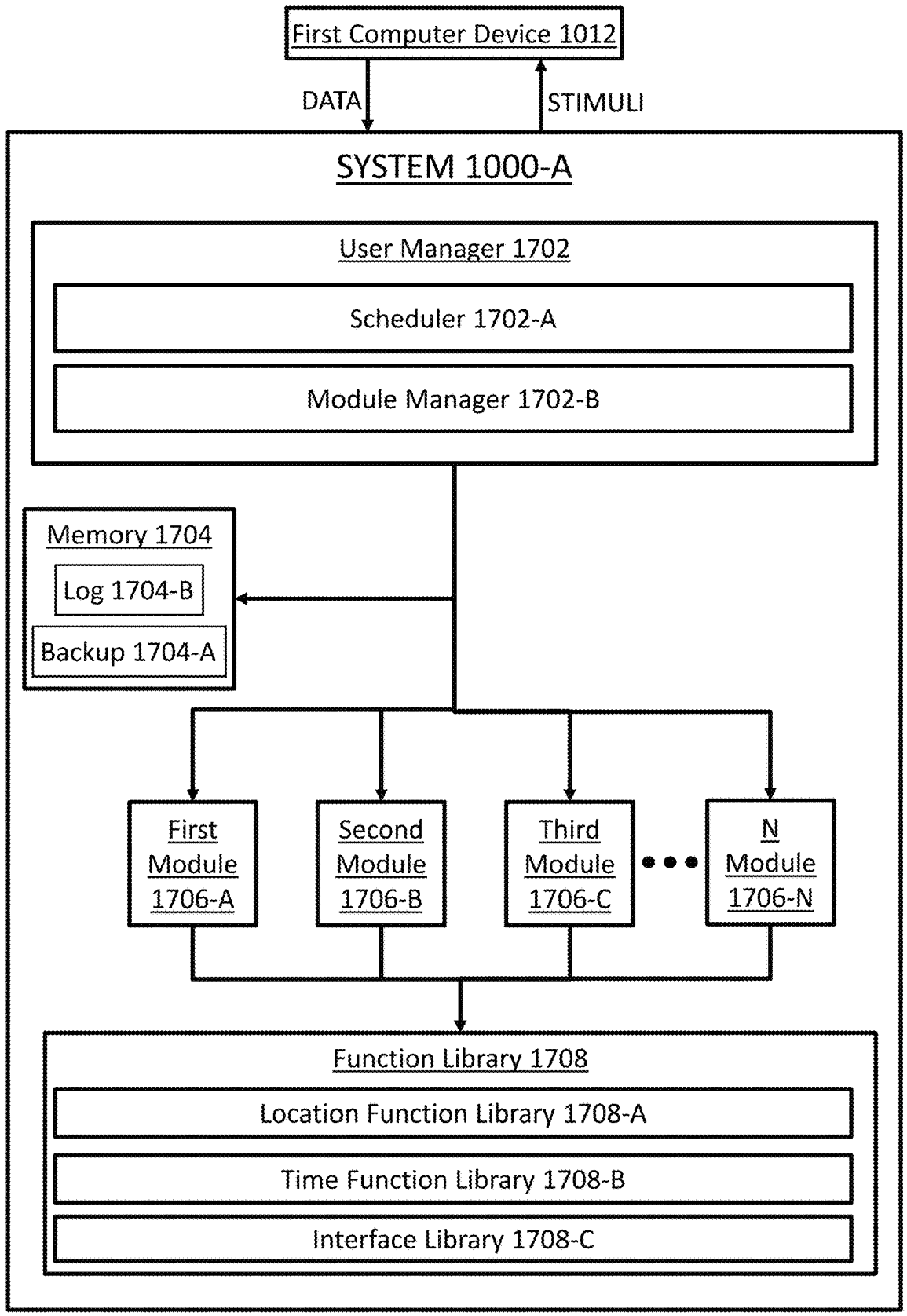
FIG. 17 is an exemplary block diagram of the system of FIG. 1 selecting a stimulus for a user associated with the first computer device and/or the second computer device in accordance with exemplary embodiments of the present invention.
Figure 17A:
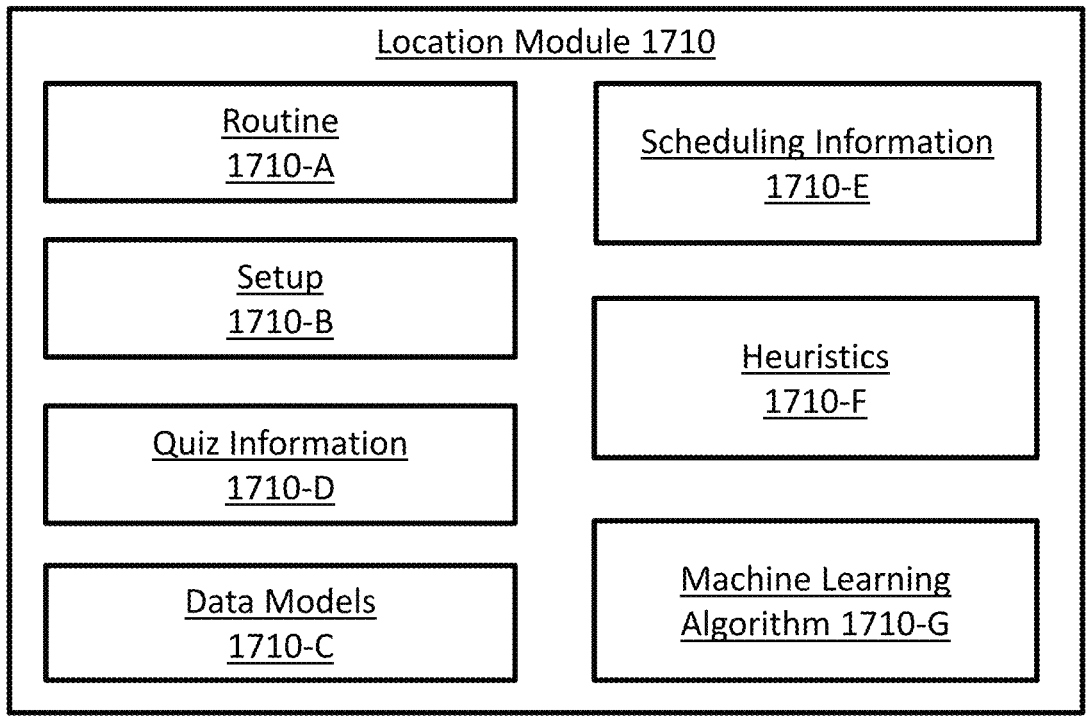
FIGS. 17A-17C are exemplary block diagrams of exemplary modules of the system of FIG. 17 in accordance with exemplary embodiments of the present invention.
Figure 17B:
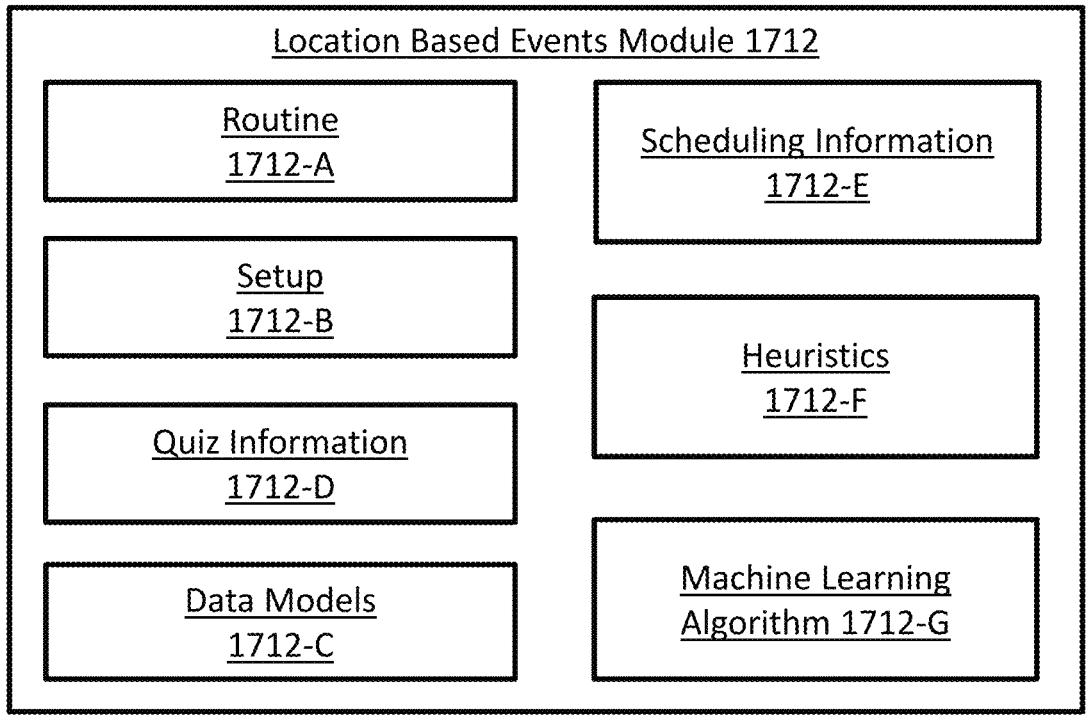
Figure 17C:
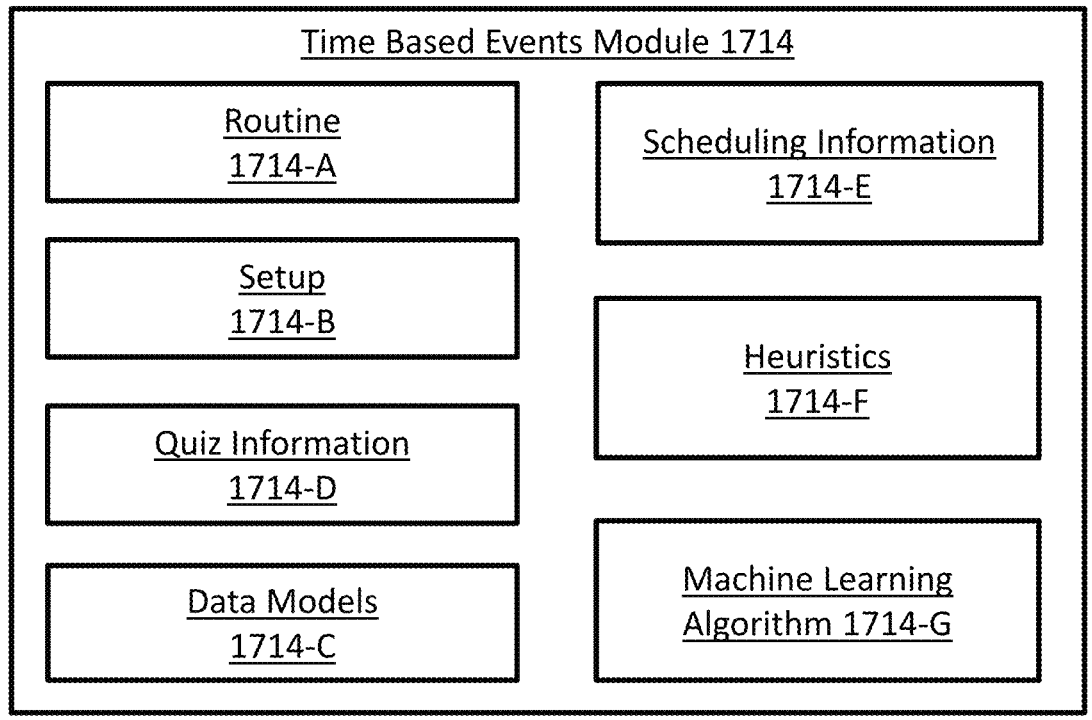
Figure 17D:
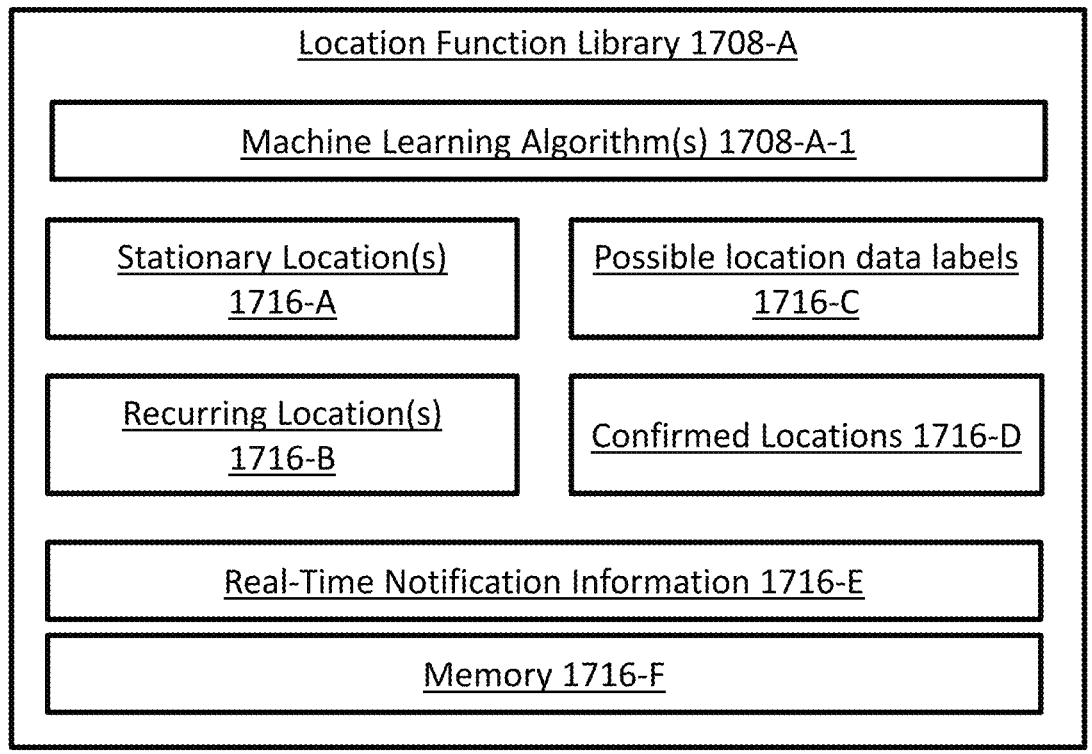
FIGS. 17D-17G are exemplary block diagrams of exemplary function libraries of the system of FIG. 17 in accordance with exemplary embodiments of the present invention.
Figure 17E:
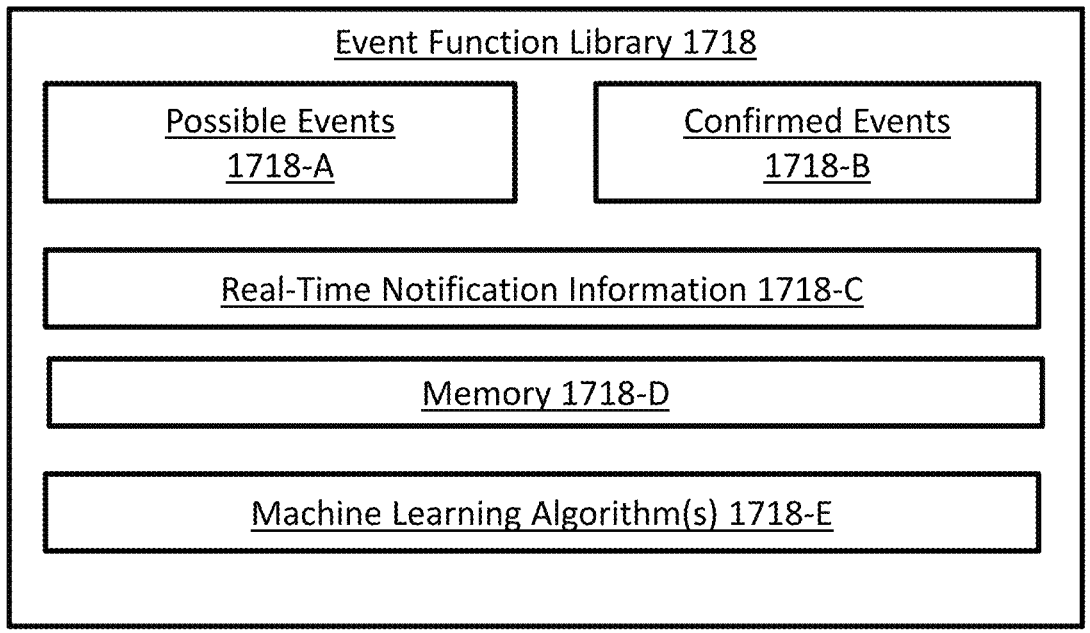
Figure 17F:
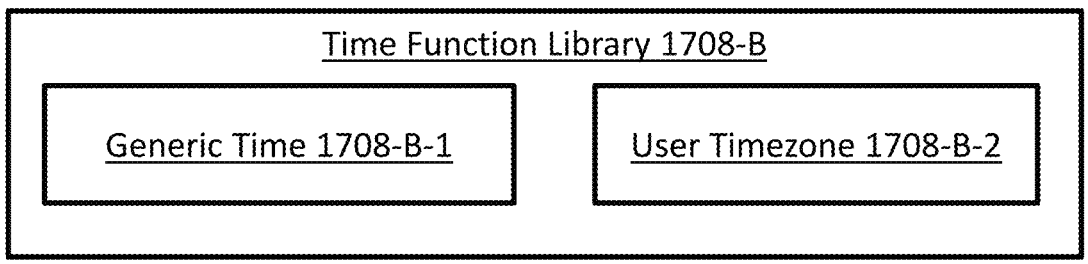
Figure 17G:
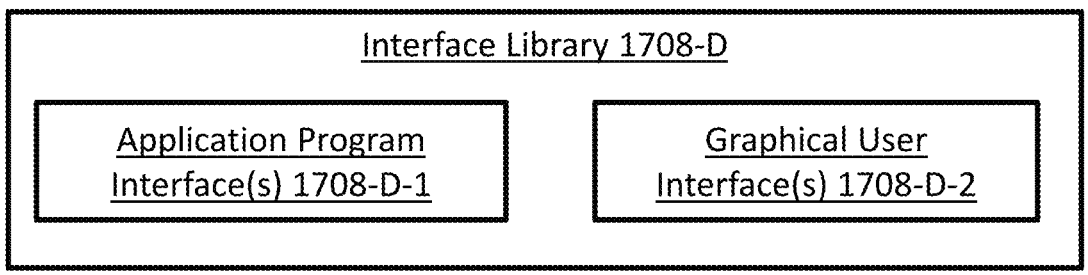

In embodiments the location module 1710, location-based events module 1712, and the time-based events module 1714 may correspond to the first module 1706-A, the second module 1706-B, and the third module 1706-C of FIG. 17 respectively.

In embodiments, step S1606 may occur as data is collected in step S1604. In embodiments, step S1606 may occur after all data is collected over the first amount of time in step S1604. In embodiments, the raw data and/or filtered data may be stored by the system 1000-A in log 1704-B. In embodiments, the raw data and/or filtered data may be stored by the system 1000-A in backup 1704-A. In embodiments, the raw data may be stored in log 1704-B and the filtered data may be stored in backup 1704-A. In embodiments, the raw data may be stored in backup 1704-A and the filtered data may be stored in log 1704-B.

The process illustrated in FIG. 16 may continue with a step S1608. At step S1608, in embodiments, the system 1000 may obtain a first machine learning algorithm. In embodiments, when enough data is obtained and labelled, the labelled data (e.g., the labelled recurring locations) can be fed into a heuristic and/or machine learning algorithm which can be used to predict user activity in advance. To feed the labelled data into a machine learning algorithm, in embodiments, the system may first obtain the machine learning algorithm. In embodiments, each user, or in some cases groups of users, (e.g., users that are customers of the system) will have one or more dedicated machine learning modules that can be used to predict that user (or group of users) present or future activities. In embodiments, different users (or groups of users) may have different models (e.g., data models 1710-C, 1712-C, and/or 1714-C) some of which may be shared (for example, models may be shared between users that work together and frequently go out to lunch together during lunchtime on business days, to name a few).

The process illustrated in FIG. 16 may continue with step S1610. At step S1610, in embodiments, the system 1000 may generate a situation data set by providing the current state data set to the first machine learning algorithm. The current data set generated in step S1606 (and/or the training data set generated in step S1606) may be input into the obtained first machine learning algorithm. In embodiments, if the input is a current data set, the output of the first machine learning algorithm may be a situation data set. The situation data set (e.g., situation information data set 1312B), in embodiments may be used as an input for a second machine learning algorithm to select one or more stimuli and corresponding trigger(s). The training data set, in embodiments, may be used to train the second machine learning algorithm.

In embodiments where machine learning is used, as mentioned above, the labelled lifestyle information may be used as a training set for the machine learning algorithm. In embodiments, the historical data will include various data streaming from e.g., a user's mobile device (e.g., a mobile phone), and the labels will be answers (or responses) to stimuli.

In embodiments, the process of training the first machine learning algorithm over a first amount of time (i.e., steps S1604-S1610) may be repeated (S1611). For example, the first iteration of steps S1604-S1606 may result in the generation and storage of a training data set associated with the first user and the second (and/or remaining iterations) iteration may result in the generation of a situation data set and/or a current state data set, to name a few. In embodiments, steps S1604-S1610 may be repeated a plurality of times. In embodiments, steps S1604-S1610 may not be repeated.

The process illustrated in FIG. 16 may continue with step S1612. In embodiments, at step S1612 the system may obtain a second machine learning algorithm. In embodiments, the situation data set (and/or training data set to train the second machine learning algorithm) may be fed into a heuristic and/or machine learning algorithm which can be used to select one or more stimuli and corresponding trigger(s) in advance. To feed the labelled data into a machine learning algorithm, in embodiments, the system may first obtain the machine learning algorithm. In embodiments, each user, or in some cases groups of users, (e.g., users that are customers of the system) will have one or more dedicated machine learning modules that can be used to predict that user (or group of users) present or future activities. In embodiments, different users (or groups of users) may have different models (e.g., data models 1710-C, 1712-C, and/or 1714-C) some of which may be shared (for example, models may be shared between users that work together and frequently go out to lunch together during lunchtime on business days, to name a few).

The process illustrated in FIG. 16 may continue with step S1614. In embodiments, at step S1614, a first stimulus including a first trigger is generated by the system. In embodiments, the first stimulus and corresponding trigger is selected by the system by inputting the generated situation data set to the second machine learning algorithm. The output, in embodiments, may be the first stimuli and one or more triggers designed to provide a push notification in real time to the first user via the first user device (and/or another associated device). The stimulus, in embodiments, may be based on location prediction(s) made by the location function library 1708-A, event prediction(s) made by the event function library 1718, time from the time function library 1708-B, user preferences (e.g., the user has excluded one or more stimuli), available stimulus information 1310C (e.g., stimuli available to use on the first user), user stimuli information 1312D (e.g., stimuli used on the first user), stimulus response information 1314B (e.g., how the first user has responded to stimuli in the past), and/or a combination thereof. The trigger, in embodiments, may include one or more of the following: a location (e.g., a radius of a location), a calendar date, a time, an event (e.g., waking up), biometric data (e.g., increase in steps, heart rate, sleep, etc.), meeting with one or more collogues, and/or a combination thereof.

In embodiments, one or more modules and/or machine learning algorithms may be used to select a stimulus and corresponding trigger—e.g., the location function library 1708-A, the event function library 1718, and/or the time function library 1708-B, to name a few. For example, the system may predict one or more locations the first user will be present using past information via the location function library 1708-A. The predicted locations (predicted in advance using past information) may be used as part of the stimulus. For example, if the first user always buys a candy bar at a local grocery store, the location function library 1708-B may predict the grocery store location and use said prediction to guide the first user to a healthier choice. The location function library 1708-A (shown in connection with FIG. 17D) in embodiments, may include one or more of the following: machine learning algorithm(s) 1708-A-1 (e.g., to predict one or more locations based on past information), stationary location(s) 1716-A (e.g., a list of each stationary location), recurring location(s) 1716-B (e.g., a list of each recurring location), possible location(s) 1716-C (e.g., a list of each predicted location data label associated with each recurring location), confirmed location(s) 1716-D (e.g., a list of each confirmed location), real-time notification information 1716-E (e.g., machine-readable instructions representing one or more real-time notifications associated with locations of stimuli), and/or memory 1716-F (e.g., to store locations predicted, stimuli selected, and/or triggers selected by the location function library 1708-A), to name a few.

As another example, the system may predict one or more events the first user may undertake using past information via the event function library 1718. The predicted events (predicted in advance using past information) may be used as part of the stimulus. For example, if the first user always eats lunch at an unhealthy restaurant, the event function library 1718 may predict the unhealthy restaurant lunch and use said prediction to guide the first user to a healthier choice. The event function library 1718 (shown in connection with FIG. 17E) in embodiments, may include one or more of the following: machine learning algorithm(s) 1718-E (e.g., to predict one or more events based on past information), possible event(s) 1718-A (e.g., a list of each predicted events associated with each recurring location), confirmed event(s) 1718-B (e.g., a list of each confirmed event), real-time notification information 1718-C (e.g., machine-readable instructions representing one or more real-time notifications associated with events of stimuli), and/or memory 1718-F (e.g., to store events predicted, stimuli selected, and/or triggers selected by the events function library 1718), to name a few.

As another example, the system may utilize the time function library 1708-B to determine times associated with selected stimuli and corresponding trigger. Real-time notifications, in embodiments, may require an accurate time reading associated with the first user. If, for example, time is not available on the first user device, the time function library 1708-B may determine the most recent user time zone (e.g., via user time zone 1708-B-2) and/or may determine a default time associated with the user (e.g., via generic time 1708-B-1).

In embodiments, the interface library 1708-D (shown in connection with FIG. 17G) may generate a graphical user interface (e.g., via graphical user interface(s) 1708-D-2) associated with the selected stimulus to be displayed on a device associated with the first user (e.g., the first user device).

The process illustrated in FIG. 16, in embodiments, may continue with step S1616. At step S1616, the first stimulus is sent to the first computing device. In embodiments, the first stimulus and corresponding trigger may be sent to the computing device such that, upon the trigger being activated, a real-time notification is displayed to the user. In embodiments, the first stimulus and corresponding trigger may be sent via an application programming interface (which may be set up via application program interface(s) 1708-D-1).

The steps of the process described in connection with FIG. 16 may be rearranged or omitted.

Referring back to FIG. 10-A, in embodiments, the system 1000 (e.g., utilizing the machine learning algorithm 1016-1) may determine an appropriate time, date, and/or location to select and/or send a stimulus to the first user. For example, if the first user's goal is to get healthier, the system 1000 may select the morning to send a stimulus to encourage the first user to go out for a run. Continuing the example, if the system 1000 has collected data that indicates the first user had a late night, the system 1000 may not send a stimulus in the morning because the system 1000 may determine that the healthier option is to sleep and/or may determine that the first user is less likely to go out for a run when the first user is more tired than usual. If, continuing the example, the first user has recently bought running shoes, the system 1000 may wait a predetermined amount of time to select and send a stimulus to encourage the first user to buy a new pair of running shoes.

In embodiments, the system 1000 may utilize one or more API's associated with third-party websites and/or vendors to select and generate a stimulus. For example, if the stimulus selected was a healthier eating option, the system 1000 may, using the API associated with FOURSQUARE®, and geo-location data associated with the first user collected by location sensor(s) 710 and/or GPS Sensor(s) 732 to determine the first user is near Restaurant A which offers healthy options (e.g., utilizing information from Vendor System 40-1). The generated stimulus, may also include the menu of Restaurant A (e.g., from an API associated with Yelp®), pictures of the healthier options (e.g., from an API associated with Yelp®) and/or an option to make a reservation (e.g., from an API associated with OpenTable.com®), to name a few.

At step S1018, in embodiments, the manager module may send the first stimulus to a first computing device associated with the first user. In embodiments, the system 1000 may generate a message including machine readable instructions to display the selected first stimulus on a device associated with the first user (e.g., the first computer device 1012, the second computer device 1014). The message including the machine-readable instructions and the first stimulus, may be sent by the system 1000 to the device(s) associated with the first user 10 via network 100. In embodiments, upon receipt of the message, the device(s) associated with the first user 10 may display a push notification as shown in connection with FIG. 13A.

In embodiments, the selected first stimulus may require the acceptance of the first user. For example, once the first stimulus was sent to a device associated with the first user, the first user may have the option of selecting whether the first user will perform the first stimulus. In embodiments, multiple stimuli are selected and sent by the system 1000 to a device associated with the first user. The first user, in embodiments, may have the option to choose one or more of the stimuli. In embodiments, when the first user accepts or declines (or answers "maybe" or an equivalent thereof) the device associated with the first user may generate and send a message including data indicating the choice of the first user. If the first user declines the first stimulus, in embodiments the collection module may determine and store the result of the first stimulus as a failed stimulus. If the first user accepts and/or does not decline the first stimulus, in embodiments, the collection module may begin collecting updated information about the first user, particularly searching for data relevant to the first stimulus.

Turning to FIG. 10-B, the process continues at step S1020, with system 1000 collecting, by a collection module, updated information about the first user. For example, the system 1000 may be collecting data associated with the first user to determine whether the first user is acting on the selected and transmitted first stimulus. The system 1000, in embodiments, may collecting information from one or more of the following: one or more of the third-party information systems 30-1 ... 30-N (e.g., if the stimulus is to eat a healthy meal at Location A, social/professional network system 38 may determine the first user checked in at Location A), the vendor system 40-1 (e.g., if the stimulus is to eat a healthy meal at Location A, the vendor system 40-1 may indicate whether the first user used a coupon associated with the meal at Location A), the personal user device 10-1 (e.g., if the stimulus is to eat a healthy meal at Location A, the location sensor(s) 710 may indicate whether the first user was at Location A), and/or the optional second personal user device 10-1A (e.g., if the stimulus is to eat a healthy meal at Location A, Global Positioning System Sensor(s) 732 may indicate whether the first user was at Location A), to name a few.

At step S1022, in embodiments, the collection module determines whether the first stimulus was successful. In embodiments, the collection module may determine whether the first stimulus was successful by analyzing the collected information. For example, if the first stimulus was to walk 10,000 steps, the collection module may determine that the first stimulus was successful when the pedometer(s) 720 registers 10,000 steps since the stimulus was either accepted by the first user and/or sent by the system 1000 (and/or within a predetermined amount of time). Similarly, if the first stimulus was to walk 10,000 steps, the collection module may determine that the first stimulus was not successful if the pedometer(s) 720 does not register 10,000 steps since the stimulus was either accepted by the first user and/or sent by the system 1000 (and/or within a predetermined amount of time). In embodiments, the collection module may determine the first stimulus was successful, even if the first user did not achieve the predetermined goal (e.g., 10,000 steps). For example, if the first user typically registers 2,000 steps a day, and, in response to the stimulus, the first user registered 8,500 steps, the collection module of the system 1000 may determine the first stimulus was successful because the first user walked significantly more steps than usual. The measure of success, in embodiments, may be based on the user and information associated with the user (e.g., if the user is more active, eats healthier, etc. than typical for that specific user, the system 1000 may register the stimulus as a success).

At step S1024, in embodiments, the collection module generates stimulus response information indicating either success of the first stimulus or failure of the first stimulus. In embodiments, stimulus response information may include the effect a stimulus had on a particular user. For example, if the system 1000 is trying to get the user to eat healthier, the system 1000 may send stimuli that give coupons for healthy meals. If those coupons are used, the collection module 1008 may receive information indicating that the stimulus used resulted in a positive result—e.g., the user used the coupon for a healthy meal which indicates the user had a healthy meal. The stimulus response information may be stored such that the collection module 1008 may be used by the manager module 1006 to determine what kind of stimulus has worked in the past.

At step S1026, in embodiments, the collection module sends to the personal information module, the stimulus response information. In embodiments, the personal information module may receive the stimulus response information from the collection module for the purposes of storage (e.g., in the lifestyle database 1002-1) and access to the stimulus response information (e.g., to increase the likelihood of success for the next stimulus using the stimulus response information).

At step S1028, in embodiments, the collection module sends to the stimulus module, the stimulus response information. In embodiments, the stimulus module may receive the stimulus response information from the collection module for the purposes of storage (e.g., in the available stimulus database 1004-2) and access to the stimulus response information (e.g., to increase the likelihood of success for the next stimulus using the stimulus response information).

In embodiments, steps S1026 and S1028 may be performed simultaneously and/or substantially simultaneously. In embodiments, the stimulus response information may be stored such that the stimulus module and/or the personal information module may access the stimulus response information. In embodiments, the steps of the process described in connection with FIGS. 10-A and 10-B may be rearranged or omitted.

FIGS. 22A-22F are exemplary flow charts of processes for providing a stimulus to a personal user device associated with a first user in accordance with exemplary embodiments of the present invention. In embodiments, the process for providing a stimulus may begin with a step S2202. At step S2202, in embodiments, a lifestyle modification computer system to encourage at least one selected change in lifestyle related behavior may be provided. As discussed above, the stimulus may be provided by a lifestyle modification computer system. The lifestyle modification computer system may provide stimuli to a plurality of users of an interactive electronic network. In embodiments, the lifestyle modification computer system may include a plurality of databases and a plurality of modules, to name a few.

The plurality of databases, in embodiments, may include one or more of the following: the lifestyle database 1002-1, the user profile database 1016-1, the available stimulus database 1004-2, the stimulus database 1004-1, and/or memory 1704. The lifestyle database 1002-1, in embodiments, may include one or more of the following: first raw time-stamped streaming data and/or location data labels associated with the first raw time-stamped data. The first raw time-stamped data may be raw time-series data obtained from a portable mobile device. In embodiments, the first raw-time stamped streaming data may include one or more sets of time-stamped sensor data (e.g., the data displayed in connection with FIG. 18). The one or more sets of time-stamped sensor data may be obtained, in embodiments, from one or more of the following: (1) one or more devices associated with a first user; (2) one or more devices associated with one or more users of the plurality of users; (3) one or more third-parties (e.g., vendor system 40-1, employer hr system 32, health insurance system 34, medical system 36, social/professional network system 38, and/or a combination thereof, to name a few) and/or a combination thereof, to name a few.

The user profile database 1016-1, in embodiments, may include one or more of the following: location information, event stream information, goal information, and/or budget information, to name a few. Location information, in embodiments, may include location data labels associated with the first user. For example, each confirmed location data label (e.g., Address 1 corresponds to the first user's home) associated with each recurring location may be stored in connection with the location information. Location information, as described herein, may be similar to the location information 752 described in connection with FIG. 7A, the description of which applying herein.

Event stream information, in embodiments, may include one or more previously identified event streams (e.g., the event stream illustrated in FIG. 20B). Each previously identified event stream, in embodiments, may include: more than one time-sequenced location data labels associated with the first user; type of stimulus information (e.g., the category of stimulus offered—weight, stress, health, to name a few), and/or a combination thereof, to name a few.

The goal information, in embodiments, may be information indicating one or more goals selected by the first user. The one or more goals may be a goal in lifestyle behavior. The goals, in embodiments, may be selected from a list of available goals and/or may be manually input by the first user. Each goal, in embodiments, may have an associated category of goal in lifestyle behavior. The categorization of the goals, in embodiments, may assist the lifestyle modification computer system in pooling data from multiple users with similar goals. The goal information, in embodiments, may be similar to goal information 1322A described in connection with FIG. 1B, the description of which applying herein.

The budget information, in embodiments, may indicate an available budget to provide stimuli to the first user. In embodiments, the budget information may include budgets for each user of the plurality of users. The budgets for each user may be one or more of the following: a per-user budget (e.g., each user gets the same budget); a per-goal budget (e.g., each selected goal has an associated budget for each user that selects said goal); a budget that is time dependent (e.g., a daily budget, a weekly budget, a monthly budget, a quarterly budget, and/or an annual budget, to name a few), and/or a combination thereof, to name a few. The budget information, in embodiments, may be similar to budget information 1320A described in connection with FIG. 1B, description of which applying herein.

The available stimulus database 1004-2, in embodiments, may include one or more of the following: available stimulus items, type of stimulus information for one or more available stimulus items, cost information for one or more available stimulus items, availability information for one or more available stimulus items, and/or a combination thereof. In embodiments, available stimulus items may refer to rewards associated with one or more stimuli—e.g., a coupon, points, to name a few. Each available stimulus item, in embodiments, may have a corresponding type (e.g., type of stimulus information), cost (e.g., cost information), and/or availability (e.g., availability information). In embodiments, the type of stimulus may be similar to the categorization of goal. For example, each type of stimulus may be categorized by goals the stimulus may be associated with. Cost, in embodiments, may refer to the cost associated with the available stimulus item. Cost may be used to determine whether a stimulus is to be sent. For example, if the stimulus includes an available stimulus item with a cost exceeding the user's remaining budget, the stimulus may not be sent. As another example, if the cost does not exceed the user's remaining budget the stimulus may be sent. As another example, if the cost does not exceed the user's remaining budget, the stimulus may not be sent because the cost is too high with respect to the user's remaining budget. Availability, in embodiments, may be information that includes a respective time period when an available stimulus item is available. For example, if the available stimulus item is a coupon to go to an outdoor pool in New York, the available stimulus item may only have an availability of the summer.

The stimulus database 1004-1, in embodiments, include query information which may include one or more of the following: one or more queries, stimulus information associated with the one or more queries, and/or outcome information associated with the one or more queries, to name a few. One or more queries, in embodiments, may refer to one or more inputs made by the lifestyle modification computer system to one or more machine learning algorithms (e.g., machine learning algorithm, 1006-1). A query, for example, may refer to an event stream (e.g., the event stream illustrated in FIG. 20B) used as an input to a machine learning algorithm to determine whether a stimulus should be selected and sent to the first user. Each query, in embodiments, may have corresponding stimulus information (e.g., the output of the machine-learning algorithm resulting from the inputted query), and/or corresponding outcome information (e.g., the outcome of the stimulus selected—e.g., positive, negative, neutral, to name a few). In embodiments, a query may only have corresponding stimulus information. For example, an event stream used as a query may receive an output indicating a stimulus should not be sent. Thus, continuing the example, the query would have corresponding stimulus information but no outcome information because no stimulus was sent.

In embodiments, the stimulus database 1004-1 may include queries, stimulus information, and outcome information associated with the first user. In embodiments, the stimulus database 1004-1 may include one or more queries, stimulus information, and outcome information associated with the first user and one or more additional users of the plurality of users. In embodiments, the plurality of queries includes queries (and/or associated stimulus information and/or outcome information) associated with one or more additional users having goals in lifestyle behavior in the same or similar category of goal in lifestyle behavior as the goal(s) selected by the first user.

In embodiments, the plurality of modules may include one or more of the following: personal information module 1002, situation module 1016, training set module 1018, stimulus module 1004, manager module 1006, collection module 1008, location module 1710, location-based events module 1712, time-based events module 1714, and/or a combination thereof, to name a few. In embodiments, the above modules may be combined and/or further segregated. One or more of the plurality of modules, in embodiments, may be operatively connected to the plurality of databases and/or one another, to name a few. In embodiments, one or more of the plurality of modules may include one or more of the following: one or more processor(s), memory, a communication portal, and/or one or more machine-readable instructions, to name a few. The lifestyle modification computer system, in embodiments, may be similar to system 1000 described above in connection with FIGS. 1, 1A-1, 1A-2, 1A-3, 1B-1F and/or system 1000-A described in connection with FIGS. 17 and 17A-G, the descriptions of which applying herein.

The process for providing a stimulus to the first user, in embodiments, may continue with a step S2204. At step S2204, in embodiments, the personal information module 1002 may obtain second raw time-stamped streaming data. The second raw time-stamped streaming data, in embodiments, may include one or more sets of time-stamped sensor data. In embodiments, the second raw time-stamped streaming data may include sensor data and/or additional data that is not sensor data (e.g., metadata, identifiers, to name a few). The one or more sets of time-stamped sensor data may be obtained from one or more of the following: (1) a first user device associated with the first user (e.g., first computer device 1012); (2) a second user device associated with the first user (e.g., second computer device 1014); (3) one or more devices associated with one or more users of the plurality of users; (4) one or more third-parties (e.g., vendor system 40-1, employer hr system 32, health insurance system 34, medical system 36, social/professional network system 38, and/or a combination thereof, to name a few) and/or a combination thereof, to name a few.

The one or more sets of time-stamped sensor data, may include a first set of time-stamped sensor data associated with a first time period (e.g., past 10 minutes, 30 minutes, hour, hours, day, days, to name a few). The first set of time-stamped sensor data may include one or more of the following: time-stamped location information and/or time-stamped motion information, to name a few. The time-stamped location information, in embodiments, may indicate the first user device was located at a first location at a first time (e.g., the time 12:04 PM) during at the first time period (e.g., a time range 12:00 PM-3:00 PM). For example, the first user device was located in times square the past 30 minutes. The time-stamped motion information, in embodiments, may be associated with movement of the first user device at the first time and/or associated with movement of the first user device around the first time (e.g., between 12:00 PM and 12:10 PM, between 12:03:30 PM and 12:04:30 PM, to name a few).

The process for providing a stimulus to the first user may continue with a step S2206. At step S2206, in embodiments, the personal information module 1002, may process the second raw time-stamped streaming data in real-time to determine if the first location has a corresponding first location data label. To determine whether the first location has a corresponding first location data label, in embodiments, the personal information module 1002 may compare the time-stamped location information of the second raw time-stamped streaming with the location data labels associated with the first user stored with the location information. If a corresponding location data label is found ("yes" at step S2208), the personal information module 1002 may update the lifestyle database 1002-1 to include the second raw time-stamped streaming data labelled with its corresponding location data label. The personal information module 1002 may, in embodiments, notify the situation module 1016 of the updated lifestyle information. In embodiments, the personal information module 1002 may send the second raw time-stamped streaming data with its corresponding location data label to the situation module 1016. If a corresponding location data label is not found ("no" at step S2208) the process may continue with the steps illustrated in connection with FIG. 22D, described in more detail below, the description of which applying herein.

Figure 22B:
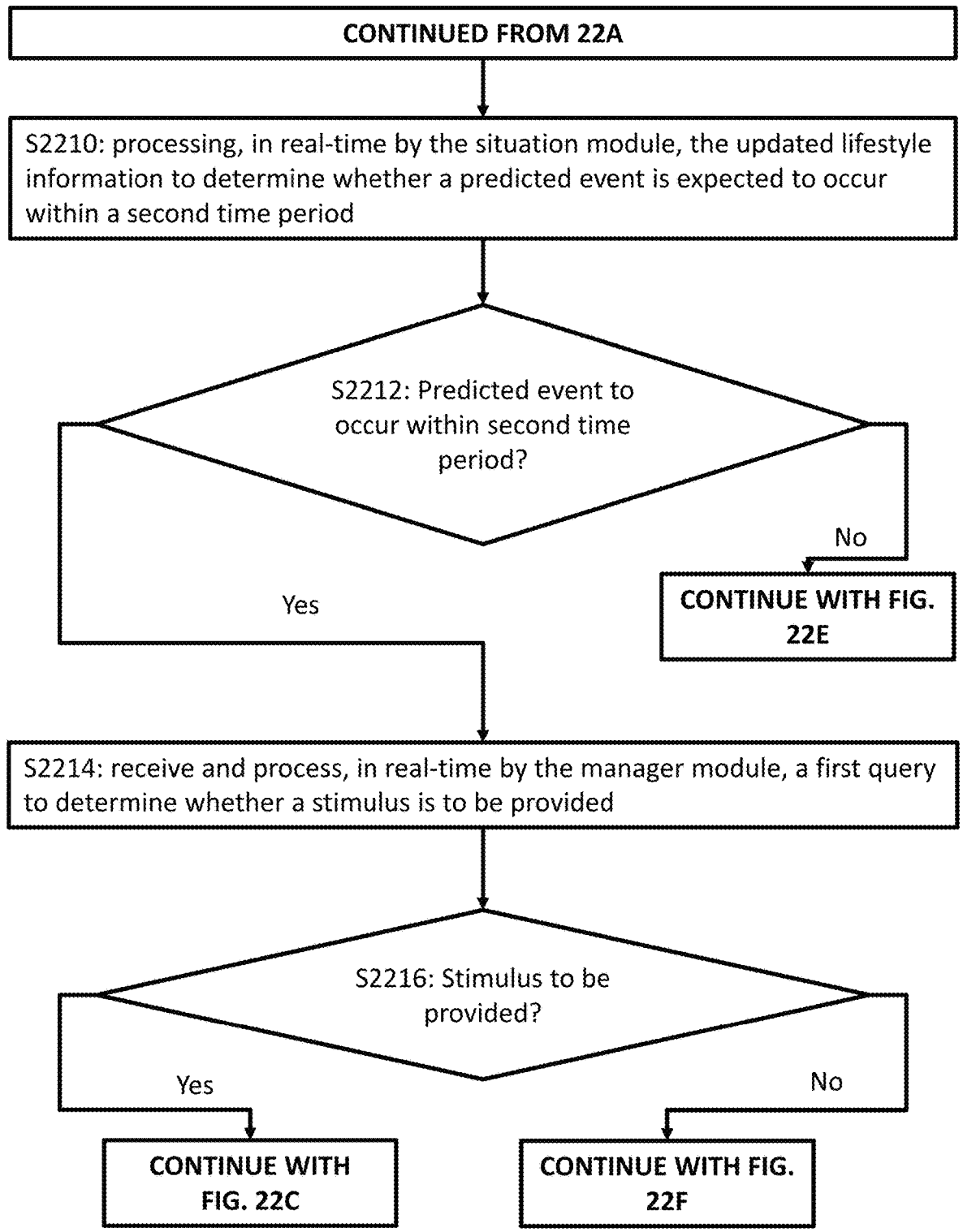

The process of providing a stimulus to a first user may continue with FIG. 22B. Referring to FIG. 22B, the process may continue with a step S2210. At step S2210, in embodiments, the situation module 1016 may process the updated lifestyle information in real-time to determine whether a predicted event is expected to occur within a second period of time (e.g., within 1 minute, within 5 minutes, within 10 minutes, within 30 minutes, within an hour, within 6 hours, within 12 hours, within a day, within a week, within a month, within a year, to name a few). To predict a future event based on past events, in embodiments, the stimulus module 1016 may obtain the updated lifestyle information (including the second raw time-stamped streaming data with its corresponding first location data label) and/or a second plurality of sets of time-stamped sensor data and, for each set of the second plurality of sets, a corresponding location data label (e.g., from the lifestyle database 1002-1 via the personal information module 1002). Each set of the second set may, in embodiments, be sequentially related by time interval and/or within a threshold period of time (e.g., within the past 12 hours, within the past 6 hours, within the past hour, within the past day, week, month, quarter, year, to name a few). The second set, in embodiments, may include each set of time-stamped sensor data associated with the second period of time (e.g., if the second period of time is between 1 and 1:30 PM, the second sent may include each set of time-stamped sensor data that occurred between 1 and 1:30 PM). The second set, in embodiments, may include less than each set of time-stamped sensor data associated with the second period of time.

In embodiments, the situation module 1016 may generate a first event stream designed to reflect past and current locations and corresponding movements associated with a user's routine over time (e.g., over the past 3 hours and future 3 hours, over the calendar day, to name a few). The event stream, in embodiments, may organize confirmed locations (and/or events) by time, order of locations (and/or events), and/or a combination thereof. An exemplary event stream is shown in connection with FIG. 20B. In embodiments, the generated event stream herein may utilize confirmed events and locations, which, in embodiments, may remove any "?"—as there are no unknowns in the generated event stream (in this example). In embodiments, the generated event stream may include unknowns and thus "?". In embodiments, the situation module 1016 may generate a plurality of event streams, each of which organized by timestamp and associated with each respective location data label.

Once generated, the situation module 1016 may analyze the first event stream (and/or the plurality of event streams) against one or more previously identified event streams of the event stream information stored in the user profile database 1016-1 (and/or against routine information—e.g., routine 1710-A, 1712-A, 1714-A; and/or against one or more data model(s) 1710-C, 1712-C, 1714-C). The situation module 1016 may determine that one or more of the previously identified event streams matches the generated first event stream above a predetermined threshold (e.g., past three locations match, past two locations match, to name a few). The match may require only a portion of a previously identified event stream to match with the generated first event stream.

In embodiments, if the situation module 1016 matches previously identified event stream(s) with the generated first event stream, the situation module 1016 may determine whether the matched previously identified event stream(s) indicate whether an event (e.g., going to work, going home, going to lunch, going to dinner, going to sleep, to name a few) is expected to occur within a second time period (e.g., within the next 30 minutes, within the next 10 minutes, within the next hour, within the next 6 hours, within the next day, to name a few). In embodiments, the lifestyle modification computer system may utilize said prediction as a trigger to select and send a real-time notification (e.g., a stimulus) to the first user. If an event is predicted to occur within the second period of time, the situation module 1016 may send the generated first event stream as a first query to the manager module 1006. If an event is not predicted to occur within the second period of time ("no" at step S2212) the process may continue with the steps illustrated in connection with FIG. 22E, described in more detail below, the description of which applying herein.

The process for providing a stimulus to a first user may continue with step S2214. At step S2214, in embodiments, the manager module 1006 may receive and process the first query in real-time to determine whether a stimulus is to be provided to the first user. To determine whether a stimulus is to be provided to the first user, in embodiments, the manager module 1006 may obtain a first machine-learning algorithm (e.g., machine learning algorithm 1006-1) with a training data set (e.g., training data set 1018) provided by the training data set module 1018. The first query (the generated first event stream) may be provided as a data input to the first machine-learning algorithm. The output of the machine-learning algorithm, in embodiments, may be stimulus information, which may indicate whether a stimulus is to be provided to the first user. The first stimulus information, in embodiments, may include a first type of stimulus information (e.g., indicating a first category of stimulus to be provided). The first stimulus information, in embodiments, may be sent by the manager module 1006 to the stimulus module 1004 (as shown in connection with FIG. 1A-3). If the first stimulus information indicates no stimulus is to be provided to the first user ("no" at step S2216) the process may continue with the steps illustrated in connection with FIG. 22F, described in more detail below, the description of which applying herein.

The training data set, in embodiments, may include one or more previously identified event streams associated with the first user. Each previously identified event stream, in embodiments, is tagged with stimulus information which may indicate a respective stimulus offered to the first user and a corresponding outcome. In embodiments, the training data set may include one or more previously identified event streams associated with one or more users of the plurality of users.

The first machine learning algorithm, in embodiments, may be similar to the machine learning algorithm 1006-1 described above in connection with FIGS. 1A-1, 1A-2, and 1A-3, the description of which applying herein. The training data set, in embodiments, may be similar to the training data set 1018 described above in connection with FIGS. 1A-1, 1A-2, and 1A-3, the description of which applying herein.

Figure 22C:
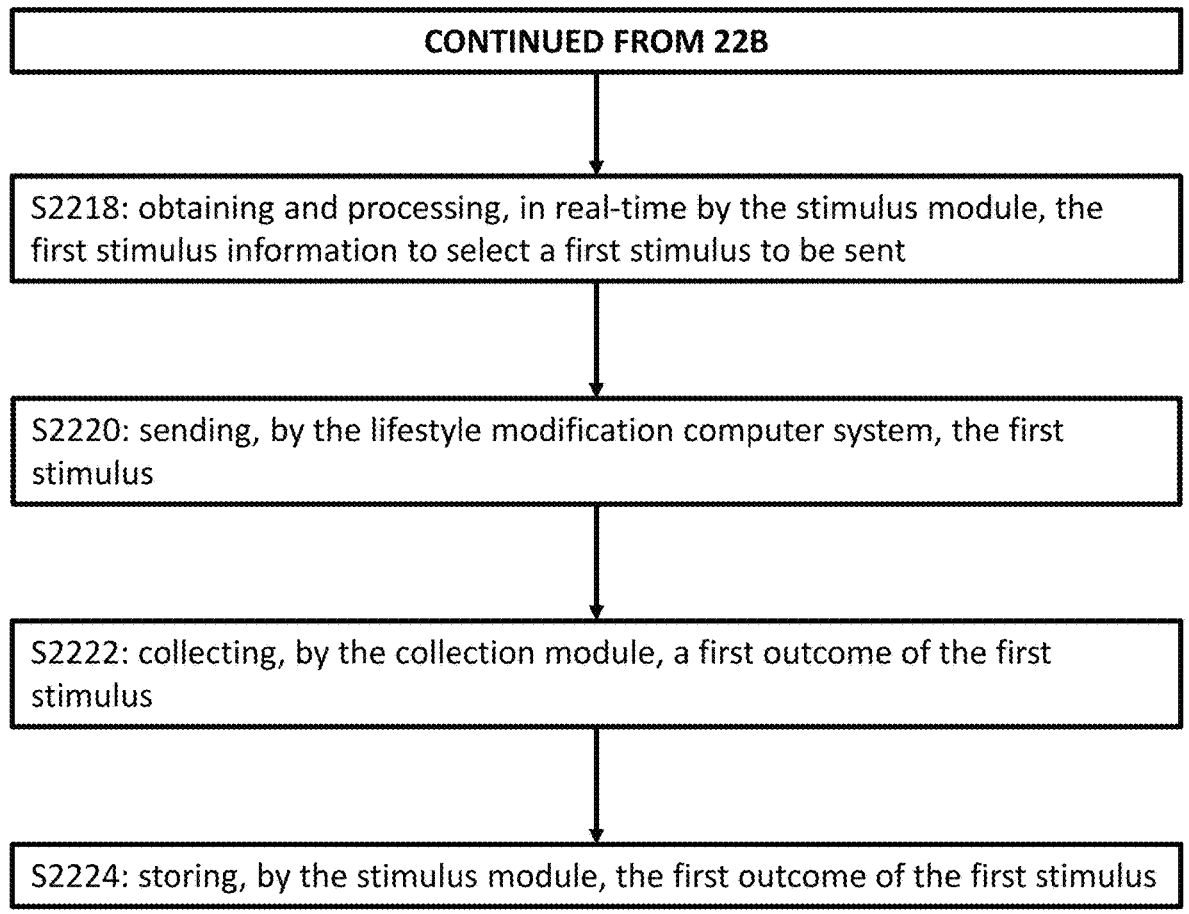

The process of providing a stimulus to a first user may continue with FIG. 22C. Referring to FIG. 22C, the process may, in embodiments, continue with a step S2218. At step S2218, in embodiments, the stimulus module 1004 may obtain and process the first stimulus information in real-time to select a first stimulus to be sent. In embodiments, the first stimulus includes one or more available stimulus items (e.g., obtained from an available stimulus module via a third-party vendor). In embodiments, the selection of the first stimulus may be based on one or more of the following: the predicted event, the available budget associated with the first user, the available stimulus items (e.g., obtained from the available stimulus database 1004-2 via the stimulus module 1004 and/or via an available stimulus module of the lifestyle modification computer system), cost(s) associated with the available stimulus items, the current weather near the first user (e.g., if it is raining, the stimulus may not be go for a run outside), outcome information, and/or a combination thereof. In embodiments, the available stimulus items are of the same type of stimulus associated with the first user's selected goal(s). In embodiments, the outcome information includes outcomes indicating a positive outcome. In embodiments, the outcome information includes both positive and negative outcomes. In embodiments, the stimulus module 1004 may determine that there are no stimuli associated with the first stimulus information (e.g., the first stimulus is unavailable). For example, the stimulus selected may cost more than the first user's available budget. The determination that one or more stimuli is unavailable may be based on one or more of the following: cost information, available budget, no stimuli associated with the stimulus information, a lack of user responses to stimuli, user preferences (e.g., stimuli are not to be sent during one or more time intervals, a blacklist of types of stimuli, whitelist of types of stimuli, to name a few), and/or a combination thereof, to name a few. If no stimuli is selected, in embodiments, the stimulus module 1004 may store the first stimulus information and/or the first query (and/or that no stimulus was selected) in the stimulus database 1004-1.

The first stimulus, in embodiments, may be situationally targeted with respect to the first user's selected one or more lifestyle goals such that the first stimulus is sent to provide a real-time notification to the first user. In embodiments, the first stimulus is situationally targeted based on the predicted event, which was predicted in advance by the lifestyle modification computer system based on prior event streams.

The process of providing a first stimulus to the first user may continue with a step S2220. At step S2220, in embodiments, the lifestyle modification computer system sends the first stimulus. In embodiments the lifestyle modification computer system sends the first stimulus to a device associated with the first user (e.g., the first computer device 1012, the second computer device 1014, to name a few). In embodiments the lifestyle modification computer system sends the first stimulus to a device associated with a second user. In embodiments the lifestyle modification computer system sends the first stimulus to a device associated with the first user (e.g., the first computer device 1012, the second computer device 1014, to name a few) and a device associated with a second user. In embodiments, the first stimulus may be sent to one or more of the following: (1) one or more devices associated with a first user; (2) one or more devices associated with one or more users of the plurality of users; (3) one or more third-parties (e.g., vendor system 40-1, employer hr system 32, health insurance system 34, medical system 36, social/professional network system 38, and/or a combination thereof, to name a few) and/or a combination thereof, to name a few.

The lifestyle modification computer system, in embodiments, may send the first stimulus by first sending the first stimulus from the stimulus module 1004 to the manager module 1006, which sends the first stimulus. In embodiments, the stimulus module 1004 may send the selected stimulus. The lifestyle modification computer system, in embodiments, may send the first stimulus by first sending the first stimulus from the stimulus module 1004 to the collection module 1008, which sends the first stimulus.

The process of providing a first stimulus to the first user may continue with a step S2222. At step S2222, in embodiments, the collection module 1008 collects a first outcome of the first stimulus (e.g., what the first user did or did not do as a result of the first stimulus). In embodiments, the first outcome may be obtained from one or more of the following: (1) one or more devices associated with a first user; (2) one or more devices associated with one or more users of the plurality of users; (3) one or more third-parties (e.g., vendor system 40-1, employer hr system 32, health insurance system 34, medical system 36, social/professional network system 38, and/or a combination thereof, to name a few) and/or a combination thereof, to name a few. The collection module 1008, in embodiments, may send the collected first outcome to the stimulus module 1004 to store. Step S2222, in embodiments, may be similar to step S1020 described in connection with FIG. 10B and/or step S1120 described in connection with FIG. 11B, the descriptions of which applying herein.

The process of providing a first stimulus to the first user may continue with a step S2224. At step S2224, in embodiments, the stimulus module 1004 may store the first outcome of the first stimulus. In embodiments, the process may repeat, e.g., at step S2204 with the personal information module 1002 obtaining third raw time-stamped streaming data. The process may continue repeating and providing stimuli to the first user.

Figure 21A:
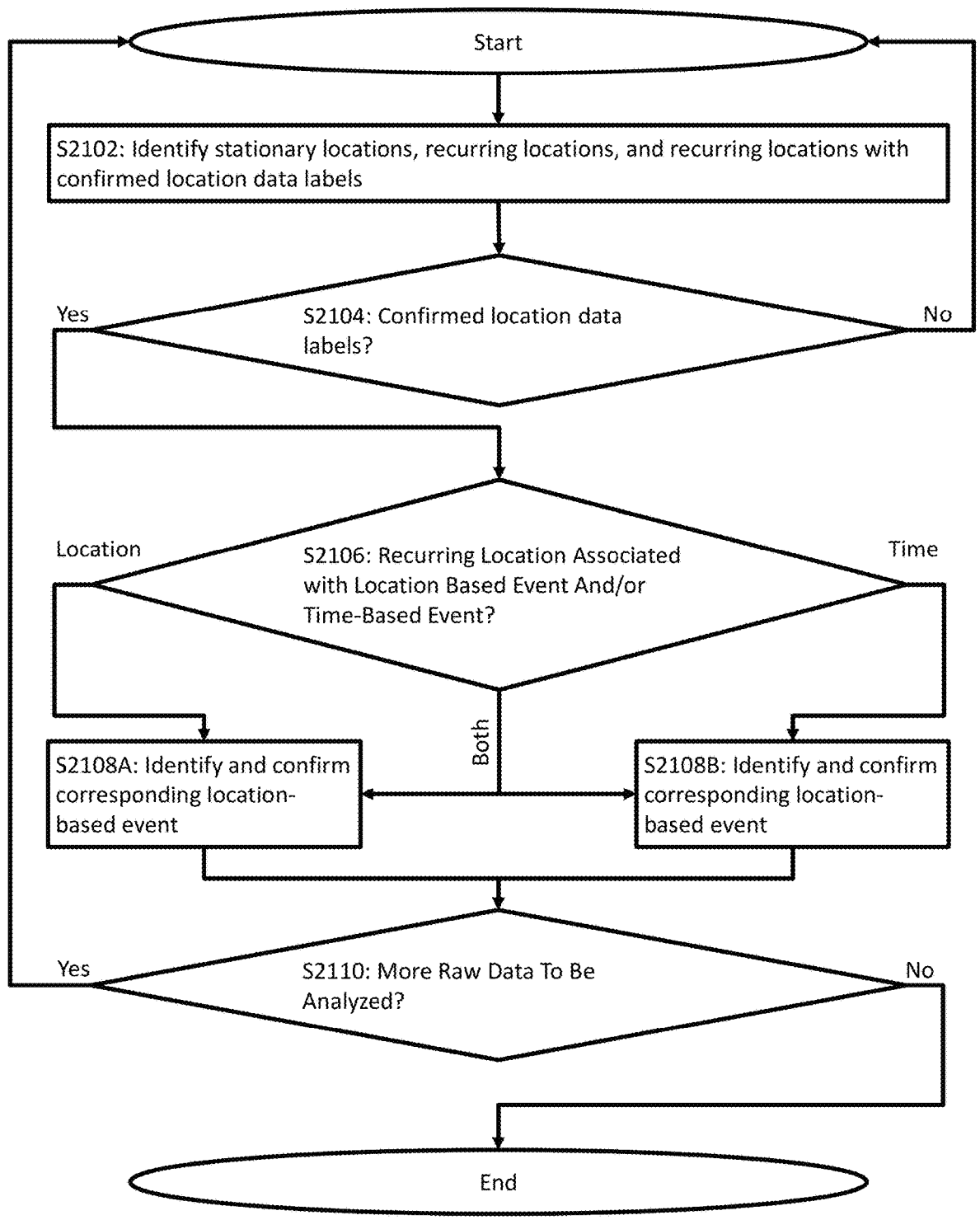
Figure 21B:
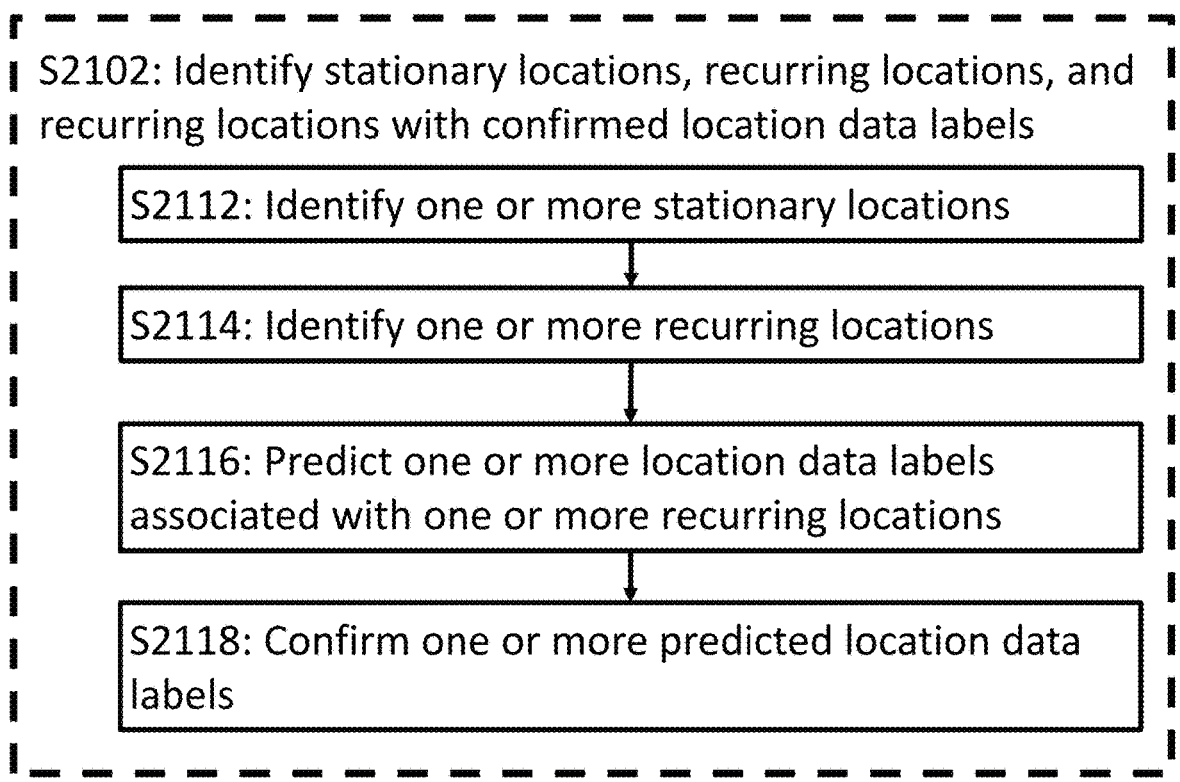
Figure 21C:
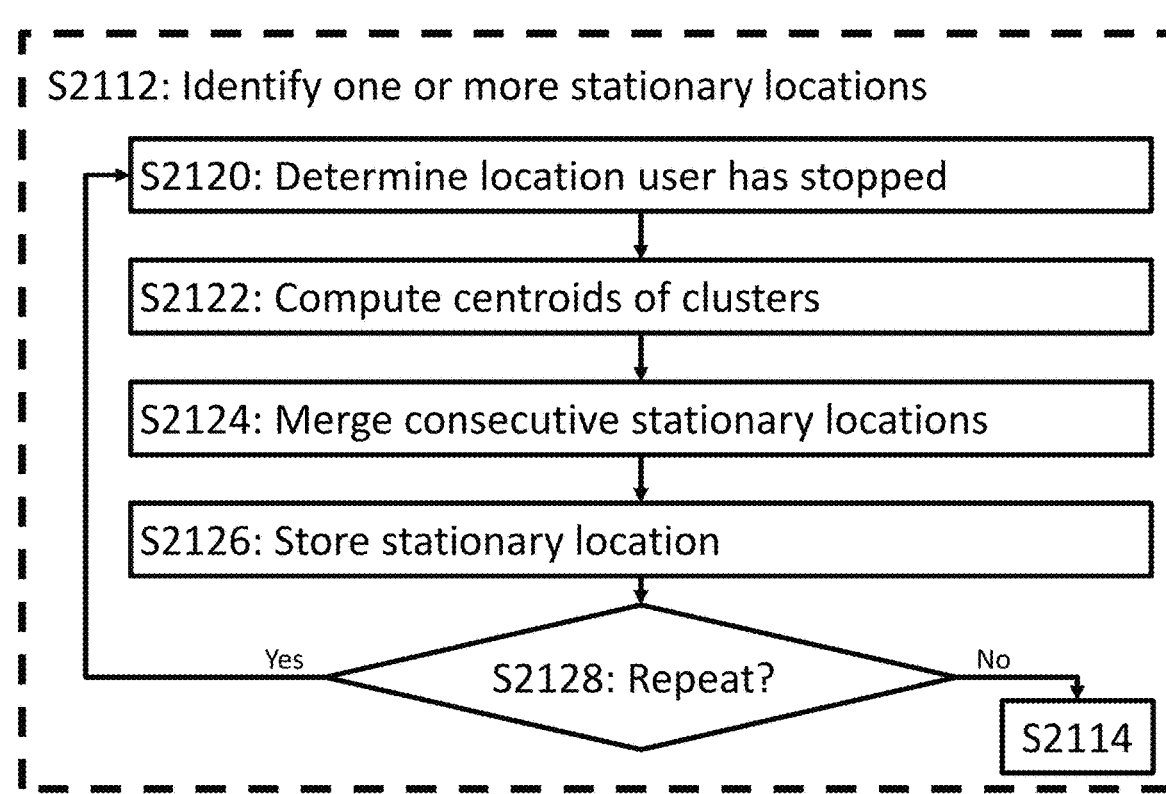
Figure 21D:
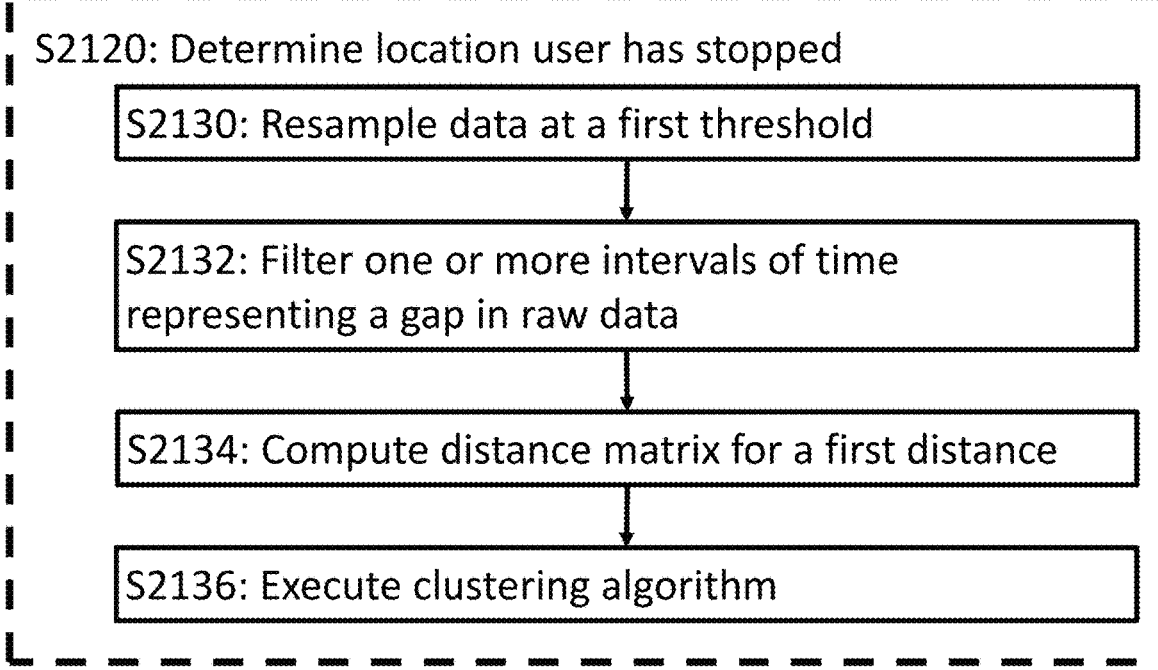
Figure 21E:
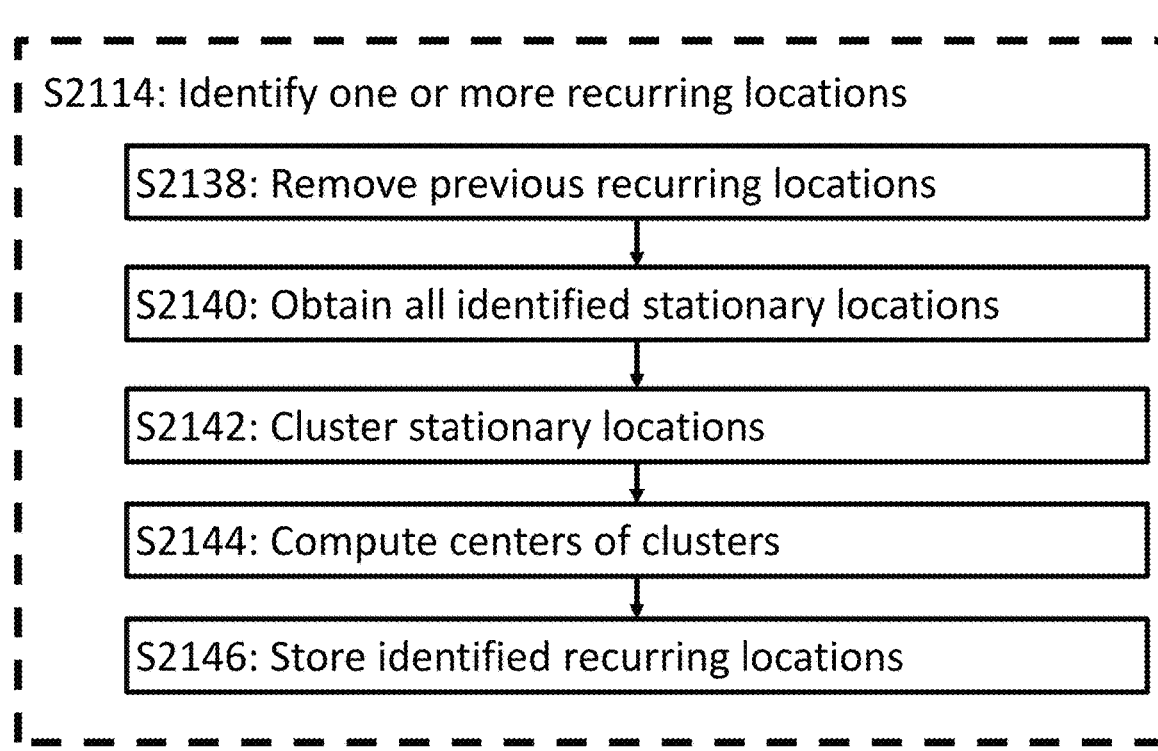

Referring back to FIG. 22A, in embodiments, a corresponding location data label is not found at step S2206 ("no" at step S2208). The process may continue with FIG. 22D. Referring to FIG. 22D, in embodiments, the process may continue with step S2226. At step S2226, in embodiments, the personal information module 1002 may determine that no location data label associated with the first location is stored in the location information. The process may continue with step S2228. In embodiments, at step S2228, the personal information module 1002 may send the second raw time-stamped streaming data to the location module 1710 to analyze, predict, and/or confirm a corresponding location data label and/or a corresponding event—the process of which is described in more detail in connection with the description of FIGS. 21A through 21M, the descriptions of which applying herein.

Referring back to FIG. 22B, in embodiments, the situation module 1016 may not predict an event to occur within the second period of time at step S2210 ("no" at step S2212). The process may continue with FIG. 22E. Referring to FIG.

22E, in embodiments, the process may continue with one or more alternatives. In embodiments, a first alternative is a step S2232. At step S2232, in embodiments, the situation module 1016 may notify the personal information module 1002, causing the personal information module 1002 to continue to analyze the second raw time-stamped streaming data for a second location (e.g., return to step S2204). In embodiments, a second alternative, the process ends.

Figure 22D:
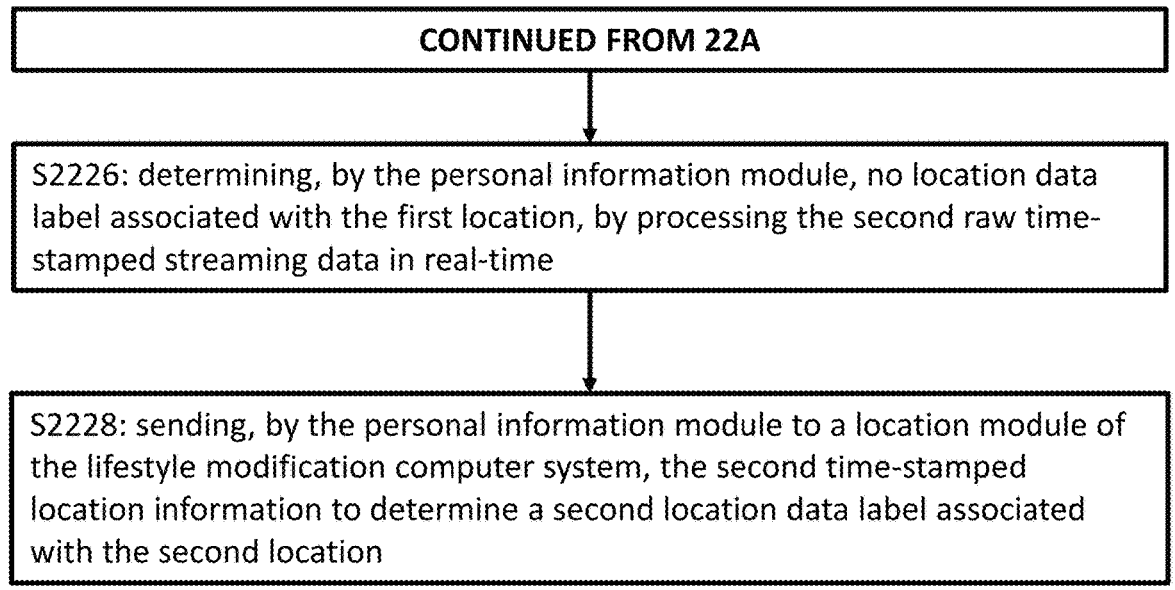
Figure 22E:
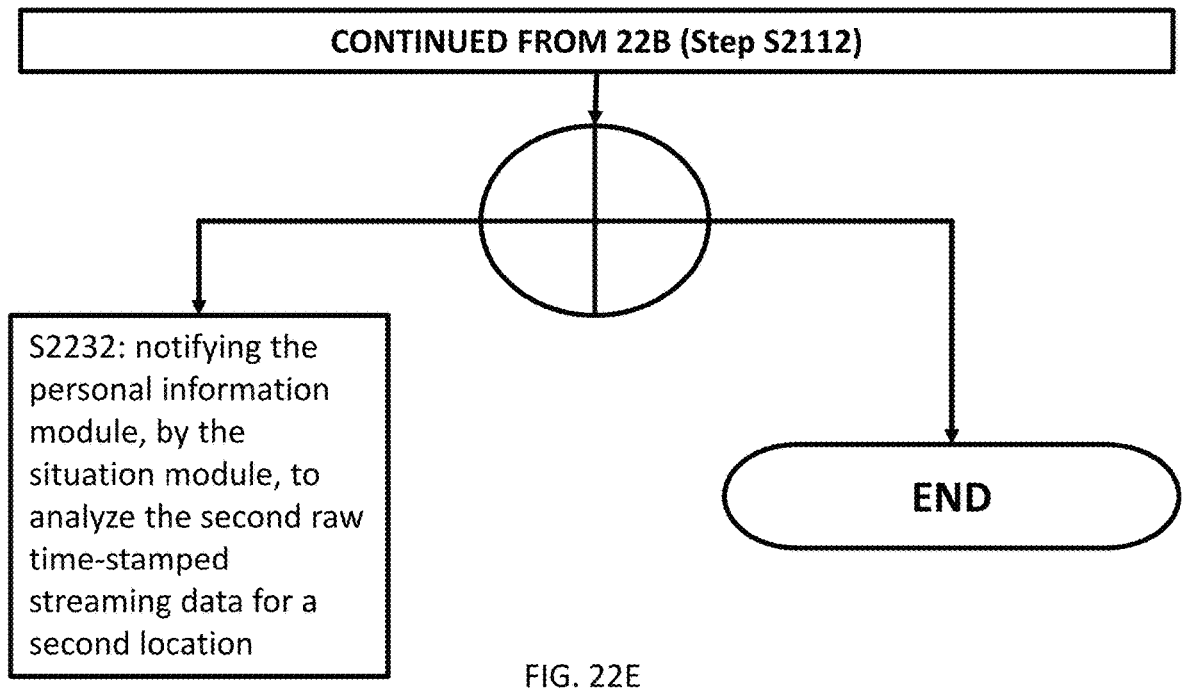
Figure 22F:
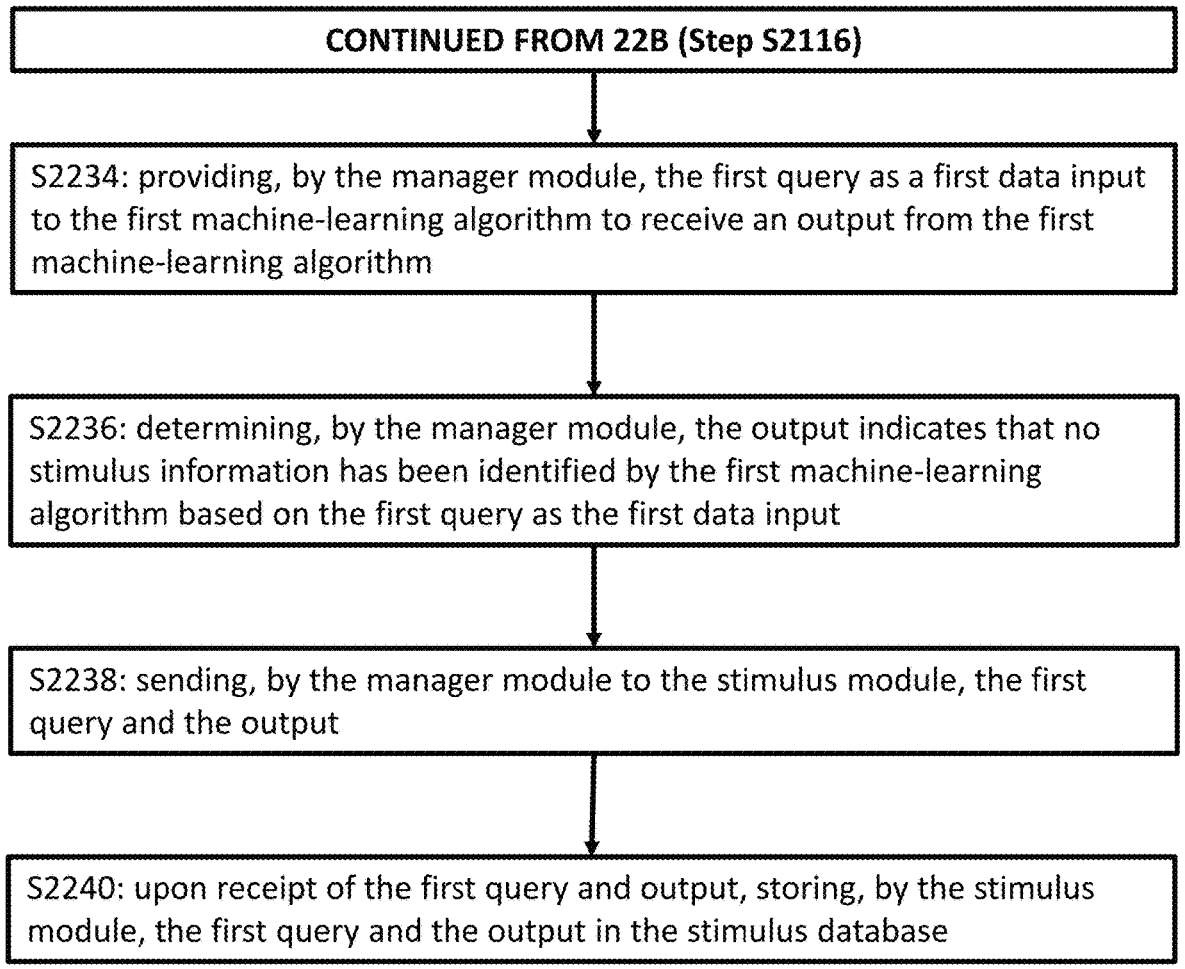

Referring back to FIG. 22B, in embodiments, the first stimulus information indicates no stimulus is to be provided to the first user ("no" at step S2216). The process may continue with FIG. 22F. Referring to FIG. 22F, in embodiments, the process may continue with a step S2234. At step S2234, in embodiments, the manager module 1006 may provide the first query as a first data input to the first machine learning algorithm to receive an output from the first machine-learning algorithm. At step S2236, in embodiments, the manager module 1006 may determine the output indicates that no stimulus information (and/or stimulus information indicates that no stimulus is to be provided) has been identified by the first machine-learning algorithm based on the first query as the first data input. The process may continue with a step S2238. At step S2238, in embodiments, the manager module 1006 sends the first query and the output to the stimulus module 1004. Upon receipt of the first query and output, at step S2240 in embodiments, the stimulus module 1004 may store the first query and the output in the stimulus database 1004-1.

The processes of FIG. 22A through 21F may be repeated. In embodiments, the steps of the processes described in connection with FIG. 22A through FIG. 22F may be rearranged or omitted.

Referring back to FIG. 1A, the system 1000 in accordance with exemplary embodiments of the present invention to encourage a selected change in health-related behavior of at least a first user of a plurality of users of an interactive electronic network is described.

The system 1000, in embodiments, may include one or more of the following: a personal information module 1002, a situation module 1016, stimulus module 1004, training set module 1018, manager module 1006, and/or collection module 1008, to name a few. The system 1000 may perform the steps illustrated in connection with FIGS. 10-A-10-B, FIGS. 11A-11B and/or FIGS. 12A-12D, the descriptions of which applying herein.

Figure 11A:
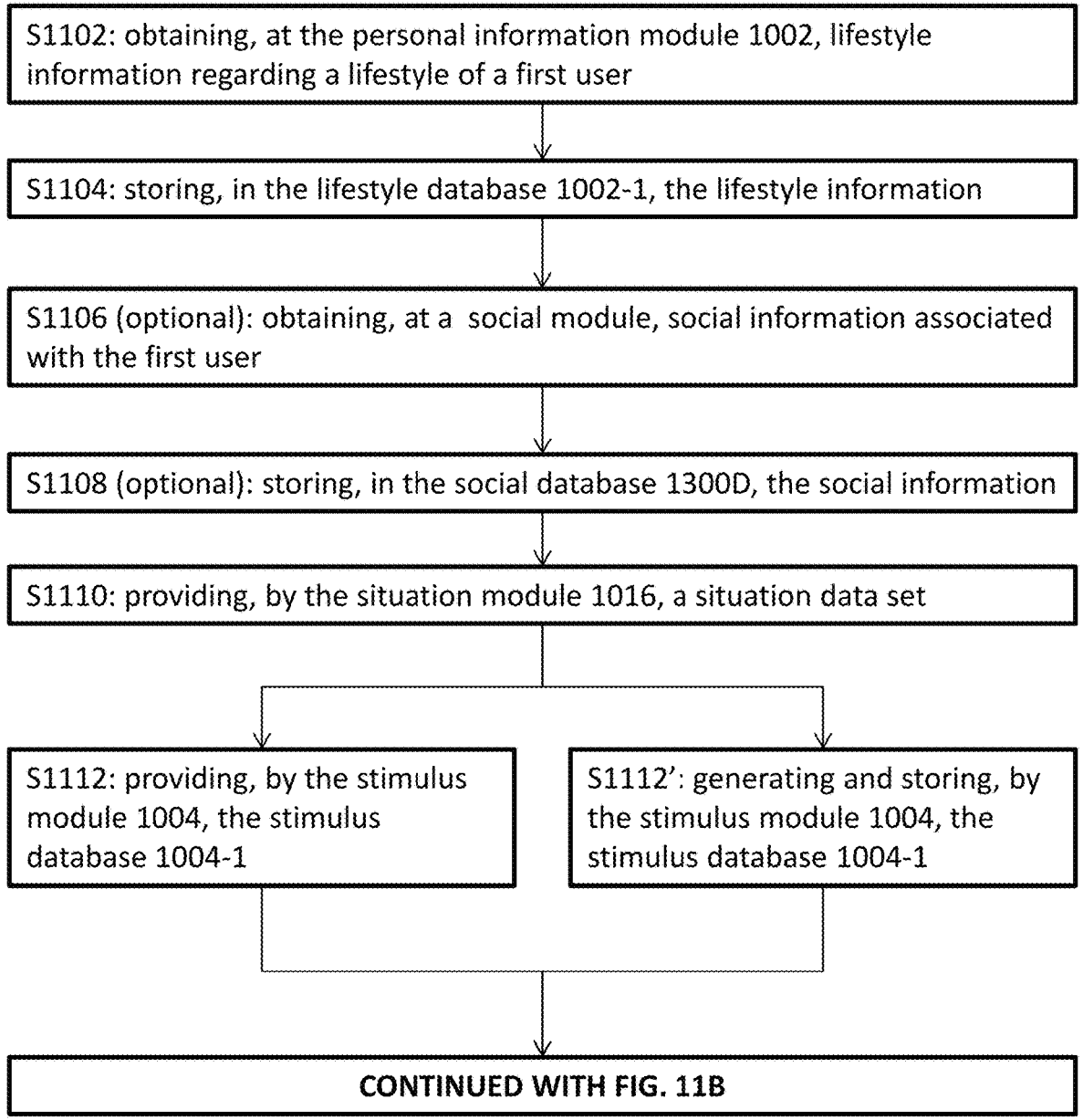
FIGS. 11A-11B are exemplary flow charts illustrating a process for encouraging a selected change in behavior of at least a first user of a plurality of users of an interactive electronic network in accordance with exemplary embodiments of the present invention.

Referring to FIG. 1A, the personal information module 1002 may include first one or more processors operatively connected to a first memory device and first machine readable instructions. Referring to FIG. 11A, in embodiments, the first one or more processors may be configured to execute the first machine readable instructions to obtain (step S1102) and store (step S1104) in one or more lifestyle databases 1002. Referring to FIG. 1B, lifestyle information 1308, in lifestyle database 1002, may include lifestyle information associated with one or more users, such as a first user. Examples of lifestyle information 1308 includes: identity information 1310A associated with an identity of the first user; health-related attribute information 1312A associated with at least one health-related attribute of the first user; health kit information 1315A associated with health conditions and/or actions effecting health of the first user; sensor information 1314A associated with one or more computer devices associated with one or more users, such as the first user; prior purchase information 1316A associated with purchases made by and/or associated with the first user; activity information 1318A indicative of activities engaged in by and/or associated with the first user within; budget information 1320A associated with an available budget for use in providing stimulus to the first user; and goal information 1322A associated with the selected change in behavior, to name a few.

Figure 7A:
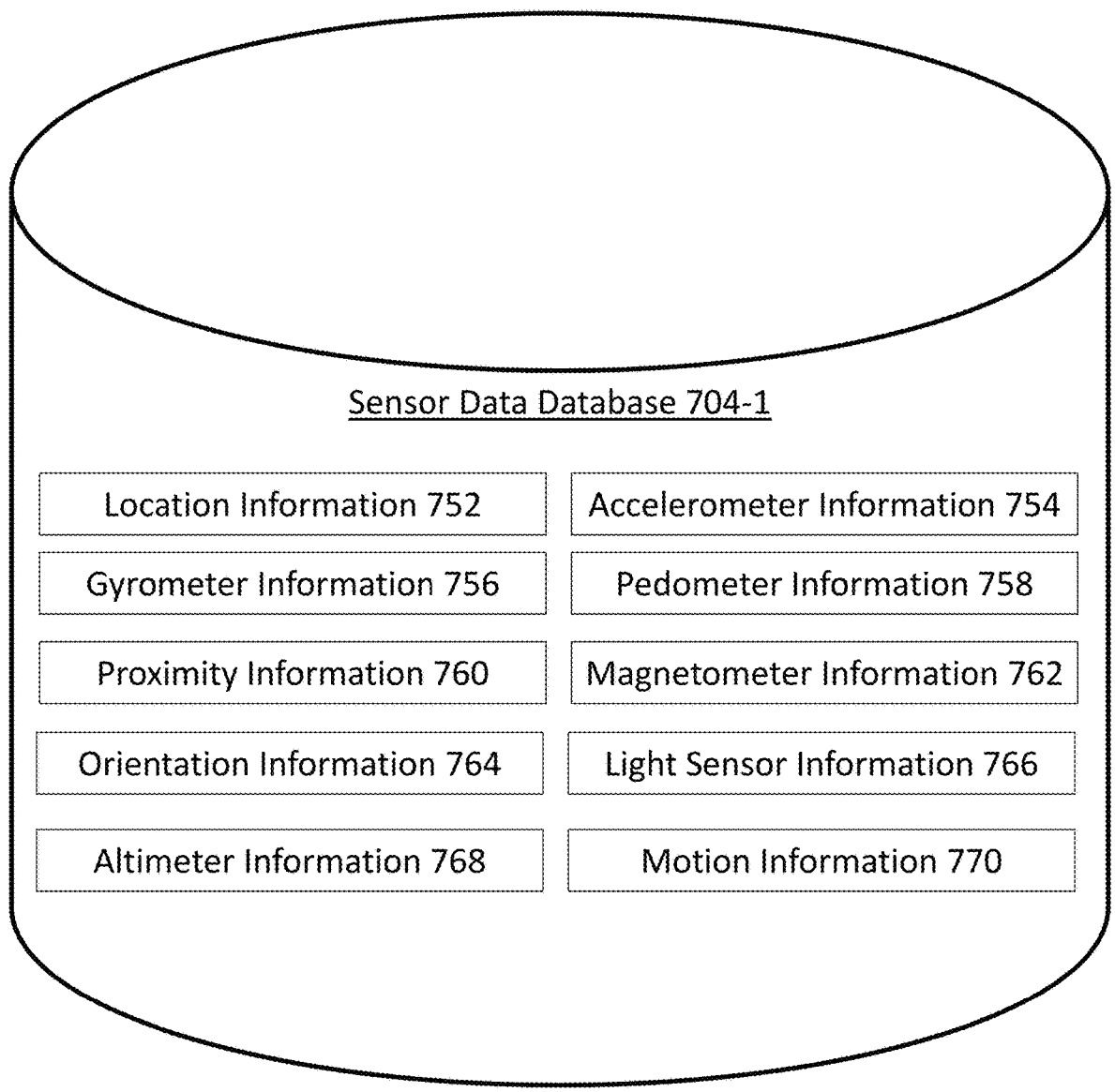
FIG. 7A illustrates an exemplary sensor data database in accordance with exemplary embodiments of the present invention.
Figure 7B:
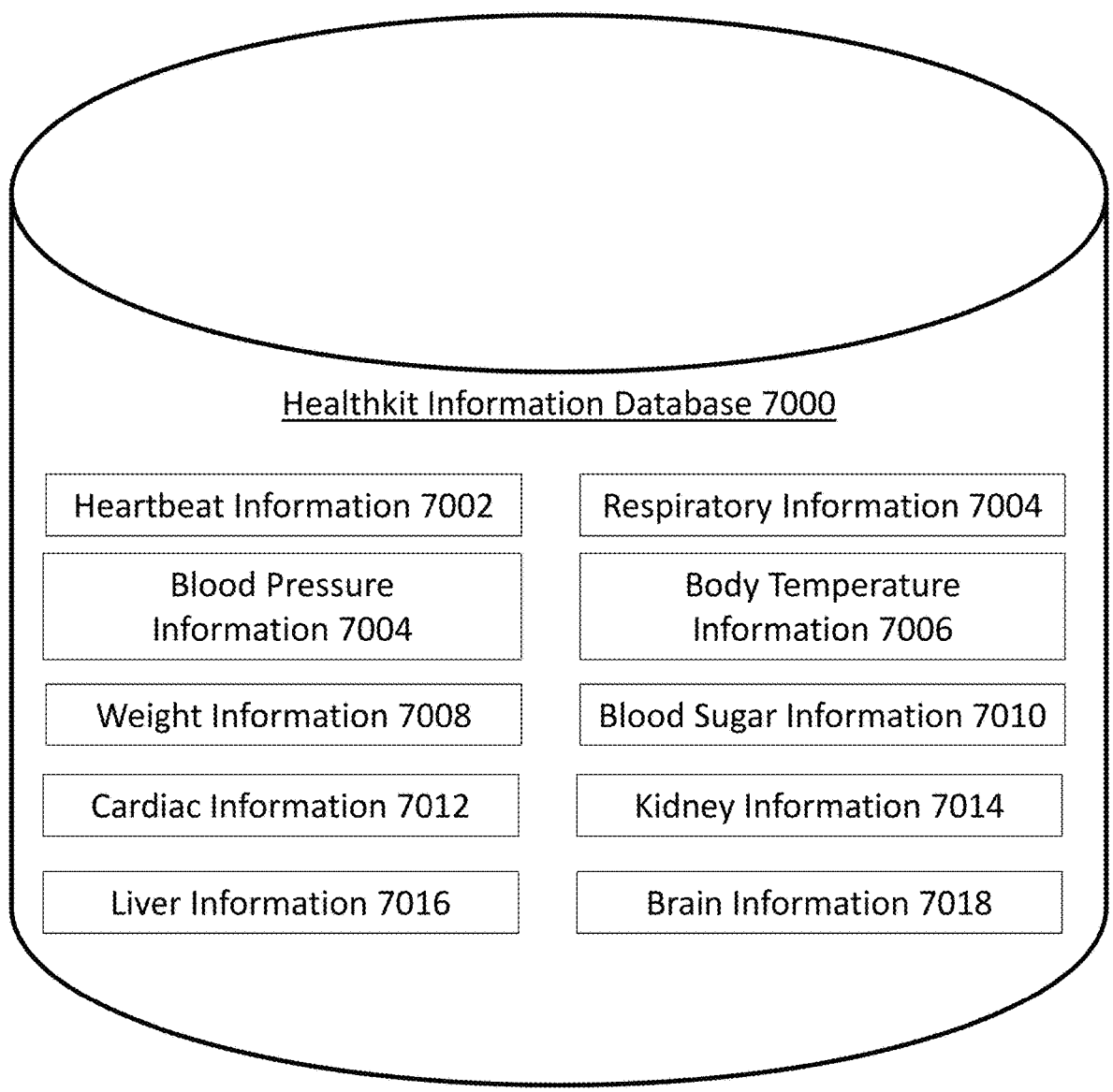
FIG. 7B illustrates an exemplary health kit data set in accordance with exemplary embodiments of the present invention.

In embodiments, as shown in FIG. 7A, sensor information 1314A may include various kinds of information taken from sensors on one or more computer devices associated with a user. For example, sensor information 1314A may include location information associated with location information and/or movement information of the first computer device at a first respective time, accelerometer information generated by at least one accelerometer of the first computer device at a second respective time; gyrometer information generated by at least one gyrometer of the first computer device at third respective time; pedometer information generated by at least one pedometer of the first computer device at a respective fourth time; proximity information generated by at least one proximity sensor of the first computer device at a fifth respective time; magnetometer information generated by at least one magnetometer sensor of the first computer device at a sixth respective time; orientation information associated with degrees of rotation the first computer device makes around three physical axes at a seventh respective time; light sensor information generated by at least one light sensor of the first computer device at an eight respective time; altimeter information associate with a change in altitude pressure of the first computer device at a ninth respective time, to name a few. In embodiments, sensor information 1314A may also include motion information associated with acceleration, attitude, rotation, and magnetic data of the first computer device at a respective time.

Referring to FIG. 11A, in embodiments, the system 1000 may further include a social module (not shown) which may include seventh one or more processors operatively connected to at least a seventh memory device and seventh machine readable instructions. The social module may be operatively connected to the personal information module 1002 and/or the manager module 1006. The seventh one or more processors may be configured to execute the seventh machine readable instructions to obtain (step S1106) and store (step S1108) in one or more social databases 1300D, social information associated with the first user. The social information (such as social connection information 1308D) may include social network information 1301D, and professional colleague information 1312D. In embodiments, at least one user (e.g., a second user) is a professional colleague connection of the first user and the third computer device is associated with the second user. The social network information 1301D may comprises one or more other users (such as a second user) that are social network connection (s). The social module may be operatively connected to the situation module 1018.

Referring back to FIG. 1A, in embodiments, a situation module 1016 may include second one or more processors operatively connected to at least a second memory device and second machine readable instructions. The situation module 1016 may be operatively connected to the personal information module 1002. Referring to FIG. 11A, the second one or more processors may be configured to execute the second machine readable instructions to provide a situation data set (step S1108) by performing the following steps, as illustrated in FIGS. 12A and 12B. Referring to FIGS. 12A and 12B, in steps S1202 and S1202', the situation module 1016 accesses the lifestyle information 1308A provided by the personal information module 1002. In steps S1204 and S1204', the situation module 1016 arranges the lifestyle information based at least on chronology to include information from a first predetermined time period to provide a current state data set associated with a current state of the first user. Referring to FIG. 12B, in a step S1206', the situation module 1016 may access prior current state information associated with prior current states of the first user. Referring to FIG. 12A, in step 1206, the situation module provides the current state data set to a machine learning algorithm trained by the prior lifestyle information arranged chronology with situation provided as a label. In embodiments, the situation data set may be provided based on the current state data set and the prior current state information as indicated in step S1208'.

In embodiments, the execution of the second machine readable instructions by the situation module further includes the following steps. The situation module 1016 accesses, prior to providing the situation information data set, the social network information provided by the social module. The situation module 1016 filters, prior to providing the situation information data set, the social network information based at least on the time the situation module 1016 provides the situation data set based on the filtering of the social network information and the filtering of the lifestyle information.

The machine learning algorithm in the situation module provides as its output a situation data set associated with a situation of the first user. The situation data set associated with the first user may be stored in memory and sent as a query to the manager module 1006, as discussed below.

Referring to FIG. 12B, in embodiments, the situation module 1016, in step S1208', may provide a situation data set associated with the first user based on the current state data set and the prior current state information. Referring to FIGS. 12A and 12B, in steps S1208 and S1210', the situation data set associated with the first user may be stored in memory of system 1000.

In embodiments, the machine learning algorithm may utilize one or more of the following: a neural network a deep learning neural network; Cloud Forest; DBSCAN; gradient boosting algos; and/or a combination thereof, to name a few.

Referring back to FIG. 1A, a stimulus module 1004 may include a third one or more processors operatively connected to a third memory device and third machine readable instructions. Referring to FIG. 11A, the third one or more processors may be configured to execute the third machine readable instructions to provide a stimulus database 1004-1 using the second memory device (step S1112). In embodiments, the stimulus database 1004-1 comprises stimulus information including, for each prior stimulus of a plurality of prior stimuli: (1) the respective prior stimulus; (2) a respective situation data set associated with the respective prior stimulus; and (3) respective stimulus response information associated with the respective prior stimulus. In embodiments, the third one or more processors may be configured to execute the third machine readable instructions to generate and store the stimulus database 1004-1 (step S1112').

Figure 11B:
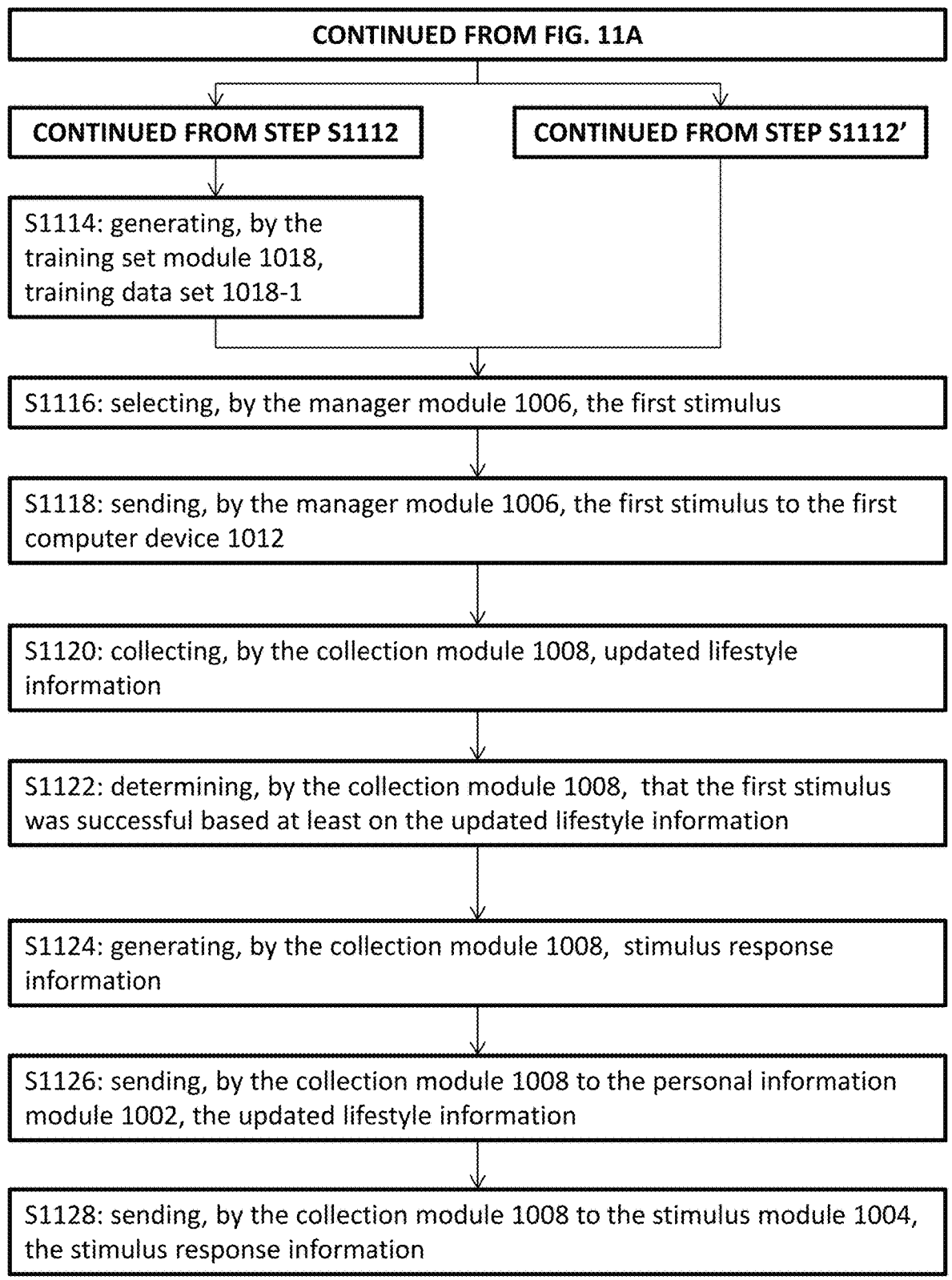

Referring back to FIG. 1A, a training set module, 1008 may include fourth one or more processors operably connected to a fourth memory device and fourth machine readable instructions, the training set module operatively connected to the stimulus module. Referring to FIG. 11B, the fourth one or more processors may be configured to execute the fourth machine readable instructions to generate a training data set (S1114) by performing the following steps, as illustrated with respect to FIG. 12C. Referring to FIG. 12C, in step S1210, the training set module 1008 may access the stimulus information 1310B stored in the stimulus database 1308B. In step S1212, the training set module 1008 may filter the stimulus information 1310B based at least on the stimulus information (such as available stimulus options) from available stimulus database 1004-2. In step S1214, the training set module 1008 may provide the training data set 1018-1 based on the application of the filter criteria to the stimulus information 1310B. In step S1216, the training set module 1008 may store the training data set 1018-1.

Referring back to FIG. 1A, a manager module 1006 may include fifth one or more processors operatively connected to at least a fifth memory device and fifth machine readable instructions. The manager module 1006 may be operatively connected to the situation module 1016 and the training set module 1018. Referring to FIG. 11B, the fifth one or more processors may be configured to execute the fifth machine readable instructions to select the first stimulus (step S1116) by the following steps as illustrated in FIG. 12D. Referring to FIG. 12D, in step S1218, the manager module 1006 may receive the situation data set from the situation module 1016. In step S1220, the manager module 1006 may provide the situation data set to a second machine learning algorithm 1006-1 trained by the training data set 1018-1 with stimulus provided as a label (see, e.g., FIG. 1F). Referring back to FIG. 1A, as a result of these steps, the machine learning algorithm 1006-1 in the manager module 10016 may select a stimulus (e.g., the first stimulus) and a time to send the such stimulus to a designated computing device associated with the designated user (e.g., the first computer device associated with the first user). Referring back to FIG. 11B, thereafter, the managing module 1006 and/or some other component of the system 1000 sends the first stimulus to the first computer device associated with the first user (step S1118).

Referring to FIG. 1A, a collection module 1008 may include sixth one or more processors operatively connected to a sixth memory device and sixth machine readable instructions. Referring to FIG. 11n, the sixth one or more processors may be configured to execute the sixth machine readable instructions to collect updated lifestyle information after the first stimulus is transmitted to the first computing device associated with the first user (step S1120). The updated lifestyle information may include information collected from at least: (1) the first computer device associated with the first user; (2) a second computer device associated with the first user; and/or (3) a third computer device associated with a second user associated with the first user via social media, professional affiliation or the interactive electronic network. In embodiment, the updated information may include at least updated lifestyle information.

At a step S1122, after collecting the updated information, in embodiments, the collection module 1008 may determine, based at least on the updated lifestyle information, whether the first stimulus was successful (and/or the degree to which is was successful or unsuccessful). In embodiments, the collection module 1008 may determine the first stimulus to be successful in varying degrees, unsuccessful in varying degrees and/or to have little or no effect on the desired behavior or outcome. Thereafter, at step S1124, the collection module 1008 may generate stimulus response information associated with success of the first stimulus. In embodiments, at step S1126, the collection module 1008, may send the updated lifestyle information to the personal information module 1002 to be added to the lifestyle database 1002-1. In embodiments, at step S1128, the collection module 1008 may send the stimulus response information, including the first stimulus and the situation data set, to the stimulus module 1004 to be added to the stimulus database 1004-1.

In embodiments, the order of these steps may vary, such as step S1126 may come either before, after or simultaneous with step S1124.

In embodiments, the steps associated with the processes described in connection with FIGS. 11A-B and 12A-D may be rearranged or omitted.

Referring back to FIG. 1A, in embodiments, the fifth one or more processors may be further configured to execute the fifth machine readable instructions to determine when the first user is within a predetermined proximity of the second user by performing the following steps. In embodiments, the situation module 1016 may access, prior to providing the situation information, social proximity information provided by the manager module. Next, in embodiments, the situation module 1016 may filter, prior to providing the situation information, the social proximity information based at least on the time. In embodiments, the process may follow with the situation module 1016 providing the situation information based on: (1) the filtering of the social proximity information; (2) the filtering of the social network information; and (3) the filtering of the lifestyle information. In embodiments, proximity may be determined based on locations of two or more user within: same cell tower, a predetermine distance x, the same city block, the same building, the same room, the same floor, the same business location (e.g., office, restaurant, etc.)

In embodiments, the proximity may be determined based on (1) determining a computer device associated with the second user is within range of the same cell tower as at least one of the first computer device or the second computer device; (2) determining the computer device associated with the second user is within a predetermined distance of at least one of the first computer device or the second computer device; (3) determining the computer device associated with the second user and at least one of the first computer device and the second computer device are in a first building; (4) determining the electronic device associated with the second user and at least one of the first computer device or the second computer device are within a first city block; (5) determining the electronic device associated with the second user and at least one of the first computer device or the second computer device are in a first room of a second building; and/or (6) determining the electronic device associated with the second user and at least one of the first computer device or the second computer device are within a first place of business.

In embodiments, the stimulus response information may be further provided from, e.g., a fourth computer device associated with a third user of the interactive electronic network associated with the first user via professional association, a fifth computer device associated with a fourth user of the interactive electronic network, wherein the fourth user is not linked via social media or professional affiliation to the first user; a sixth computer device associated with a fifth user of the interactive electronic network associated with the first user via professional association; and/or a seventh computer device associated with a sixth user of the interactive electronic network, wherein the sixth user is not linked via social media or professional affiliation to the first user.

In embodiments, the stimulus response information is provided based on updated lifestyle information indicating whether the first stimulus provided positive results relative to the selected change.

In embodiments, the health-related attribute information may include: (1) heartbeat information; (2) respiratory information; (3) blood pressure information; (4) body temperature information; (5) height information; and/or (6) weight information, to name a few.

In embodiments, at least a portion of the health-related attribute information may be provided by the first user via one or more computer devices associated with the first user.

In embodiments, at least a portion of the health-related attribute information may be provided by one or more healthcare providers.

In embodiments, the manager module 1006 may send the first stimulus to the first computer device by performing the following steps. The manager module 1006 generates, after selecting the first stimulus, first machine-readable instructions including a first graphical user interface (GUI), wherein the first GUI represents the first stimulus and comprises: (1) a first message based on at least the first stimulus; and (2) impending first choice information being based on at least the impending first choice and the selected change. The manager module 1006 sends the first machine-readable instructions to the first computer device, wherein, upon receiving the first machine-readable instructions, the first computer device executes the first machine-readable instructions which causes the first GUI to be displayed on a display screen of the first computer device.

In embodiments, the collection module 1008 may perform the following additional steps. The collection module 1008 determines that the stimulus response information indicates that the first stimulus resulted in positive results relative to the selected change. The collection module generates, in response to determining the first stimulus resulted in positive results, display machine-readable instructions including a first graphical user interface (GUI), wherein the first GUI comprises a first message based on at least one of: (1) the positive results; (2) the first stimulus, and (3) the stimulus response information. The collection module sends the display machine-readable instructions to at least one of the user's computer devices. Upon receiving the first machine-readable instructions, one or more of the computer devices may execute the first machine-readable instructions to cause the first GUI to be displayed on a display screen of that device. In embodiments, the devices may be a portable computing device (such as a smart phone, a tablet, a phablet, or a laptop) and a wearable device.

Figure 14A:
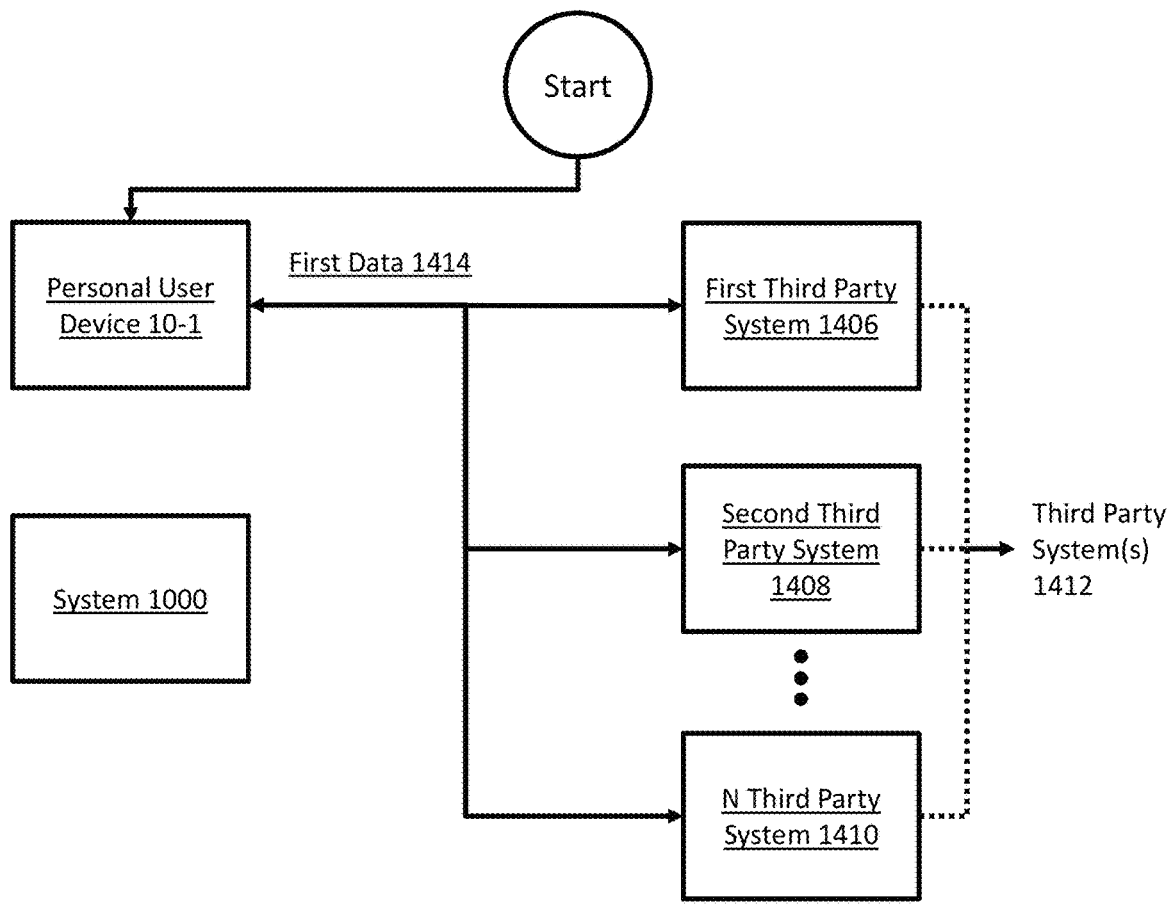
FIGS. 14A-14E are illustrative block diagrams illustrating a process for selecting a stimulus in accordance with exemplary embodiments of the present invention.

FIGS. 14A-14E are exemplary block diagrams illustrating an exemplary process for selecting a stimulus in accordance with exemplary embodiments of the present invention. In embodiments, an exemplary process for selecting a stimulus may begin with FIG. 14A. FIG. 14A illustrates a personal user device 10-1 sending and/or receiving first data 1414 to/from the third-party systems 1412 over network 100. The first data 1414 sent from the personal user device 10-1 to the third-party system 1412, in embodiments, may be in response to a request or call from the third-party systems 1412. In embodiments, the first data 1414 may be sent to the third-party system 1412 from the personal user device 10-1 at regular intervals. In embodiments, the first data 1414 may be sent to the third-party system 1412 from the personal user device 10-1 in response to an input on the personal user device 10-1 and/or in response to a request for information (e.g., the location) by the personal user device 10-1. In embodiments, the system may communicate directed with the third-party systems 1412 over network 100.

As an example, in embodiments, the personal user device 10-1 may be sending data relevant to a weather application supported by the first third-party system 1406. Continuing the example, the first data 1414 may include metadata, sent from the personal user device 10-1 to the first third-party system 1406, indicating a current location of the personal user device 10-1. As another example, the personal user device 10-1 may be sending data relevant to a health tracking application supported by the second third-party system 1408. Continuing the example, the first data 1414 may include metadata, sent from the personal user device 10-1 to the second third-party system 1408, indicating the number of steps the user associated with the personal user device 10-1 is taking.

The third-party systems 1412, in embodiments, may include the first third-party system 1406, the second third-party system 1408 . . . the N third-party system 1410, to name a few. In embodiments, the third-party systems 1412 may include one or more systems that support one or more of the following mobile applications: messaging mobile applications, health mobile applications, dating mobile applications, map mobile applications, driving mobile applications, music mobile applications, and/or weather mobile applications to name a few. The third-party system(s) 1412, in embodiments, may each include one or more of the following: a display, a network connection interface, communications circuitry, one or more processors, and/or memory, to name a few. The components of each of the third-party system(s) 1412 may be similar to the components of the system 1000, the first computer device 1012, and/or the second computer device 1014 each described above in connection with FIGS. 1A-1 and 1A-2, the descriptions of which applying herein.

Figure 14B:
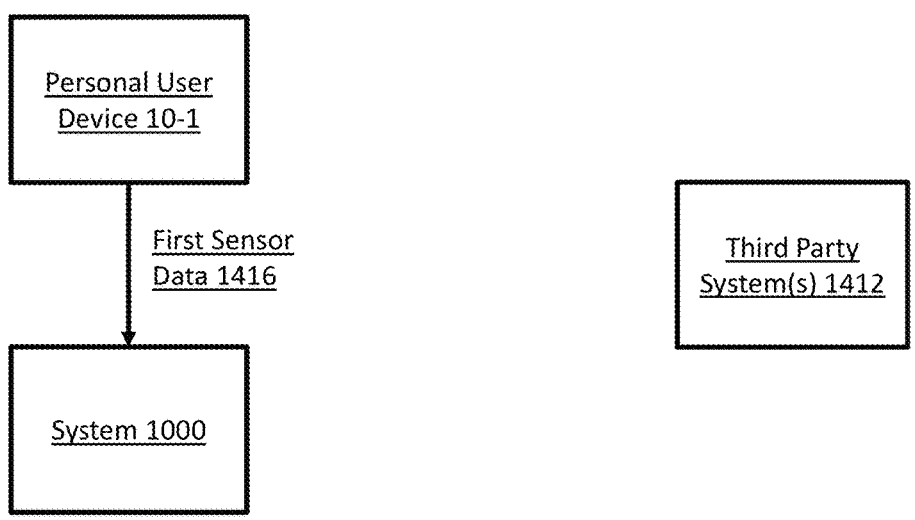

In embodiments, the exemplary process for selecting a stimulus may continue with FIG. 14B. FIG. 14B illustrates a personal user device 10-1 sending first sensor data 1416 to the system 1000 over network 100. The process for sending first sensor data 1416 from the personal user device 10-1 to the system 1000 may begin with the personal user device 10-1 obtaining data. The data obtained and/or the first sensor data 1416, in embodiments, may include one or more of the following: sensor data, connection data, calendar data (e.g., from Apple Proprietary HealthKit 728 and/or Google Proprietary Google Fit 730), identity data (e.g., from Apple Proprietary HealthKit 728 and/or Google Proprietary Google Fit 730), health-related attribute data (e.g., from Apple Proprietary HealthKit 728 and/or Google Proprietary Google Fit 730), prior purchase data, activity data, goal data, user preferences data, contact data (e.g., from Apple Proprietary HealthKit 728 and/or Google Proprietary Google Fit 730) and/or medical data (e.g., from Apple Proprietary HealthKit 728 and/or Google Proprietary Google Fit 730). In embodiments, each piece of data, when obtained by the personal user device 10-1 (e.g., sensor data is obtained by one or more sensor devices), may include the data obtained, the type of data obtained, and a timestamp. The timestamp may indicate one or more of the following: when the data was obtained, when the data was created, and/or when the data was sent to the system 1000. When data is sent from the aforementioned one or more sources, in embodiments, each piece of data may include the obtained data and the relative timestamp associated with the relative piece of data.

The obtained data, in embodiments, may be transformed into the first sensor data 1416 by being processed by one or more processor(s) of the personal user device 10-1 and formatted by the personal user device 10-1. The first sensor data 1416 may, as shown in FIG. 14B, be sent by the personal user device 10-1 to the system 1000 via network 100. In embodiments, as shown in connection with FIG. 14E, the first sensor data 1416 may be received by the system 1000 at the personal information module 1002. The system 1000, in embodiments, may also store the received first sensor data 1416 in the lifestyle database 1002-1. In embodiments, the first sensor data 1416 may be organized by the relative timestamp and/or be time sliced based on the relative timestamp. For example, the lifestyle database 1002-1 may organize the first sensor data 1416 by user (e.g., the user associated with the personal user device 10-1) and, within each user's information, by relative timestamp. Continuing the example, the lifestyle database 1002-1 may organize the first sensor data 1416 in the order of the most recent creation time to the least recent creation time.

Figure 14C:
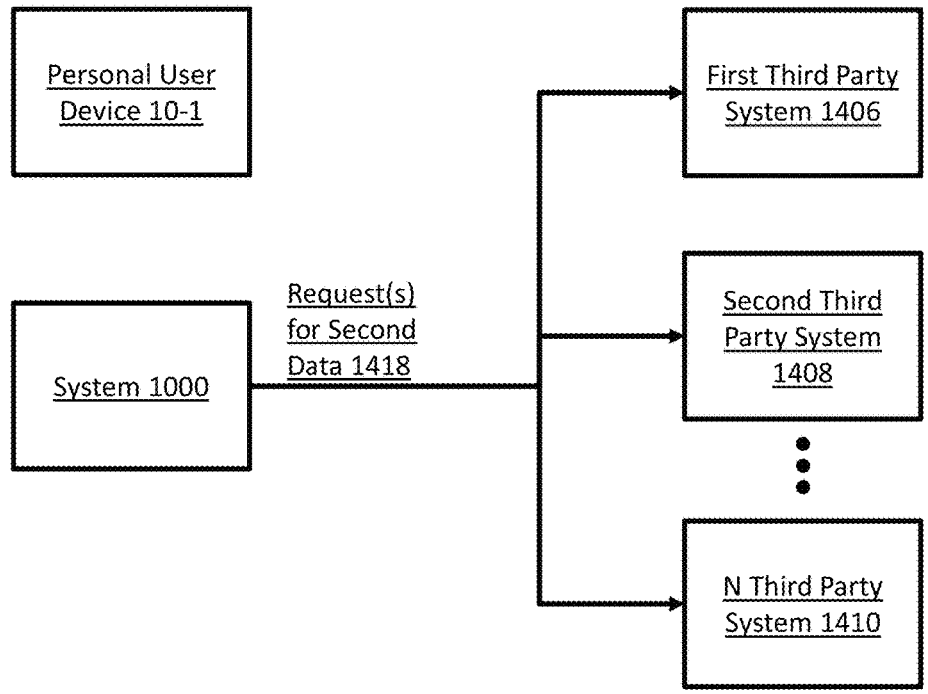
Figure 14D:
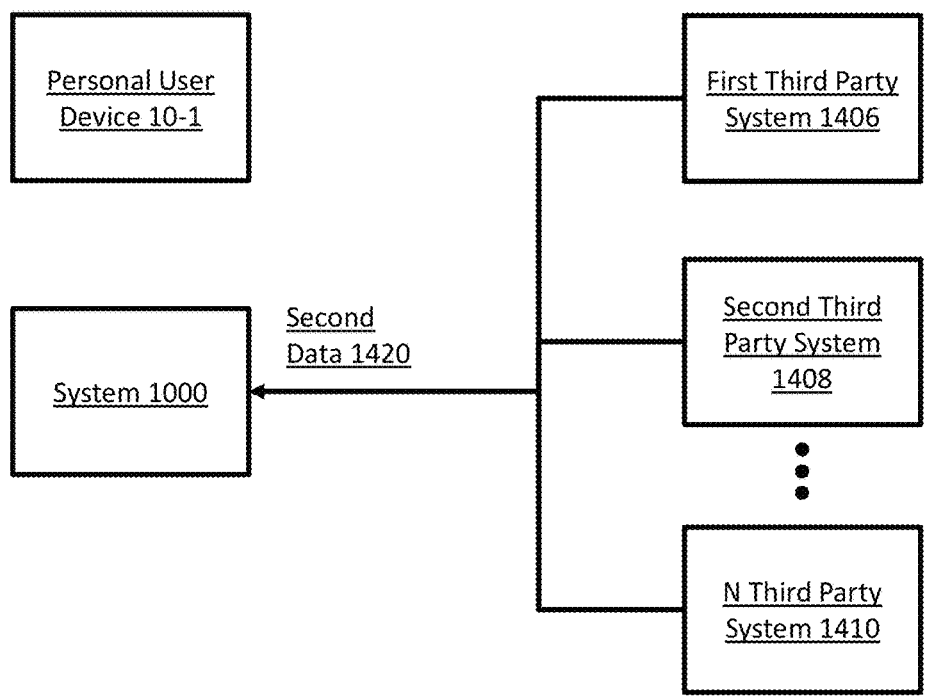
Figures 1, 14D:
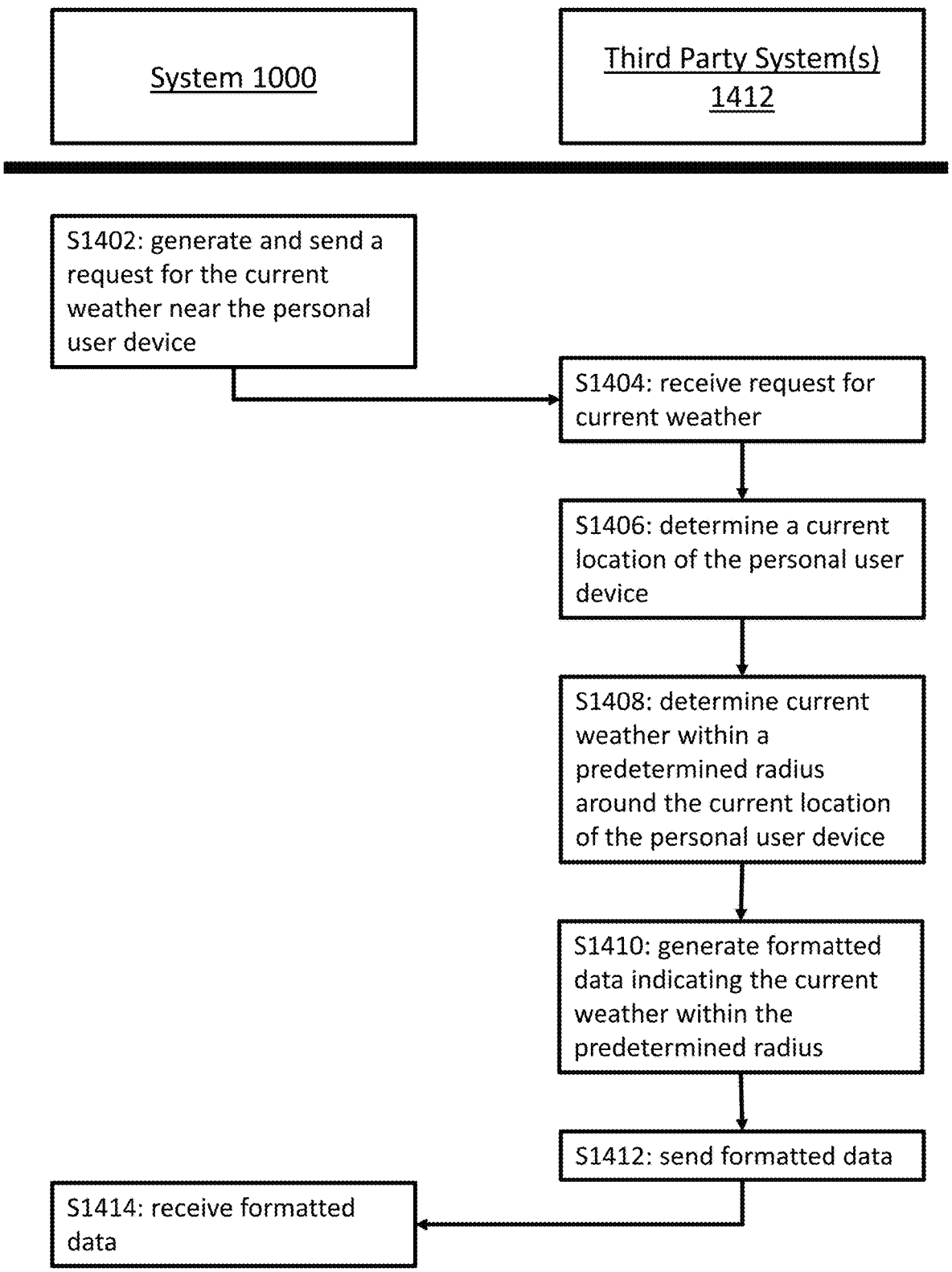
Figures 2, 14D:
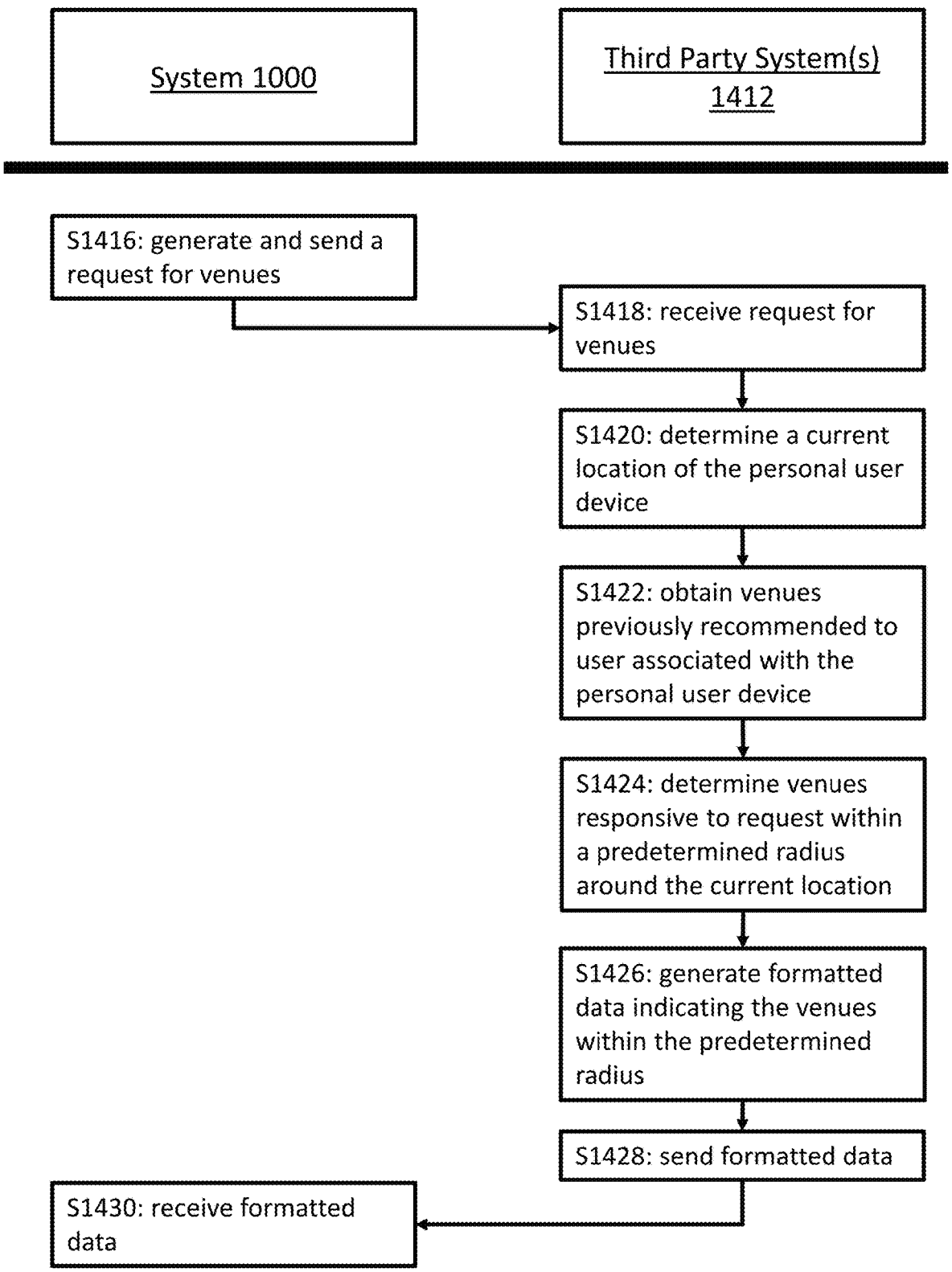

In embodiments, the exemplary process for selecting a stimulus may continue with FIGS. 14C-D. FIG. 14C illustrates the system 1000 requesting data from the third-party system(s) 1412. FIG. 14D illustrates the system 1000 receiving the requested data from the third-party system(s) 1412. In embodiments, the system 1000 may be requesting data associated with the user associated with the personal user device 10-1. For example, the request(s) for second data 1418 may include requests for: the weather at the personal user device 10-1 location; events near (e.g., within a predetermined radius) the personal user device 10-1, restaurants near (e.g., within a predetermined radius) the personal user device 10-1 location; and/or activities near (e.g., within a predetermined radius) the personal user device 10-1 location, to name a few. Continuing the example, the second data 1420 may include data indicating: the weather at the personal user device 10-1 location; events near (e.g., within a predetermined radius) the personal user device 10-1, restaurants near (e.g., within a predetermined radius) the personal user device 10-1 location; and/or activities near (e.g., within a predetermined radius) the personal user device 10-1 location, to name a few. Exemplary processes for requesting and receiving the second data 1420 are described in connection with FIGS. 14D-1 and 14D-2, the descriptions of which applying herein.

First, referring to FIG. 14D-1, in embodiments, the system 1000 may request the third-party system(s) 1412 for the weather at the personal user device 10-1 location. In embodiments, the process for requesting the weather at the personal user device 10-1 location may begin at step S1402. At step S1402, in embodiments, the system 1402 may generate and send a request for the current weather near (e.g., within a predetermined radius) the personal user device 10-1. The request (e.g., the request for second data 1418) may be sent by the system 1000 to the third-party system(s) 1412 (e.g., a weather micro-service) via network 100. In embodiments, the third-party system(s) 1412 may include a micro-service.

The process for requesting the weather at the personal user device 10-1 location may continue with step S1404. At step S1404, the third-party system(s) 1412 may receive the request for the current weather. The request, in embodiments, may be received by one or more of the third-party system(s) 1412. The process for requesting the weather at the personal user device 10-1 location may continue with step S1406. At step S1406, in embodiments, the third-party system(s) 1412 may determine a current location of the personal user device 10-1 (e.g., first data 1414). The current location, may be determined using previously obtained data (e.g., the first data 1414) and/or by requesting the location of the personal user device 10-1 by sending a request (e.g., call) to the personal user device 10-1 and receiving metadata indicating the current location of the personal user device 10-1, to name a few.

The process for requesting the weather at the personal user device 10-1 location may continue with step S1408. At step S1408 the third-party system(s) 1412 may determine the current weather within a predetermined radius around the current location of the personal user device 10-1. The current weather may be accessed via one or more databases and/or weather service providers. The predetermined radius, in embodiments, may be determined by the system 1000 based on the type of stimulus. For example, if the stimulus sent to the user is a challenge to go for a run, the predetermined radius may be large enough to determine whether the user will encounter adverse weather during a run. As another example, if the example is to eat at a healthy restaurant, the predetermined radius may include the user's location and the restaurant's location.

The process for requesting the weather at the personal user device 10-1 location may continue with step S1410. In embodiments, at step S1410, the third-party system(s) 1412 generate formatted data indicating the current weather within the predetermined radius. In embodiments, the data gathered by the third-party system(s) 1412 may be normalized or otherwise formatted to be compatible with the system 1000. In embodiments, the system 1000 may have format requirements based on the hardware and/or software associated with the system 1000. The process for requesting the weather at the personal user device 10-1 location may continue with step S1412. At step S1412, in embodiments, the third-party system(s) 1412 may send the formatted data (e.g., the second data 1420) to the system 1000 over network 100. The formatted data (e.g., the second data 1420), at step S1414 in embodiments, may be received by the system 1000.

In embodiments, the following is exemplary code for obtaining weather data near (e.g., within a predetermined radius) the location of the personal user device 10-1 in accordance with exemplary embodiments of the present invention:
  extract userID & (latLong)
  weather_API(latLong)
  Transform data
  save data to persistent DB As a second example, referring to FIG. 14D-2, in embodiments, the system 1000 may request one or more third-party system(s) 1412 for information relevant to a venue. In embodiments, the system 1000 may be gathering data for a stimulus related to a restaurant, event, and/or activity associated with a venue. The process for obtaining data for a stimulus associated with a venue, in embodiments, may begin with step S1416. At step S1416, in embodiments, the system 1402 may generate and send a request for venues near (e.g., within a predetermined radius) the personal user device 10-1. The request (e.g., the request for second data 1418) may be sent by the system 1000 to one or more of the third-party system(s) 1412 (e.g., 4Square) via network 100. In embodiments, the third-party system(s) 1412 may include a micro-service.

The process for requesting venues at the personal user device 10-1 location (and/or a planned route the personal user device 10-1 typically takes or is planning on making) may continue with step S1418. At step S1418, the third-party system(s) 1412 may receive the request for venues. The request, in embodiments, may be received by one or more of the third-party system(s) 1412. The process for requesting venues within a predetermined radius of the personal user device 10-1 location (and/or a planned route the personal user device 10-1 typically takes or is planning on making) may continue with step S1420. At step S1420, in embodiments, the third-party system(s) 1412 may determine a current location of the personal user device 10-1 (e.g., first data 1414). The current location, may be determined using previously obtained data (e.g., the first data 1414) and/or by requesting the location of the personal user device 10-1 by sending a request (e.g., call) to the personal user device 10-1 and receiving metadata indicating the current location of the personal user device 10-1, to name a few. In embodiments, the third-party system(s) 1412 may use frequented locations—e.g., the user's place of work, commute to work, home, and/or any planned trips, to name a few (e.g., using the first data 1414).

The process for requesting venues may continue with step S1422. At step S1422, in embodiments, the third-party system(s) 1412 may obtain venues previously recommended to the user associated with the persona user device 10-1 ("Previous Venue Information"). In embodiments, the Previous Venue Information may be stored locally by one or more of the third-party system(s) 1412. If, in embodiments, the Previous Venue Information is stored locally and/or in memory operatively connected to the third-party system(s) 1412, the third-party system(s) 1412 may access the Previous Venue Information. In embodiments, to obtain the Previous Venue Information, the third-party system(s) 1412 may generate and send a request to the system 1000 over network 100. The request, in embodiments, may be a request for the Previous Venue Information. In response, in embodiments, the system 1000 may obtain and send data indicating and/or including the Previous Venue Information. In embodiments, the Previous Venue Information may be venues that have been previously recommended, within a predetermined amount of time (e.g., the past month, past week, past year, to name a few) to the user associated with the persona user device 10-1. In embodiments, the Previous Venue Information may be venues that have been previously recommended and are associated with a stimulus that has achieved positive results. In embodiments, the Previous Venue Information may be venues that have been previously recommended and are associated with a stimulus that has achieved negative and/or not positive results.

In embodiments, the following is exemplary code for obtaining Previous Venue Information in accordance with exemplary embodiments of the present invention:
  extract (latLong)
  restaurant_list_fetch(latLong, 100 m radius)
  for(venue in venueList) {
    sort_venues(venue list)
  }
  extract (recommended_venue)
  if(reward_ref exists in persistence_DB) {
    save_in_persistence_DBO
    if(menu_list available in recommended_venue){
    create_reward_parent_in_persistence_DB( )
    save_reward_parent_in_persistence_DB( )
    }
  }
  else {
    create_unique_reward_refo
  }

The process for requesting venues may continue with step S1424. At step S1424, in embodiments, the third-party system(s) 1412 may determine venues responsive to the system 1000's request (e.g., the request(s) for second data 1418) within a predetermined radius around the current location. In embodiments, the third-party system(s) 1412 may generate a list of venues based on one or more of the following: (1) the type of request from the system 1000 (e.g., a request for an event, a request for a restaurant, a request for a concert, to name a few); (2) the Previous Venue Information; (3) the weather near (e.g., within a predetermined radius) the location of the venue; (4) the weather near (e.g., within a predetermined radius) the location of the personal user device 10-1; (5) identity information associated with the user associated with the personal user device 10-1; (6) attribute information associated with the user associated with the personal user device 10-1; (7) health condition information associated with the user associated with the personal user device 10-1; (8) movement information associated with the user associated with the personal user device 10-1; (9) lifestyle information associated with the user associated with the personal user device 10-1; (10) social information associated with the user associated with the personal user device 10-1; and/or (11) stimulus condition information associated with the user associated with the personal user device 10-1, to name a few.

In embodiments, the responsive venues may be filtered by the third-party system(s) 1412 in view of the Previous Venue Information. For example, if a previous venue is on the generated list of venues and is also associated with a previous stimulus that was unsuccessful, the third-party system(s) 1412 may filter out the previous venue. As another example, if a previous venue is on the generated list of venues and is also associated with a previous stimulus that was given as part of a stimulus within a predetermined amount of time (e.g., within the past week), the third-party system(s) 1412 may filter out the previous venue. As another example, if a previous venue is on the generated list of venues and is also associated with a previous stimulus that was both successful and given as part of successful stimulus outside a predetermined amount of time (e.g., a month ago), the third-party system(s) 1412 may not filter out the previous venue. In embodiments, the third-party system(s) 1412 may filter the generated list of venues based on one or more of the following: (1) the type of request from the system 1000 (e.g., a request for an event, a request for a restaurant, a request for a concert, to name a few); (2) the Previous Venue Information; (3) the weather near (e.g., within a predetermined radius) the location of the venue; (4) the weather near (e.g., within a predetermined radius) the location of the personal user device 10-1; (5) identity information associated with the user associated with the personal user device 10-1; (6) attribute information associated with the user associated with the personal user device 10-1; (7) health condition information associated with the user associated with the personal user device 10-1; (8) movement information associated with the user associated with the personal user device 10-1; (9) lifestyle information associated with the user associated with the personal user device 10-1; (10) social information associated with the user associated with the personal user device 10-1; and/or (11) stimulus condition information associated with the user associated with the personal user device 10-1, to name a few. For example, if the attribute information indicates that the user is allergic to peanuts, the third-party system(s) 1412 may filter out venues that offer food including peanuts. In embodiments, the third-party system(s) 1412 may continue filtering the generated list of venues until the filtered list of venues is equal to and/or below a predetermined amount of venues (e.g., 1 venue, 2, venues, 3, venues . . . N venues, to name a few).

In embodiments, the following is exemplary code for obtaining and filtering venues in accordance with exemplary embodiments of the present invention:

```
extract location coordinates (latLong)
if(not_already_fetched_within_100  m_radius_of_lat-
   Long) {
   fetch_venues(latLong, 100 m radius)
}
else {
   if(venues data older then 7 days) {
   fetch_venues(latLong, 100 m radius)
   }
   Extract totalVenueCount
   if(totalVenueCount>4) {
   recommender_microservice( )
   }
}
```

The process for requesting venues may continue with step S1426. In embodiments, at step S1426, the third-party system(s) 1412 generate formatted data indicating the venues within the predetermined radius. In embodiments, the indication of venues may be the venues left on the generated list after the above described filtering process has been completed. In embodiments, the data gathered by the third-party system(s) 1412 may be normalized or otherwise formatted to be compatible with the system 1000. In embodiments, the system 1000 may have format requirements based on the hardware and/or software associated with the system 1000. The process for requesting venues may continue with step S1412. At step S1428, in embodiments, the third-party system(s) 1412 may send the formatted data (e.g., the second data 1420) to the system 1000 over network 100. The formatted data (e.g., the second data 1420), at step S1430, in embodiments, may be received by the system 1000.

The steps of the processes described in connection with FIG. 14D-1 and/or FIG. 14D-2 may be rearranged or omitted. For the purposes of the processes described in connection with FIG. 14D-1 and/or FIG. 14D-2, third-party system(s) 1412 may refer to one or more third-party systems.

Figure 14E:
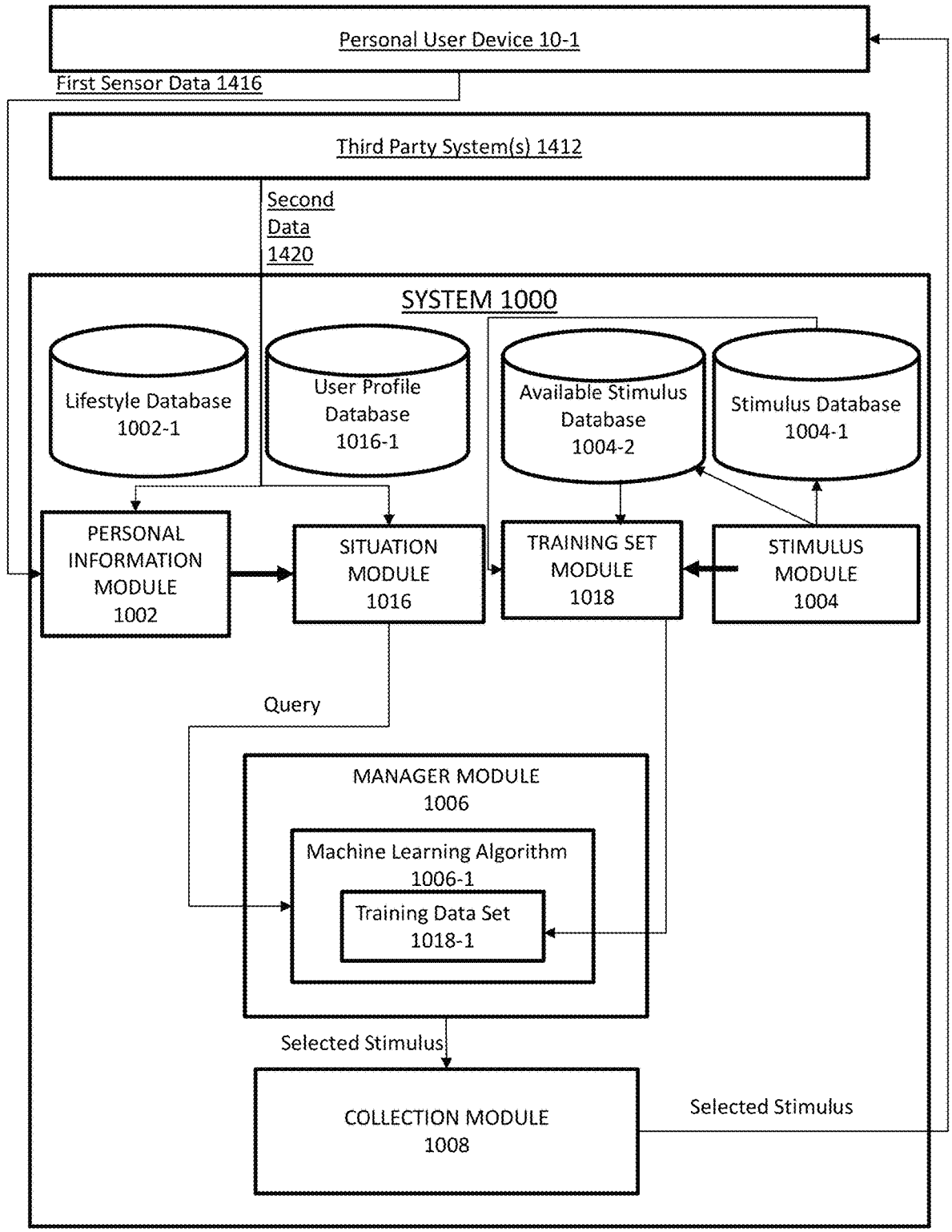

In embodiments, the exemplary process for selecting a stimulus may continue with FIG. 14E. Referring to FIG. 14E, the personal user device 10-1, in embodiments, sends the first sensor data 1416 to the system 1000. The system 1000, in embodiments, may receive the first sensor data 1416 at the personal information module 1002. In embodiments, one or more of the third-party system(s) 1412 may send the second data 1420 to the system 1000. The system 1000 in embodiments, may receive the second data 1420 at the personal information module 1002 and/or the situation module 1016. The system 1000, in embodiments, based at least a portion on the first sensor data 1416 and/or the second data 1420 may select a stimulus. In embodiments, prior to selecting, generating, and/or sending a stimulus to the personal user device 10-1, the system 1000 may obtain notification information associated with the personal user device 10-1. The notification information, in embodiments, may indicate the amount of notifications the system 1000 has sent to the personal user device 10-1. In embodiments, notification information may indicate the amount of notifications the system 1000 has sent to the personal user device 10-1 over a predetermined amount of time (e.g., day, week, month, year, to name a few). If, in embodiments, the notification information indicates that the system 1000 has sent too many notifications to the personal user device 10-1 (e.g., too many in view of standards set by companies associated with the personal user device 10-1—e.g., Apple, Google, Samsung, to name a few), the system 1000 may not generate a stimulus until a predetermined amount of time has passed (e.g., day, week, month, year, to name a few). In embodiments, the system 1000 may generate a message including the selected stimulus. The generated message, in embodiments, may be sent to the personal user device 10-1.

In embodiments, the processes shown in connection with FIGS. 14A-14E may occur simultaneously or in a different order. In embodiments, the processes shown in connection with FIGS. 14A-14E may continue until the system 1000 determines a stimulus should be generated and sent to the personal user device 10-1. This determination may be based on one or more of the following: user preferences, the machine learning algorithm 1006-1, available stimuli, sensor data (e.g., location, weather, to name a few), and/or the time, to name a few.

Figures 1, 15:
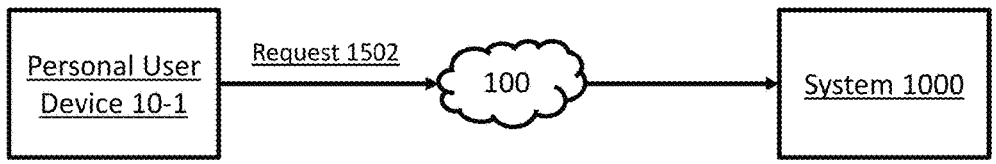
Figures 2, 15:
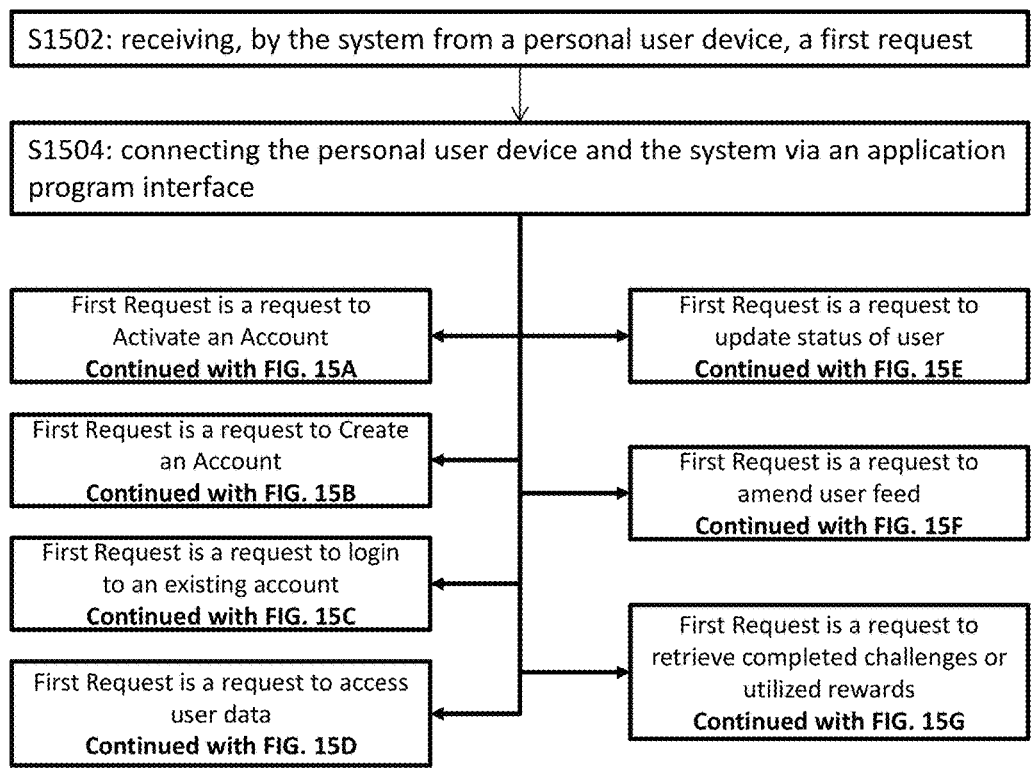

In embodiments, the system 1000 may receive one or more requests from the personal user device 10-1. Referring to FIG. 15-1, in embodiments, the personal user device 10-1 may send a request 1502 to the system 1000 over network 100. An exemplary process for receiving the request 1502 is described in connection with FIG. 15-2, the description of which applying herein.

Referring to FIG. 15-2, an exemplary process for receiving the request 1502 is shown. The process, in embodiments, for receiving and processing the request 1502 may begin at step S1502. In embodiments, at step S1502, the system 1000 receives the request 1502 from the personal user device 10-1. In embodiments, in response to the request 1502, at step S1504, the personal user device 10-1 and the system 1000 may be connected via an application programming interface (API). In embodiments, the following is exemplary code for creating an API gateway between the system 1000 and the personal user device 10-1 in accordance with exemplary embodiments of the present invention:

HTTP_request_from_client( )
api_gateway_routes_request(request_path)
extract_respective_fields_as_per_path( )
call_to_backed_server_api( )
response_json_creation( )
give_HTTP_response_to_client( )

The process with respect to FIG. 15-2 may continue in a variety of ways (illustrated in FIGS. 15A-15G), depending on the type of request received by the system 1000. For exemplary and brevity purposes, the processes described in connection with FIGS. 15A-15G account for one or more of the following types of requests: account activation, creating an account; login to an existing account; access user data; updating the status of a user; amending the user feed; and/or retrieve completed challenges or utilized rewards, to name a few. Persons of ordinary skill in the art understand that request 1502 may be a different request. The processes described in connection with FIGS. 15-2, and 15A-15G are intended to be illustrative, not limiting.

Figure 15A:
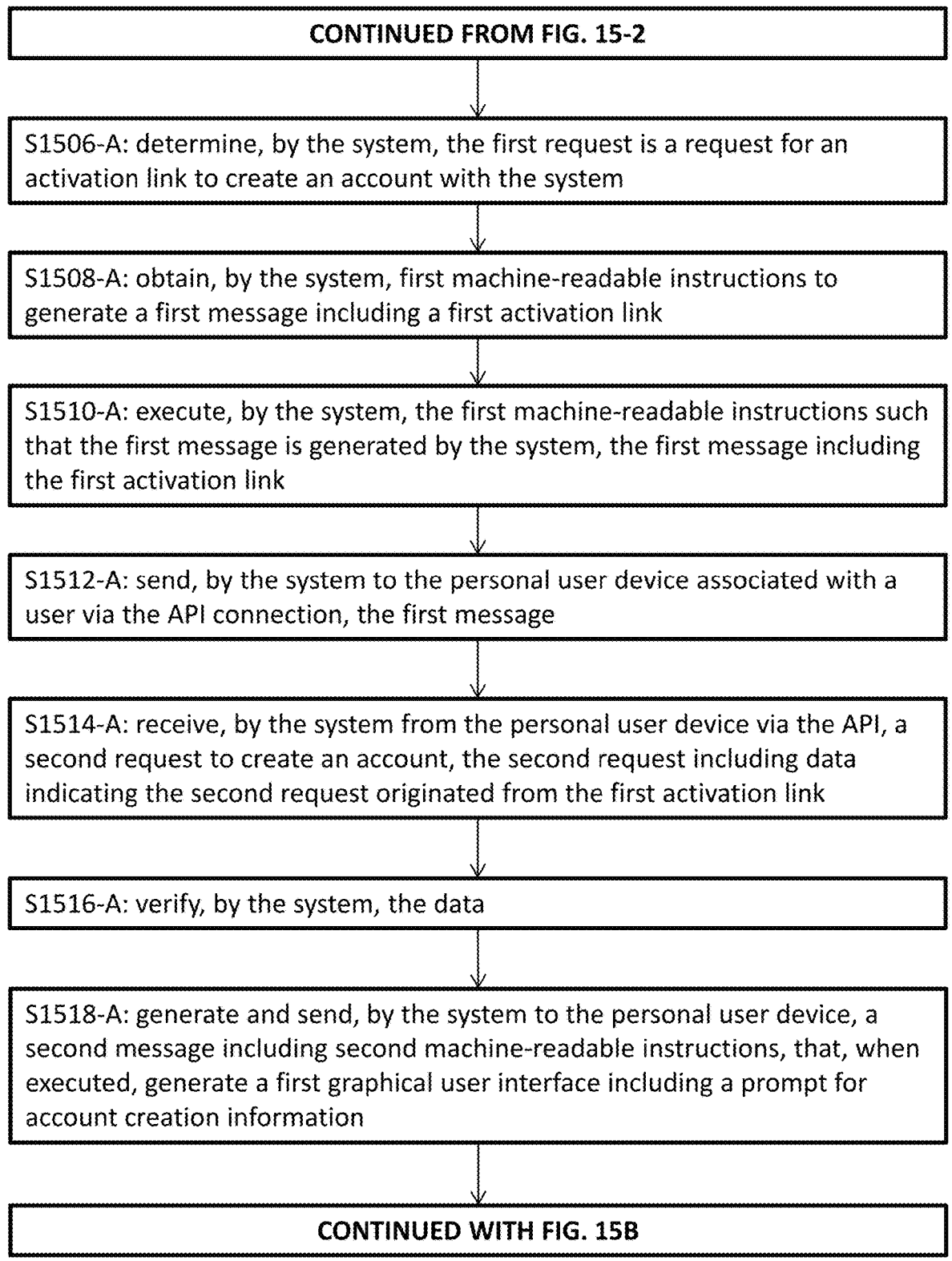
FIG. 15A is an exemplary block diagram illustrating a personal user device transmitting a request to the system in accordance with exemplary embodiments of the present invention.

In embodiments, the request 1502 is a request to activate an account for the user associated with the personal user device 10-1. In such embodiments, the process for receiving and processing the request 1502, in embodiments, may continue with FIG. 15A. Referring to FIG. 15A, the process for receiving and processing a request to activate an account may begin with step S1506-A. In embodiments, at step S1506-A, the system 1000 may determine that the request 1502 is a request for an activation link to create an account with the system 1000.

The process for receiving and processing the request 1502, in embodiments, may continue with step S1508-A. In embodiments, at step S1508-A, the system 1000 may obtain first machine-readable instructions to generate a first message including a first activation link. In embodiments, the first machine-readable instructions may have been previously generated and/or stored by the system 1000 in memory operatively connected to the system 1000. In embodiments, the first activation link may be a unique link such that when a user activates (e.g., selects, clicks on, etc.) the activation link, the system 1000 can verify one or more of the following: when the link was generated, where the request for the first activation link was received from, and/or who the link was generated for, to name a few. In embodiments, the first activation link is a "one-time use" activation link (e.g., the link can only be activated one time).

The process for receiving and processing the request 1502, in embodiments, may continue with step S1510-A. In embodiments, at step S1510-A, the system 1000 may execute the first machine-readable instructions. The execution of the first machine-readable instructions, in embodiments, may result in the generation of the first message. The first message, in embodiments, may include the first activation link. In embodiments, at step S1512-A, the system 1000 may send the generated first message to the personal user device 10-1 via the API and network 100. The first message, in embodiments, may include machine-readable instructions, that, upon receipt of the first message, cause the personal user device 10-1 to display a graphical user interface (GUI) including the first activation link. In embodiments, the first message may be one or more of the following: an SMS message; an MMS message; a push-notification; an in-application message; an RCS message; an electronic-mail message; a telephonic message, and/or a combination thereof, to name a few. Upon receipt of the first message, in embodiments, the first activation link may be activated by the user associated with the personal user device 10-1. In embodiments, the link may be activated by any suitable electronic device associated with the user associated with the personal user device 10-1. The activation of the activation link, in embodiments, may cause the personal user device 10-1 (and/or another electronic device associated with the user associated with the personal user device 10-1) to generate and send a second request. The second request, in embodiments, may be an account creation request. In embodiments, the second request may include data (e.g., metadata) indicating that the second request originated from the first activation link.

The process for receiving and processing the request 1502, in embodiments, may continue with step S1514-A. In embodiments, at step S1514-A, the system 1000 may receive the second request via the API and/or network 100. The second request, in embodiments, may include data (e.g., metadata) indicating that the second request originated from the first activation link. The data (and/or the second request), in embodiments at step S1516-A, maybe verified by the system 1000. Verification, in embodiments, may include one or more of the following: (1) verifying the data indicating the origination of the second request; (2) verifying the user; (3) verifying the second request; and/or (4) verifying the personal user device 10-1, to name a few.

The process for receiving and processing the request 1502, in embodiments, may continue with step S1518-A. In embodiments, at step S1518-A, the system 1000 may generate (e.g., by obtaining and executing machine-readable instructions) and send, to the personal user device 10-1, a second message including second machine-readable instructions, that, when executed, generate a first GUI including a prompt for account creation information. The second message, in embodiments, may be sent from the system 1000 to the personal user device 10-1 via the API and/or network 100. In embodiments, the second message may be one or more of the following: an SMS message; an MMS message; a push-notification; an in-application message; an RCS message; an electronic-mail message; a telephonic message, and/or a combination thereof, to name a few. Upon receipt of the second message, in embodiments, the second machine-readable instructions may be executed by the personal user device 10-1, causing the personal user device 10-1 to display the first GUI. In embodiments, the requested account creation information associated with the user may be input into the appropriate fields associated with the first GUI displayed on the personal user device 10-1 and sent to the system 1000 via the API and/or network 100. Account creation information, in embodiments, may include one or more of the following: (1) user credentials, (2) identity information associated with the user associated with the personal user device 10-1; (3) attribute information associated with the user associated with the personal user device 10-1; (4) health condition information associated with the user associated with the personal user device 10-1; (5) movement information associated with the user associated with the personal user device 10-1; (6) lifestyle information associated with the user associated with the personal user device 10-1; (7) social information associated with the user associated with the personal user device 10-1; and/or (8) stimulus condition information associated with the user associated with the personal user device 10-1, to name a few.

Figure 15B:
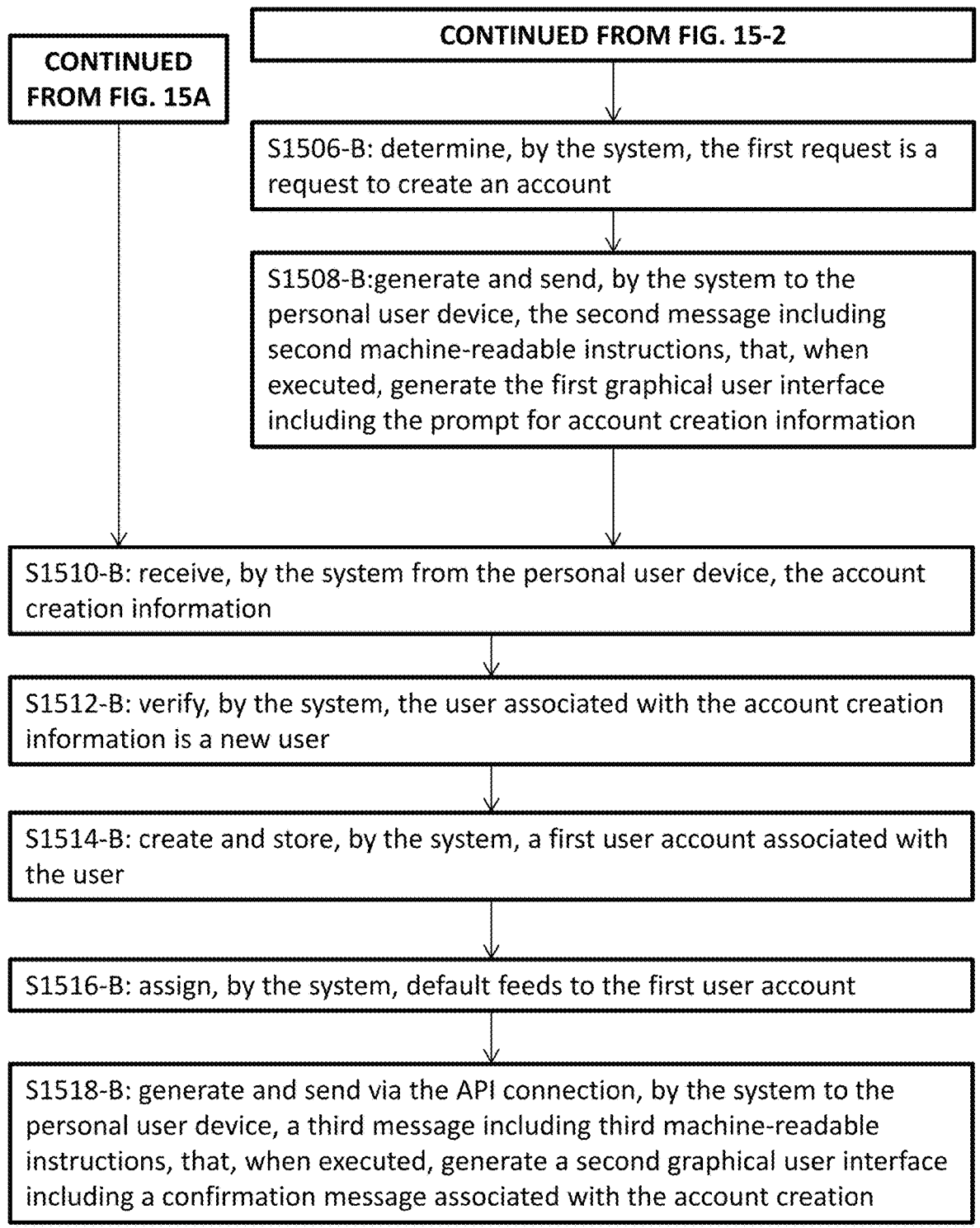

The process described in connection with FIG. 15A, in embodiments, may continue with steps S1510-B through S1518-B of FIG. 15B, the description of which applying herein.

In embodiments, the request 1502 is a request to create an account with the system 1000 for the user associated with the personal user device 10-1. In such embodiments, the process for receiving and processing the request 1502, in embodiments, may continue with FIG. 15B. Referring to FIG. 15B, the process for receiving and processing a request to create an account may begin with step S1506-B. In embodiments, at step S1506-B, the system 1000 may determine that the request 1502 is a request to create an account with the system 1000.

The process for receiving and processing the request 1502, in embodiments, may continue with step S1508-B. In embodiments, at step S1508-B, the system 1000 may generate (e.g., by obtaining and executing machine-readable instructions) and send, to the personal user device 10-1, a second message including second machine-readable instructions, that, when executed, generate a first GUI including a prompt for account creation information. The second message, in embodiments, may be sent from the system 1000 to the personal user device 10-1 via the API and/or network 100. In embodiments, the second message may be one or more of the following: an SMS message; an MMS message; a push-notification; an in-application message; an RCS message; an electronic-mail message; a telephonic message, and/or a combination thereof, to name a few. Upon receipt of the second message, in embodiments, the second machine-readable instructions may be executed by the personal user device 10-1, causing the personal user device 10-1 to display the first GUI. In embodiments, the requested account creation information associated with the user may be input into the appropriate fields associated with the first GUI displayed on the personal user device 10-1 and sent to the system 1000 via the API and/or network 100. Account creation information, in embodiments, may include one or more of the following: (1) user credentials, (2) identity information associated with the user associated with the personal user device 10-1; (3) attribute information associated with the user associated with the personal user device 10-1; (4) health condition information associated with the user associated with the personal user device 10-1; (5) movement information associated with the user associated with the personal user device 10-1; (6) lifestyle information associated with the user associated with the personal user device 10-1; (7) social information associated with the user associated with the personal user device 10-1; and/or (8) stimulus condition information associated with the user associated with the personal user device 10-1, to name a few.

The process for creating an account and/or the continued process of creating an account through an activation link, may continue with step S1510-B. At step S1510-B, in embodiments, the system 1000 may receive the account creation information associated with the user from the personal user device 10-1. The account creation information, in embodiments at step S1512-B may be verified by the system 1000. For example, the system 1000 may verify that the user associated with the personal user device 10-1 is a new user and/or the personal user device 10-1 has not been used to create an account. In embodiments, the system 1000 may verify that the account creation information is sufficient to create a new account. For example, the system 1000 may check the strength of the user credentials. As another example, the system 1000 may verify the user through an e-mail address.

The process for creating an account may continue with step S1514-B. At step S1514-B, in embodiments, the system 1000 may create and store a first user account associated with the user associated with the personal user device 10-1. The first user account, in embodiments, may be created using the account creation information. In embodiments, the first user account and information associated with the first user account may be stored by the system 1000 in memory operably connected to the system 1000 (e.g., in the lifestyle database 1002-1 and/or the user profile database 1016-1, to name a few).

Once the first user account has been created, in embodiments at step S1516-B, the system 1000 may assign defaults to the first user account. The defaults, in embodiments, may include one or more of the following: a default feed (e.g., the feeds shown in connection with the screen shots of FIGS. 9A-9B and 13B-13C), default settings, and/or default user preferences, to name a few. In embodiments, the system 1000 may assign the defaults by storing the defaults in a manner such that the defaults are associated with the first user account.

In embodiments, the process of creating an account may continue with step S1518-B. At step S1518-B, in embodiments, the system 1000 may generate (e.g., by obtaining and executing machine-readable instructions) and send a third message to the personal user device 10-1 via the API and/or the network 100. The third message, in embodiments, may include third machine-readable instructions, that, when executed, cause the personal user device 10-1 to display a second GUI including a confirmation message associated with the creation of the first user account.

Figure 15C:
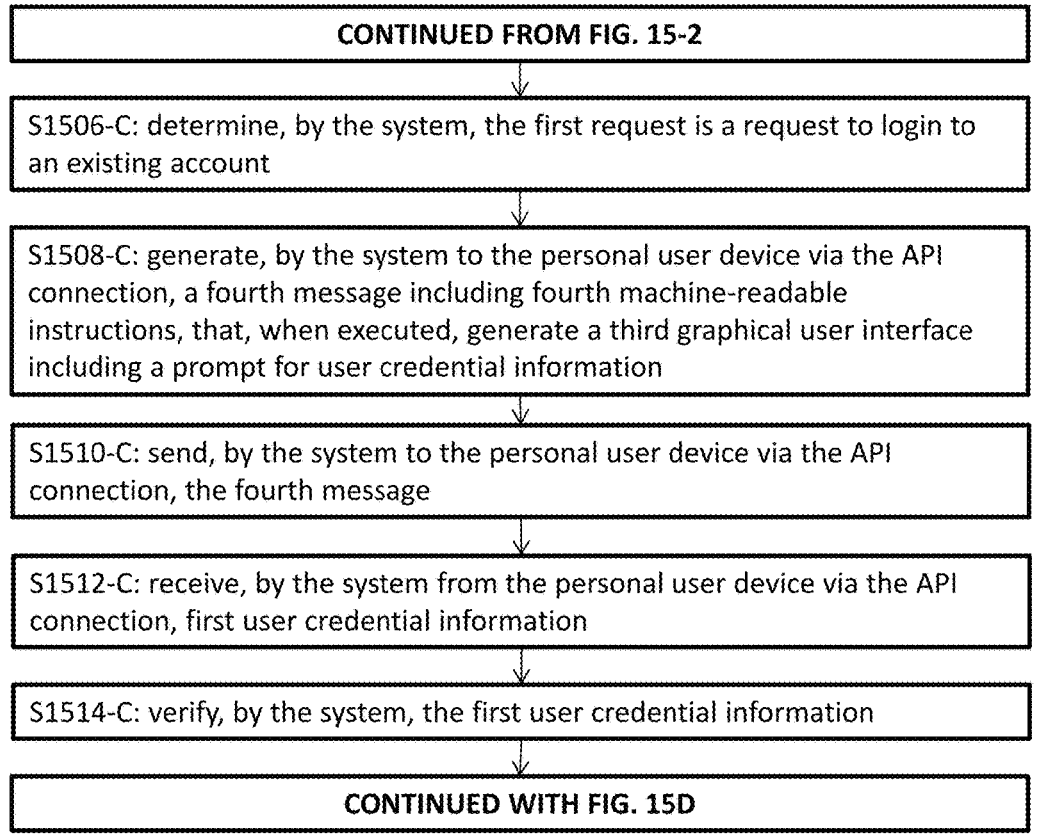

In embodiments, the request 1502 is a request to login to an existing account. In such embodiments, the process for receiving and processing the request 1502, in embodiments, may continue with FIG. 15C. Referring to FIG. 15C, the process for receiving and processing a request to login to an existing account may begin with step S1506-C. In embodiments, at step S1506-C, the system 1000 may determine that the request 1502 is a request to login to an existing account with the system 1000.

The process for logging into an existing account with the system 1000, in embodiments, may continue with step S1508-C. In embodiments, at step S1508-C, the system 1000 may generate (e.g., by obtaining and executing machine-readable instructions) and send (at step S1510-C) a fourth message to the personal user device 10-1 via the API and/or the network 100. The fourth message, in embodiments, may include fourth machine-readable instructions, that, when executed, cause the personal user device 10-1 to display a third GUI including a prompt for user credential information. Upon receipt of the fourth message, in embodiments, the fourth machine-readable instructions may be executed by the personal user device 10-1, causing the personal user device 10-1 to display the third GUI. In embodiments, the requested credential information associated with the user may be input into the appropriate fields associated with the third GUI displayed on the personal user device 10-1 and sent to the system 1000 via the API and/or network 100.

The process for logging into an existing account with the system 1000, in embodiments, may continue with step S1512-C. In embodiments, at step S1512-C, the system 1000 may receive, from the personal user device 10-1 via the API and/or network 100, the user credential information. At step S1514-C, in embodiments, the system 1000 (e.g., via login module 3005) verifies the user credential information. If the user credential information cannot be verified, the system 1000 may generate and send a notification to the personal user device 10-1 (via API and/or network 100) indicating the user credentials could not be verified. In embodiments, if the user credential information is verified, the process may continue with step S1508-D through S1510-D of FIG. 15D, the descriptions of which applying herein.

Figure 15D:
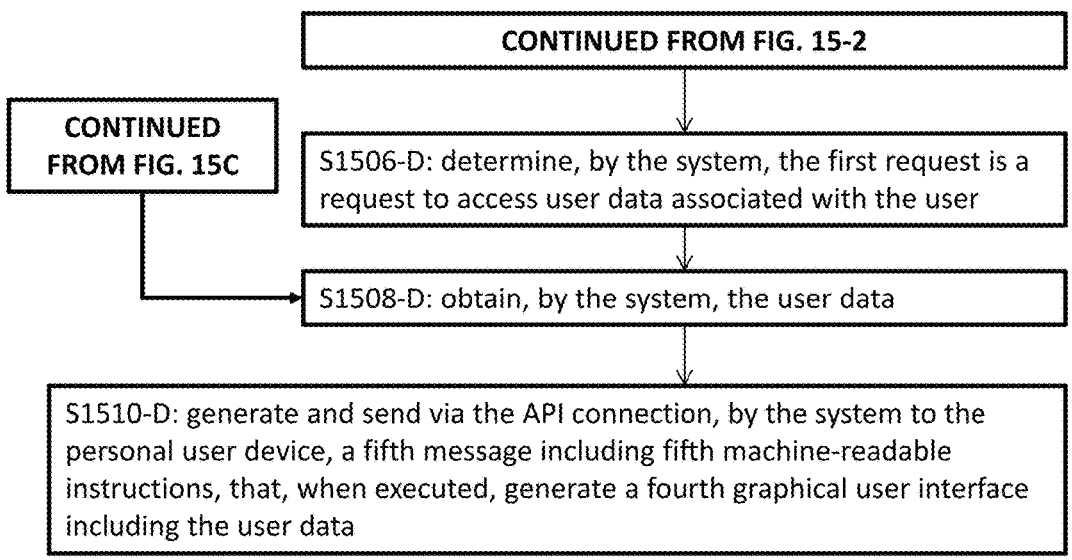

In embodiments, the request 1502 is a request to access user data associated with the user associated with the personal user device 10-1. In such embodiments, the process for receiving and processing the request 1502, in embodiments, may continue with FIG. 15D. Referring to FIG. 15D, the process for receiving and processing a request to access user information may begin with step S1506-D. In embodiments, at step S1506-D, the system 1000 may determine that the request 1502 is a request to access user information associated with an existing account with the system 1000.

The process for providing access to user data, in embodiments, may continue with step S1508-D. At step S1508-D, in embodiments, the system 1000 may obtain the user data. The user data, in embodiments, may be obtained by accessing one or more of the following: memory operatively connected to the system 1000; the lifestyle database 1002-1, the user profile database 1016-1, the available stimulus database 1004-2, the stimulus database 1004-1, and/or a combination thereof, to name a few.

In embodiments, the process for providing access to user data may continue with step S1510-D. At step S1510-D, in embodiments, the system 1000 may generate (e.g., by obtaining and executing machine-readable instructions) and send a fifth message to the personal user device 10-1 via the API and/or the network 100. The fifth message, in embodiments, may include fifth machine-readable instructions, that, when executed, cause the personal user device 10-1 to display a fourth GUI including the user data. In embodiments, the user data may be shown in the form of a feed (e.g., the feeds shown in connection with the screen shots of FIGS. 9A-9B and 13B-13C). Upon receipt of the fifth message, in embodiments, the fifth machine-readable instructions may be executed by the personal user device 10-1, causing the personal user device 10-1 to display the fifth GUI (e.g., the screenshots illustrated in connection with FIGS. 9A-9G and 13A-13L).

In embodiments, the following is exemplary code for granting access to and providing user data in accordance with exemplary embodiments of the present invention:

receive_query_requests_from_API_gateway(query)
insert_data_to_Backend_DB(sensorData)
check_event_present_for_user_around_his_location( )
add_event_data_to_cache_DB(event_data)
insert_user_profile_data(name, age, weight, height, gender)
fetch_user_feed_data(userID)
remove_expired_feeds_for_user(userID)
sort_feeds_based_on_feedWeights( )
sends_response_to_APIgateway( )

Figure 15E:
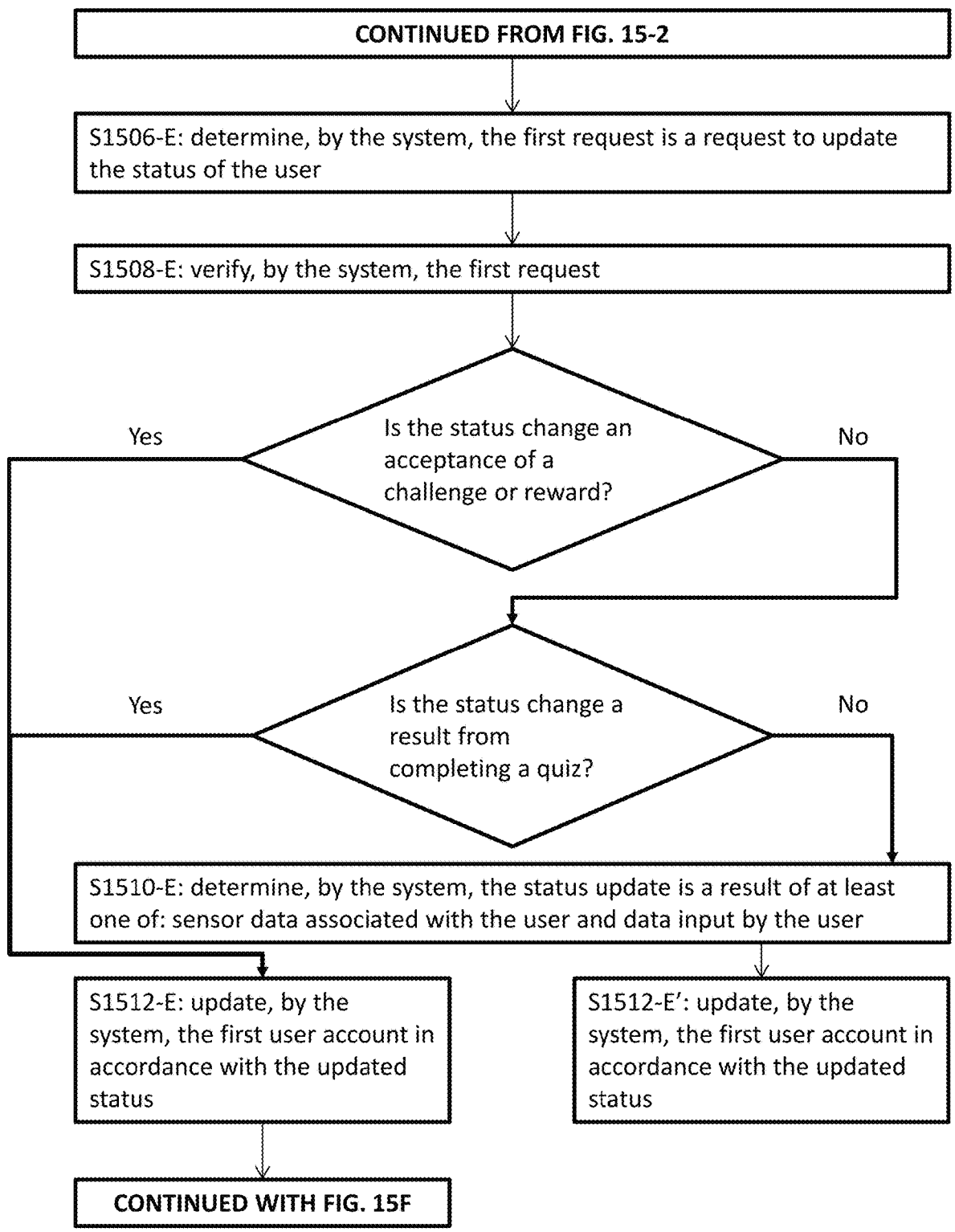

In embodiments, the request 1502 is a request to update the status of a user associated with the user associated with the personal user device 10-1. In such embodiments, the process for receiving and processing the request 1502, in embodiments, may continue with FIG. 15E. Referring to FIG. 15E, the process for receiving and processing a request to update the status of a user may begin with step S1506-E. In embodiments, at step S1506-E, the system 1000 may determine that the request 1502 is a request to update the status of a user associated with an existing account with the system 1000. The request 1502, in embodiments at step S1508-E, may be verified by the system (e.g., via a request and verification of user credentials associated with the user making the request).

In embodiments, the requested status change is an acceptance of a challenge or a reward and/or the result of completing a quiz. In such embodiment, the process of processing a request to update the status of a user may continue with step S1512-E. In embodiments, at step S1512-E, the system 1000 may update the first user account in accordance with the updated status. For example, if the user accumulated points for completing a challenge and/or a quiz, the points may be assigned to the user's account. Continuing the example, the points may be assigned by storing the points in one or more of the following: memory operatively connected to the system 1000; the lifestyle database 1002-1, the user profile database 1016-1, the available stimulus database 1004-2, the stimulus database 1004-1, and/or a combination thereof, to name a few. In embodiments, the process for updating the status of a user may continue with steps S1508-F through S1510-F described below in connection with FIG. 15F, the description of which applying herein.

In embodiments, the requested status change is not an acceptance of a challenge or a reward and/or not the result of completing a quiz. In such embodiment, the process of processing a request to update the status of a user may continue with step S1510-E. In embodiments, at step S1510-E, the system 1000 may determine the status update is a result of at least one of the following: sensor data received from the personal user device 10-1 and/or data input manually by the user associated with the personal user device 10-1, to name a few.

The process, in embodiments, may continue at step S1512-E' where the system 1000 may update the first user account in accordance with the updated status. For example, if the user if time ran out on a challenge (e.g., the user only walked 7500 of 10000 required steps), the result of the challenge (e.g., incomplete) may be assigned to the user's account. Continuing the example, the points may be assigned by storing the result of the challenge in one or more of the following: memory operatively connected to the system 1000; the lifestyle database 1002-1, the user profile database 1016-1, the available stimulus database 1004-2, the stimulus database 1004-1, and/or a combination thereof, to name a few.

In embodiments, the following is exemplary code for updating the status of a user in accordance with exemplary embodiments of the present invention:

```
for(every 30 secs) {
   check_event_data_from_cache_DB( )
   extract(eventFeedID)
}
check_time_based_events_inpersistence_DB( )
check_notification_count(time: last one day)
if(is_user_is_not_notified for a feedID) {
   send_notification(userID)
   update_sent_notifications_in_backend(userID)
   add_feed_to_userdetails_in_backend(userID, feedID)
}
```

Figure 15F:
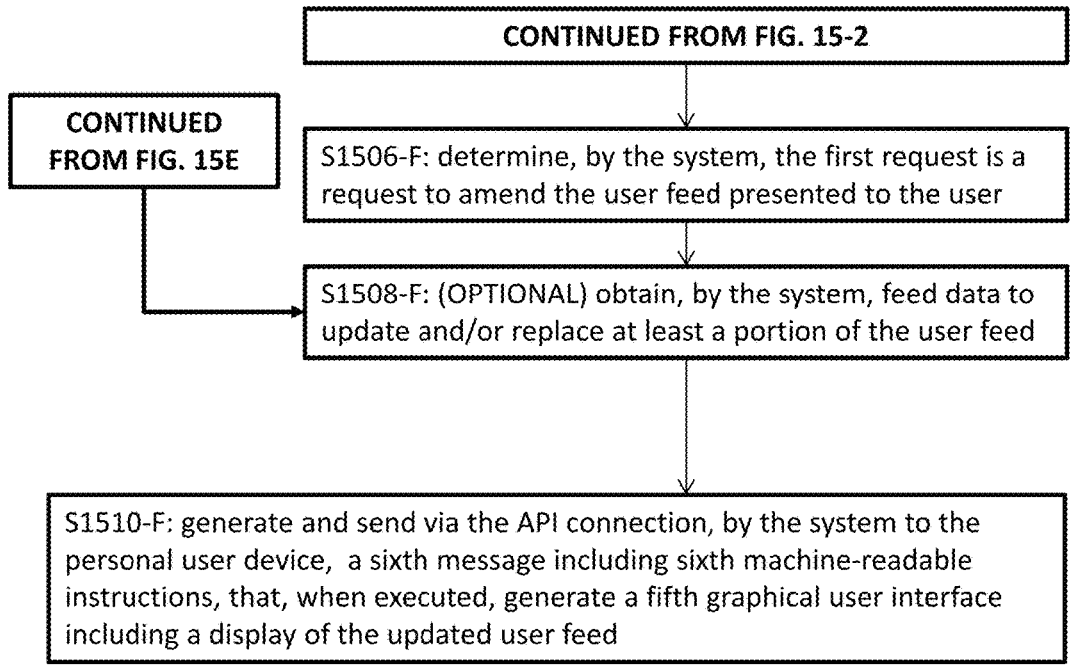

In embodiments, the request 1502 is a request to amend the user feed (e.g., the feeds shown in connection with the screen shots of FIGS. 9A-9B and 13B-13C) of a user associated with the user associated with the personal user device 10-1. In such embodiments, the process for receiving and processing the request 1502 (and/or the process of updating the status of a user), in embodiments, may continue with FIG. 15F. Referring to FIG. 15F, the process for receiving and processing to amend the user feed may begin with step S1506-F. In embodiments, at step S1506-F, the system 1000 may determine that the request 1502 is a request to amend the user feed of a user associated with an existing account with the system 1000.

The process for amending the user feed, in embodiments, may optionally continue with step S1508-F. At step S1508-F, the system, in embodiments, may obtain feed data to update and/or replace at least a portion of the user feed. The feed information, in embodiments, may include one or more of the following: a quiz, a challenge, a message, and/or a combination thereof, to name a few. The feed data, in embodiments, may have been previously generated and stored in one or more of the following: memory operatively connected to the system 1000; the lifestyle database 1002-1, the user profile database 1016-1, the available stimulus database 1004-2, the stimulus database 1004-1, and/or a combination thereof, to name a few.

In embodiments, the process for amending the user feed may continue with step S1510-F. At step S1510-F, in embodiments, the system 1000 may generate (e.g., by obtaining and executing machine-readable instructions) and send, to the personal user device 10-1, a sixth message including sixth machine-readable instructions, that, when executed, generate a fifth GUI including a display of the updated user feed. The sixth message, in embodiments, may be sent from the system 1000 to the personal user device 10-1 via the API and/or network 100. In embodiments, the sixth message may be one or more of the following: an SMS message; an MMS message; a push-notification; an in-application message; an RCS message; an electronic-mail message; a telephonic message, and/or a combination thereof, to name a few. Upon receipt of the sixth message, in embodiments, the sixth machine-readable instructions may be executed by the personal user device 10-1, causing the personal user device 10-1 to display the fifth GUI.

Figure 15G:
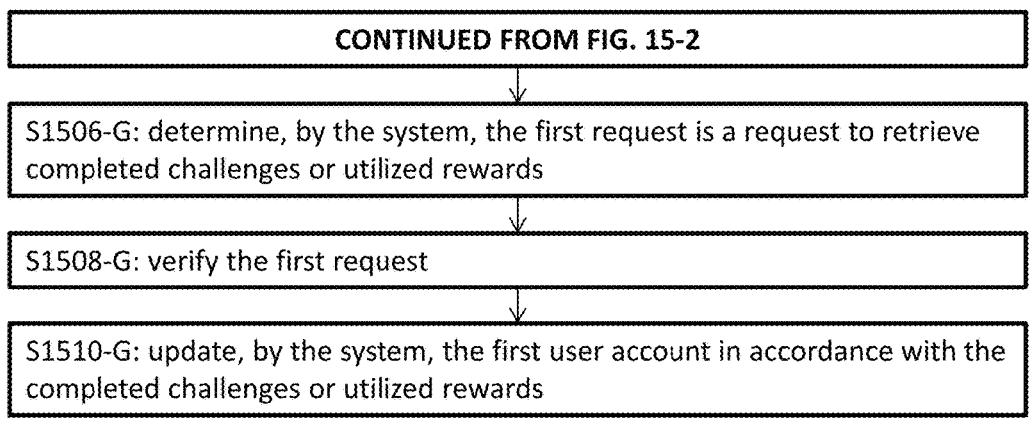

In embodiments, the request 1502 is a request to retrieve completed challenges and/or retrieve utilized rewards, each associated with the user associated with the personal user device 10-1. In such embodiments, the process for receiving and processing the request 1502, in embodiments, may continue with FIG. 15G. Referring to FIG. 15G, the process for receiving and processing a request to retrieve completed challenges and/or retrieve utilized rewards associated with a user may begin with step S1506-G. In embodiments, at step S1506-G, the system 1000 may determine that the request 1502 is a request to retrieve completed challenges and/or retrieve utilized rewards associated a user associated with an existing account with the system 1000. The request 1502, in embodiments at step S1508-G, may be verified by the system 1000 (e.g., via a request and verification of user credentials associated with the user making the request). Once verified, in embodiments at step S1510-G, the system 1000 may update the user account in accordance with the completed challenges and/or utilized rewards (e.g., by updating one or more of: memory operatively connected to the system 1000; the lifestyle database 1002-1, the user profile database 1016-1, the available stimulus database 1004-2, the stimulus database 1004-1, and/or a combination thereof, to name a few).

The steps of the processes described in connection with FIGS. 15-2, 15A, 15B, 15C, 15D, 15E, 15F, and/or 15G may be rearranged or omitted.

EXAMPLES

The following is a non-exhaustive list of use case Examples of the prompt and stimulus features provided to users of personal user devices 10-1 . . . 10-n in accordance with embodiments of the present invention.

Example 1: Third-Party Sets Up a Challenge for User to Complete 10000 Steps a Day and Get Rewarded Via Incentives A third-party, such as an employer, sets up a challenge for its employees to complete 10000 steps a day for a reward incentive. The information associated with the challenge is inputted at third-party user information systems 30-1 . . . 30-n and communicated to personal data system 20 via network 100. Processor 2010 of personal data system 20 identifies the appropriate personal user devices 10-1 . . . 10-n that qualify for the challenge and issue challenge data to the personal user devices 10-1 . . . 10-n of the qualified users, where it is stored as stimulus data 3060.

A user receives, at one or more of the personal user devices 10-1 . . . 10-n via mobile application software 3000, a notification about the new challenge, which is to be rewarded with a predetermined number of points if the user walks 10000 steps in a day. In embodiments, the notification may be a push notification, as shown in connection with FIG. 13A. For example, as shown in FIG. 13A, a notification about a healthy eating option near (e.g., within a predetermined radius) the user associated with the one or more personal devices 10-1 . . . 10-n.

The user taps on the notification, which in turn opens mobile application software 3000 where user accepts the challenge via user interface module 3010. Stimulus data 3060 and user profile data 3045 at personal user device(s) 10-1 . . . 10-n is updated with the accepted challenge.

The updated user profile data 3045 recorded at personal user device(s) 10-1 . . . 10-n is sent to personal data system 20 where it is stored (user profile data 2014). Device (API) data 3055 is, thereafter, recorded at the personal user device(s) 10-1 . . . 10-n and periodically sent to personal data system 20 for storage (Recorded User Device (API) data 2018). Related user data 2020, which may include user profile data 3045, device (API) data 3055, and stimulus data 3060 of personal user device(s) 10-1 . . . 10-n associated with one or more related users, is, likewise, periodically retrieved by personal data system 20 and stored.

Processor 2010 at personal data system 20 executes one or more algorithmic processes to analyze the periodically stored user data and to monitor the progress of user challenge completion.

On successful completion of the challenge, an alert/stimulus is sent to the personal user device(s) 10-1 . . . 10-n informing the user about the completion.

Additionally, personal data system executes one or more behavioral tracking processes based on the above and records any changes in a user profile data 2014 in accordance with the periodically stored user data in the course of completing or not completing the challenge.

If the change is: positive, user response to the stimulus is also captured, if required, user tags, which may be maintained with user feedback data 2024 at personal data system 20, are updated. If the change is negative, process repeats.

Example 2: Better Sleep Regime Recommendations Sent to User

User data is retrieved from user profile data 2014 and user records are retrieved from recorded user device (API) data 2018. Processor 2010 at personal data system 20 executes one or more algorithmic processes to analyze the retrieved data to determine a user's sleep pattern. Third-party user data 2016 is retrieved to generate a better sleep regime recommendation.

A stimulus is transmitted from stimulus module 2032 of personal data system 20 to stimulus transceiver module 3020 of personal user device(s) 10-1 . . . 10-n. User interface module 3010 provides a display of the stimulus to the user and the user clicks at the stimulus (a better sleep regime).

Mobile application software 3000 continuously, periodically, on demand, or based on predetermined conditions records device (API) data 3055 via API module 3040 and user response data 3065 via user interface module 3010. Personal data system 20 is periodically updated with the newly recorded user data via stimulus transceiver module 3020 or another network interface to network 100. Personal data system 20 monitors the periodically updated recorded user device (API) data 2018 along with user feedback data 2024. Stimulus impact on user behavior is tracked and stored at user profile data 2014 and user feedback data 2024 and one or more user tags are updated at user profile data 2014 and the process is repeated based on specific conditions, for example, a predetermined improvement threshold.

Example 3: Weekly Pattern Determination

User data is retrieved from user profile data 2014 and user records are retrieved from recorded user device (API) data 2018. Processor 2010 at personal data system 20 executes one or more algorithmic processes to analyze the retrieved data to determine a user's activity pattern. Personal data system 20 conducts continuous analysis of the user's activity pattern data to derive daily and weekly activities. The derived user activity daily and weekly patterns are stored in user profile data 2014.

Regular activities are continuously, periodically, on demand, or based on predetermined conditions compared over regular periods to identify any changes at personal data system 20. Based on the derived patterns and third-party user data 2016, personal data system 20 determines one or more stimuli from vendor and stimulus data 2022 to suggest parallel action/choice to the user at personal user device(s) 10-1 . . . 10-n.

Personal data system 20 continues behavioral tracking through personal user device(s) 10-1 . . . 10-n in accordance with the above and detects for any changes. User feedback from personal user device(s) 10-1 . . . 10-n is stored in user feedback data 2024 when outcome is positive or specific requirements are met according to the stimuli.

Example 4: Real Time Bidding for Vendor

For equipment, items, services, memberships, and the like, a user at personal user device(s) 10-1 . . . 10-n is provided with better recommendations by facilitating real-time bidding among vendors. Based on user profile data 2014 and/or user feedback data 2024, personal data system 20 determines a particular need for a user. Personal data system 20 retrieves user recommendations from vendor and stimulus data 2022 and queries vendor systems 40-1 . . . 40-n for real time bidding on fulfilling the determined need. Vendor systems 40-1 . . . 40-n may include corresponding vendor coupon data sets 40A-1-40A-n which reflect available coupons or deals that the system may use as stimulus. Personal data system 20 prioritizes the vendors based on bidding results and stores the recommendation priority in vendor and stimulus data 2022.

One or more highest recommended choices is retrieved from vendor and stimulus data 2022 and forwarded to the user at personal user device(s) 10-1 . . . 10-n. The forwarded recommendation(s) is also stored in user profile data 2014. Personal user device(s) 10-1 . . . 10n records and relays user feedback on the shown recommendation(s) and the user feedback is stored in user feedback data 2024.

Example 5: Recommendation to the User

Related to Example 4, a user at personal user device(s) 10-1 . . . 10-n is provided with recommended (or discounted or otherwise user incentivized) equipment, items, services, memberships, and the like, based on the user's profile, activity level, etc. Processor 2010 at personal data system 20 retrieves user profile data 2014 and recorded user device (API) data 2018 for a combined analysis with third-party user data 2016 and vendor and stimulus data 2022 using one or more algorithmic processes. One or more recommendations are identified based on the analysis and corresponding one or more stimuli are generated at stimulus module 2032 and transmitted to the user at personal user device(s) 10-1 . . . 10-n.

Personal user device(s) 10-1 . . . 10n records and relays user feedback on the recommendation(s) and the user feedback is stored in user feedback data 2024. User tags are updated in user profile data 2014 along with the feedback recorded in user feedback data 2024.

Example 6: Third-Party Puts Up a Timely Query/Quiz for the User

A third-party, through programming and/or input at third-party user information systems 30-1 . . . 30-n, defines a collection of queries and quizzes for users. These queries and quizzes are received at personal data system 20 and stored as third-party user data 2016. When appropriate based on preset conditions defined by the third-party in the query data, one or more of the queries and quizzes are forwarded to mobile application software 3000 at personal user device(s) 10-1 . . . 10-n and the user is prompted to answer questions about, for example, his/her preferred choice between honey and sugar as a routine food option, and is rewarded for answering.

Accordingly, user profile data 2014 and recorded user device (API) data 2018 is continuously, periodically, on demand, or based on predetermined conditions analyzed along with query data collected from third-party user data 2016 by processor 2010 using one or more algorithmic processes to determine the appropriate time, condition, and query(ies) for users at personal user device(s) 10-1 . . . 10-n. Stimuli corresponding to the determined queries are sent to the identified users at personal user device(s) 10-1 . . . 10-n informing about the query(ies) using the stimulus module 2032. The user's responses to the query stimuli are relayed to personal data system 20 and recorded in the user feedback data 2024. Based on these responses, user profile data 2014 is also updated.

Example 7: Third-Party Provides a Survey for the User, to Record his/her Routine Schedule and Habits Related to Example 6, a third-party, through programming and/or input at third-party user information systems 30-1 . . . 30-n, defines a survey for users. The survey is received at personal data system 20 and stored as third-party user data 2016. When appropriate based on preset conditions defined by the third-party in the survey data, the survey is forwarded to mobile application software 3000 at personal user device(s) 10-1 . . . 10-n and the user is prompted to answer questions about his/her daily diet schedule and eating-habits via user interface module 3010. Points may be rewarded to users for taking up the survey, or other incentives may be offered.

Accordingly, user profile data 2014 and recorded user device (API) data 2018 is continuously, periodically, on demand, or based on predetermined conditions analyzed along with survey data collected from third-party user data 2016 by processor 2010 using one or more algorithmic processes to determine the appropriate time, condition, and survey for users at personal user device(s) 10-1 . . . 10-n. Stimuli corresponding to the determined surveys are sent to the identified users at personal user device(s) 10-1 . . . 10-n informing about the survey using the stimulus module 2032. User answers to the stimuli are relayed to personal data system 20 and stored in the user feedback data 2024. Based on these answers, user profile data 2014 is also updated.

Example 8: User is Suggested to Join a Group or Network and is Given Subscription Discounts as Incentive A user is given a suggestion to join a nearby Cycling group. Processor 2010 at personal data system 20 retrieves and analyzes user profile data 2014 and recorded user device (API) data 2018 along with related user data 2020 to determine commonalities among related users. Based on the retrieved data, processor 2010 executes one or more algorithmic processes to determine the best available social group for a user to join.

Once a group has been identified for a particular user, a stimulus with group information is generated and transmitted to personal user device(s) 10-1 . . . 10-n of the user, informing about the group and the procedure to join. User reaction to the stimulus is relayed to personal data system 20 and recorded in user feedback data 2024. Related user data 2020 is updated based on the stimulus and response. In embodiments, such a response to the stimulus may be sensor data and/or user actions on the user device screen/buttons.

On successful feedback from the user (i.e., the user joins the suggested group), stimuli for related users in the group are generated and transmitted to the personal user devices 10-1 . . . 10-n of the group participants, updating them of the new participant.

On subsequent group events, stimuli are sent to the personal user devices 10-1 . . . 10-n of group participants informing them about the on-going activities in the group. User feedback to the stimuli is relayed to personal data system 20 and updated in user feedback data 2024. One or more algorithmic processes are executed by processor 2010 at personal server 20 for determining whether each user personal regime in the group has improved.

Example 9: Building a Data Set

FIGS. 21A-21M are exemplary flowcharts of processes to build a data set (e.g., training data set 1018-1, situation information data set 1312B, to name a few) for a machine learning algorithm (e.g., machine learning algorithm 1006-1, machine learning algorithm 1712-G, machine learning algorithm 1714-G, machine learning algorithm(s) 1708-1, machine learning algorithm(s) 1718-E, to name a few). A data set, in accordance with exemplary embodiments of the present invention, is the result of transforming raw data into information, which can be utilized by heuristics and/or machine learning algorithms to transform the information into knowledge about a user's routine (e.g., locations and/or activities).

Building a data set, in embodiments, may begin at the start of the first amount of time described above in connection with FIG. 16. In embodiments, a system (e.g., system 1000, system 1000-A, to name a few) may build a data set each day, week, month, year, and/or a combination thereof. In embodiments, a data set may be built if a large change is determined and/or detected. For example, if the system determines that a country where a user is residing is under a national emergency order, the system may build a data set to better understand a routine associated with the user during the national emergency order.

For the purposes of this example, the system has already obtained raw data (e.g., time-series data from a portable personal user device (e.g., a smartphone) associated with the first user) from one or more devices and/or databases associated with a first user. Building a data set from raw data, in embodiments, may begin with step S2102. At step 2102, in embodiments, the system (e.g., via user manager 1702) may identify stationary locations, recurring locations, and recurring locations with confirmed location data labels. Referring to FIG. 21B, the system at step S2102, in embodiments, (step S2112) filters the raw data to stationary locations (e.g., via process(es) of FIGS. 21B, 21C, and/or 21D), (S2114) filters the stationary locations to recurring locations (e.g., via process(es) of FIGS. 21B and/or 21E), and filters recurring locations to recurring locations with confirmed location data labels by (step S2116) predicting location data labels for each recurring location (e.g., via process(es) of FIGS. 21B and/or 21F) and by (step S2118) confirming said predictions (e.g., via process(es) of FIGS. 21B and/or 21G). Each recurring location, if applicable, may be labelled with its corresponding confirmed location data label by the system. Referring back to FIG. 21A, in embodiments, with confirmed location data labels of recurring locations (yes at step S2104), the system (e.g., via the user manager 1702) may determine, at step S2106, whether the confirmed location data label of each recurring location indicates the respective recurring location is associated with a location-based event, a time-based event, and/or both a location based-event and a time based-event. Information associated with each respective recurring location (e.g., a confirmed location data label associated with a respective location, a timestamp associated with the respective location, to name a few) may be sent (e.g., via user manager 1702) to one or more modules of the system (e.g., location-based events module 1712 for location data labels that indicate an association with a location-based event, time-based events module 1714 for location data labels that indicate an association with a time-based event, to name a few) based on the determination in step S2106. The one or more modules may (at step S2108A (e.g., via process(es) of FIGS. 21H, 21J, and/or 21K) and/or step S2108B (e.g., via process(es) of FIGS. 21I, 21L, and/or 21M)) identify and confirm events corresponding to each respective location with a confirmed location data label. Each recurring location, if applicable, may be labelled with its corresponding confirmed event by the system.

As described above, the system, at step 2102 in embodiments, filters the obtained raw data by identifying stationary locations, recurring locations, and recurring locations with confirmed location data labels. Referring to FIG. 21B, in embodiments, the process of filtering the raw data by identifying stationary locations, recurring locations, and recurring locations with confirmed location data labels may begin at the above-mentioned step S2112 where the system (e.g., via location module 1710) identifies one or more stationary locations in the raw data. Referring to FIG. 21C, in embodiments, the system (e.g., via location module 1710), may analyze the raw data (at step S2120) to determine a first location where the first user has stopped. Referring to FIG. 21D, in embodiments, to determine the first location where the first user has stopped, the system (e.g., via location module 1710) may resample the raw data at a first threshold, which may fill gaps in the raw data and/or remove outliers from the raw data. The first threshold, in embodiments, may refer to an amount of time corresponding to a gap of data and an amount of distance corresponding to the change of distance from the last location identified before the gap of data and the first location identified after the gap of data. For exemplary purposes, resampling of the raw data at the first threshold, for example, may fill gaps within the raw data that: have a duration of less than the amount of time in the first threshold, have a distance change less than the distance in the first threshold, and/or a combination thereof. In embodiments, gaps within the raw data that exceed the first threshold may not be filled by the resampling of the raw data. Gaps which have not been filled by the resampling of the raw data at step S2132, in embodiments, may be filtered out by the system (e.g., via location module 1710).

The process for determining where the first user has stopped may continue with step S2134 where the system (e.g., via location module 1710) may compute a distance matrix for a first distance. The first distance, in embodiments, may refer to a distance indicating the user, even if moving short distances, has stopped at a location. The system, may compute a distance matrix for a first distance to detect clusters where the first user has stopped. The detected clusters, at step S2136 (and step S2122 of FIG. 21C), in embodiments, may be utilized by the system (e.g., via location module 1710) to compute centroids of clusters (e.g., using a clustering algorithm) where the user has stopped—e.g., using DBSCAN clustering (i.e. executing DBSCAN algorithm), CRNN sequencing, and/or a combination thereof, to name a few. Each centroid of each cluster, in embodiments, may refer to a stationary location. Referring back to FIG. 21C, the process of identifying one or more stationary locations may continue with step S2122 where, in embodiments, the system (e.g., via location module 1710) may compute the centroids of clusters in the portion of the raw data associated with the first location (and/or each identified stationary location).

The process of identifying one or more stationary locations may continue with step S2124 where, in embodiments, the system (e.g., via location module 1710) may merge consecutive stationary locations. For example, the raw data may indicate a plurality of data points over time where the user has stopped at a first location. Because the user has not moved (and/or has not moved outside a radius around the first location), the system (e.g., via location module 1710) may merge each consecutive data point (over time) of the plurality of data points at the first location to indicate that each consecutive data point of the plurality of data points at the first location are a part of the same instance where the first user has stopped at the first location.

The process of identifying one or more stationary locations may continue with step S2124 where, in embodiments, the system (e.g., via location module 1710) may store the first location as a stationary location (e.g., in memory 1704). In embodiments, each stationary location stored may be stored with location information corresponding to the respective stationary location. The location information, in embodiments, may include a timestamp indicating when the first user has stopped at the stationary location, a timestamp indicating when the first user left the stationary location, a time range indicating an interval of time the user spent at the stationary location, motion information associated with the first user (e.g., motion information before the first user stopped, motion information after the first user has begun to move again, and/or a combination thereof), and/or a combination thereof, to name a few.

The process of identifying one or more stationary locations may repeat (step S2128)—e.g., if more raw data is to be analyzed for stationary locations—until the raw data is analyzed and/or one or more stationary locations are identified. In embodiments, the processes of FIG. 21C and FIG. 21D may identify more than one (and/or all of) the stationary locations in the raw data, simultaneously (and/or substantially simultaneously). Once the one or more stationary locations have been identified, in embodiments, the process may continue with step S2114 of FIG. 21B.

Referring to FIG. 21B, in embodiments, the process of filtering the raw data by identifying stationary locations, recurring locations, and recurring locations with confirmed location data labels may continue at the above-mentioned step S2114 where the system (e.g., via location module 1710) identifies one or more recurring locations from the one or more stationary locations identified in step S2112. Referring to FIG. 21E, in embodiments, the system (e.g., via location module 1710), remove all previously identified recurring locations (from previous data sets)—e.g., remove all previously identified recurring locations from local memory. The system (e.g., via location module 1710), in embodiments at step S2140, may obtain all identified stationary locations from step S2112. The obtained stationary locations, in embodiments, may include corresponding information for each stationary location (e.g., location information, timestamps, time ranges, etc.). The process of identifying one or more recurring locations may continue with step S2142 where, in embodiments, the system (e.g., via the location module 1710) may input the filtered data (e.g., the stationary locations) into an algorithm to cluster the stationary locations (e.g., using the Gaussian Mixture Model). The execution of the Gaussian Mixture Model, in embodiments, may result in the identification of one or more clusters. The system, in embodiments at step S2144 may compute the centers of the clusters (e.g., compute the centroids of the clusters), resulting in one or more identified recurring locations. In embodiments, the filtered raw data including one or more recurring locations may, for each data point indicating a recurring location, include one or more of the following corresponding pieces of information: at least two start timestamps indicating each date and time the user stopped at the recurring location, at least two end timestamps indicating each date and time the user left the recurring location, at least two time ranges indicating at least two intervals of time and corresponding dates of which the user spent at the recurring location, motion information associated with the first user (e.g., motion information before each time the first user stopped at the recurring location, motion information after each time the first user left the recurring location, and/or a combination thereof), and/or a combination thereof, to name a few. Each recurring location (and/or each recurring location's corresponding information) may be stored (step S2146) by the system (e.g., via the location module 1710 in memory 1704).

Referring to FIG. 21B, in embodiments, the process of filtering the raw data by identifying stationary locations, recurring locations, and recurring locations with confirmed location data labels may continue at the above-mentioned step S2116 where the system (e.g., via location module 1710) predicts one or more location data labels associated with the one or more recurring locations identified in step S2114. Referring to FIG. 21F, the system (e.g., via the location module 1710) may, at step S2148, obtain all identified recurring locations. For each recurring location, in embodiments at step S2150, the system (e.g., via the location module 1710) may compute the hours of the week. For example, the data set may apply to an amount of time—a week. The week, in embodiments, may be mapped into a routine (e.g., routine 1710-A), by mapping each recurring location over a week long schedule. To build the routine, in embodiments, the system (e.g., via location module 1710 and/or time function library 1708-B) may convert all timestamps associated with the recurring locations to the same time zone, allowing the recurring locations to be organized as a function of time (e.g., FIGS. 18, 19A, 19B, 20A, 20B). For example, the system (e.g., via the routine 1710-A of location module 1710), may generate a timeline of recurring locations for an interval of one week (e.g., FIG. 19A). The timeline, in embodiments, may include each recurring location. In embodiments, the system may generate a timeline for each recurring location.

The generated one or more timelines (at step S2152), in embodiments, may be compared to one or more data models (e.g., data model(s) 1710-C). The data model(s) 1710-C may each represent a generic recurring location and/or a corresponding location data label (e.g., home, office, work, gym, place of worship, etc.) organized over time—for example—in timeline form (e.g., FIG. 19B). If the similarities between the generated one or more timelines and one or more data models is above a second threshold (e.g., a percentage of similarity), the system (e.g., via the location module 1710) may determine the location data label associated with the matched one or more data models and may be a potential (e.g., predicted) location data label for the one or more recurring locations corresponding to the one or more generated timelines. In embodiments, at step S2154, each match above the second threshold (and/or each match with similarities) may be confirmed by the system (e.g., via quiz information 1710-D of location module 1710).

Referring to FIG. 21B, in embodiments, the process of filtering the raw data by identifying stationary locations, recurring locations, and recurring locations with confirmed location data labels may continue at the above-mentioned step S2118 where the system (e.g., via location module 1710) confirms one or more of the location data labels predicted in step S2118. The process of confirming each match above the second threshold, in embodiments, is illustrated in connection with FIG. 21G.

Referring to FIG. 21G, in embodiments, confirming one or more of the location data labels predicted in step S2118 may be accomplished by one or more of the following: a stimulus (e.g., via steps S2156, S2158, S2160), purchase information (e.g., via prior purchase information 1316A (e.g., using a purchase made by the first user and/or a person within proximity of the first user to confirm the location of the user at the time of purchase)), social media information (e.g., via social connection information 1308D (e.g., a social connection and/or a professional colleague check in at a location) and/or using social media to confirm a predicted location data label of a location the first user checked into), information from one or more additional users (e.g., if a second user has already confirmed the location data label of the first user's recurring location, the system may use the second user's confirmed location data label to confirm the predicted location data label of the first user's recurring location), and/or a combination thereof, to name a few. For example, the system (e.g., via quiz information 1710-D of location module 1710) at step S2156, may obtain, for each predicted location data label, a stimulus (e.g., a prompt, quiz, etc.) designed to confirm each respective predicted location data label. The stimulus, in embodiments, may directly query the first user with regards to the location data label of the recurring location (e.g., did you just leave your home?). In embodiments, the stimulus may attempt to retrieve confirmation indirectly (e.g., offering a reward (e.g., a coupon, points, to name a few) for a picture of the first user's mailbox to confirm the first user's home address). The stimulus, at step S2158, may be sent by the system to the first user via a device associated with the first user. In response, at step S2160, the system may receive a stimulus response indicating whether the respective location data label is confirmed (S2162). If the location data label is confirmed, or if another location data label is confirmed as the location data label of the respective recurring location, the system may label the respective recurring location with its confirmed location data label (or the another location data label confirmed). If the location data label was not confirmed, the system may obtain a second quiz and/or filter out the recurring location from the filtered information. In embodiments, the system may not require the use of one or more stimuli to confirm location data labels of stationary and/or recurring locations.

Referring back to FIG. 21A, in embodiments, the system (e.g., via the user manager 1702) may determine whether each of the one or more confirmed location data labels indicates a location-based event (e.g., working out at the gym, seeing a movie, working at a place of employment, going shopping, etc.) and/or a time-based event (e.g., waking up, eating breakfast, eating lunch, eating dinner, going to sleep, etc.). In embodiments, the determination may be made based on one or more of the following: the confirmed location data label (e.g., the recurring location is the gym), the timestamps (e.g., the recurring location is visited at lunch time), and/or a combination thereof, to name a few. Each recurring location determined to have a corresponding location data label indicative of a location-based event may, in embodiments, be sent by the system (e.g., via the user manager 1702) to a first module (e.g., the location-based event module 1712). In embodiments, each recurring location determined to have a corresponding location data label indicative of a time-based event may be sent by the system (e.g., via the user manager 1702) to a first module (e.g., the time-based event module 1714).

If one or more of the one or more confirmed location data labels indicates a location-based event is associated with a recurring location, the process may continue with step S2108A where the system (e.g., via the location-based events module 1712) identifies (step S2164 of FIG. 21H) and confirms (step S2166 of FIG. 21H) a corresponding location-based event associated with one or more confirmed location data labels. Referring to FIG. 21J, the system (e.g., via the location-based events module 1712) may, to predict a location-based event for each recurring location with a confirmed location data label, (at step S2172) obtain location data for each confirmed location. For example, at step S2174, each recurring location with a confirmed location data label, in embodiments, may be organized by the system (e.g., via routine 1712-A of the location-based event module 1712) over time (in embodiments, similarly to the S2148 and S2150 of FIG. 21F, the descriptions of which applying herein).

The organized recurring locations (at step S2176—e.g., organized into a timeline, event stream, to name a few), in embodiments, may be compared to one or more data models (e.g., data model(s) 1712-C). The data model(s) 1712-C may each represent a generic location-based event (working out at the gym, seeing a movie, working at a place of employment, going shopping, etc.) organized over time—for example—in timeline form (e.g., FIG. 19B) and/or in event stream form (e.g., FIG. 20B). If the similarities between the organized recurring locations and one or more data models is above a third threshold (e.g., a percentage of similarity), the system (e.g., via the location module 1710) may determine the location data label associated with the matched one or more data models and may be a potential (e.g., predicted) location data label for the one or more recurring locations corresponding to the one or more generated timelines. In embodiments, at step S2178, each match above the third threshold (and/or each match with similarities) may be confirmed by the system (e.g., via quiz information 1712-D of location-based event module 1712).

Figure 21H:
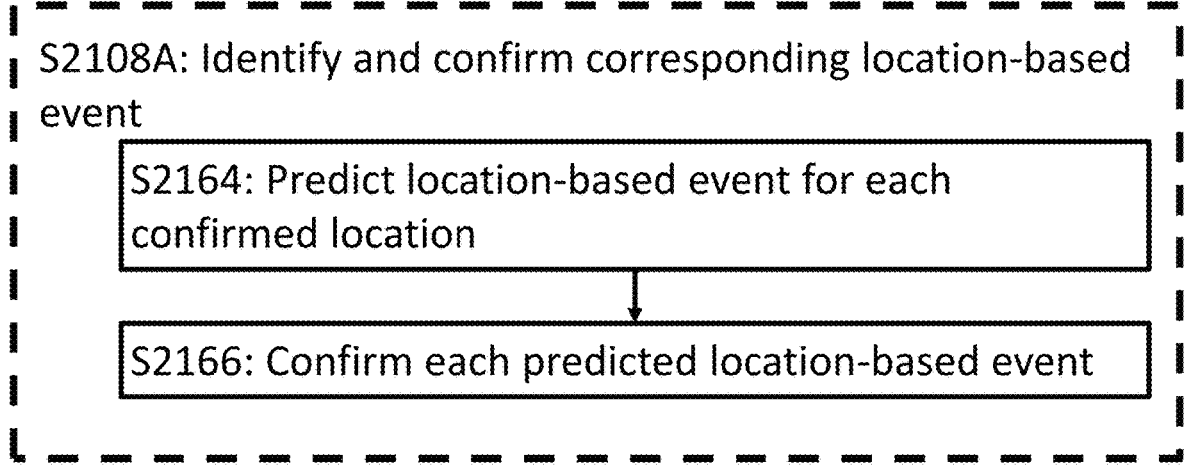

Referring to FIG. 21H, in embodiments, the process of identifying and confirming corresponding location-based event(s) may continue at the above-mentioned step S2166 where the system (e.g., via quiz information 1712-D of location-based event module 1712) confirms one or more of the events predicted in step S2164. The process of confirming each match above the third threshold, in embodiments, is illustrated in connection with FIG. 21K.

Referring to FIG. 21K, in embodiments, confirming one or more of the matches may be accomplished by one or more of the following: a stimulus (e.g., via steps S2180, S2182, S2184), purchase information (e.g., via prior purchase information 1316A (e.g., using a purchase made by the first user and/or a person within proximity of the first user to confirm the event associated with the recurring location), social media information (e.g., via social connection information 1308D (e.g., a social connection and/or a professional colleague post an activity corresponding to a checked in location) and/or using social media to confirm an event associated with the confirmed location data label of a location the first user checked into), information from one or more additional users (e.g., if a second user has already confirmed an activity associated with the first user's recurring location, the system may use the second user's confirmed activity to confirm the predicted activity associated with the first user's recurring location), and/or a combination thereof, to name a few. For example, the system (e.g., via quiz information 1712-D of location-based event module 1712) at step S2180, may obtain, for each predicted event, a stimulus (e.g., a prompt, quiz, etc.) designed to confirm each respective predicted event. The stimulus, at step S2182, may be sent by the system to the first user via a device associated with the first user. In response, at step S2184, the system may receive a stimulus response indicating whether the respective event is confirmed (S2186). If the event is confirmed, or if another event is confirmed, the system may label the respective recurring location with its confirmed corresponding event (or another event confirmed). If the event was not confirmed, the system may obtain a second quiz and/or filter out the recurring location from the filtered information. In embodiments, the system may not require the use of one or more stimuli to confirm predicted corresponding events of stationary and/or recurring locations.

If one or more of the one or more confirmed location data labels indicates a time-based event is associated with a recurring location, the process may continue with step S2108B where the system (e.g., via the time-based events module 1714) identifies (step S2168 of FIG. 21I) and confirms (step S2170 of FIG. 21I) a corresponding time-based event associated with one or more confirmed location data labels. Referring to FIG. 21L, the system (e.g., via the time-based events module 1714) may, to predict a time-based event for each recurring location with a confirmed location data label, (at step S2188) obtain location patterns associated with the recurring locations (e.g., from step S2150 and/or S2174). The system (e.g., via the time-based event module 1714) may, in embodiments, analyze the location patterns to predict an upcoming time-based event. The analysis, in embodiments, may include updating the time interval (step S2190) to enable the system to make a prediction in advance. Based on the time and location pattern, in embodiments, at step S2191, the system (e.g., via the time-based event module 1714) may predict a time-based event in advance (e.g., lunch, dinner, sleep, etc.) and a time (and/or time range) when the predicted time-based event will take place. In embodiments, before the predicted time occurs, at step S2192, the system (e.g., via quiz information 1714-D of the time-based events module 1714) may generate and send a quiz to the first user.

Figure 21I:
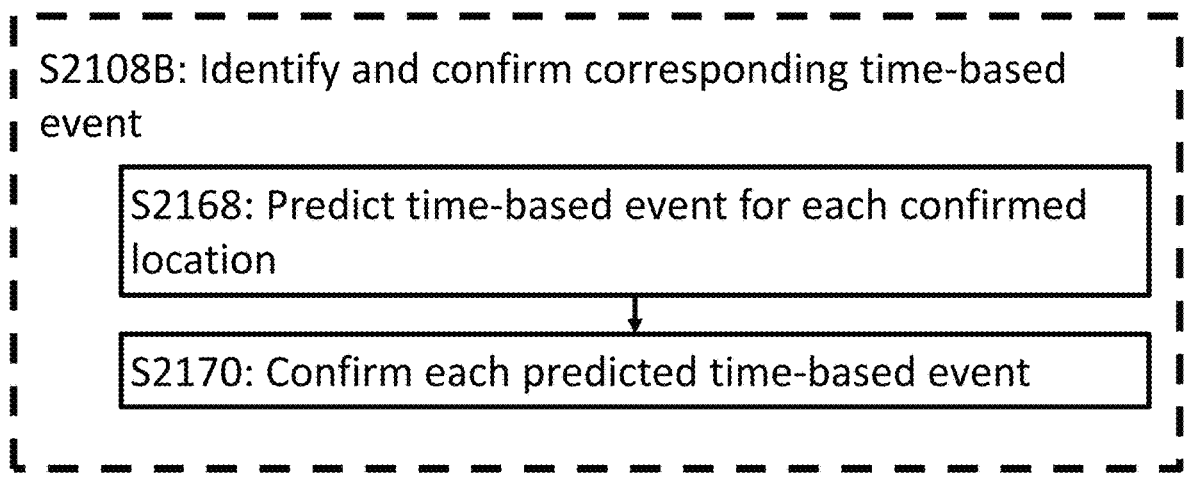
Figure 21L:
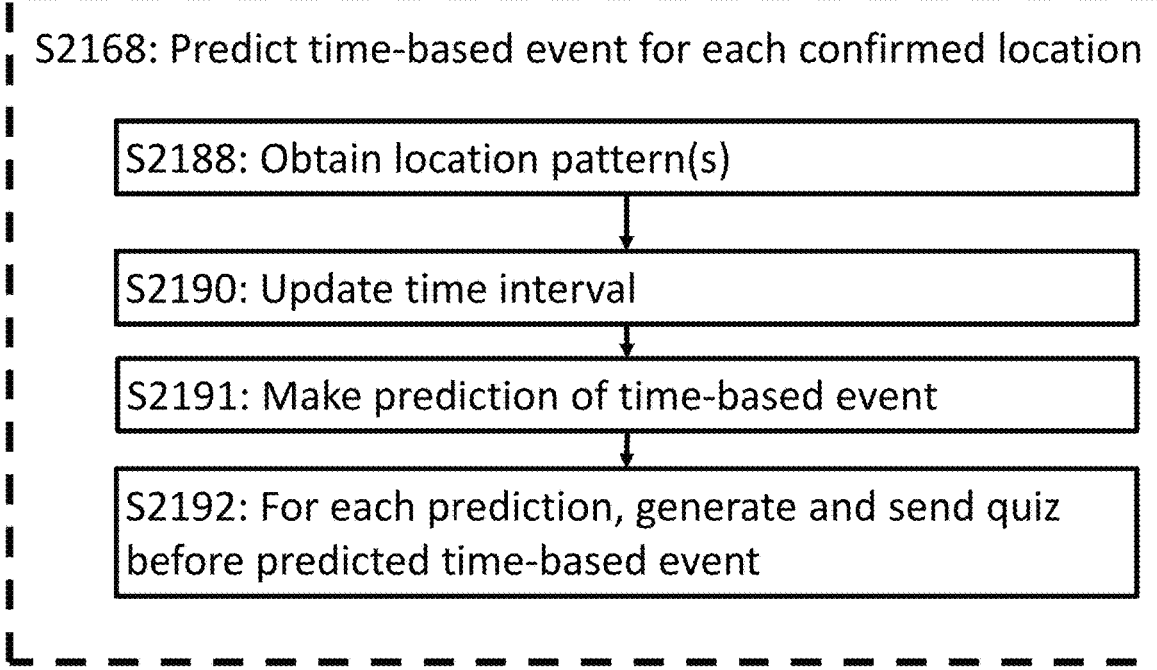

Referring to FIG. 21I, in embodiments, the process of identifying and confirming corresponding time-based event(s) may continue at the above-mentioned step S2170 where the system (e.g., via quiz information 1714-D of time-based event module 1714) confirms one or more of the events predicted in step S2168. The process of confirming each prediction, in embodiments, is illustrated in connection with FIG. 21M.

Figure 21M:
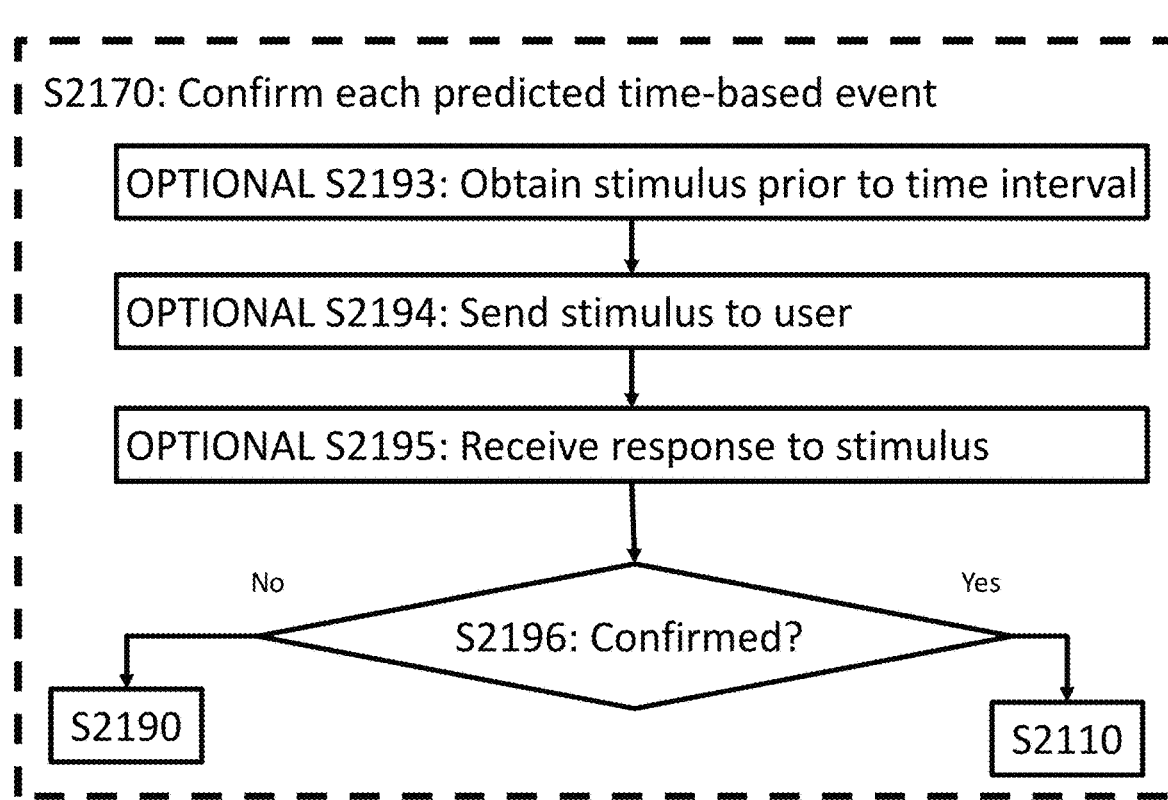

Referring to FIG. 21M, in embodiments, confirming one or more of the matches may be accomplished by one or more of the following: a stimulus (e.g., via steps S2193, S2194, S2195), purchase information (e.g., via prior purchase information 1316A), social media information (e.g., via social connection information 1308D), information from one or more additional users (e.g., one or more user event streams associated with users that are not the first user), and/or a combination thereof, to name a few. For example, the system (e.g., via quiz information 1714-D of time-based event module 1714) at step S2193, may obtain, for each predicted event, a stimulus (e.g., a prompt, quiz, etc.) designed to confirm each respective predicted event. The stimulus, at step S2194, may be sent by the system to the first user via a device associated with the first user before the predicted event was predicted to take place. For example, the stimulus may state "Are you about to have lunch?" In response, at step S2195, the system may receive a stimulus response indicating whether the respective event is confirmed (S2196). If the event is confirmed, or if another event is confirmed, the system may label the respective recurring location with its confirmed corresponding event (or another event confirmed). If the event was not confirmed, the system may update the time interval (S2190) and make another prediction to confirm. Exemplary pseudocode representing the process described in connection with FIG. 21I is located below.

```
initialization( ):
    interval = initialize_interval(
        interval_start=11:00,
        interval_end=14:00)
each_day( ):
    prediction = mean(interval)
    send a notification to the user half an hour before the prediction
    wait for the user to answer the quiz
    if user has answered very late to the quiz:
        discard_answer( )
    else
        update_interval( )
update_interval( ):
    answer_time = time when the user has answered
    if answer == 'YES':
        if answer_time > interval_end: # answered after the interval
            interval_end = answer_time
        elif answer_time < interval_start: # answered before the interval
            pass # do nothing
        else: # answered within the time interval
            interval_end = answer_time
    else if answer == 'NO':
        if answer_time > interval_end: # answered after the interval
            pass # do nothing
        elif answer_time < interval_start: # answered before the interval
            interval_start = answer_time
        else: # answered within the time interval
            interval_start = answer_time
```

In embodiments the system may not use a stimulus to confirm one or more events corresponding to one or more recurring and/or stationary locations.

In embodiments, the system (e.g., system 1000-A and/or system 1000) may model the behavior of a plurality of users associated with the system for the purposes of predicting activities. For example, the system may generate and send stimuli to a plurality of users, asking similar questions (e.g., when do you have lunch?). Continuing the example, each response from each user may be stored, resulting in a database of times when each of a plurality of users have lunch. This information, in embodiments, may assist the system in predicting a time-based event.

The processes of FIG. 21A through 21M may be repeated (S2110—e.g., if more raw data is to be analyzed). In embodiments, the steps of the processes described in connection with FIG. 21A through FIG. 21M may be rearranged or omitted.

Example 10: Exemplary Training of a Machine Learning Algorithm

To train a machine-learning algorithm to determine what stimuli may work, and determine when said stimuli may work better on a user (e.g., Bob), the system may obtain information associated with Bob over a first period of time (for the purposes of this example, a week). The information obtained by the system, for example, may be information that is used to generate data sets for the purposes of predicting behavior to better encouraging a change in said behavior to achieve Bob's goal. The data obtained may be data previously gathered by Bob's cell phone and stored by Bob's cell phone over the past week or the data may be gathered by the system in substantially real-time (e.g., the system receives and/or monitors data gathered by Bob's cell phone as Bob's cell phone is gathering the data). For the purposes of this example, the system obtains data from Bob's cell phone over a week in substantially real time.

The system, for the purposes of this example, may gather two types of information —motion information and location information in chronological order- to build a data set to describe Bob's daily activities. The motion information and location information, in embodiments, enable the system to determine locations the user has been over a period of time, such as, a few days, a week, or multiple weeks or months to name a few. The motion and location information (e.g., raw data), may have gaps—e.g., periods of time where data is unavailable or not gathered by Bob's cell phone. The gaps, continuing the example, are also used by the system to build the aforementioned data set.

One or more methods and/or specialized software algorithms may be utilized to fill the gaps—e.g., resampling at a constant rate, DBSCAN clustering, CRNN sequencing, the Gaussian Mixture model, and/or a combination thereof, to name a few.

Figure 18:
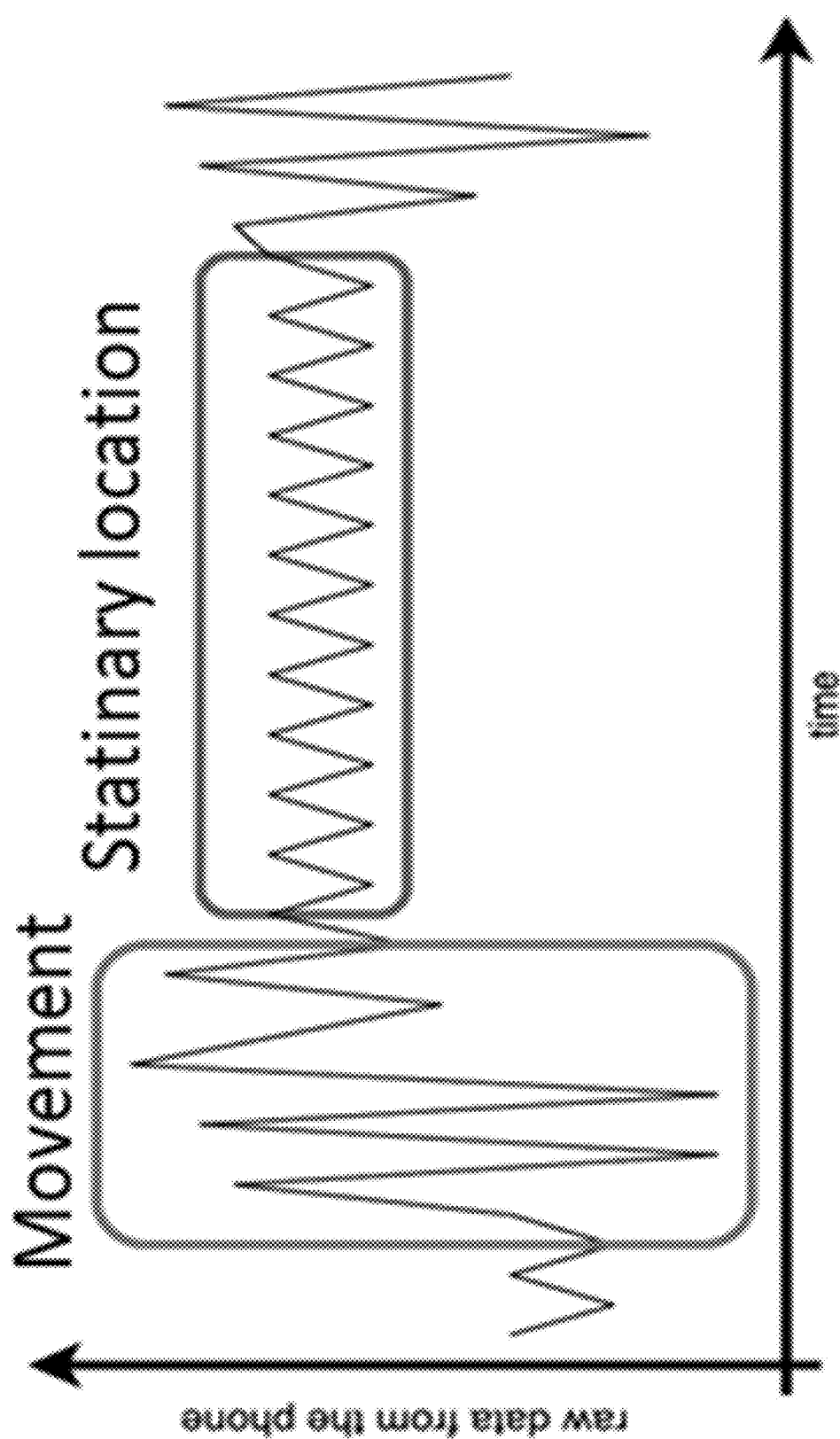
FIG. 18 is an exemplary graph of a user's movement over time in accordance with exemplary embodiments of the present invention.

Continuing the example, the system may begin to gather data from Bob's cell phone. The data may indicate, that Bob is moving. After a period of time, Bob may decide to stop at a first location, which results in the gathering of corresponding data indicating a lack of movement by the system (e.g., Bob's cell phone shows a location within a first predetermined radius over a predetermined period of time that indicates Bob and his cell phone are in a stationary location). Continuing the example, the system may store the location (e.g., in coordinates) together with the movement information prior to Bob stopping at the location. Bob may continue his day, leaving the first location and moving to a second location. This type of data gathering may continue throughout the week. For exemplary purposes, FIG. 18 illustrates data obtained from an exemplary user device including the movement prior to a stationary location and the stationary location itself.

Continuing the example, at the end of the day, Bob may travel back home. Once Bob gets home, in embodiments, he may turn off his phone, have poor cell reception, turn off his location services etc. Bob's cell phone may also prevent the gathering and/or dissemination of data. When Bob's cell phone is either not gathering data or not permitted to gather data, the system may analyze the gathered data up until the gap and right after the gap to determine whether the third location (Bob's home) may be a user-specific location. The system may analyze the data surrounding the gaps to determine whether Bob was either at or close to (e.g., within a predetermined radius) the same location at the end of the gap of time and, if within the predetermined radius, the system may determine whether Bob was in the same location for a long period of time (e.g., indicating a user-specific location). Continuing the example, the data may indicate that right before the gap, Bob was at the third location, after the gap Bob was within a predetermined radius of the third location, and the gap of time was 8 hours. This series of data may indicate to the system that Bob's home is the third location and Bob usually spends 8 hours at home between work days.

The system may continue to gather data and determine movement and locations for the entire week (e.g., or the allotted predetermined time). The extracted locations, for example may be broken up by the system into the following types of locations—user-specific places (locations associated with Bob—e.g., Bob's home, Bob's place of business, Bob's classroom etc.), public places (e.g., a park, mass-transit system, etc.) and special places (locations that are not frequented that often e.g., wedding venues, birthday party at a friend's house, funeral homes, etc.). The system may organize the extracted locations into categories because the type of location may affect the data processing required to identify the location, movement, and/or activity associated with the movement and/or the location. For example, special places may not be part of Bob's routine and predicting a special place may require more of a motion information heavy approach than a combined approach of movement, location, day, and/or time (e.g., Bob goes to work at 7:00 AM every weekday. For the purposes of this example, public places and special places may be extracted using one or more external services—for example—Google Maps, OpenStreetMap, etc. To detect user-specific places (e.g., Bob's house above), the system may utilize motion information associated with Bob, location information associated with Bob, whether locations are recurring, and gaps of data collection from Bob's cell phone. Continuing the example, the above explanation of the Bob's home may be similar to the analysis executed by the system.

Further analysis of the data may be required by the system. Continuing the example, the system may group the detected locations into separate, and sometimes overlapping, groups—e.g.,—stationary locations, recurring locations, possible locations; and confirmed locations (regardless of whether user-specific, public, and/or special). The system may extract stationary locations based on Bob's lack of movement. The system may also analyze data gathered to extract stationary locations using one or more algorithms (e.g., a machine learning algorithm, DBSCAN, and/or a gaussian mixture model, to name a few). The system may extract recurring locations by determining which of the stationary locations is visited more than once by Bob during the week. The system may extract possible locations using the gaps of data (e.g., similar to the analysis of Bob's home). To extract confirmed locations, the system may generate and send a query (e.g., a quiz, prompt, and/or a combination thereof, to name a few) to Bob's cell phone. Continuing the example, the system may send the following to Bob's cell phone:

Is the Third Location one of the following?
  A: Your home
  B: Your office
  C: None of the above Continuing the example, at the end of the day, Bob may travel back home. Once Bob gets home, in embodiments, he may turn off his phone, have poor cell reception, turn off his location services etc., resulting in data not being available for the system. Bob's cell phone may also prevent the gathering and/or dissemination of data. When Bob's cell phone is either not gathering data or not permitted to gather data, the system may analyze the gathered data up until the gap and right after the gap to determine whether the third location (Bob's home) may be a user-specific location. The system may analyze the data surrounding the gaps to determine whether Bob was either at or close to (e.g., within a predetermined radius) the same location at the end of the gap of time and, if within the predetermined radius, the system may determine whether Bob was in the same location for a long period of time (e.g., indicating a user-specific location). Continuing the example, the data may indicate that right before the gap, Bob was at the third location, after the gap Bob was within a predetermined radius of the third location, and the gap of time was 8 hours. This series of data may indicate to the system that Bob's home is the third location and Bob usually spends 8 hours at home between work days.

The system may continue to gather data and determine movement and locations for the entire week (e.g., or the allotted predetermined time). The extracted locations, for example may be broken up by the system into the following types of locations—user-specific places (locations associated with Bob—e.g., Bob's home, Bob's place of business, Bob's classroom etc.), public places (e.g., a park, mass-transit system, etc.) and special places (locations that are not frequented that often e.g., wedding venues, birthday party at a friend's house, funeral homes, etc.). The system may organize the extracted locations into categories because the type of location may affect the data processing required to identify the location, movement, and/or activity associated with the movement and/or the location. For example, special places may not be part of Bob's routine and predicting a special place may require more of a motion information heavy approach than a combined approach of movement, location, day, and/or time (e.g., Bob goes to work at 7:00 AM every weekday. For the purposes of this example, public places and special places may be extracted using one or more external services—for example—Google Maps, OpenStreetMap, etc. To detect user-specific places (e.g., Bob's house above), the system may utilize motion information associated with Bob, location information associated with Bob, whether locations are recurring, and gaps of data collection from Bob's cell phone. Continuing the example, the above explanation of the Bob's home may be similar to the analysis executed by the system.

Further analysis of the data may be required by the system. Continuing the example, the system may group the detected locations into separate, and sometimes overlapping, groups—e.g.,—stationary locations, recurring locations, possible locations; and confirmed locations (regardless of whether user-specific, public, and/or special). The system may extract stationary locations based on Bob's lack of movement. The system may also analyze data gathered to extract stationary locations using one or more algorithms (e.g., a machine learning algorithm, DBSCAN, and/or a Gaussian mixture model, to name a few). The system may extract recurring locations by determining which of the stationary locations is visited more than once by Bob during the week. The system may extract possible locations using the gaps of data (e.g., similar to the analysis of Bob's home). To extract confirmed locations, the system may generate and send a query (e.g., a quiz, prompt, and/or a combination thereof, to name a few) to Bob's cell phone. Continuing the example, the system may send the following to Bob's cell phone:

Is the Third Location one of the following?
  A: Your home
  B: Your office
  C: None of the above Bob may send the response of "A: Your home." If the system receives such a response, the third location would be categorized by the system as a confirmed location. If the system receives "B: Your office" as a response, the system may replace the possible third location determination of Bob's Home with Bob's Office. If the system receives "C:

None of the above" as a response, the system may delete the determination of Bob's home and reanalyze the data.

Continuing the example, the system may associate one or more activities with each extracted location. As an example, the activity associated with the third location is Bob's home. The activities may be determined by the system using data available to the system (e.g., system may determine the activity is a movie if the stationary location is a movie theater and Bob was there for two hours) and/or using quizzes (and/or prompts) to confirm the activity. The system may not determine an activity for each location. Where possible, the system may assign determined activities to their corresponding location. The determination of activities and locations may be done simultaneously and/or substantially simultaneously by the system.

The system may, continuing the example, use the categories of locations (stationary, recurring, possible, confirmed) to begin to build data sets to better understand Bob's actions throughout the day. The first data set may include each stationary location with each's corresponding activity, movement information, and timestamp. The second data set may include each recurring location with each's (for each visit to the recurring location) corresponding activity, movement information, and timestamp. As noted above, the first data set and the second data set may overlap. The third data set may include both of (1) each possible location with each's corresponding activity, movement information, timestamp, and whether confirmed and (2) each confirmed location with each's corresponding activity, movement, timestamp, and whether confirmed. The obtained data from Bob's cell phone is transformed by the system into data sets that are usable by the system to provide accurate and persuasive stimuli at a precise time with real-time notifications. The three data sets may be used by the system as a predictive model for Bob. Continuing the example, the data may suggest that Bob eats at an unhealthy restaurant every day on the way to work at 7:30 AM. The system may generate and send a stimulus that triggers a real-time notification when Bob is leaving his home to go to work. The notification may offer a stimulus that provides a coupon for a healthier meal on the way to work. If Bob uses the coupon, the system may determine that the stimuli was a success and store the utilized stimuli as such. If Bob does not use the coupon and still eats at the unhealthy restaurant, the system may determine that the stimuli was not a success and store the utilized stimuli as such. Each successful or unsuccessful stimuli may be stored in a data set, assisting the prediction of whether a stimulus will work.

The system may use the data sets to train one or more machine learning algorithms to select stimuli and times to present said stimuli such that data obtained by the system from Bob's cell phone may trigger a real-time push notification of the selected stimulus (a more detailed description of training a machine learning algorithm in accordance with this disclosure is located below in connection with the description of FIG. 16, the description of which applying herein). The system may use the data sets as a predictive model until the data sets have grown to a predetermined size, suitable for training a machine learning algorithm. The data sets would then be used by the system to train the machine learning algorithm.

Example 11: Exemplary Recommendations for Lowest COVID-19 Infection Risk

Related to Example 4, a user at personal user device(s) 10-1 ... 10-*n*, using mobile application software 3000 is provided with recommended locations to reduce risk of infection by disease, for example to reduce risk of infection by the severe acute respiratory syndrome coronavirus 2 (SARS CoV-2) responsible for the COVID-19 disease during the pandemic of 2020. Processor 2010 at personal data system 20 (or at system 1000) retrieves user profile data 2014, current user location data (e.g., location information 752), and recorded user device data 2018, including a historical log file of user location data (e.g., location information 752) for a combined analysis with third-party data (e.g., from third party information systems 30-1 ... 20-*n*) (for example the Israeli contact tracing feed at https://matrixdemos.blob.core.windows.net/mabar/Points.json or equivalent ones provided in various other countries) and Foursquare/Google maps data using one or more algorithmic processes. One or more recommendations are identified based on the analysis and corresponding stimuli (one or more) are generated at stimulus module 2032 and transmitted to the user at personal user device(s) 10-1 ... 10-*n*.

System 1000-A (and/or system 1000) accesses third-party data (e.g., from third party information systems 30-1 ... 20-*n*) which may include a contact tracing database and retrieves timestamped geographical coordinates of infection sources (for example, the locations, paths, and whereabouts of people confirmed to be infected with COVID-19, or displaying symptoms consistent with COVID-19). For each such record, System 1000-A (and/or system 1000) computes a risk score that that reflects how likely the user is to become infected.

An exemplary risk score calculation function for each known location within a specified radius is outlined below:
    user.loc=user.location(now)
    risk_radius=50 m
    historical_range=72 h
    connect_to_third_party_system( )
    locations=get_locations(risk_radius)
    for each location in locations {
        location.records=from third_party_system, select_records(historical_range,
    location(risk_radius))
        for each location.record in location.records: {
            location.risk.total+=normalize(0, time(now)-location.record.timestamp( ), 100)}
    location.risk.score=location.risk.total/records.count( )

Personal user device(s) 10-1 ... 10-*n* may then display the risk associated with each location as a number representing the risk score, as a color representing risk range (for example, 0-20=low risk as green, 21-69=medium risk as yellow, 70-100=high risk as red), as different graphical notations and so forth. In embodiments, the displayed risk may alert users with information regarding the number of hours that have expired since the last time a confirmed infected person has physically been in a particular building.

A challenge caused by the COVID-19 pandemic and other pandemics that may occur is the difficulty of using technology to verify and enforce social distancing regulations that may require stores and other venues to limit the number of people that may enter at any given point in time, or maintain a minimal distance from each other. Among other problems, such regulations may give rise to queues being formed at entrances of such stores and other venues. Certain users may want to minimize any waiting in queues, both in order to save time and to further minimize any further risk of exposure. To minimize queue waiting for such users, personal user device(s) 10-1 ... 10-*n* may also collect user data from user devices and data from third parties to estimate the length of the queue at each particular location. For example, users waiting in a queue will have a very clear pattern of repeatedly moving 6 feet increments (or other distance increments prescribed by social distancing regulations) and then being stationary for some time, all while they get closer and closer to the venue's entrance. This type of pattern can be recognized by location module 1710 as depicted in FIG. 18.

Personal user device(s) 10-1 . . . 10-*n* may also send quizzes or other stimuli to users, to confirm if they are indeed waiting in a queue and what is the queue length. These responses can then be sent to system 1000-A (and/or system 1000) to be shared with other users in the geographical vicinity. The users may be sent coupons usable in the venue to keep track of when users are paying for items, and thus, likely leaving the venue.

Personal user device(s) 10-1 . . . 10-*n* may also send quizzes to designated users (for example, the usher at the entrance to a store) to receive input on queue wait times.

Personal user device(s) 10-1 . . . 10-*n* may also enable a user to search for desired venues (for example, grocery stores) within a certain geographical region or vicinity (e.g., by accessing data from third party systems including, for example, Google Maps API, Apple Maps, Foursquare and the like), and to provide a sorted list of such venues according to distance, to queue wait times, to infection risk, or any variation thereof, including combined scores of these parameters. Personal user device(s) 10-1 . . . 10-*n* may further depict some or all of these venues on a map, with information about each venue overlaid over the map.

Personal user device(s) 10-1 . . . 10-*n* may also alert a user (by audio or vibration or onscreen display or any other mean) that the user is close (within a certain radius, within a geographical region, or otherwise) to an infection risk. For example, if the user is about to enter a particular store where a recent infection risk has been identified, personal user device(s) 10-1 . . . 10-*n* may then alert said user about the risk and possibly the user will not enter the store and thus reduce their own risk of infection.

While in the foregoing specification a detailed description of specific embodiments of the present disclosure was set forth, it will be understood that many of the details herein given may be varied considerably by those skilled in the art without departing from the spirit and scope of the present disclosure.

The exemplary embodiments of the present invention, as set forth above, are intended to be illustrative, not limiting. The spirit and scope of the present invention is to be construed broadly. Now that embodiments of the present invention have been shown and described in detail, various modifications and improvements thereon can become readily apparent to those skilled in the art. Accordingly, the exemplary embodiments of the present invention, as set forth above, are intended to be illustrative, not limiting. The spirit and scope of the present invention is to be construed broadly.

What is claimed:

1. A method comprising:
(a) providing a lifestyle modification computer system comprising one or more computers and including at least:
  (1) a plurality of databases stored in respective memory operatively connected to the lifestyle computer system including:
    (A) a lifestyle database comprising:
      (i) first raw time-stamped streaming data including a plurality of sets of time-stamped sensor data obtained by a first user personal mobile device associated with a first user; and
      (ii) a respective location data label associated with each set of time-stamped sensor data;
    (B) a user profile database comprising:
      (i) location information including location data labels associated with the first user;
      (ii) event stream information including previously identified event streams associated with the first user and comprising a plurality of time-sequenced location data labels associated with the first user and respective type of stimulus information associated with each respective previously identified event stream;
      (iii) goal information indicating at least one selected goal in lifestyle behavior of the first user,
        wherein the at least one selected goal in lifestyle behavior is a subset of a plurality of goals in lifestyle behaviors organized by category of goal in lifestyle behavior; and
      (iv) budget information including an available budget to provide stimuli to the first user
    (C) an available stimulus database comprising available stimulus information comprising a plurality of available stimulus items and for each available stimulus item of the plurality of available stimulus items comprising:
      (i) respective type of stimulus information including a respective categorization of the stimulation information associated with the at least one selected goal in lifestyle behavior;
      (ii) respective cost information including a respective cost associated with the respective stimulus item; and
      (iii) respective availability information including a respective time period when the respective stimulus item is available; and
    (D) a stimulus database comprising:
      (i) query information comprising:
        1. a plurality of queries;
        2. respective stimulus information associated with each query of the plurality of queries; and
        3. respective outcome information associated with each query of the plurality of queries;
  (2) a plurality of modules including:
    (A) a personal information module;
    (B) a situation module;
    (C) a training set generation module;
    (D) a stimulus module;
    (E) a manager module; and
    (F) a collection module;
(b) obtaining, by the personal information module of the lifestyle modification computer system from the first user personal mobile device, second raw time-stamped streaming data including a first set of time-stamped sensor data associated with a first time period, wherein the first set of raw time-stamped sensor data includes:
  (1) time-stamped location information associated with a location of the first user personal mobile device at a first time in the first time period; and
  (2) time-stamped motion information associated with movement of the first user personal mobile device at a first time in the first time period;
(c) upon obtaining the second raw time-stamped streaming data, processing, in real-time by the personal information module of the lifestyle modification computer system, the second raw time-stamped streaming data by the steps of:
  (1) determining, in real-time, a first location data label associated with the location of the first user personal mobile device at the first time,
    wherein the determining step is made by comparing, at least the time-stamped location information with the location information associated with the first user stored in the user profile database to determine the first location data label;
  (2) updating the lifestyle database by storing the second raw time-stamped streaming data labelled with the first location data label; and
  (3) notifying the situation module that there is updated lifestyle information;
(d) upon receiving the update notification, processing, in real-time by the situation module of the lifestyle modification computer system, the updated lifestyle information by performing, the steps of:
  (1) obtaining, by the situation module, the updated lifestyle information including the second raw time-stamped stream data with its associated first location data label and a second plurality of sets of time-stamped sensor data and corresponding location data labels,
    wherein the second plurality of time-stamped sensor data is a subset of the plurality of sets of time-stamped sensor data and each of the second plurality of sets of time-stamped sensor data is sequentially related by time interval and are within a threshold period of time;
  (2) generating, by the situation module, a first event stream organized by timestamps associated with each respective location data label corresponding to the second plurality of sets of time-stamped sensor data;
  (3) analyzing, by the situation module, the generated first event stream against event stream information obtained from the user profile database associated with the first user to determine a predicted event expected to occur within a second time period; and
  (4) upon determining the predicted event expected to occur within the second time period, sending, from the situation module to the manager module, the generated first event stream as a first query to the manager module;
(e) upon receipt of the first query, processing, in real-time by the manager module, the first query by the steps of:
  (1) providing, by the manager module, the first query as a data input to a first machine-learning algorithm with a training set provided by the training set module to generate first stimulus information to be sent to the first user personal mobile device, the first stimulus information including a first type of stimulus information indicating a first categorization of the first stimulus information associated with the at least one goal in lifestyle behavior;
    wherein the training set includes a plurality of the previously identified event streams associated with the first user, tagged with stimulus information indicating a respective stimulus offered to the first user and corresponding respective stimulus outcome information indicating one or more respective actions taken in response to the respective stimulus offered;
  (2) generating, by the manager module via the first machine-learning algorithm, the first stimulus information; and
  (3) sending the first stimulus information to the stimulus module of the lifestyle modification computer system;
(f) upon receipt of the first stimulus information, processing, in real-time by the stimulus module, the first stimulus information to select a first stimulus including a first stimulus item to be sent to the first user personal mobile device, based on available stimulus items in the available stimulus database, and outcome information in the stimulus database indicating prior outcomes of one or more stimuli offered in association with prior event streams,
    wherein the first stimulus is a first type of stimulus, and
    wherein the first stimulus is selected from available stimulus items that are associated with both the first type of stimulus and outcome information indicating a positive outcome; and
(g) sending, by the lifestyle modification computer system to the first user personal mobile device, the first stimulus,
    wherein the first stimulus is situationally targeted with respect to the at least one selected goal in lifestyle behavior such that the first stimulus is sent to provide a real-time notification to the first user via the personal mobile device; and
(h) collecting, by the collection module, a first outcome associated with the first stimulus and causing the stimulus module to update the stimulus database with at least the first query, the first stimulus, and the first outcome.

2. The method of claim 1, wherein the situational targeting of the first stimulus based on the predicted event, and
  wherein the predicted event is predicted in advance by the lifestyle modification computer system based on prior event streams.

3. The method of claim 1, further comprising:
(i) obtaining, by the personal information module from the first user personal mobile device, third raw time-stamped streaming data including a second set of time-stamped sensor data associated with a third time period obtained by the first user personal mobile device, wherein the second set of time-stamped sensor data includes:
  (1) second time-stamped location information during the second time period associated with a second location of the first user personal mobile device at a second time in the second time period; and
  (2) second time-stamped motion information associated with movement of the first user personal mobile device at the second time in the second time period.

4. The method of claim 3, wherein the third raw time-stamped data includes additional data associated with the first user personal mobile device.

5. The method of claim 3, further comprising:
(j) upon obtaining the third raw time-stamped streaming data, determining, by the personal information module, that no location data label is associated with the second location, by processing the third raw time-stamped streaming data in real-time; and
(k) sending, by the personal information module to a location module of the lifestyle modification computer system, the second time-stamped location information to establish a second location data label associated with the second location.

6. The method of claim 3, further comprising:
(j) upon obtaining the third raw time-stamped streaming data, processing, in real-time by the personal information module of the lifestyle modification computer system, the third raw time-stamped streaming data by the steps of:
  (1) determining, in real-time, a second location data label associated with the second location of the first user personal mobile device at a second time in the second time period,
  wherein the determining step is made by comparing, at least the second time-stamped location information with the location information associated with the first user stored in the user profile database to determine the second location data label;
  (2) updating the lifestyle database by storing the third raw time-stamped streaming data labelled with the second location data label; and
  (3) notifying the situation module that there is updated lifestyle information; and
(k) upon receiving the update notification, processing, in real-time by the situation module of the lifestyle modification computer system, the updated lifestyle information by performing the steps of:
  (1) obtaining, by the situation module, the updated lifestyle information including the third raw time-stamped stream data with its associated second location data label and a third plurality of sets of time-stamped sensor data and corresponding location data labels,
  wherein the third plurality of time-stamped sensor data is a subset of the plurality of sets of time-stamped sensor data and each of the third plurality of sets of time-stamped sensor data is sequentially related by time interval and within the threshold period of time;
  (2) generating, by the situation module, a second event stream organized by timestamps associated with each respective location data label corresponding to the third plurality of sets of time-stamped sensor data;
  (3) analyzing, by the situation module, the generated second event stream against event stream information obtained from the user profile database associated with the first user to determine no predicted event is expected to occur within a third time period; and
  (4) upon determining that no predicted event is expected to occur within the third time period, one of the following occurs:
    (i) the method ends; or
    (ii) the situation module notifies the personal information module to analyze the third raw time-stamped stream data for a third location.

7. The method of claim 3, further comprising:
(j) upon obtaining the third raw time-stamped streaming data, processing, in real-time by the personal information module of the lifestyle modification computer system, the third raw time-stamped streaming data by the steps of:
  (1) determining, in real-time, a second location data label associated with the second location of the first user personal mobile device at the second time period,
  wherein the determining step is made by comparing, at least the second time-stamped location information with the location information associated with the first user stored in the user profile database to determine the second location data label;
  (2) updating the lifestyle database by storing the third raw time-stamped streaming data labelled with the second location data label; and
  (3) notifying the situation module that there is updated lifestyle information; and
(k) upon receiving the update notification, processing, in real-time by the situation module of the lifestyle modification computer system, the updated lifestyle information by performing, the steps of:
  (1) obtaining, by the situation module, the updated lifestyle information including the third raw time-stamped stream data with its associated second location data label and a third plurality of sets of time-stamped sensor data and corresponding location data labels,
  wherein the third plurality of time-stamped sensor data is a subset of the plurality of sets of time-stamped sensor data and each of the third plurality of sets of time-stamped sensor data is sequentially related by time interval and within the threshold period of time;
  (2) generating, by the situation module, a second event stream organized by timestamps associated with each respective location data label corresponding to the third plurality of sets of time-stamped sensor data;
  (3) analyzing, by the situation module, the generated second event stream against event stream information obtained from the user profile database associated with the first user to determine a second predicted event expected to occur within a third time period; and
  (4) upon determining that the predicted event expected to occur within the third time period, sending, from the situation module to the manager module, the generated second event stream as a second query to the manager module;
(l) upon receipt of the second query, processing, in real-time by the manager module, the second query by the steps of:
  (1) providing, by the manager module, the second query as a second data input to the first machine-learning algorithm with the training set provided by the training set module to receive an output from the first machine-learning algorithm;
  (2) determining, by the manager module, the output indicates that no stimulus information has been identified by the first machine-learning algorithm based on the second query as the second data input; and
  (3) sending, by the manager module to the stimulus module, the second query and the output; and
(m) upon receipt of the second query and output, storing, by the stimulus module, the second query and the output in the stimulus database.

8. The method of claim 3, further comprising:
(j) upon obtaining the third raw time-stamped streaming data, processing, in real-time by the personal information module of the lifestyle modification computer system, the third raw time-stamped streaming data by the steps of:
  (1) determining, in real-time, a second location data label associated with the second location of the first user personal mobile device at the second time period,
  wherein the determining step is made by comparing, at least the second time-stamped location information with the location information associated with the first user stored in the user profile database to determine the second location data label;
(2) updating the lifestyle database by storing the third raw time-stamped streaming data labelled with the second location data label; and
(3) notifying the situation module that there is updated lifestyle information; and
(k) upon receiving the update notification, processing, in real-time by the situation module of the lifestyle modification computer system, the updated lifestyle information by performing, the steps of:
(1) obtaining, by the situation module, the updated lifestyle information including the third raw time-stamped stream data with its associated second location data label and a third plurality of sets of time-stamped sensor data and corresponding location data labels,
wherein the third plurality of time-stamped sensor data is a subset of the plurality of sets of time-stamped sensor data and each of the third plurality of sets of time-stamped sensor data is sequentially related by time interval and within the threshold period of time;
(2) generating, by the situation module, a second event stream organized by timestamps associated with each respective location data label corresponding to the third plurality of sets of time-stamped sensor data;
(3) analyzing, by the situation module, the generated second event stream against event stream information obtained from the user profile database associated with the first user to determine a second predicted event expected to occur within a third time period; and
(4) upon determining that the predicted event expected to occur within the third time period, sending, from the situation module to the manager module, the generated second event stream as a second query to the manager module;
(l) upon receipt of the second query, processing, in real-time by the manager module, the second query by the steps of:
(1) providing, by the manager module, the second query as a second data input to the first machine-learning algorithm to generate second stimulus information to be sent to the first user personal mobile device, the second stimulus information including a second type of stimulus information indicating a second categorization of the second stimulus information associated with the at least one goal in lifestyle behavior;
(2) generating, by the manager module via the first machine-learning algorithm, the second stimulus information; and
(3) sending the second stimulus information to the stimulus module of the lifestyle modification computer system;
(m) upon receipt of the first stimulus information, determining, in real-time by the stimulus module, a second stimulus corresponding to the second stimulus information is unavailable; and
(n) upon determining the second stimulus is unavailable, storing, by the stimulus module, the second query and the second stimulus information.

9. The method of claim 1, wherein the budget information further includes respective available budgets for each user of a plurality of users of an interactive electronic network associated with the lifestyle modification computer system, and
wherein the plurality of users includes the first user.

10. The method of claim 9, wherein one or more users of the plurality of users is associated with a monthly budget.

11. The method of claim 9, wherein one or more users of the plurality of users associated with the same budget.

12. The method of claim 1, wherein the budget information includes a budget for each at least one selected goal.

13. The method of claim 1, wherein the at least one selected goal includes a plurality of selected goals.

14. The method of claim 1, wherein the plurality of queries includes queries associated with one or more users associated with one or more goals in lifestyle behavior in the same category of goal in lifestyle behavior as the at least one goal in lifestyle behavior of the first user.

15. The method of claim 1, wherein the respective outcome information for each query of the plurality of queries includes outcomes of one or more stimuli offered to one or more additional users associated with one or more goals in lifestyle behavior in the same category of goal in lifestyle behavior as the selected at least one goal in lifestyle behavior of the first user.

16. The method of claim 1, wherein, prior to step (d), the personal information module sends the second raw-time stamped streaming data with its associated first location data label to the situation module.

17. The method of claim 1, wherein the obtained second plurality of sets of time-stamped sensor data and corresponding location labels includes less than all of the second plurality of sets of time-stamped sensor data within the threshold period of time.

18. The method of claim 1, wherein the threshold period of time is one of the following:
(i) 1 calendar day
(ii) 12 hours;
(iii) 6 hours;
(iv) 1 hour; and
(v) 30 minutes.

19. The method of claim 1, wherein the first event stream includes a plurality of event streams, each organized by timestamps associated with its respective location data label.

20. The method of claim 1, wherein the first event stream is organized further by one or more of the following:
(i) each event included in the first event stream's respective timestamp; and
(ii) a routine associated with the first user.

21. The method of claim 1, wherein the second period of time is less than 10 minutes.

22. The method of claim 1, wherein the first stimulus is sent to a second user personal mobile device associated with a second user.

23. The method of claim 1, wherein the first outcome is collected from at least one of the following:
(i) the first user personal mobile device;
(ii) a second electronic device associated with the first user;
(iii) a second user personal mobile device associated with a second user; and
(iv) a third party computer system.

24. The method of claim 1, wherein the first stimulus is sent from the stimulus module to the manager module and then from the manager module to the first user personal mobile device.

25. The method of claim 1, wherein the first stimulus is sent to the first user personal mobile device by the stimulus module.

26. The method of claim 1, wherein the first stimulus is sent from the stimulus module to the collection module and then from the collection module to the first user personal mobile device.

27. The method of claim 1, wherein the first machine-learning algorithm is utilizes a neural network.

28. The method of claim 1, wherein the training set further includes a plurality of previously identified event streams associated with a second user.

\* \* \* \* \*